(12) United States Patent
Khaskin

(10) Patent No.: US 11,465,966 B2
(45) Date of Patent: Oct. 11, 2022

(54) CYCLOPROPANATION METHOD

(71) Applicant: OKINAWA INSTITUTE OF SCIENCE AND TECHNOLOGY SCHOOL CORPORATION, Okinawa (JP)

(72) Inventor: Eugene Khaskin, Okinawa (JP)

(73) Assignee: OKINAWA INSTITUTE OF SCIENCE AND TECHNOLOGY SCHOOL CORPORATION, Okinawa (JP)

( * ) Notice: Subject to any disclaimer, the term of this patent is extended or adjusted under 35 U.S.C. 154(b) by 12 days.

(21) Appl. No.: 16/635,475

(22) PCT Filed: Aug. 17, 2018

(86) PCT No.: PCT/JP2018/030472
§ 371 (c)(1),
(2) Date: Jan. 30, 2020

(87) PCT Pub. No.: WO2019/035479
PCT Pub. Date: Feb. 21, 2019

(65) Prior Publication Data
US 2021/0238133 A1 Aug. 5, 2021

Related U.S. Application Data

(60) Provisional application No. 62/547,232, filed on Aug. 18, 2017.

(51) Int. Cl.
*C07C 315/04* (2006.01)
*B01J 31/18* (2006.01)
*B01J 31/20* (2006.01)
*B01J 31/22* (2006.01)
*B01J 31/24* (2006.01)
*C07D 295/096* (2006.01)
*C07D 333/18* (2006.01)

(52) U.S. Cl.
CPC ......... *C07C 315/04* (2013.01); *B01J 31/1805* (2013.01); *B01J 31/189* (2013.01); *B01J 31/20* (2013.01); *B01J 31/226* (2013.01); *B01J 31/2495* (2013.01); *C07D 295/096* (2013.01); *C07D 333/18* (2013.01); *B01J 2231/4288* (2013.01); *B01J 2531/821* (2013.01); *B01J 2531/825* (2013.01); *C07B 2200/05* (2013.01); *C07C 2601/02* (2017.05); *C07C 2601/16* (2017.05)

(58) Field of Classification Search
None
See application file for complete search history.

(56) References Cited

PUBLICATIONS

U.S. Appl. No. 62/547,232, Eugene Khaskin—owned by Applicant, filed Aug. 18, 2017.
PCT/JP2018/030472 published as WO2019035479, Feb. 21, 2019, Okinawa Institute Of Science And Technology School Corporation—owned by Applicant.
Written opinion and search report for PCT/JP2018/030472, dated Feb. 21, 2019, Okinawa Institute Of Science And Technology School Corporation—owned by Applicant.
Appel et al., Scope and Limitations of Cyclopropanations with Sulfur Ylides. J. Am. Chem. Soc. 132: 17894-17900 (2010).
Benoit et al., Diastereoselective Borocyclopropanation of Allylic Ethers Using a Boromethylzinc Carbenoid. J. Am. Chem. Soc. 139: 1364-1367 (2017).
Brandt et al., Synthesis of substituted tetrahydrofurans via intermolecular reactions of y-chlorocarbanions of 3-substituted 3-chloropropylphenyl sulfones with aldehydes. Tetrahedron 66: 3378-3385 (2010).
Chanthamath et al., Enantioselective Cyclopropanation of a Wide Variety of Olefins Catalyzed by Ru (II)—Pheox Complexes. Acc. Chem. Res., 49, 2080-2090 (2016).
Gianatassio et al., Strain Release Amination. Science 351(6270): 241-246 (2016).
Jankins et al., Three-Component [1+1+1] Cyclopropanation with Ruthenium (II). Organometallics 37: 2609-2617 (2018).
Jin et al., Enantioselective Sulfonation of Enones with Sulfonyl Imines by Cooperative N-Heterocyclic-Carbene/Thiourea/Tertiary-Amine Multicatalysis. Angew. Chem. Int. Ed. 52: 12354-12358 (2013).
Muller et al., Asymmetric Copper-Catalyzed Carbozincation of Cyclopropenes en Route to the Formation of Diastereo- and Enantiomerically Enriched Polysubstituted Cyclopropanes. J. Am. Chem. Soc. 137: 15414-15417 (2015).
Shitama et al., Asymmetric Simmons—Smith Reaction of Allylic Alcohols with Al Lewis Acid/N Lewis Base Bifunctional Al (Salalen) Catalyst. Angew. Chem. Int. Ed. 47: 2450-2453 (2008).
Skarzewski et al., A new and efficient route to homochiral y-hydroxysulfoxides and y-hydroxysulfones. Tetrahedron: Asymmetry 13: 2105-2111 (2002).
Tsunoda et al., Arylmethyl phenyl sulfones, a new carbon nucleophile for Mitsunobu-type alkylation. Tetrahedron Lett. 40: 7359-7362 (1999).
Welbes et al., Synthesis of Cyclopropanes via Pd (II/IV)-Catalyzed Reactions of Enynes. J. Am. Chem. Soc. 129: 5836-5837 (2007).

*Primary Examiner* — Joseph R Kosack
(74) *Attorney, Agent, or Firm* — Brian S. Boyer; Syndicated Law, PC

(57) ABSTRACT

A cyclopropanation method includes reacting an alcohol, an ester, or an aldehyde with a sulfone in an organic solvent containing a base providing a counter cation to form a cyclopropane; and isolating the cyclopropane. When using the alcohol or ester, the organic solvent further contains a catalyst having an alcohol dehydrogenation activity.

26 Claims, 97 Drawing Sheets

Previous Methods

Corey-Chaikosky ylide mediated cyclopropanation

Simmons-Smith cyclopropanation via diiodomethane

Metal catalyzed carbene cyclopropanation of olefins

Invention

Ru catalyzed cyclopropanation of alcohols

Classical Julia Olefination

Julia, 1973

Modified Julia Olefination of Aldehydes

Julia, 1991

Catalytic Olefination of Alcohols

Milstein, 2015

Initial Screening of Unsymmetrical Esters

Reactions of Symmetrical Esters

CYCLOPROPANATION METHOD

This application is a national stage application, filed under 35 U.S.C. 371, of International application no. PCT/JP2018/030472, filed Aug. 17, 2018, which claims the benefit of U.S. provisional application No. 62/547,232, filed on Aug. 18, 2017, each application of which is hereby incorporated herein by reference in its entirety.

TECHNICAL FIELD

This invention relates generally to cyclopropanation, and more particularly to a method of cyclopropanation, a compound having a cyclopropane structure, and a use thereof.

BACKGROUND

Cyclopropanes are an important structural motif in many biosynthetic pathways and are present in a large number of natural products.[1] (References are cited in the last paragraph of this specification) Due to the high ring strain present in this structural motif, compounds bearing it have found use in the pharmaceutical industry as drugs and antibiotics, and as useful precursors in the synthesis of industrially relevant compounds.[2] However, the high ring strain presents many synthetic challenges, with the most common pathways proceeding through the generation of reactive carbene and ylide species, requiring a number of synthetic steps, often generating stoichiometric amounts of waste, and/or requiring large (>5 mol %) amounts of catalyst.

The cyclopropanation reaction has been mostly limited to olefin precursors. Historical examples include the Simmons-Smith cyclopropanation, which uses multiple equivalents of zinc, where catalytic zinc reagents have recently been utilized,[3] and the Corey-Chaykovsky cyclopropanation, part of a class of cyclopropanation reactions characterized as Michael initiated ring closure,[4] (FIG. 1) where olefins are attacked with dimethylsulfonium ylides.[5] Other popular methods for synthesizing cyclopropanes include metal-catalyzed additions of carbenes formed from the decomposition of diazo reagents,[6] organocatalysis,[4g, 4i, 7] ene-yne catalyzed ring closure,[8] and metal-catalyzed additions to cyclopropenes.[9] These approaches are in the vast majority of cases specific to polar or electron deficient olefins, where a β-carbon substituent often acts as a directing group for the cyclopropanation reagent.

Due to the value of the cyclopropane architecture in designing novel antibiotics and reagent libraries, and as intermediates in natural product or drug candidate syntheses, new types of cyclopropane derivatives are currently of high interest.

SUMMARY OF INVENTION

One embodiment of the invention is a cyclopropanation method of reacting alcohol, ester, or aldehyde with sulfone to form a cyclopropane.

In one embodiment using alcohol or ester, the cyclopropanation method includes reacting an alcohol or an ester with a sulfone in a presence of a base providing a counter cation such as a potassium cation, a catalyst having an alcohol dehydrogenation activity, and an organic solvent to form a cyclopropane; and isolating the cyclopropane.

In one embodiment using aldehyde, the cyclopropanation method includes reacting an aldehyde with a sulfone in a presence of a base providing a counter cation such as a potassium cation and an organic solvent to form a cyclopropane; and isolating the cyclopropane.

Another embodiment of the invention is a compound having a cyclopropane structure that can be formed by the method.

One embodiment is exemplified in FIG. 1. As shown in FIG. 1, a product can have a cyclopropane structure with two or three new stereocenters and a possible quaternary carbon, formed from achiral starting materials.

Moreover, in the embodiment of this invention in FIG. 1 (Invention), the products of the cyclopropanation reaction may be relatively rare examples of electron rich cyclopropane products that also possess an excellent leaving group at the quaternary carbon center. The aryl sulfone functional group bound directly to a cyclopropane unit, introduces a push-pull effect conducive to ring opening reactions,[10] and has been recently used in an elegant C—N bond coupling technique by the Baran group.[11] Ring opening reactions of push-pull cyclopropanes in organic synthesis, including ring expansion, have been summarized previously.[12] A large limiting factor for the cyclopropane mediated C—N coupling protocol is the accessibility of the sulfone cyclopropane reagent that has to be prepared via multi-step synthesis.[11b, 13] The method of coupling alcohols directly with sulfones can offer facile entrance to a large number of diverse, polarized sulfonated cyclopropanes in one step.

The method of the invention offers advantages over previous methods by giving control over substituents on all three carbons of the ring with excellent diastereoselectivity and without the need of any prefunctionalization to form complex olefins or sensitive diazo reagents.

166.1(2), C16-C11-C1-C3−124.5(3), C26-C21-C2-C3−157.9(3), C301-C31-C3-C2−91.3(4), C302-C301-C31-C3−174.7(3).

Figure 94:
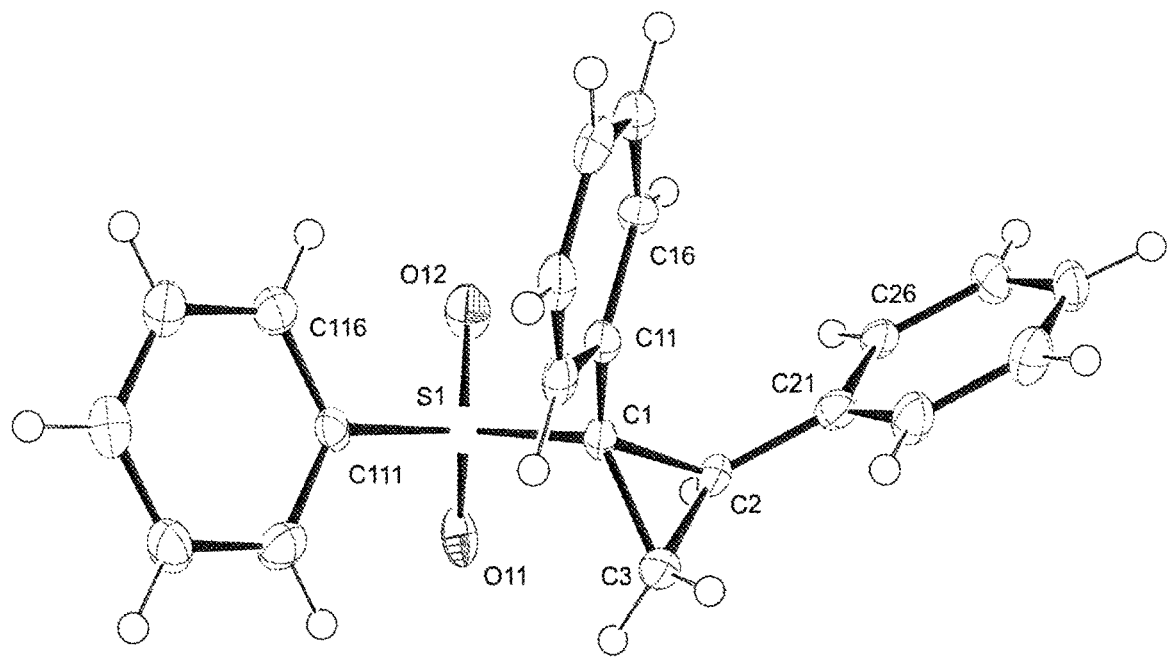

FIG. 94 illustrates ORTEP diagram showing 50% probability anisotropic displacement ellipsoids of non-hydrogen atoms for compound 7 according to single crystal X-ray diffraction data. Selected interatomic distances [Å], valence and dihedral angles [°]: C1-C2 1.537(8), C2-C3 1.489(9), C1-C3 1.508(8), C1-S1 1.795(6), C1-C11 1.479(8), C2-C21 1.504(8), C3-C1-C2 58.5(4), C1-C2-C3 59.8(4), C1-C3-C2 61.7(4), S1-C1-C11 113.7(4), C116-C111-S1-C1 96.8(5), C111-S1-C1-C3 100.3(5), C16-C11-C1-C3 132.4(6), C26-C21-C2-C3 172.8(5).

Figure 95:
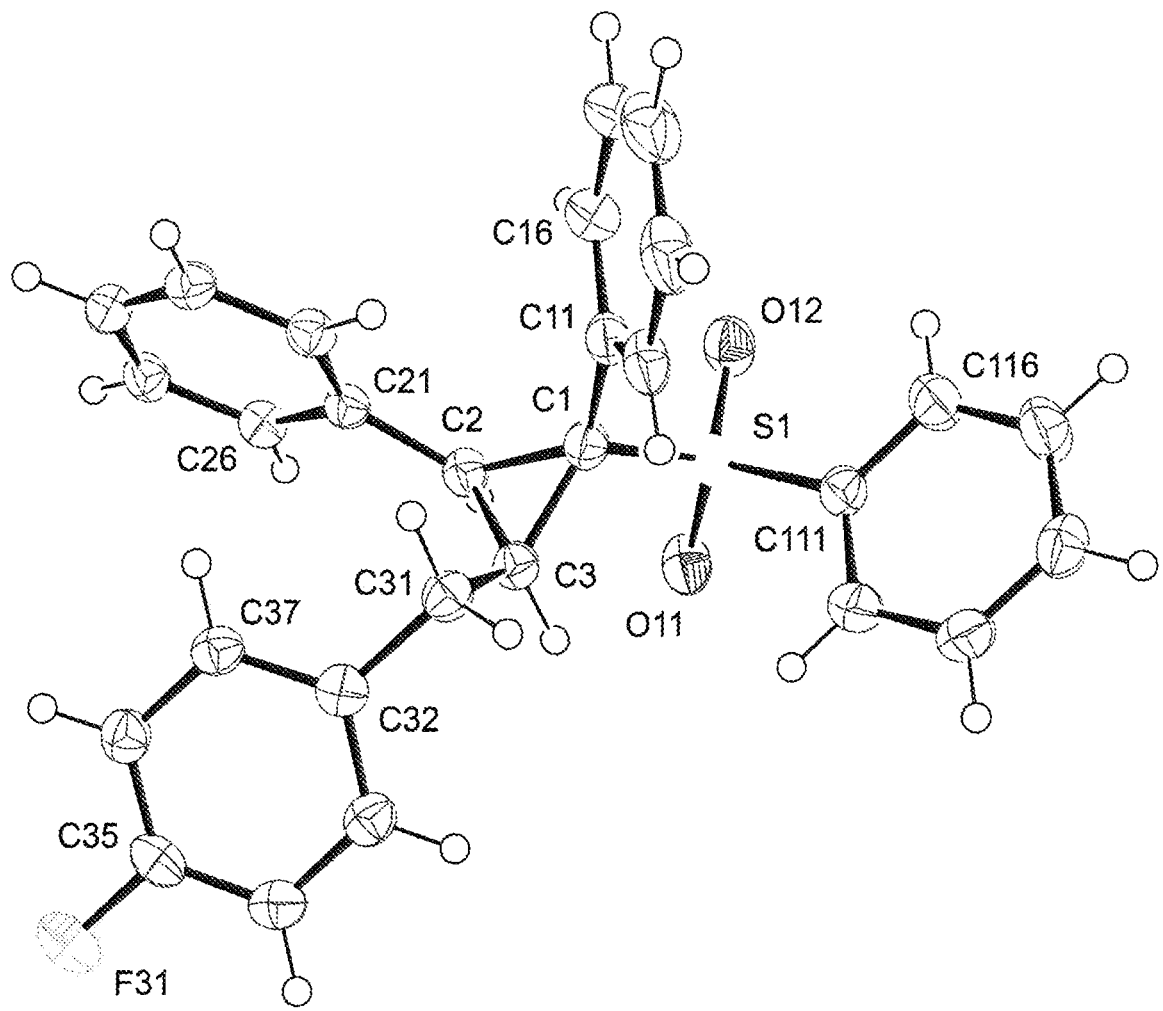

FIG. 95 illustrates ORTEP diagram showing 50% probability anisotropic displacement ellipsoids of non-hydrogen atoms for compound 8 according to single crystal X-ray diffraction data. Selected interatomic distances [Å], valence and dihedral angles [°]: C1-C2 1.535(2), C2-C3 1.522(2), C1-C3 1.515(2), S1-C1 1.7945(18), C1-C11 1.498(2), C2-C21 1.493(2), C3-C31 1.518(2), C35-F31 1.363(2), C2-C1-C3 59.86(11), C1-C2-C3 59.44(11), C2-C3-C1 60.70(11), S1-C1-C11 111.78(12), C116-C111-S1-C1−111.11(17), C16-C11-C1-C3−137.16(19), C26-C21-C2-C3−122.02(18), C32-C31-C3-C2 80.9(2), C37-C32-C31-C3−98.60(19).

Figure 96:
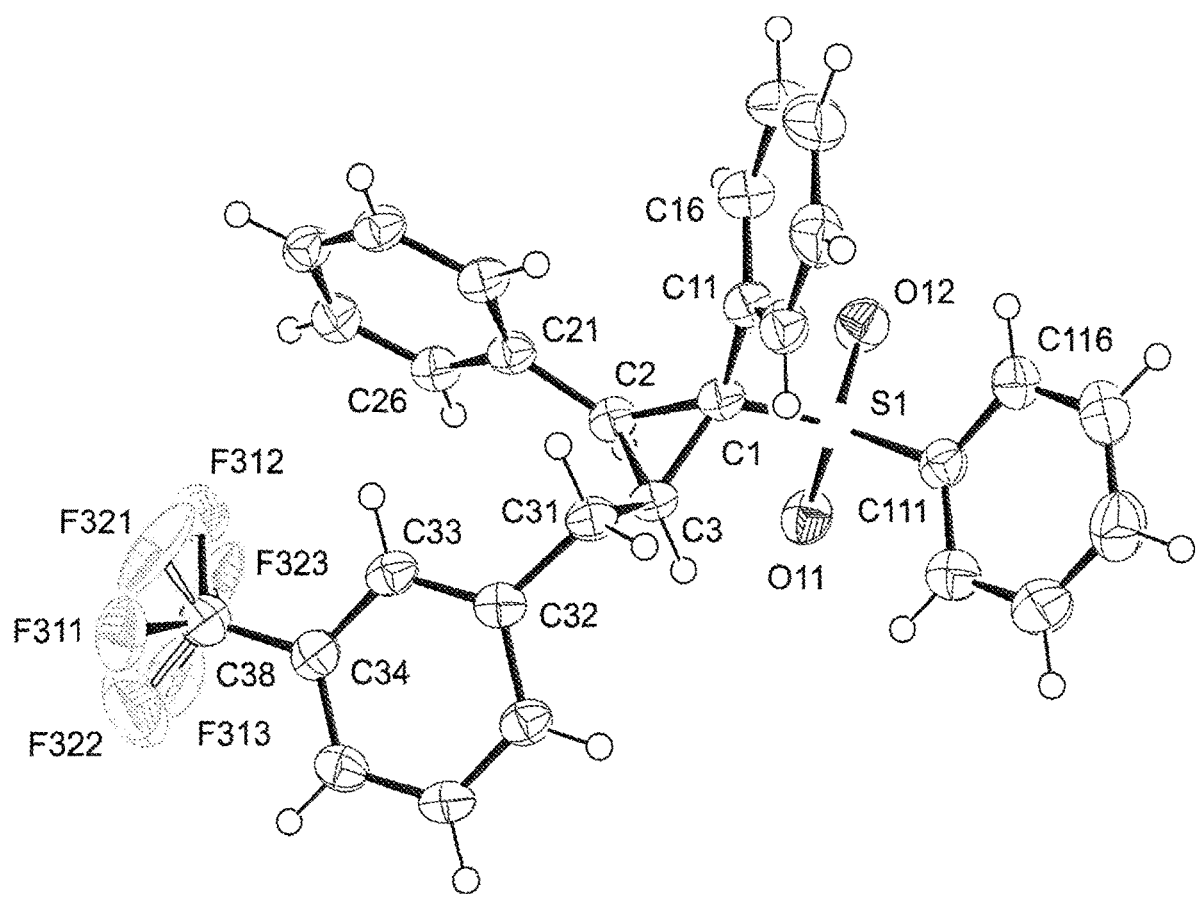

FIG. 96 illustrates ORTEP diagram showing 50% probability anisotropic displacement ellipsoids of non-hydrogen atoms for compound 9 according to single crystal X-ray diffraction data. Selected interatomic distances [Å], valence and dihedral angles [°]: C1-C2 1.527(3), C2-C3 1.524(2), C1-C3 1.510(3), S1-C1 1.7955(19), C1-C11 1.500(3), C2-C21 1.495(3), C3-C31 1.518(2), C34-C38 1.494(3), C38-F311 1.330(3), C38-F321 1.249(10), C2-C1-C3 60.23(12), C1-C2-C3 59.32(12), C2-C3-C1 60.45(12), S1-C1-C11 111.41(13), C116-C111-S1-C1−91.12(17), C111-S1-C1-C3−86.49(15), C16-C11-C1-C3−140.25(19), C26-C21-C2-C3 121.73(19), C32-C31-C3-C2 85.6(2), C33-C32-C31-C3−92.0(2). The minor component of the disordered trifluoromethyl group is shown in "open bond" type.

Figure 97:
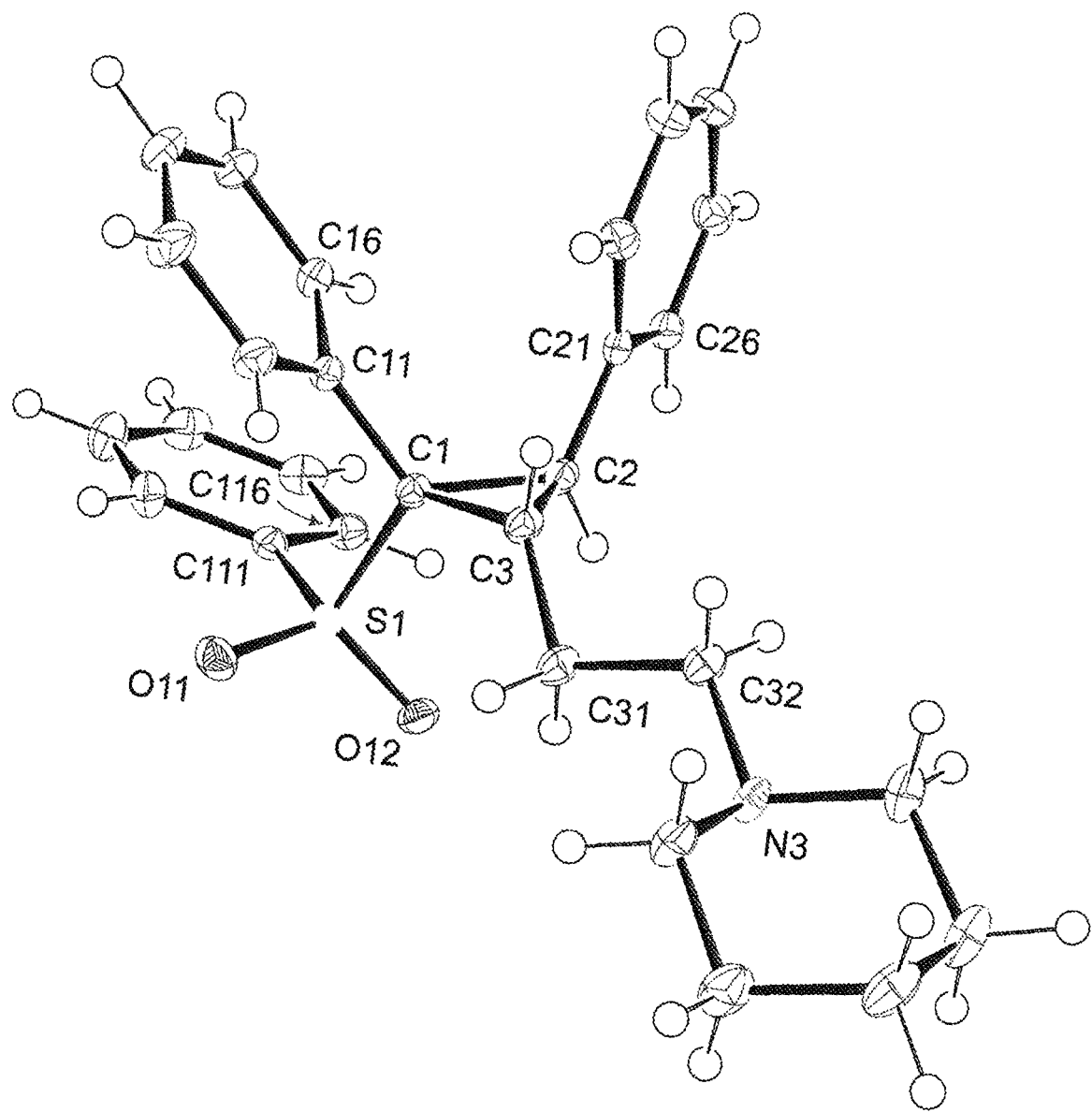

FIG. 97 illustrates ORTEP diagram showing 50% probability anisotropic displacement ellipsoids of non-hydrogen atoms for compound 12 according to single crystal X-ray diffraction data. Selected interatomic distances [Å], valence and dihedral angles [°]: C1-C2 1.5392(16), C2-C3 1.5091(17), C1-C3 1.5160(17), C1-S1 1.7786(13), C1-C11 1.5008(16), C2-C21 1.4912(18), C3-C31 1.5148(17), N3-C32 1.4655(16), C2-C1-C3 59.20(8), C1-C2-C3 59.63(8), C2-C3-C1 61.17(8), S1-C1-C11 112.46(9), C116-C111-S1-C1 84.32(11), C111-S1-C1-C3−158.84(9), C16-C11-C1-C3 126.05(13), C26-C21-C2-C3 167.91(11), C32-C31-C3-C2 86.91(14).

Figure 98:
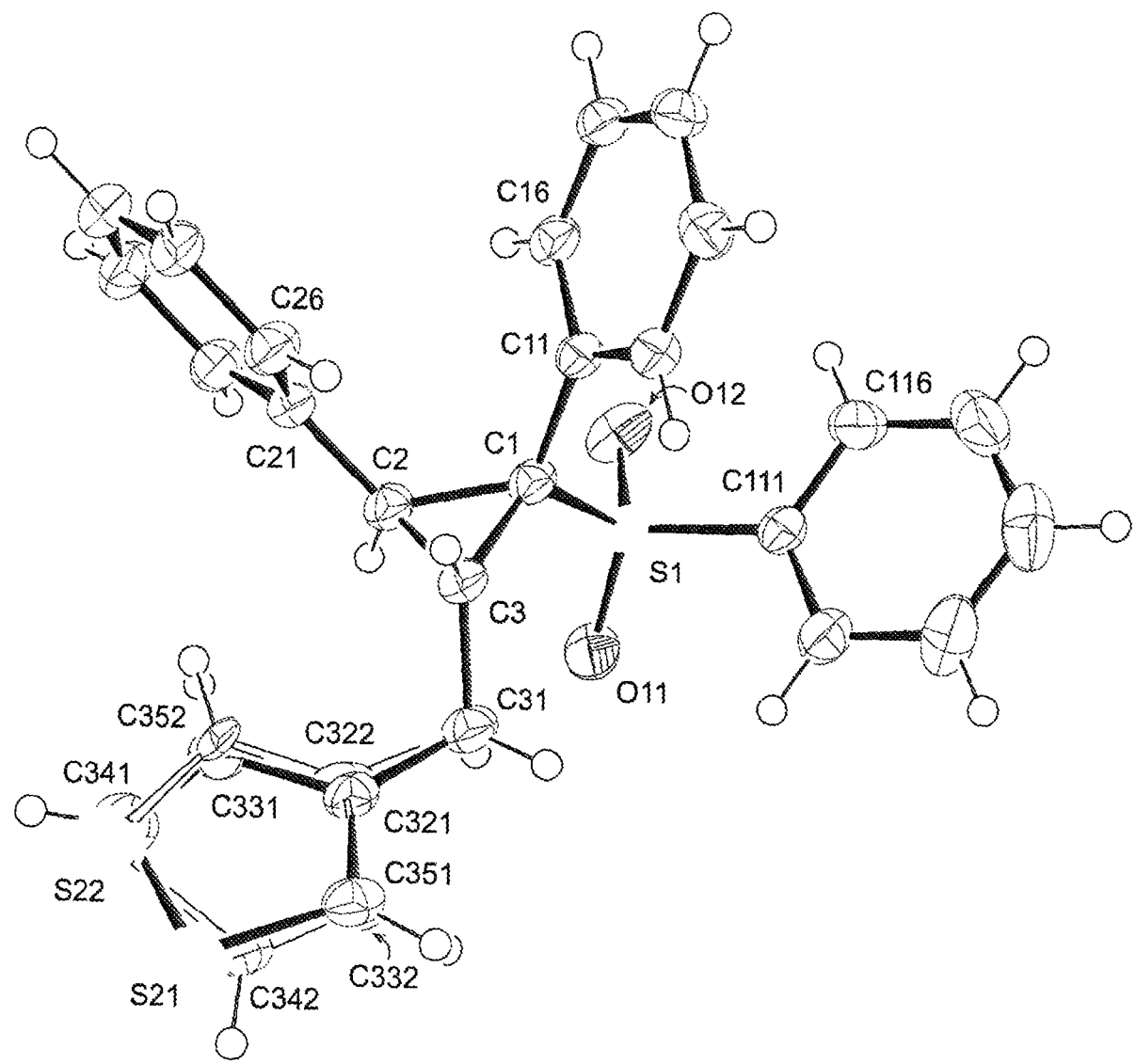

FIG. 98 illustrates ORTEP diagram showing 50% probability anisotropic displacement ellipsoids of non-hydrogen atoms for compound 13 according to single crystal X-ray diffraction data. Selected interatomic distances [Å], valence and dihedral angles [°]: C1-C2 1.538(3), C2-C3 1.512(3), C1-C3 1.523(3), S1-C1 1.7845(19), C1-C11 1.501(3), C2-C21 1.493(2), C3-C31 1.518(3), S21-C341 1.745(9), S21-C351 1.691(7), S22-C342 1.779(13), S22-C352 1.68(2), C2-C1-C3 59.22(13), C1-C2-C3 59.91(13), C2-C3-C1 60.88(13), S1-C1-C11 103.43(9), C341-S21-C351 91.6(4), C342-S22-C352 89.7(11), C116-C111-S1-C1−95.49(19), C111-S1-C1-C3−95.62(17), C16-C11-C1-C3−132.93(19), C26-C21-C2-C3 11.9(3), C321-C31-C3-C2−86.6(3), C322-C31-C3-C2−156.5(10), C351-C321-C31-C3−129.3(5), C352-C322-C31-C3 38(2). The minor component of the disordered thiophene moiety is shown in "open bond" type.

Figure 99:
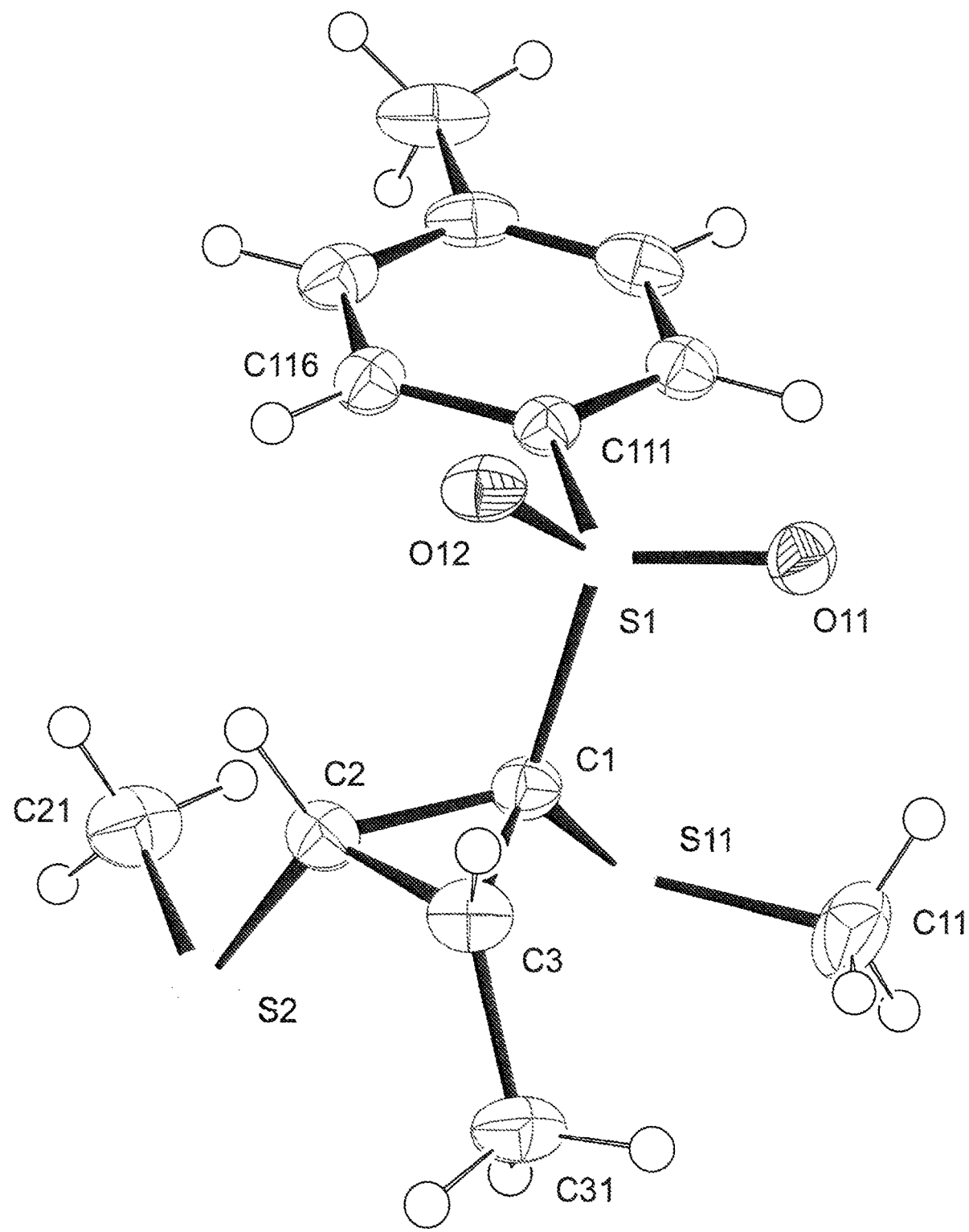

FIG. 99 illustrates ORTEP diagram showing 50% probability anisotropic displacement ellipsoids of non-hydrogen atoms for compound 15 according to single crystal X-ray diffraction data. Selected interatomic distances [Å], valence and dihedral angles [°]: C1-C2 1.525(4), C2-C3 1.491(4), C1-C3 1.537(4), S1-C1 1.779(3), S11-C1 1.772(3), S11-C11 1.800(4), S2-C2 1.769(3), S2-C21 1.788(4), C2-C1-C3 58.3(2), C1-C2-C3 61.3(2), C2-C3-C1 60.46(19), S1-C1-S12 114.90(16), C1-S11-C11 102.54(17), C2-S2-C21 98.94(16), C116-C111-S1-C1 74.4(3), C111-S1-C1-C3−152.2(2), C11-S11-C1-C3−72.6(3), C21-S2-C2-C3−159.6(3), C31-C3-C2-S2 2.2(4).

Figure 100:
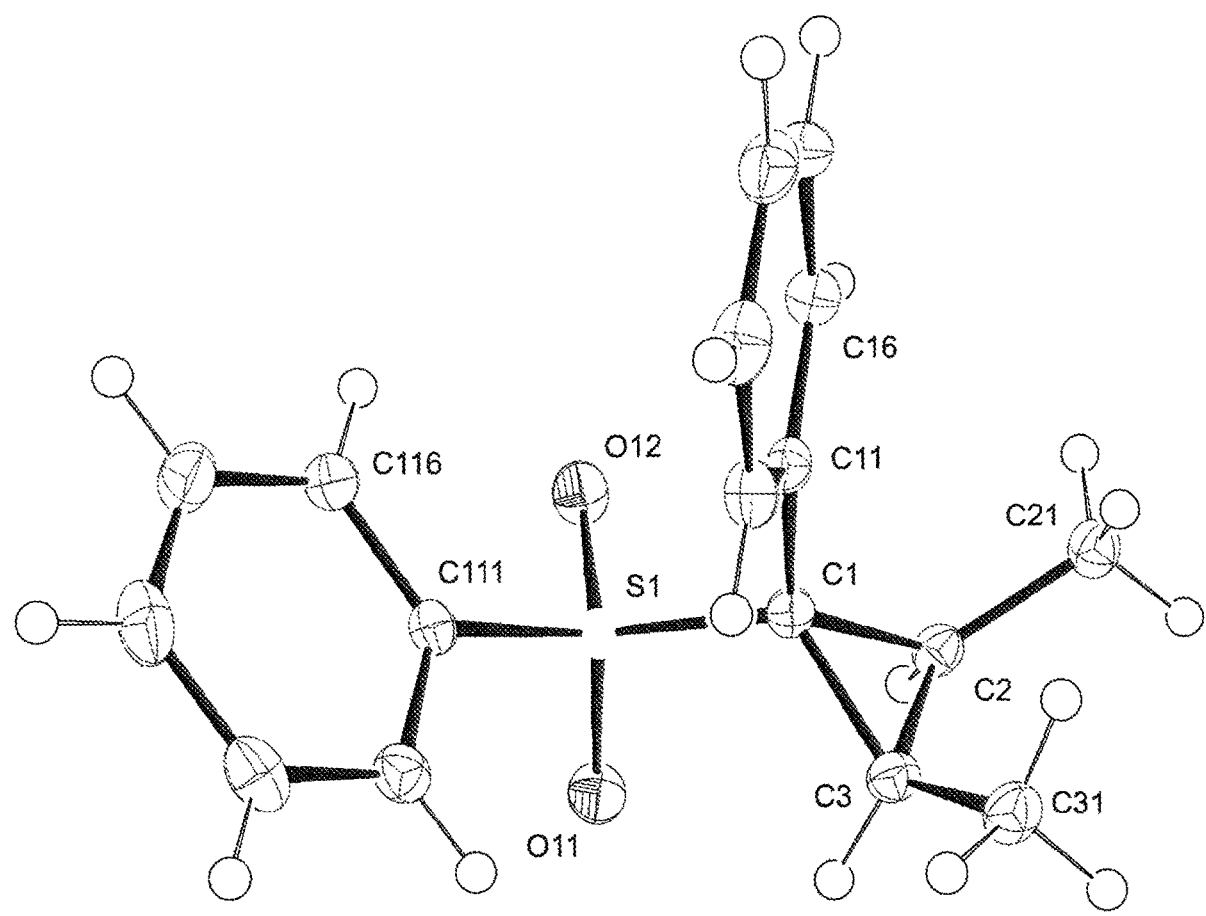

FIG. 100 illustrates ORTEP diagram showing 50% probability anisotropic displacement ellipsoids of non-hydrogen atoms for compound 24 according to single crystal X-ray diffraction data. Selected interatomic distances [Å], valence and dihedral angles [°]: C1-C2 1.5282(15), C2-C3 1.5104(16), C1-C3 1.5245(16), C1-S1 1.7837(12), C1-C11 1.4969(15), C2-C21 1.5080(16), C3-C31 1.5043(17), C2-C1-C3 59.31(7), C1-C2-C3 60.22(7), C2-C3-C1 60.47(7), S1-C1-C11 112.31(8), C116-C111-S1-C1 107.13(10), C111-S1-C1-C3 103.28(9), C16-C11-C1-C3 131.54(12).

DESCRIPTION OF EMBODIMENTS

Detailed Description of the Preferred Embodiment

The preferred embodiments of the present invention are described below. Although the preferred embodiments of the present invention have been described herein, the description is merely illustrative. Further modification of the invention herein disclosed will occur to those skilled in the respective arts and all such modifications are deemed to be within the scope of the invention as defined by the appended claims.

The following are definitions of terms used herein.

"Alkyl" by itself or as part of another substituent refers to a saturated hydrocarbon group. "Alkyl" may be a linear or branched group having the number of carbon atoms when it is designated (i.e., $C_{1-8}$ means one to eight carbon atoms). "Cycloalkyl" is an alkyl group that is cyclic. Examples of alkyl groups include methyl, ethyl, n-propyl, isopropyl, n-butyl, t-butyl, isobutyl, and sec-butyl, etc. Examples of cycloalkyl groups include cyclohexyl, cyclopentyl, (cyclohexyl)methyl, cyclopropylmethyl, bicyclo[2.2.1]heptane, bicyclo[2.2.2]octane, etc. Alkyl groups can be substituted or unsubstituted, unless otherwise indicated. Examples of substituted alkyl include haloalkyl, perhaloalkyls, thioalkyl, aminoalkyl, and the like.

"Aryl" refers to an aromatic hydrocarbon group having a single ring (monocyclic) or multiple rings (bicyclic, etc.), which can be fused together or linked covalently. Aryl groups with 6-10 carbon atoms are preferred, where this number of carbon atoms can be designated by $C_{6-10}$, for example. Examples of aryl groups include phenyl and naphthalene-1-yl, naphthalene-2-yl, biphenyl and the like. Aryl groups can be substituted or unsubstituted, unless otherwise indicated.

"Heterocycloalkyl" refers to a saturated or unsaturated non-aromatic ring containing at least one heteroatom (typically 1 to 5 heteroatoms) selected from nitrogen, oxygen, sulfur or silicon. The heterocyclyl ring may be monocyclic or bicyclic. Preferably, these groups contain 0-5 nitrogen atoms, 0-2 sulfur atoms and 0-2 oxygen atoms. More preferably, these groups contain 0-3 nitrogen atoms, 0-1 sulfur atoms and 0-1 oxygen atoms. Examples of heterocycloalkyl groups include pyrrolidine, piperidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-dioxide, piperazine, pyran, pyridone, 3-pyrroline, thiopyran, pyrone, tetrahydrofuran, tetrahydrothiophene, quinuclidine and the like.

"Heteroaryl" refers to an aromatic group containing at least one heteroatom, where the heteroaryl group may be monocyclic or bicyclic. Examples include pyridyl, pyridazinyl, pyrazinyl, pyrimidinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiazolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, oxadiazolyl, thiadiazolyl, pyrrolyl, thiazolyl, furyl or thienyl.

Suitable substituents may include halogen, —CN, —CO$_2$R', —C(O)R', —C(O)NR'R'', oxo (=O or —O$^-$), —OR', —OC(O)R', —OC(O)NR'R''—NO$_2$, —NR'C(O)R'', —NR'''C(O)NR'R'', —NR'R'', —NR'CO$_2$R'', —NR'S(O)R'', —NR'S(O)$_2$R''', —NR'''S(O)NR'R'', —NR'''S(O)$_2$NR'R'', —SR', —S(O)R', —S(O)$_2$R', —S(O)$_2$NR'R'', —NR'—C(NHR'')=NR''', —SiR'R''R''', —N$_3$, substituted or unsubstituted C$_{1-8}$ alkyl, substituted or unsubstituted C$_{2-8}$ alkenyl, substituted or unsubstituted C$_{2-8}$alkynyl, substituted or unsubstituted C$_{6-10}$ aryl, substituted or unsubstituted 5- to 10-membered heteroaryl, and substituted or unsubstituted 3- to 10-membered heterocyclyl. The number of possible substituents range from zero to the total number of substitutable hydrogen atoms.

The term catalysis or "catalyzed" refers to a process in which a relatively small amount of a material increases the rate of a chemical reaction and is not itself consumed in the reaction.

The term "catalytic amount" refers to a substoichiometric amount of the catalyst relative to a reactant.

The term "chiral" refers to a molecule or conformation which is not superimposable with its mirror image partner.

"Complex" refers to a coordination compound formed by the union of one or more electronically rich molecules or atoms capable of independent existence with one or more electronically poor molecules or atoms, which is also capable of independent existence.

"Diastereomer" refers to one of a group of stereoisomers which is not related to another stereoisomer of the group as a mirror image.

"Diastereoselective" refers to a process which favors production of one of the two possible diastereomers of a reaction product. For example, a chemical reaction would be diastereoselective if it produces the two diastereomers of a chiral product in unequal amounts. Such a reaction is said to exhibit diastereoselectivity.

"Enantiomer" refers to one of a pair of molecular species that are mirror images of each other and not superimposable.

"Stereoisomer" refers to isomers of identical constitution (i.e. bond connectivity), but which differ in their arrangement in space.

"Stereoselective" refers to preferentially forming one stereoisomer over another in a chemical reaction. If the stereoisomers are enantiomers, the chemical reaction is an enantioselective reaction. If the stereoisomers are diastereomers, the chemical reaction is a diastereoselective reaction.

In one embodiment, a cyclopropanation method includes reacting an alcohol, an ester, or an aldehyde with a sulfone in an organic solvent containing a base providing a counter cation such as a potassium cation to form a cyclopropane; and isolating the cyclopropane.

The organic solvent further contains a catalyst having an alcohol dehydrogenation activity when the alcohol or the ester is used for the reaction.

The alcohol may be selected from any alcohols that enable the cyclopropanation. For example, the alcohol may be an alkyl, cycloalkyl, heterocyclyl, aryl, or heteroaryl alcohol. Preferably, the alcohol is a primary alcohol. In one embodiment, the alcohol is R$^1$CH$_2$OH, in which R$^1$ may be hydrogen, alkyl, or cycloalkyl, and the alkyl is optionally intervened by oxygen, sulfur, or nitrogen (e.g. imino). R$^1$ may be saturated or unsaturated, and preferably a double bond does not exist between a β carbon and a γ carbon of the alcohol. R$^1$ may be unsubstituted or substituted with at least one substituent selected from alkyl, cycloalkyl, heterocycloalkyl, aryl, and heteroaryl, and preferably the β carbon of the alcohol is unsubstituted, and the substituent may be further substituted or unsubstituted.

For example, the alkyl may be C$_{1-5}$, C$_{1-8}$, or C$_{1-10}$alkyl, the cycloalkyl may be C$_{3-6}$, C$_{3-8}$, or C$_{3-10}$ cycloalkyl, the heterocycloalkyl may be C$_{3-8}$, C$_{3-10}$, or C$_{3-12}$ heterocycloalkyl, the aryl may be C$_{6-8}$, C$_{6-10}$, or C$_{6-12}$ aryl, and the heteroaryl may be C$_{5-8}$, C$_{5-10}$, or C$_{5-12}$ heteroaryl.

Examples of the alcohol includes, but not limited to, the following compounds:

[Chem. 1]

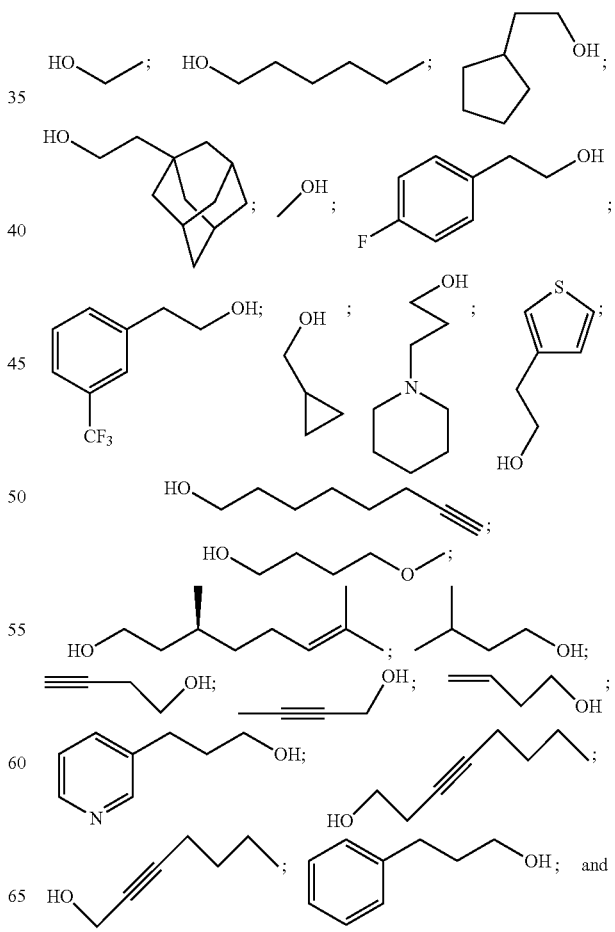

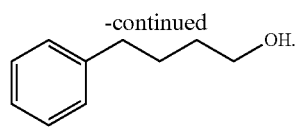

The ester may be selected from any esters that enable the cyclopropanation. For example, the ester may he may be an alkyl, cycloalkyl, heterocyclyl, aryl, or heteroaryl ester of an alkyl, cycloalkyl, heterocyclyl, aryl, or heteroaryl carboxylic acid. In one embodiment, the ester is formed from $R^1$ $CH_2OH$ and $R^2COOH$. $R^1$ may be hydrogen, alkyl, or cycloalkyl, and the alkyl is optionally intervened by oxygen, sulfur, or nitrogen. $R^1$ may be saturated or unsaturated, and preferably a double bond does not exist between a β carbon and a γ carbon of the alcohol. $R^1$ may be unsubstituted or substituted with at least one substituent selected from the group consisting of alkyl, cycloalkyl, heterocycloalkyl, aryl, and heteroaryl, and preferably the β carbon of the alcohol is unsubstituted. The substituent may be further substituted or unsubstituted. $R^2$ may be saturated or unsaturated alkyl, saturated or unsaturated cycloalkyl, saturated or unsaturated heterocycloalkyl, aryl, or heteroaryl. $R^2$ may be unsubstituted or substituted.

For example, the alkyl may be $C_{1-5}$, $C_{1-8}$, or $C_{1-10}$ alkyl, the cycloalkyl may be $C_{3-6}$, $C_{3-8}$, or $C_{3-10}$ cycloalkyl, the heterocycloalkyl may be $C_{3-8}$, $C_{3-10}$, or $C_{3-12}$ heterocycloalkyl, the aryl may be $C_{6-8}$, $C_{6-10}$, or $C_{6-12}$ aryl, and the heteroaryl may be $C_{5-8}$, $C_{5-10}$, or $C_{5-12}$ heteroaryl.

Examples of the ester include, but not limited to, the following compounds:

[Chem. 2]

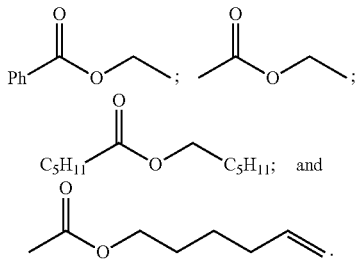

The aldehyde may be selected from any aldehydes that enable the cyclopropanation. For example, the aldehyde is an alkyl, cycloalkyl, heterocyclyl, aryl, or heteroaryl aldehyde. In one embodiment, the aldehyde is paraformaldehyde or $R^3$ CHO, in which $R^3$ may be hydrogen, alkyl, or cycloalkyl, and the alkyl is optionally intervened by oxygen, sulfur, or nitrogen. $R^3$ may be saturated or unsaturated, and preferably a double bond does not exist between a β carbon and a γ carbon of the aldehyde. $R^3$ may be unsubstituted or substituted with at least one substituent selected from the group consisting of alkyl, cycloalkyl, heterocycloalkyl, aryl, and heteroaryl, and preferably the α carbon of the aldehyde is unsubstituted. The substituent may be further substituted unsubstituted.

For example, the alkyl may be $C_{1-5}$, $C_{1-8}$, or $C_{1-10}$ alkyl, the cycloalkyl may be $C_{3-6}$, $C_{3-8}$, or $C_{3-10}$ cycloalkyl, the heterocycloalkyl may be $C_{3-8}$, $C_{3-10}$, or $C_{3-12}$ heterocycloalkyl, the aryl may be $C_{6-8}$, $C_{6-10}$, or $C_{6-12}$ aryl, and the heteroaryl may be $C_{5-8}$, $C_{5-10}$, or $C_{5-12}$ heteroaryl.

Examples of the aldehyde include, but not limited to, the following compounds:

[Chem. 3]

and $C_5H_{11}CHO$.

The sulfone may be selected from any sulfones that enable the cyclopropanation. In one embodiment, the sulfone may be represented by $R^4CH_2SO_2R^5$. $R^4$ may be hydrogen, alkyl, alkylthio, cycloalkyl, heterocycloalkyl, aryl, or heteroaryl. $R^4$ may be unsubstituted or substituted. $R^4$ may be saturated or unsaturated. Preferably, a bond between a β carbon and a γ carbon in $R^4$ of the sulfone is saturated. $R^5$ may be unsubstituted or substituted aryl or heteroaryl.

For example, the alkyl may be $C_{1-5}$, $C_{1-8}$, or $C_{1-10}$ alkyl, the alkylthio may be $C_{1-5}$, $C_{1-8}$, or $C_{1-10}$ alkylthio, the cycloalkyl may be $C_{3-6}$, $C_{3-8}$, or $C_{3-10}$ cycloalkyl, the heterocycloalkyl may be $C_{3-8}$, $C_{3-10}$, or $C_{3-12}$ heterocycloalkyl, the aryl may be $C_{6-8}$, $C_{6-10}$, or $C_{6-12}$ aryl, and the heteroaryl may be $C_{5-8}$, $C_{5-10}$, or $C_{5-12}$ heteroaryl.

Examples of the sulfone include, but not limited to, the following compounds:

[Chem. 4]

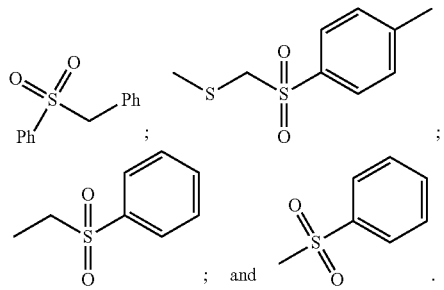

Other examples may be found in Lopchuk, J. M., et al., J. Am. Chem. Soc. 2017, 139, 3209-3226;

One species of sulfones may be used alone. Alternatively, two or more different sulfones may be used together in one reaction.

The Bordwell $pK_a$ table[S2] can be used to determine the $pK_a$ of the sulfone substrates. In the case of a mixed sulfone reaction, this can be used to help predict which sulfone will act as the leaving group and which one will remain in the cyclopropane. The most acidic sulfone will remain in the cyclopropane product while the less acidic sulfone will only donate the R-group ($R^4$ in the above formula) and lose the sulfone. In the case where the $pK_a$s are very close, large amounts of homo coupling may be observed in addition to some mixed products. For example, the benzyl phenyl sulfone and methyl thiomethyl ether phenyl sulfone have very similar $pK_a$, 23.4 and 23.5 respectively, so this reaction may produce less amounts of mixed product. The amount of the mixed product may be at least 50%.

The base may be selected from any bases that enable the cyclopropanation. In one embodiment, the base is selected from ones that can provide a counter cation such as a potassium cation or cesium cation during the cyclopropanation reaction. For example, the base is one having potassium. The base may be at least one selected from potassium hydroxide, potassium methoxide, potassium ethoxide, potassium propoxide, potassium butoxide, potassium tert-butoxide (KOtBu), potassium bis(trimethylsilyl)amide (KHMDS), and potassium hydride.

An amount of the base may be any amount that enables the cyclopropanation reaction and selected by one of ordinary skill in the art. The amount of the base may be 50 to 350 mol %, 100 to 300 mol %, or 150 to 250 mol % with respect to an amount of the alcohol or the ester. For example, the amount of the base is more than 100 mol %.

The catalyst may be selected from any catalysts that enable the cyclopropanation. For example, any catalyst that is active in alcohol dehydrogenation to aldehydes at high temperatures such as 80 or 120° C. can be used. Also, the catalyst may be a Pt, Cu, Fe, Mn, Cr, Co, Pd, Ru, V, Ni, or Os catalyst. In another embodiment, the catalyst may be $TiO_2$, $CeO_2$, cupper chromite, copper/alumina, ZnO, ZnO/CuO, or Pt/Alumina. For example, the catalyst is a metal complex such as a Ru complex or an Os complex. The Ni catalyst may be $NiBr_2$ or $NiBr_2(PPh_3)_2$.

Specific examples of the ruthenium catalyst include, but not limited to, ruthenium metal, ruthenium nanoparticles, ruthenium on carbon, ruthenium oxide, ruthenium sulfide, ruthenium hydroxide, fluoride ruthenium, ruthenium chloride, ruthenium bromide, iodide ruthenium, ruthenium sulfate, ruthenium acid or a salt thereof (e.g., and ammonium ruthenate), perruthenate or salts thereof (e.g., tetrapropylammonium perruthenate), inorganic compounds such as inorganic ruthenium complexes [e.g., hydroxy ruthenium halide (hydroxy ruthenium chloride, etc.), ruthenium hexamine halides (hexamine ruthenium chloride), ruthenium nitrosyl, hexa-halo ruthenate, or a salt thereof (sodium hexachlororuthenate)], ruthenium cyanide, organic compounds such as organic ruthenium complexes [e.g., Triruthenium dodecacarbonyl (0), dicar-bonyltris(triphenylphosphinc) ruthenium (II), diacetatodicar-bonylbis(triphenylphosphine)ruthenium (II), dichlorotris(triphenylphosphine)ruthenium (II), dihydri-dotetrakis(triphenylphosphine)ruthenium dichlorobis(acetonitrile)bis(ttiphenylphosphine)ruthenium (II), and ruthenocene, etc.].

Preferably, the catalyst is a Ru (II) complex. A ruthenium (II) is any ruthenium metal with an oxidation state of 2+.

Examples of the catalyst include, but not limited to, the following compounds:

[Chem. 5]

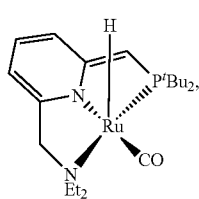

A

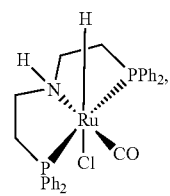

B

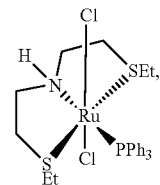

C

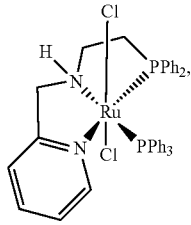

D

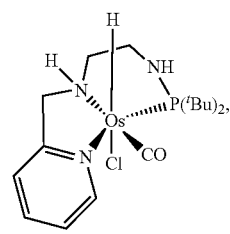

E $RuCl_3$, and $NiBr_2$.

Amount of the catalyst may be any amount that enables the cyclopropanation and selected by one of ordinary skill in the art. The amount of the catalyst may be at least 0.1, 0.2, 0.3, 0.4, or 0.5 mol % with respect to an amount of the alcohol or the ester. The amount of the catalyst may be at most 10, 9.0, 8.0, 7.0, 6.0, 5.0, 4.0, 3.0, 2.0, or 1.0 mol % with respect to an amount of the alcohol or the ester. For example, the amount may be 0.1 to 10 mol %, 0.1 to 4.0 mol %, 0.1 to 3.0 mol %, or 0.2 to 1.0 mol % with respect to an amount of the alcohol or the ester.

The organic solvent may be selected from ether based solvents and aromatic hydrocarbons. Examples of the organic solvent include, but not limited to, tetrahydrofuran, dioxane, 1,2-dimethoxyethane, benzene, and toluene.

Preferably, the solvent is anhydrous. The solvent can also contain water in an amount of less than three equivalents with respect to an amount of the alcohol, the ester, or the aldehyde. In one embodiment, water does not substantially affect the cyclopropanation reaction at one equivalent.

In the cyclopropanation reaction, the molar ratio of sulfone:ester, alcohol, or aldehyde is preferably approximately 2:1. Each cyclopropane molecule results from the coupling of two sulfone and one alcohol/ester/aldehyde units. This molar ratio can produce purer products and a better yield.

In another embodiment, the cyclopropanation reaction can be carried out with sulfone; ester, alcohol, or aldehyde: and a cyano compound. All the reaction conditions and reactants may be as described above except for the cyano compound. The cyano compound can be any cyano compounds that enable the cyclopropanation reaction. For example, some embodiments of the cyano compound can be represented by $R^{11}CH_2CN$, in which $R^{11}$ is hydrogen, alkyl, or cycloalkyl, and the alkyl or cycloalkyl is optionally intervened by oxygen, sulfur, or nitrogen (e.g. imino). $R^{11}$ may be saturated or unsaturated. $R^{11}$ may be unsubstituted or substituted with at least one substituent selected from alkyl, cycloalkyl, heterocycloalkyl, aryl, and heteroaryl, and the substituent may be further substituted or unsubstituted. For example, the alkyl may be $C_{1-5}$, $C_{1-8}$, or $C_{1-10}$ alkyl, the cycloalkyl may be $C_{3-6}$, $C_{3-8}$, or $C_{3-10}$ cycloalkyl, the heterocycloalkyl may be $C_{3-8}$, $C_{3-10}$, or $C_{3-12}$ heterocycloalkyl, the aryl may be $C_{6-8}$, $C_{6-10}$, or $C_{6-12}$ aryl, and the heteroaryl may be $C_{5-8}$, $C_{5-10}$, or $C_{5-12}$ heteroaryl. One example of this reaction can be illustrated as follows:

[Chem. 6]

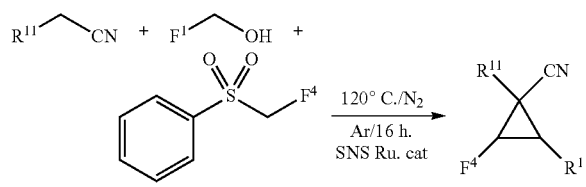

in which $R^{11}$, $R^1$, $R^4$ are as described above. More specifically, for example, this reaction can be carried out as follows:

[Chem. 7]

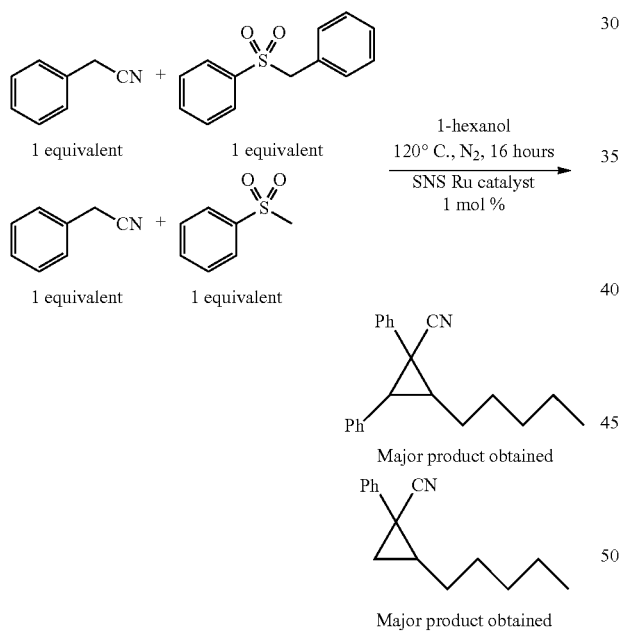

Cyano cyclopropanes are very valuable substrates as the cyano group is very polar and can be easily modified into an amine or other types of functional groups.

The products of the method may be isolated by any conventional method. For example, HPLC or column chromatography may be used. In one embodiment, the isolating is carried out by a chiral chromatography. In one embodiment, the product is crystalized.

The cyclopropanation reaction may be carried out in an open system or a closed system. For example, the reaction is carried out at an atmosphere of inert gas such as nitrogen and argon. The closed system is preferable in one embodiment. A conventional reaction container may be used. The reaction container is suitably equipped with a stirrer. The open system is preferred in another embodiment that large amounts of substrate are reacted and a substantial $H_2$ pressure is expected to be generated.

The reaction may be carried out at any temperature that enables the cyclopropanation. A person of ordinary skill in the art can choose an appropriate temperature. For example, the temperature is above the room temperature (room temperature=approximately 20 to 25° C.). For example, the temperature is 60° C. or more, preferably 80° C. or more, and more preferably 100° C. or more. The temperature may be 200° C. or less and preferably 150° C. or less. In one embodiment, the reaction is carried out at approximately 120° C.

The reaction may be carried out for any time period that enables the cyclopropanation. A person of ordinary skill in the art can select an appropriate time period. The reaction time may be at least 5, 10, 15, 25, or 50 hours. For example, the reaction time is 5 to 100 hours, preferably 10 to 75 hours (for example, 72 hours), and more preferably 15 to 25 hours (for example, 16 hours).

A yield of the product may be any value. For example, the yield is 10% or more, 20% or more, 30% or more, 40% or more, 50% or more, 60% or more, or 70% or more.

Examples of the compound having a cyclopropane structure that can be formed by the method include, but not limited to, the following compounds:

[Chem. 8]

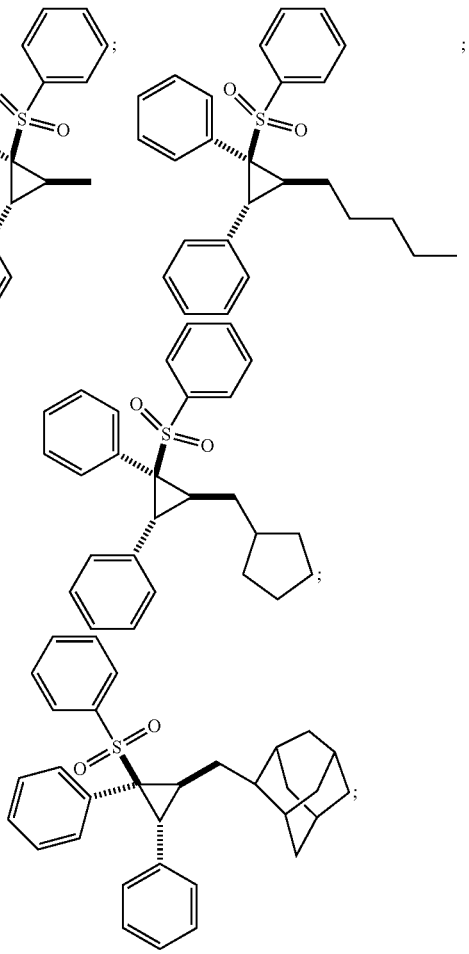

-continued
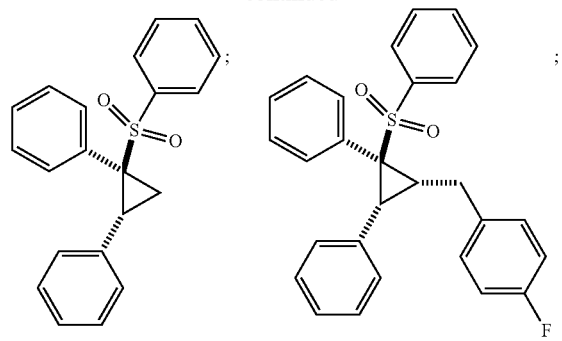
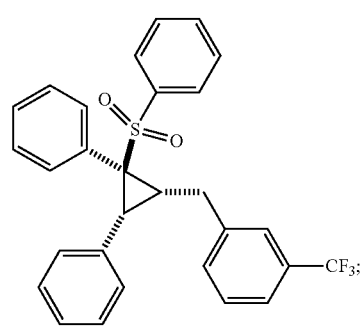
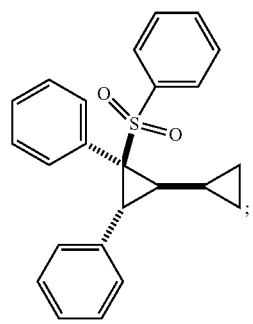
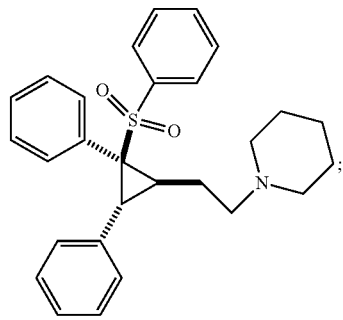
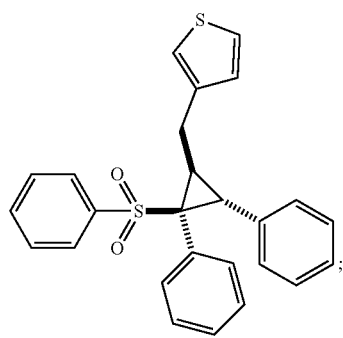
-continued
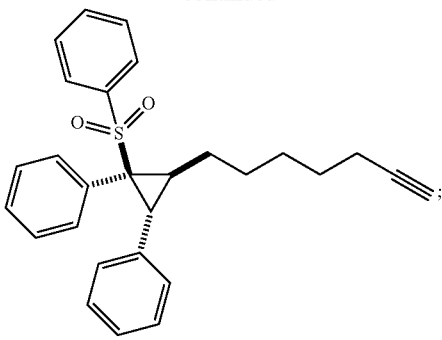
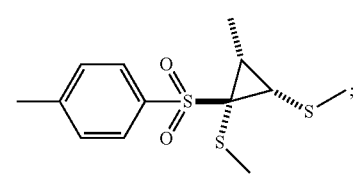
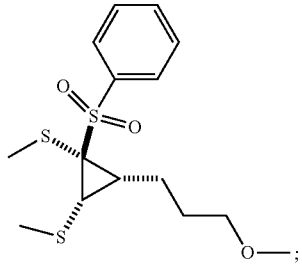
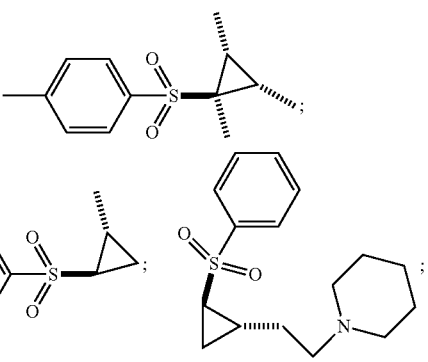
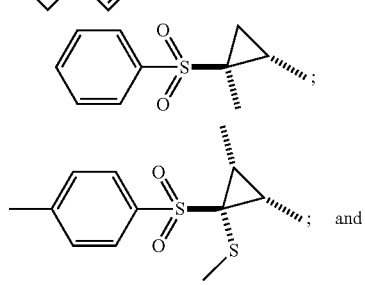

-continued

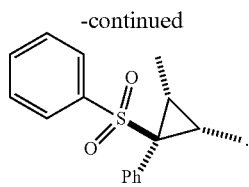

One embodiment of the invention is directed to a compound having a cyclopropane structure formed by the aforementioned method.

In one embodiment, the compound having a cyclopropane structure may be formed as follows:

[Chem. 9]

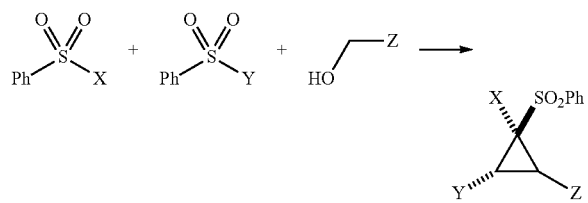

in which $PhSO_2CH_2X$, $PhSO_2CH_2Y$, and $ZCH_2OH$ may be selected from the aforementioned sulfones and alcohols.

Figure 1:
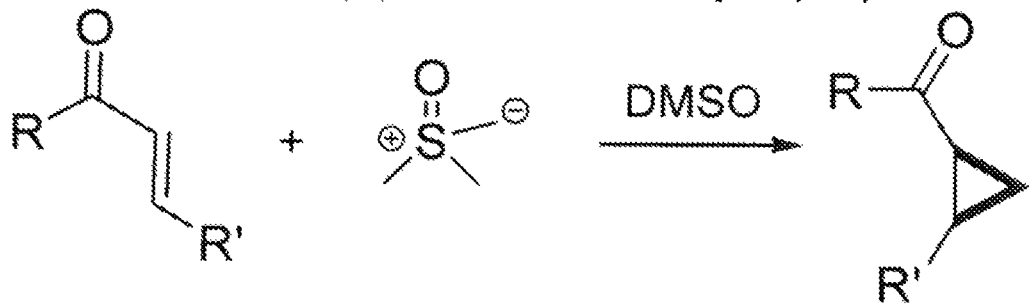
FIG. 1 illustrates an overview of cyclopropanation methods.
Figure 1:
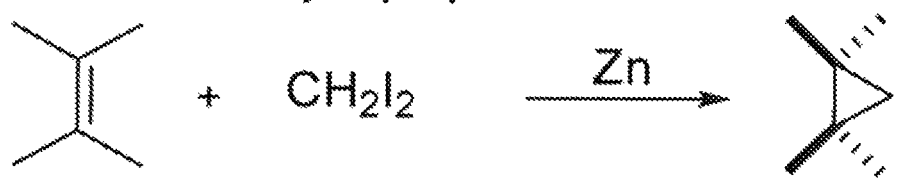
Figure 1:
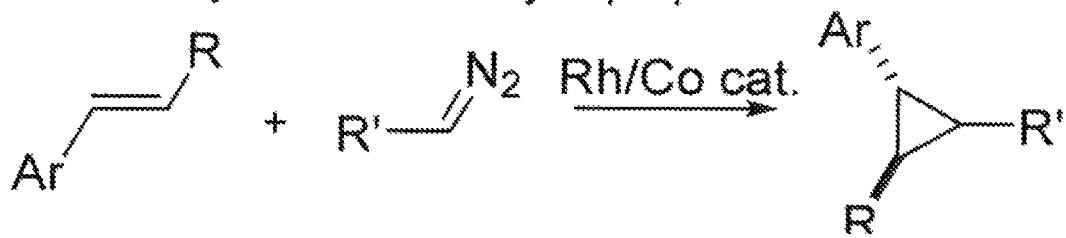
Figure 1:
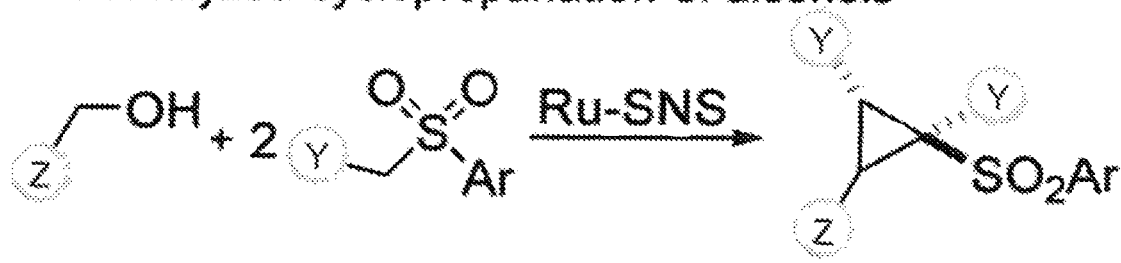
Figure 1:
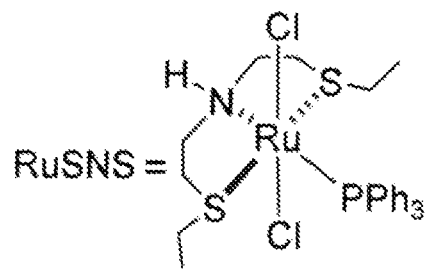

A reaction scheme of another embodiment is shown in Invention of Figure I. In FIG. 1, $ArSO_2Y$ and $ZOH$ may be selected from the aforementioned sulfones and alcohols.

The compound having a cyclopropane structure may be represented by:

[Chem. 10]

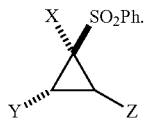

In this formula, X and Y may be derived from the aforementioned sulfones, and Z may be derived from the aforementioned alcohols, aldehyde, or esters.

Another embodiment of the invention is directed to a use of a compound having a cyclopropane structure that can be formed by the method. The use may be for producing drugs and antibiotics in the pharmaceutical field or as useful precursors in the synthesis of industrially relevant compounds.

Another embodiment of the invention is a method including reacting an alcohol represented by $R^6CH_2OH$ or an ester represented by $R^7COOCH_2R^8$ with a sulfone represented by $R^6CH_2$ or an ester represented by $R^7COOCH_2R^8$ with a sulfone represented by $R^9Ch_2SO_2R^{10}$ to produce a compound represented by $R^6CH_2CHR^9SO_2R^{10}$ or $R^8CH_2CHR^9SO_2R^{10}$ and isolating the product. $R^6$, $R^7$, $R^8$, $R^9$, and $R^{10}$ may be inde-pendently selected from alkyl, cycloalkyl, hetcrocycloalkyl, aryl, and heteroaryl. The alcohol, ester, and sulfone may be selected from those described above. In this reaction, the aforementioned catalyst, solvent, and base may be used at the aforementioned conditions (e.g. amount, temperature, etc.). For example, as a catalyst,

[Chem. 11]

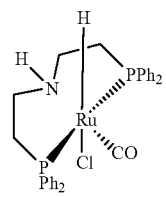

is used, and the amount of the catalyst is, for example, 2 mol %.

Examples

General Specifications: Reagents and Instrumentation

All solvents and reagents for the reactions were weighed out and dispensed in an inert atmosphere, nitrogen MBraun Unilab pro glovebox unless otherwise stated. Anhydrous toluene was purchased from Kanto Chemical Company with no extra drying or redistilling techniques. Benzyl Phenyl Sulfone was purchased from TCI Chemicals, KHMDS and Ru-SNS (Aldrich No. 746339) were purchased from Sigma Aldrich. All alcohols and sulfones were purchased from TCI Chemicals, Sigma Aldrich, Alfa Aesar or Oakwood Chemicals with no extra drying or redistilling. NMR spectra were collected on a JEOL ECZ 600R JEOL ECZ 400S spectrometer unless otherwise noted. $^{19}F$ peaks are measured relative to hexafluoro benzene. $^1H$ and $^{13}C$ chemical shifts are reported referenced to $CDCl_3$ peaks. All NMR analysis was performed with MestReNova. GC/MS data was performed on a Shimadzu QP2010-Ultra equipped with an SH-Rxi-1 ms 60 meter column with mesitylene standard added after reaction completion. HRMS were obtained on a Thermo LTQ OrbitrapXL with a nanospray interface. Most compounds had both an $[M]^+$ and $[M+NH_4]^+$ detected. X-ray analysis was performed on a Rigaku Xtal LAB ProDS spectrometer with a Dectris Pilatus 3R 200K-A detector using a copper radiation source.

Initial Studies and Optimization.

Figure 2:
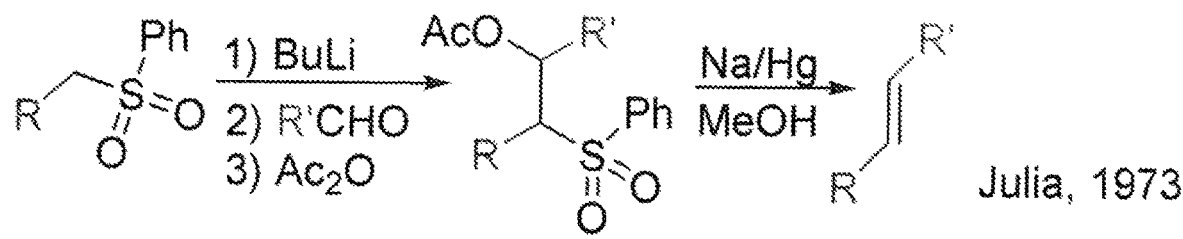
FIG. 2 illustrates Julia olefination and related reactions.
Figure 2:
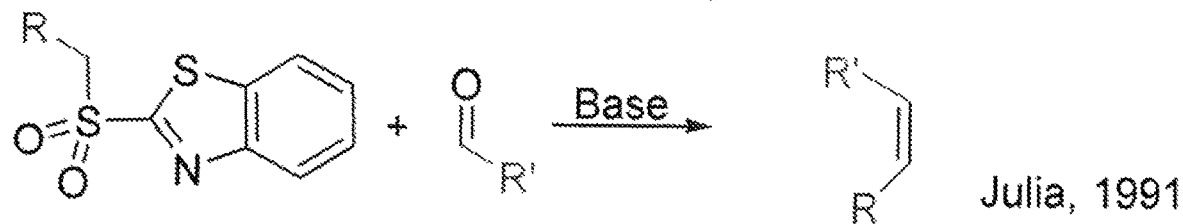
Figure 2:
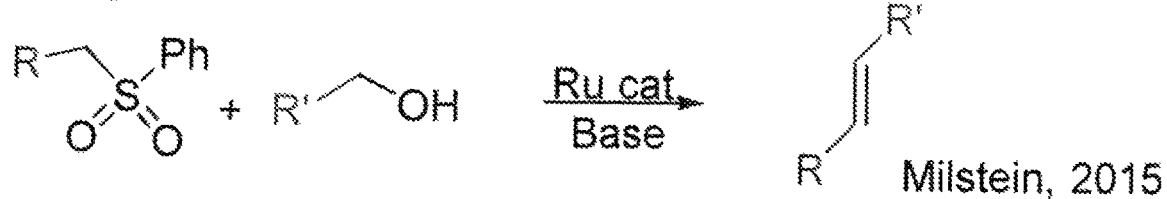

In 2014, Milstein and Srimani reported on a Julia-like olefination reaction of alcohols (FIG. 2) in the presence of a Ru catalyst[14] that was previously used in the acceptorless dehydrogenation of alcohols and amines to form substrates such as esters, amines, and imines. Similar to the above mentioned report, various other products can be obtained by introducing other substrates that can capture the intermediate aldehyde.[15] Although the Julia olefination requires reduction of a vinyl sulfone intermediate in order to form the highly trans selective olefin,[16] the olefins obtained via Ru catalysis did not need an external reductant and some substrates reacted to give products in high (>70%) isolated yields. The Julia reaction can be modified to use specialized reagents that release $SO_2$ without the need for a reductant (FIG. 2),[17] however, simple sulfones only were used in the Milstein procedure. The authors were not certain why the olefin was produced in one step, without generating a Julia-like intermediate, but one possibility is that the hydrogen generated in situ from dehydrogenation of alcohol was active in reducing the unobserved intermediate. The reaction was limited to benzylic alcohols; octanol, the only aliphatic substrate tested, reacted with dimethylsulfone to give a complicated mixture of products.

Pursuant to the inventor's recently published report on the ester metathesis of unsymmetrical esters,[18] the inventor was interested to see if the commercially available Gusev SNSRu catalyst (structure given in Table 2 as catalyst C)[19] active in the ester scrambling reaction could show novel reactivity in other systems. Revisiting the original chemistry with unsymmetrical esters instead of alcohols, as shown in FIG. 3, the inventor confirmed the original Milstein coupling results between the benzylic alcohol part of the ester and alkyl/aryl sulfones.

Figure 3:
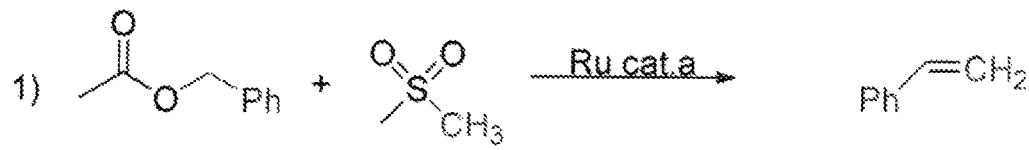
FIG. 3 illustrates reactions of esters with sulfones under catalytic conditions. In this figure, a) Conditions: 100 mol % sulfone to substrate, with Gusev catalyst (0.5 mol %), 110 mol % KOtBu, $N_2$ atmosphere, 16 hours, 80° C., closed vessel. Afterwards quench with aq. $NH_4Cl$, extraction.
Figure 3:
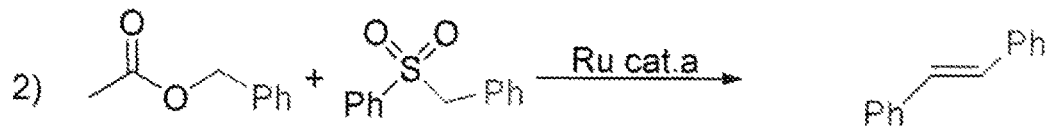
Figure 3:
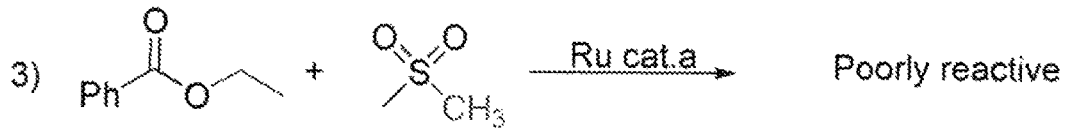
Figure 3:
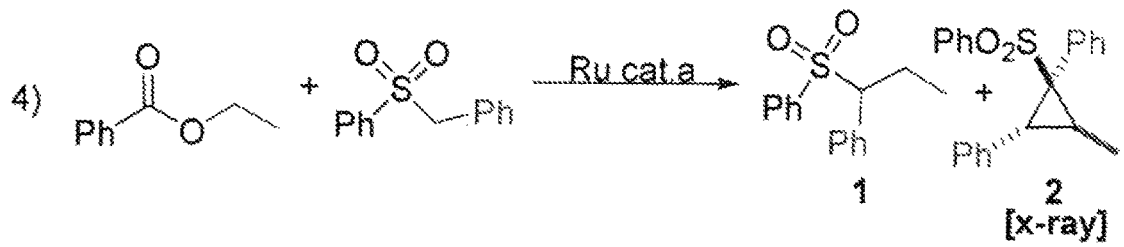
Figure 3:
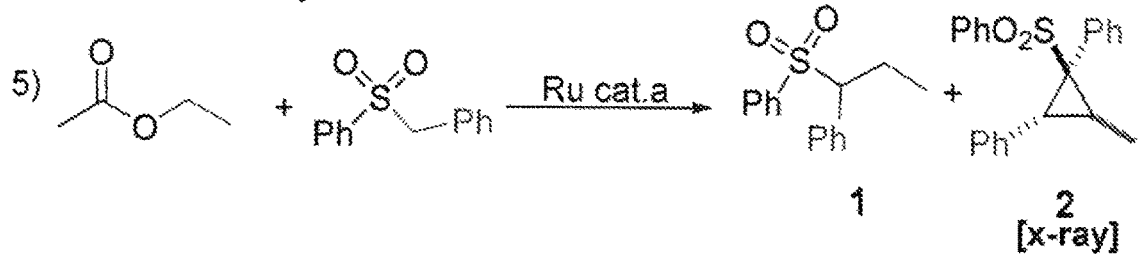
Figure 3:
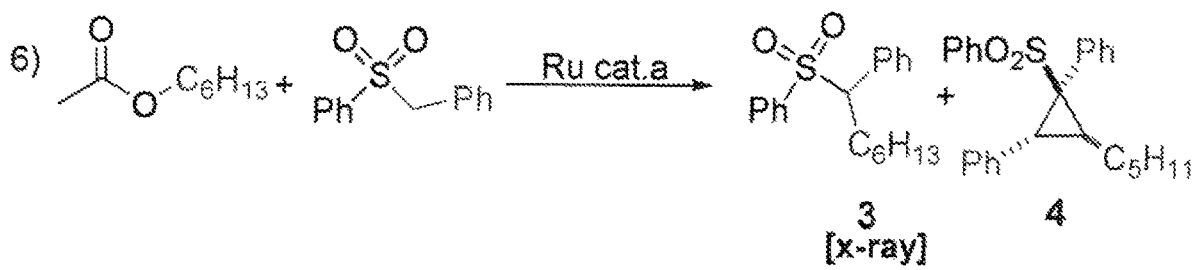

The inventor thus observed the olefin products, styrene and stilbene, which were produced when benzyl acetate reacted with dimethyl sulfone and benzyl phenyl sulfone, respectively (FIG. 3; eq. 1,2). Intriguingly, the activity of these ester substrates suggests that the hydrogen formed in situ in the original Milstein system cannot act as a reductant of a proposed β-OH sulfone intermediate, hinting at a more complex mechanism for the earlier reported reaction. Another unexpected outcome was obtained in the reaction of an alkyl alcohol ester. Thus, when ethyl benzoate ester and benzyl phenyl sulfone were coupled, the inventor observed only trace styrene formation and two new products that at the time could not be identified based on the crude NMR spectra alone (FIG. 3; eq. 4). To avoid trace styrene that presumably arose as a byproduct of ester metathesis, the inventor used the symmetrical ester ethyl acetate on a 1 mmol scale to cleanly form and isolate the same products, which were labelled as unknown compounds 1 and 2 (FIG. 3; eq. 5). Product 1 was isolated as a white solid, and 2 could be crystallized by slow evaporation of acetone solution. Symmetrical ester hexyl hexanoate gave products 3 and 4, which are analogues of 1 and 2 but with an extra $C_4H_8$ unit (FIG. 3; eq. 6), with 3 crystallized via slow evaporation of acetone solution and 4 isolated as a gel. The structures of 2 and 3 were unambiguously identified by single crystal X-ray diffraction analysis (FIG. 4), showing excellent agreement with NMR data, and allowed the inventor to make structural assignments and identify related compounds 1 and 4. Both the linear and the cyclopropane product were unexpected based on previously known chemistry and in both cases, the linear product was minor and was about half the amount of the cyclopropane.

According to NMR and single crystal X-ray diffraction data, cyclopropane products 2 and 4 have a fixed stereochemistry with regard to the two aryl groups, and were obtained with one diastereomer being predominant. Each cyclopropane molecule appears to result from the coupling of two sulfone and one alcohol units. Chiral HPLC resolution of a 50 mg sample of 2 allowed for the separation, isolation, and crystallization of the (1R,2S,3R)-2 and (1S, 2R,3S)-2 enantiomers. While quaternary center sulfone cyclopropanes have been reported in the literature,[11b, 13b, 20] their syntheses are multi-step, often involving the preparation of an advanced thioether intermediate and its subsequent oxidation. The synthetic method of this example requires only an ester, sulfone, base and the catalyst: all components that are commercially available and cheap.

Reaction with ethyl acetate gave the same amount of products 1 and 2 as the one carried out with ethyl benzoate, without the presence of trace styrene, confirming that it is only the alcohol part of the ester that is transformed into products.

In FIG. 3, Eqs. 1 and 2, benzyl acetate gave olefinic products as described above. Interestingly, no traces of products 1 and 2 could be seen in reaction 2 in FIG. 3, presumably due to the fast rate of reaction to form the styrene. However, traces of styrene could be observed in reaction 4 in FIG. 3. Reaction 3 in FIG. 3 also indicates that purely alkyl sulfones are not active in the cyclopropanation reaction. That the aryl part of the ester does not participate in the reaction at all is striking since it is further established that the Ru catalyst is only responsible for dehydrogenating the alcohol to aldehyde and it is the latter's reaction with sulfone mediated by a counter cation such as a potassium cation that is responsible for cyclopropanation. Reaction of ester in the absence of catalyst did not result in formation of cyclopropanation.

Cyclopropanation of Alcohols.

Since only the alcohol unit of the ester reacted in the mixed ester experiments, the inventor quickly established that it was possible to replace the ester by an alcohol or an aldehyde. As two equivalents of sulfone are required for the synthesis of one cyclopropane, a 200 mol % amount was used for all reactions during optimization. Qualitative optimization of this promising transformation with the SNS Gusev catalyst (catalyst C in Table 2) via GC/MS data (Table 1) against an internal standard, showed that the yield of minor linear product 3 could be lowered significantly when two equivalents of sulfone were used, increasing the yield of 4 in turn. The initial screen (Table 1) also showed that the catalyst is responsible for only dehydrogenating the starting alcohol; however, the rate of aldehyde formation can affect the production as starting from an aldehyde led to far lower yields of the final cyclopropane product (entries 1-2), presumably due to disproportionation/condensation reactions in the presence of large amounts of strong base. The catalyst is also responsible for producing 3 by eliminating the OH group from what is likely a Julia-like intermediate species. Reactions with aldehyde and without catalyst (Table 1; entry 2) showed no 3 by GC/MS. The formation of byproducts may thus be minimized by optimizing conditions and choosing the right catalyst.

Entry 4 (Table 1) confirmed that a counter cation such as a potassium cation worked in non-catalytic amounts, with sodium acting to shut down the coupling. $RuCl_3$ was also a viable homogenous catalyst under the reaction conditions (entry 6), reaching ca. 17 TON, but also giving unidentified, relatively low-boiling byproducts in the GC/MS trace, Interestingly, even $NiBr_2$ was active to some extent, however the number of byproducts and unreacted alcohol significantly exceeded that of even $RuCl_3$. The identity of the base (Table 1, entry 3) also can affect the production since sodium gave no product.

TABLE 1

Establishing viability of alcohols as substrates

| Entry | Cat. (mol %) | b or c | Additive | Base | Yield of 4 (GCMS) |
|---|---|---|---|---|---|
| 1 | C (0.2) | b | none | KHMDS | 21% |
| 2 | none | b | none | KHMDS | 22% |
| 3 | C (0.2) | c | none | NaHMDS | no reaction |
| 4 | C (0.2) | c | KBr 10% mol | NaHMDS | trace |
| 5 | C (0.2) | c | none | KHMDS | quantitative |
| 6 | $RuCl_3$ (5.0) | c | none | KHMDS | 85% |
| 7 | C (0.2) | c | Hg drop | KHMDS | quantitative |
| 8 | $RuCl_3$ (5.0) | c | Hg drop | KHMDS | 18% |
| 9 | $NiBr_3$ (2.0) | c | none | KHMDS | 18% |
| 10 | C (0.2) | c | $H_2$ 1 atm | KHMDS | 76% |

Conditions: 0.2 mmol b or c, 200 mol % sulfone, 210 mol % base, $N_2$ closed vessel

TABLE 2

Optimization of cyclopropanation reaction conditions.

| Entry | Cat. (mol %) | T (° C.) | Solvent | Base | Yield of 4 (GCMS) |
|---|---|---|---|---|---|
| 1 | A (2) | 80 | Toluene | KHMDS | 80%[a] |
| 2 | B (3) | 80 | Toluene | KHMDS | 11% |
| 3 | C (0.5) | 80 | Toluene | KHMDS | 70% |
| 4 | D (0.5) | 80 | Toluene | KHMDS | 54% |
| 5 | E (2) | 80 | Toluene | KHMDS | 41% |
| 6 | C (0.5) | 80 | Toluene | NaOH | 0% |
| 7 | C (0.5) | 80 | Toluene | LiHMDS | 0% |
| 8 | C (0.5) | 80 | Toluene | NaHMDS | 0% |
| 9 | C (0.5) | 80 | Toluene | KOtBu | 70%[a] |
| 10 | C (0.5) | 120 | Toluene | KHMDS | quantitative |
| 11 | C (0.2) | 120 | Toluene | KHMDS | quantitative |
| 12 | C (0.5) | 80 | THF | KHMDS | 35% |
| 13 | C (0.5) | 80 | THF | KOtBu | 0% |

0.2 mmol hexanol scale, 200 mol % sulfone, 210 mol % base, $N_2$ closed vessel.
[a]Significant amount of linear product 3 was obtained.

Catalyst optimization.

The identity of the dehydrogenation catalyst may be one factor to minimize formation of byproduct 3 and to enable a steady rate of aldehyde formation. A short catalyst screening (Table 2) showed that a number of commercially available Ru and Os catalysts active in alcohol dehydrogenative coupling to give esters were also competent in the cyclopropanation reaction. The preferred catalyst was the $SNSR_u$ Gusev catalyst C tested initially.[19] The commercially available Milstein catalyst A[21] was also reasonably active, albeit at a higher loading; however, the presence of byproduct 3 was more. Takasago catalyst B that is normally quite active in alcohol coupling and ester hydrogenation chemistry,[22] was less active for this transformation. Catalysts D[23] and E,[24] although active and with the latter showing that efficient transformation is not limited to ruthenium, were also less active. The identity of the base, and its associated alkali metal cation, again affected the reaction, with KHMDS giving visibly better outcomes than KOtBu, and LiHMDS or NaHMDS not leading to any cyclopropane formation. THF solvent was less active than toluene when KHMDS was used as a base, and using both THF and KOtBu resulted in no cyclopropane product. The number of solvents that catalysts A-E can be exposed to in the presence of strong base is limited to ether based ones and aromatic hydrocarbons. However, increasing the temperature to 120° C. in toluene (reactions were performed in a closed vessel) led to significant improvements in the yield of cyclopropanation products, with linear products appearing as trace species or not being detected by GCMS at all. Significantly, diastereoselectivity of 4 was not affected by increasing the reaction temperature.

Substrate Scope and Formation of Cross-Coupled Products.

Upon settling on optimized conditions (Table 2, entries 10-11) the inventor attempted cyclopropanation with a number of alcohols at the 1 mmol scale, using benzyl phenyl sulfone as the model sulfone because of its low cost and its ability to form crystalline products, which were helpful in determining diastereoselective trends. With catalyst C, reaction outcome was not significantly affected by retaining the low catalyst loading of 0.2 mol % for ethanol and hexanol. However, for some other alcohols, unless purity is guaranteed or distillation is performed, it is better to use as much as 1 mol % catalyst. In most cases in FIG. 5, coupling was carried out with 1 mol % of catalyst (some substrates at 0.5 mol %), and on a larger scale (1 mmol) than during the optimization procedure used in Tables 1 and 2, in order to obtain significant amounts of material after isolation by flash column chromatography and demonstrate the practical utility of the current method.

Figure 5:
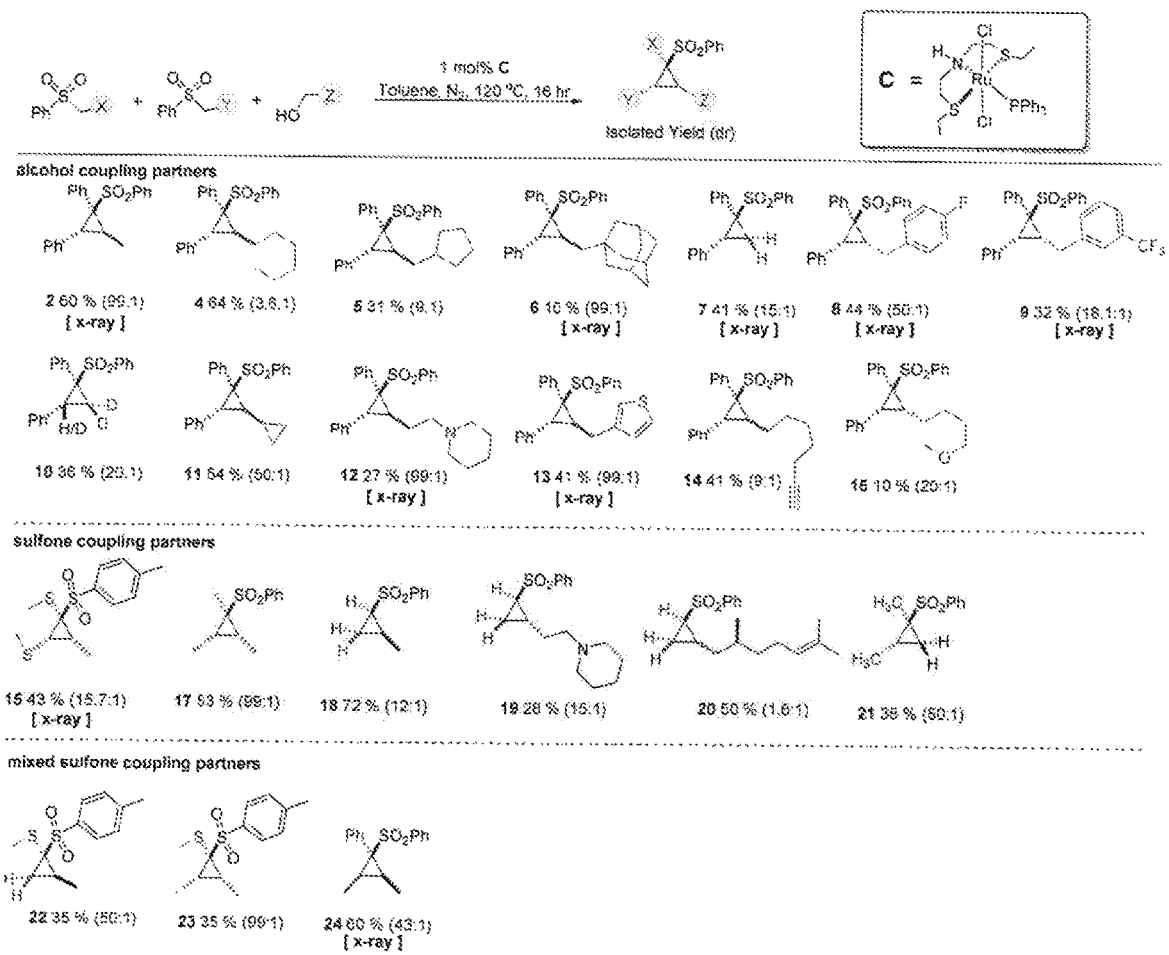
FIG. 5 illustrates compounds obtained in the course of coupling of alcohols with sulfones. Relative configuration of the major diastereomer is presented. All substrates with 1 mol % C except 6, 16, 18, 20 (0.5 mol % C). Substrate 7 can be synthesized from 2-butyne-1-ol or 3-butyne-1-ol under the same conditions but with a 72 h reaction time. 8 and 9 required 72 h of reaction time. Substrate 21 synthesized from paraform and no catalyst. 1 and 3 are byproducts isolated during synthesis of 2 and 4 from esters.

In FIG. 5, besides simple alkyl alcohols, which in themselves include diverse entries such as adamantyl and cyclopropyl alcohols (products 6, 11), the reaction conditions also proved amenable to fluorine (8, 9), sulfur (13), nitrogen (12, 19) and oxygen (16) atom modified alcohols. Fluorine atom containing substrate 2-para-fluorophenyl ethanol was cyclopropanated in 44% isolated yield after a longer, 3 days reaction time (8). Some substrates allowed for their isolation in impressive ca. 70% yield range; however, even reaction yields of ca. 10-40% for highly complex products obtained from simple starting materials greatly outperform all other viable approaches for their synthesis. Interestingly, isobutanol was unreactive, but cyclopropyl alcohol gave product 11 in good yields. For the latter alcohol, the steric hindrance on the 13 carbon is smaller than for a free Me group however. The importance of sterics for ring closure is illustrated by the low yield of product 6.

Significantly, amine containing substrate piperdine-4-propanol gave acceptably large (ca. 30%) isolated yields of product 12. Methanol was also amenable to cyclopropanation under the reaction conditions to give the corresponding C3-unsubstituted cyclopropane sulfone 7. Interestingly, the same product 7 was observed after long reaction times with 2-butyn-1-ol and 3-butyn-1-ol, hinting at a complicated rearrangement mechanism accompanied by formal C—C bond cleavage. In these cases, however, the reaction requires long reaction times of 72 hours to achieve similar 40% yields.

Other commercially available sulfones such as ethyl phenyl sulfone and methylthiomethyl based sulfones also reacted to give good yields of products 15-24. Methanol does not react with ethyl phenyl sulfone to give acceptable yields of cyclopropane. However, substituting methanol for paraformaldehyde and performing the reaction without catalyst, the inventor was able to isolate product 21 in a yield of 38%. Overall, since the products are difficult to obtain by other methods, even at a low isolated yield of 10% that is seen for 6, the current one-step procedure is vastly superior. Recently, a procedure has been published by the Baran group for the synthesis of a large number of diverse sulfones in a one-step, iron catalyzed reaction from a number of easily accessible vinyl sulfone precursors.[11a] These sulfones can be utilized in the current method to give a large range of diverse cyclopropanes.

The inventor performed a number of "mixed sulfone" reactions in order to extend the utility of the current method by introducing substituents from two different sulfones on the ring carbons (FIG. 5). Using one equivalent of each sulfone often led to selective reactions for cross-coupled products, with relatively small amounts of the homocoupling cyclopropane that could be mostly separated out after column chromatography. The selectivity could be predicted based on $pK_a$ differences between the two sulfones (See Table 3), with the more acidic sulfone remaining on the ring as this sulfone is the first to capture the in situ produced aldehyde. Compounds 23 and 24 retained observable amounts of homocoupling product after column chromatography (yield is given for only the desired cyclopropane). However, HPLC separation could provide pure product.

TABLE 3

Abbreviated $pK_a$ table

| Substrate pKa H$_2$O | (DMSO) |
|---|---|
| SULFONES | |
| Ph–S(O)(O)–CH$_2$–X | |
| X = H | (29.0) |
| CH$_3$ | (31.0) |
| t-Bu | (31.2) |
| Ph | (23.4) |
| CH=CH$_2$ | (22.5) |
| CH=CHPh | (20.2) |
| CCH | (22.1) |
| CCPh | (17.8) |
| COPh | (11.4) |
| COMe | (12.5) |
| OPh | (27.9) |
| N$^+$Me$_3$ | (19.4) |
| CN | (12.0) |
| NO$_2$ | (7.1) |
| SMe | (23.5) |
| SPh | (20.5) |
| SO$_2$Ph | (12.2) |
| PPh$_2$ | (20.2) |
| Ph–S(O)(O)–CHPh$_2$ | (22.3) |
| Me–S(O)(O)–Me | (31.1) |
| CF$_3$–S(O)(O)–Me | (18.8) |
| CF$_3$–S(O)(O)–i-Pt | (21.8) |
| CF$_3$–S(O)(O)–cyclopropyl | (26.6) |
| Et–S(O)(O)–Et | (32.8) |
| (PhSO$_2$)$_2$CH$_2$Me | (14.3) |

Figure 6:
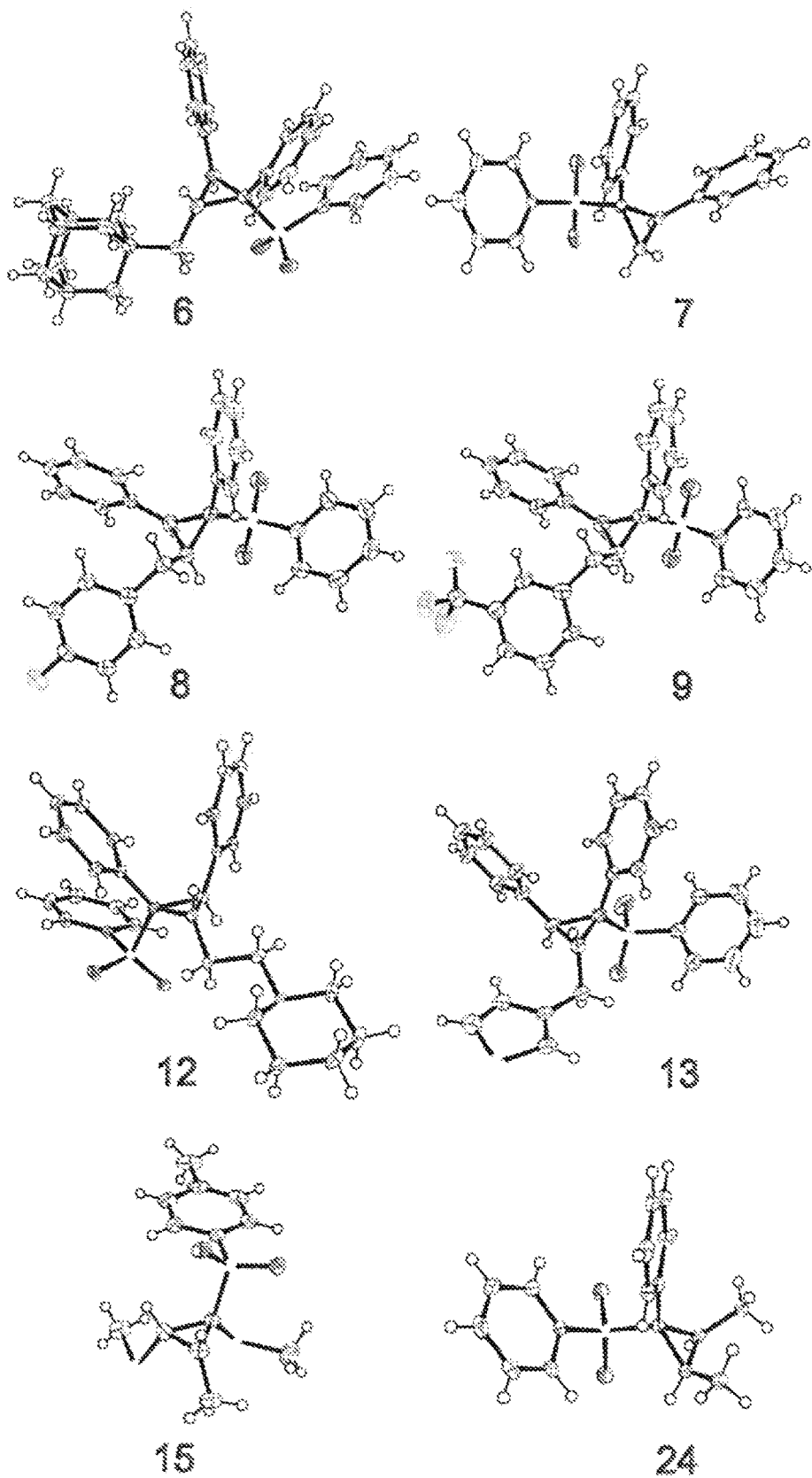
FIG. 6 illustrates ORTEP projections of cyclopropanes 6-9, 12, 13, 15, and 24 showing anisotropic displacement ellipsoids at the 50% probability level.

A lot of the cyclopropanes synthesized by the inventor are relatively non-polar, and manage to crystallize well after column chromatography via slow evaporation of solvent. Suitable single crystals were studied by means of X-ray diffraction (FIG. 6).

Figure 4:
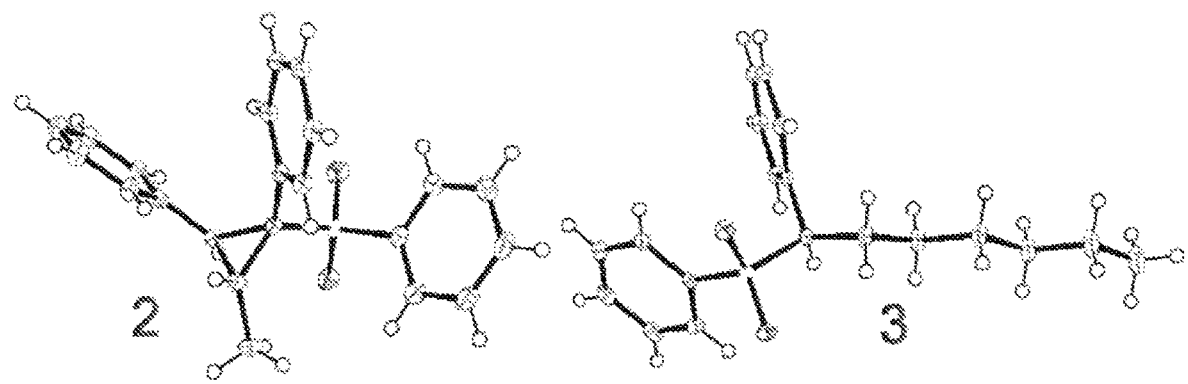
FIG. 4 illustrates ORTEP projections of cyclopropane 2 and linear product 3 showing anisotropic displacement ellipsoids at 50% probability level.

The crystallographic data in the drawings contain full experimental details regarding data collection and structure refinement. FIGS. 4 and 6 illustrate molecular structure and configuration of compounds analyzed. Interestingly, racemic samples of cyclopropanes 2 and 6 crystallize in the Sohncke space group P2$_1$ of the monoclinic crystal system as conglomerates of enantiomer crystals, which makes direct resolution of their racemates possible. The other substances studied form racemic compounds in crystals, containing both enantiomers in the unit cell.

A number of other alcohols could be cyclopropanated, but some resulted in mixtures that could not be easily separated by column chromatography, or gave products in low yields. Some sulfones are unreactive under the current conditions, or give trace yields of cyclopropane (dimethylsulfone, cyanomethyl phenyl sulfone, etc). Other substrates such phenyl allyl sulfone were reactive, but a large number of byproducts with similar polarity were also produced. Table 4 shows these substrates that includes an olefinic alcohol and other nitrogen containing substrates.

TABLE 4

Other substrate for the cyclopropanation reaction.

GROUP A: No cyclopropane reactivity

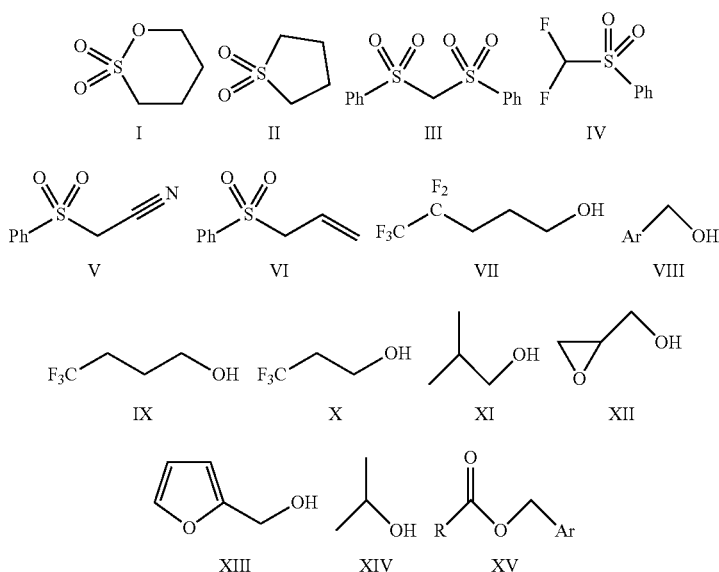

GROUP B: Some reactivity; no cyclopropane or very little cyclopropane

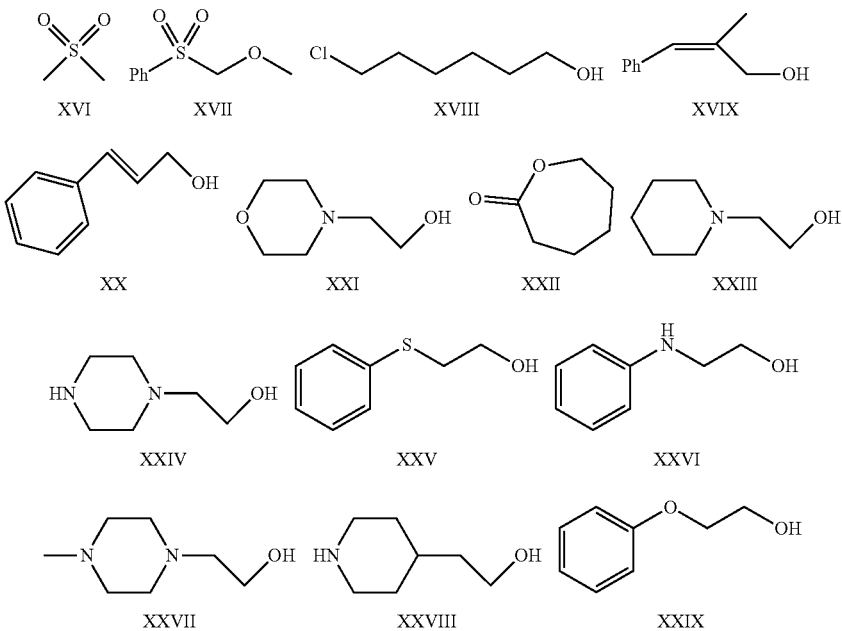

TABLE 4-continued

Other substrate for the cyclopropanation reaction.

GROUP C: Good reactivity for cyclopropane; unexpected product obtained or poor dr.

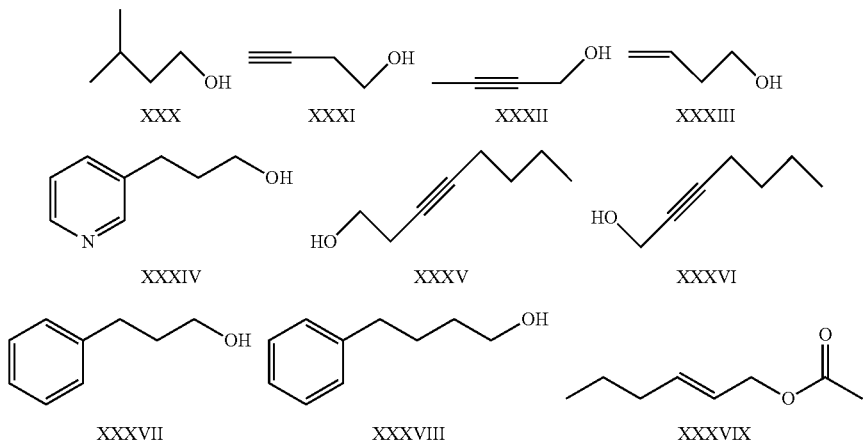

For Group A, usually no significant consumption of starting material was observed with one of the starting substrates. This was particularly true for the fluorinated alcohols. Substance VIII is a general class of aryl alcohols, which react to give olefins as reported previously.[S4] Functional groups on the sulfone that are next to the carbon that is connected to the sulfur are deleterious for cyclopropanation. Compound XI and related compounds show that β carbon substitution generally means that the reaction will not proceed. A counterpoint is compound 11 where the reaction proceeds in good yield, and compounds such as 9 and 8. However there the cone angle is smaller than with a free Me group. Compounds XII and XIII are not stable under the reaction conditions. Secondary alcohols (and ketones) don't work in general, and the general class of aromatic esters XV react in the same way as VIII to give olefins.

For Group B, some reactivity was observed, and undetermined products were observed. For some compounds, the inventor could not observe cyclopropanes with the right M⁺ or the approximate expected retention time by GC/MS. Sulfonate XVI (and II), suggest that an aryl sulfone works for reactivity, while sulfone XVII is likely not stable under the reaction conditions. For compound XVIII, activation of the CCl bond likely occurs during the reaction, probably by the Ru catalyst, preventing yield of products. This result means that the reaction is limited under the current conditions to not tolerating alkyl C—X bonds as in compound XVIII. Compound XVIX gives an olefin product to a moderate degree despite β carbon substitution. Secondary amines such as XXIV and XXVII actually do react to give trace cyclopropane according to GC/MS. However, in general, if the 6 membered ring is bonded to the β carbon, reactivity is low. Compounds XXV, XXVI, and XXIX rearranged with heteroatom-C bond cleavage during the reaction and even though some cyclopropane was obtained, it was mostly compound 2.

In Group C, good reactivity was obtained. XXX had a crude d. r. of 4:1. Compounds XXXI, XXXII, XXXV, and XXXVI all reacted after 72 hours of heating to give the same compound 7. The same reactivity pattern of ultimate CC cleavage occurs if the triple bond is located on the β or γ carbon. Compound XXXIII gave some hydrogenated product with low d. r. that was very difficult to separate on the column. Compounds XXXIV and XXXVII worked to give cyclopropane, but there were significant amounts of olefin byproduct, where the bond between the β or γ carbon has also been dehydrogenated. Compound XXXVIII worked well, showing that once the aryl group is past the γ carbon, reaction proceeds well without olefin byproduct. Compound XXXVIX worked well, but with low d. r. and it is similar to compound 20, which shows that double bonds can be tolerated in the reaction.

Mechanistic discussion. Previous methods for the diastereoselective synthesis of cyclopropanes, which are summarized in FIG. 1, often required low temperatures to enable selectivity. The inventor was thus interested in obtaining insight into the unusual mechanism of the current reaction. In 1991, Julia showed that addition of sulfone carbon anions could be catalyzed by nickel complexes to add across double bonds and give cyclopropanes in various degrees of diastereoselectivity.[25] Other examples in the literature showed that carbanions can add to sulfone substituted olefins to give cyclopropanes where the sulfone functionality is maintained,[26] or is eliminated. In the case of elimination, the SO₂Ph moiety likely leaves as a benzene sulfinate.[25, 27]

Analyzing the results in Table 1, the inventor concluded that the reaction first proceeds to form the aldehyde and it is the aldehyde which reacts with two sulfone anions, presumably in a stepwise manner with the lower $pK_a$ sulfone reacting first, as mixed sulfone reactions showed that selectivity is possible (FIG. 5). Cyclopropanation of methanol-d₄ (FIG. 5, compound 10) showed that the carbon atom from the alcohol was still fully deuterated, with the other sulfone based CH being partially deuterated due to exchange with the D atom of methanol's OD, showing that exchange does not occur after the formation of the initial aldehyde or of any of the intermediates.

Based on Table 2, it is also clear that the formally non-coordinating HMDS anion improves activity of potassium in closing the cyclopropane ring. THF, which can compete for binding potassium, is less preferable for the reaction. The combination of KOtBu and THF led to no product.

The dehydrogenation catalyst is active at lower temperatures as can be seen from earlier reports.[18-19] It likely initially forms the aldehyde intermediate (and also forms 3 later as a byproduct), while the K+ mediated cyclization may require high temperatures. As noted above, 3 forms in greater amounts when there are less than 2 equivalents of sulfone present, and also at lower temperatures. The byproduct 3 was not observed in Table 1 entry 2 where hexanal and no catalyst was used, suggesting that formation of 3 is catalyst mediated.

Large amounts of byproducts 1 and 3 were isolated in the initial pre-screening experiments that could be used in interrogating the mechanism. The inventor treated isolated 3 with one equivalent of base and sulfone under the catalytic reaction conditions with and without catalyst and in the presence or absence of 1 eq. of water, since water is a likely product of the cyclopropanation reaction (Scheme 1 below). In both cases, the intermediate was completely unreactive. Since 3 fails to give the final product 4, its presence is preferably minimized by using high reaction temperatures and catalysts that do not lead to its formation as easily (i.e. C, but not A). Addition of water to the catalytic reaction did not lead to an appreciable effect at 1 equivalent of water to substrate, but proved deleterious to the reaction outcome at 3 equivalents, with no cyclopropane product being detected (Scheme 1). This could be due to the alcohol dehydrogenation catalyst being shut down in the presence of excess water, or the formation of carboxylate byproducts, which can deleteriously affect catalysis in toluene.[15a] Another possibility is that instead of acting to shut down the Ru catalyst, water can bind the potassium and prevent efficient cyclization. However, addition of molecular sieves to catalytic reactions did not change their outcome.

The non-reaction of vinyl sulfone (Scheme 1) suggests that olefin species are not likely intermediates in contrast with the earlier results obtained by Julia.[25] A catalytic reaction with hexanol set up with an open system under a flow of argon gas that would allow generated $H_2$ to escape did not alter the initial yields or selectivities of the reaction when sampling the mixture after 1 and 2 hours, further arguing against an olefin intermediate mechanism.

Scheme 1. Mechanistic investigation reactions

[Chem. 12]

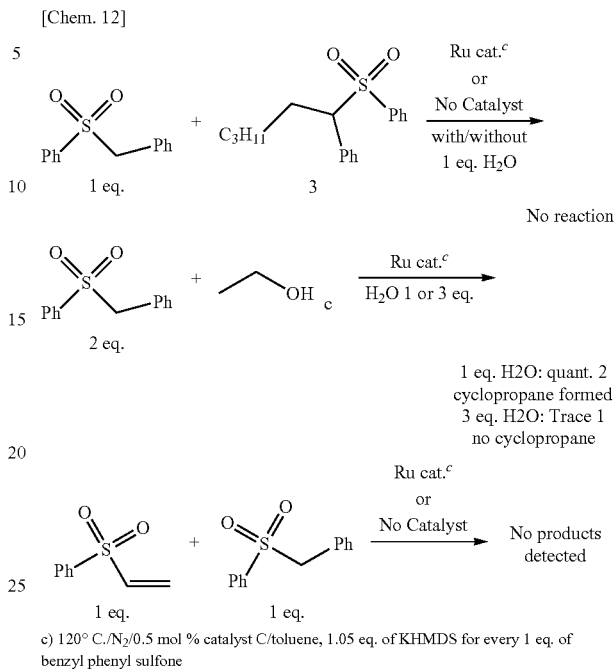

c) 120° C./$N_2$/0.5 mol % catalyst C/toluene, 1.05 eq. of KHMDS for every 1 eq. of benzyl phenyl sulfone Based on the above mechanistic studies and previous literature examples, although the claim scope is not limited thereto, the inventor suggests the following mechanism outlined in Scheme 2 below. Initial formation of an intermediate aldehyde, either free or metal complex bound, is followed by attack of a sulfone anion to create intermediate i. In mixed sulfone reactions, intermediate i is formed from the most acidic sulfone species. In the case of the catalyst mediated side reaction, intermediate i can lose water to give iii and eventually form 3. In the main pathway, intermediate i is templated by K+, that could be ligated by HMDS− or tBuO−, to react concertedly in a four electron three center cyclization with another sulfone equivalent to give product 4 directly with loss of water and sulfinate (presumed intermediate ii), where the stereochemistry is set by the K+templating effect.

Scheme 2. Proposed Mechanism

[Chem. 13]

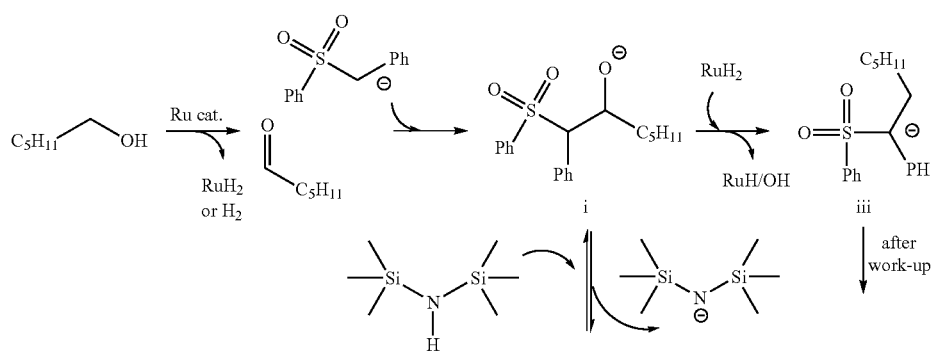

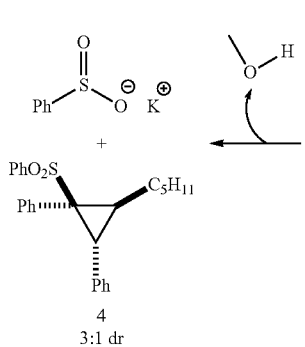

4
3:1 dr

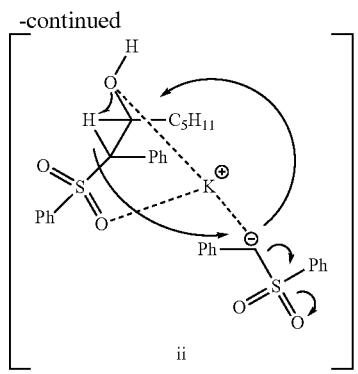

ii $$\underset{\text{3}}{\text{[structure of compound 3]}}$$

Interestingly, fluorine containing cyclopropanes 8 and 9, and oxygen containing 16 have a trans configuration of the alcohol moiety to the remaining sulfone. Since these electronegative atoms are far away from the cyclopropane core, an electronic effect is less likely than F/O being bound to potassium in the transition state, leading to the observed stereochemistry that differs from other cases. For products 17, 23, and 24, meso compounds are formed preferentially, possibly reflecting the different coordination environment around the potassium when smaller sulfones are used.

All reactions in FIG. 1, Table 1, and Scheme 1 were carried out on a 0.2 mmol scale of alcohol or ester substrate in 11 mL screwcap vials. The reaction vials were loaded in the glovebox with the requisite amount of alcohol or ester, and an amount concordant with the table entry was added of appropriate sulfonate, catalyst and base. All the solid reagents were measured out into the vial first, then 4 mL of toluene were added and the liquid reagents were added afterwards. At this point, an Hg droplet was added to the two reactions where a test for catalyst homogeneity was carried out. The vials were closed with the cap and wrapped with electric tape and parafilm. Afterwards the vials were removed from the glovebox and heated at 80° C. or 120° C. as indicated for 16 hours. Mesitylene internal standard was added on a 1-1 alcohol to mesitylene ratio. Afterwards 4 mL of saturated $NH_4Cl$ solution was added and after shaking to neutralize, the organic layer was sampled by GC/MS. Where yields were necessary to determine optimized conditions for latter catalytic reactions, a conversion factor was determined for isolated hexyl cyclopropane product X to mesitylene of ~2:1 and this was used to calculate the given yields of total cyclopropane products, without regard to dr ratio. The same conversion ratio was used to estimate yields of products when ethanol or ethyl benzoate ester was used. Finally, although some of the yields were quantitative, the close polarity of the linear product and the two diastereomer products, as well as the starting material, led to lower overall isolated yields of a particular diastereomer.

Experimental procedures and conditions for Table 2 and FIG. 5 are as follows. General procedure for closed system: To an oven dried 100 mL Schlenk flask in a $N_2$ glovebox, benzyl phenyl sulfone (464 mg, 2 mmol), KHMDS (410 mg, 2.05 mmol) and Ru-SNS (6.3 mg, 0.01 mmol) were dissolved in 10 mL of Toluene. The alcohol or ester (1 mmol) was added to the reaction mixture, the vessel was sealed and stirred at 120° C. for 12 hours. The reaction time was different for some cyclopropane entry as indicated. The reaction was allowed to cool to room temperature, then quenched with 5 mL of saturated $NH_4Cl$ solution. The mixture was extracted with 20 mL of Ethyl Acetate×3 and the organic layers were collected and dried over $MgSO_4$. The solvent was concentrated under vacuum and purified by flash silica chromatography with a gradient of 100:0→88:12 (Hexane:Ethyl Acetate). Fractions where an overly large amount of minor diastereomer, byproduct, or starting material was present along with the desired product were discarded.

General procedure for open system: To an oven dried 100 mL three neck flask in a $N_2$ glovebox, benzyl phenyl sulfone (464 mg, 2 mmol), KHMDS[a] (410 mg, 2.05 mmol) and Ru-SNS[b] (6.3 mg, 0.01 mmol) were dissolved in 15 mL of Toluene. The alcohol or ester (1 mmol) was added to the reaction mixture via microsyringe, the vessel was sealed and removed from the glove box. A reflux condenser was attached and the reaction was stirred at 100° C. for 12 hours under a flow of Ar. The reaction was allowed to cool to room temperature, then quenched with 5 mL of saturated $NH_4Cl$ solution. The mixture was extracted with 20 mL of Ethyl Acetate×3 and the organic layers were collected and dried over $MgSO_4$. The solvent was concentrated under vacuum and purified by flash silica chromatography with a gradient of 100:0→88:12 (Hexane:Ethyl Acetate). Fractions where an overly large amount of minor diastereomer, byproduct, or starting material was present along with the desired product were discarded.

Cyclopropanes Stereochemistry Assignments.

In cases where crystal structures were not obtained, the relative stereochemistry was assigned based on the NOESY effect between protons on the ring and the two phenyl groups. If both cyclopropane protons showed coupling to the phenyl ring as shown below:

[Chem. 14]

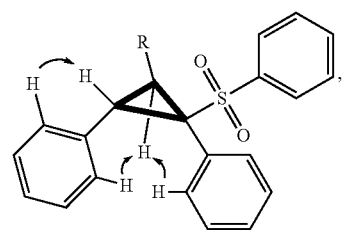

NOESY effect of cyclopropanes but not to each other, then the protons were assigned as trans. Additionally, the coupling constant was measured in 1H NMR and used to help confirm cis/trans relationship. However, in the case of benzyl phenyl sulfonate the coupling values accepted in the literature (7-9 for cis and 5-7 for trans) are not helpful, as the trans compounds (as confirmed by X-Ray for some of them) have couplings of ~8 Hz, which is a record for trans cyclopropanes. See also structural assignment in compound 7, which has been obtained via a multi-step procedure previously.[53]

Cyclopropanes obtained in the above experiments and NMR characterization are shown below.

[Chem. 15]

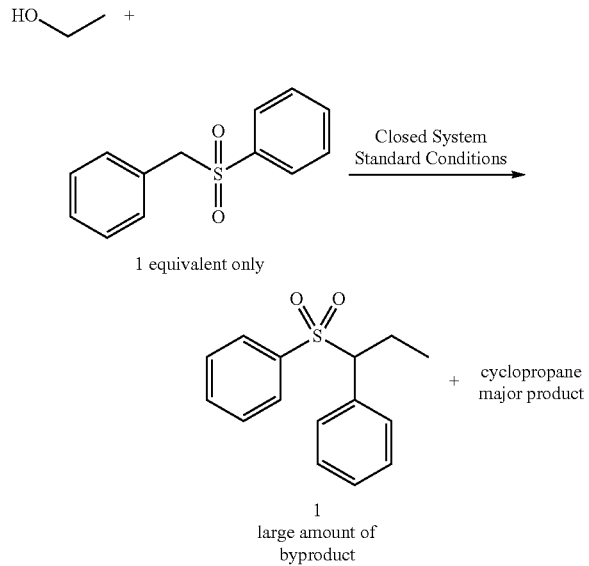

Physical State: White Solid

Since this is a byproduct in the reaction when only one equivalent of sulfone is used, the yield was not determined. It is slightly more polar than the cyclopropane and can be separated on the column at a slightly polar gradient (15% Et$_2$O to hexanes as opposed to 10% for the cyclopropane). The product contains a very minor cyclopropane impurity (see peak at ~3.45 ppm).

Figure 7:
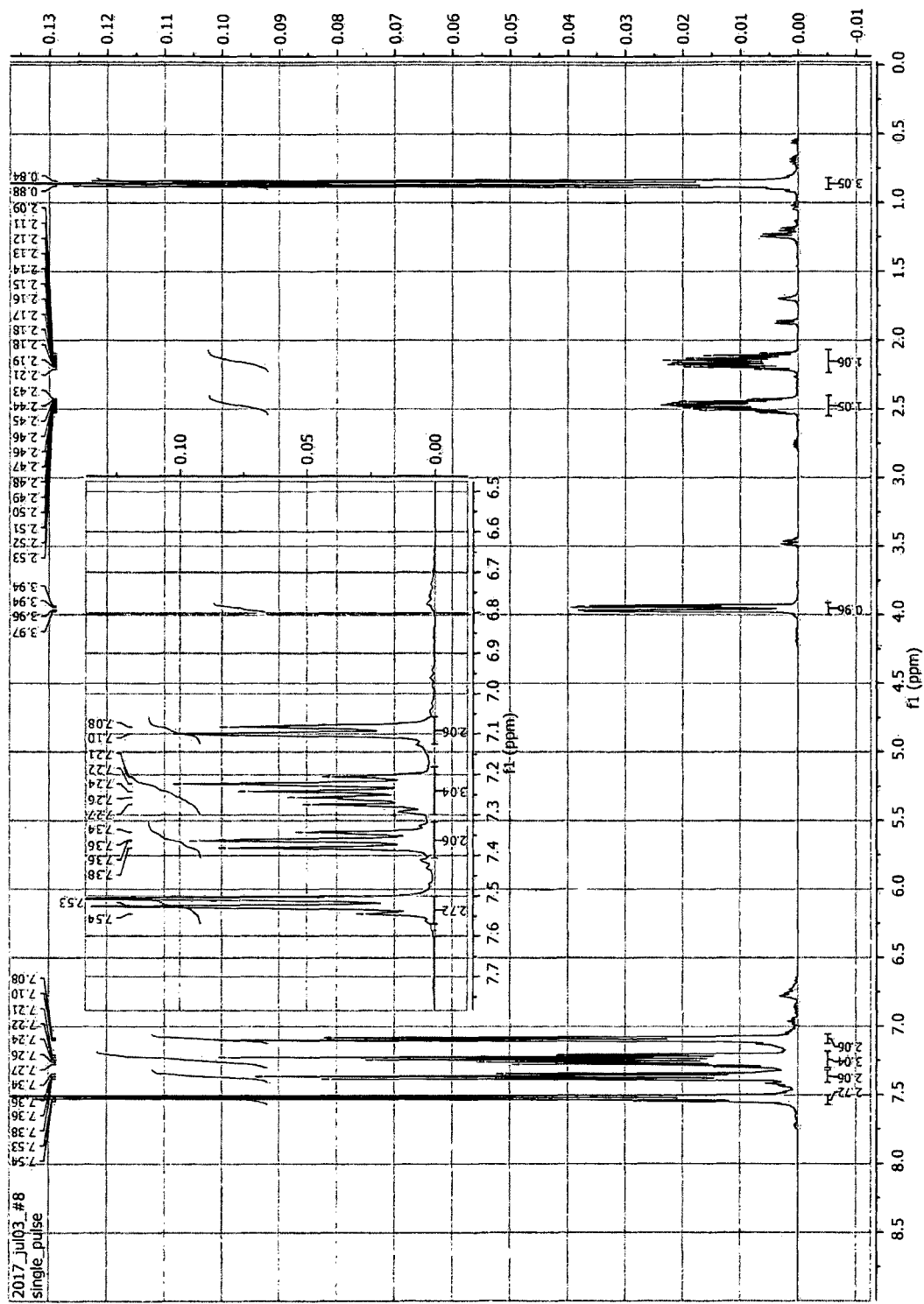
FIG. 7 illustrates $^1H$ NMR of Compound 1.

FIG. 7 illustrates $^1$H NMR (400 MHz, Chloroform-d) δ 7.57-7.48 (m, 3H). 7.41-7.32 (m, 2H), 7.30-7.18 (m, 3H), 7.09 (d, J=6.8 Hz, 2H), 3.95 (dd, J=11.6, 3.7 Hz, 1H), 2.55-2.40 (m, 1H), 2.24-2.07 (m, 1H), 0.86 (t, J=7.4 Hz, 3H).

Figure 8:
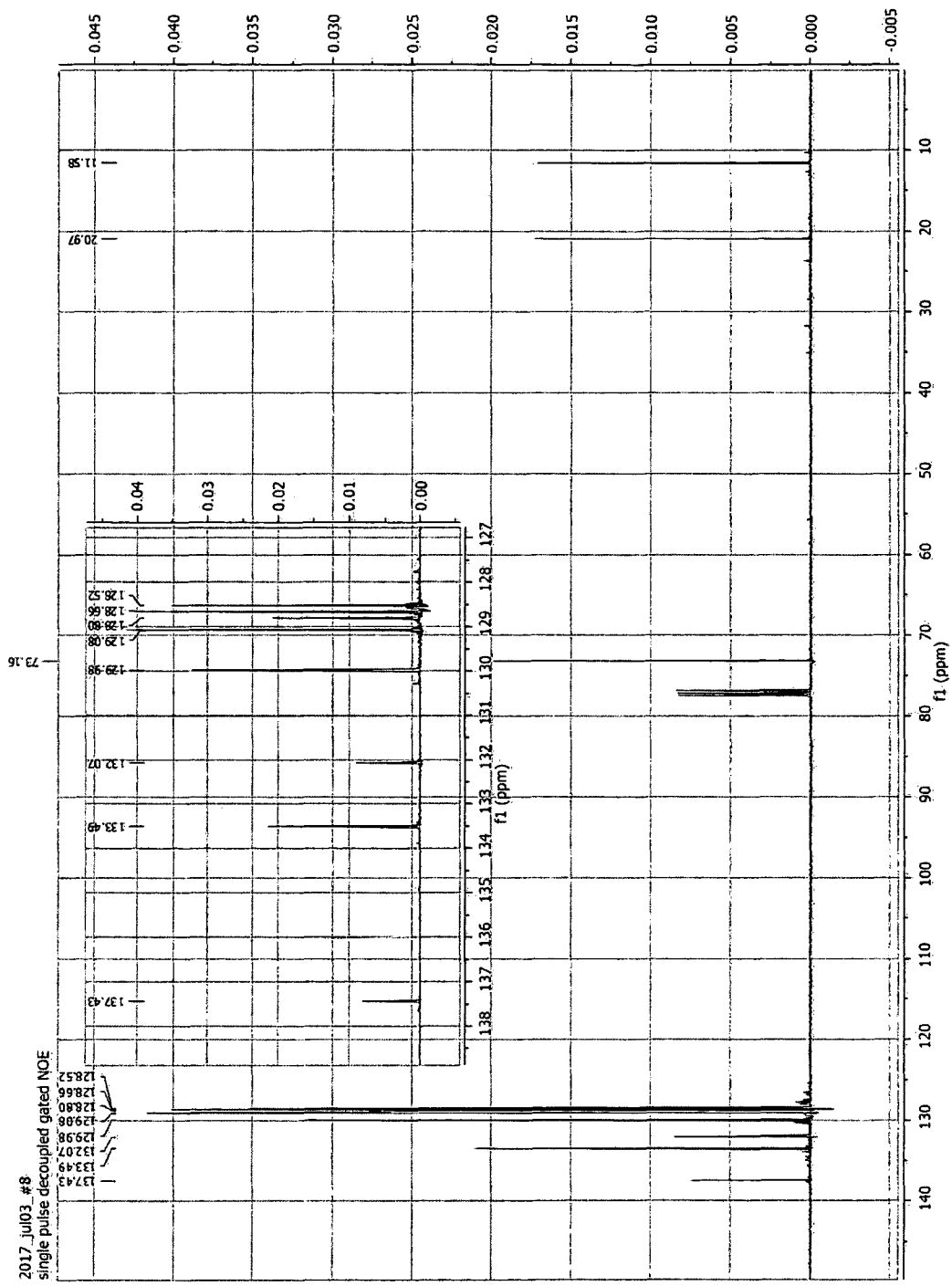
FIG. 8 illustrates $^{13}C$ NMR of Compound 1.

FIG. 8 illustrates $^{13}$C NMR (101 MHz, Chloroform-d) δ 137.43, 133.49, 132.07, 129.98, 129.08, 128.80, 128.66, 128.52, 73.16, 20.97, 11.58.

HRMS: [M+H]$^+$ Expected 261.0944; Obtained 261.0951

[Chem. 16]

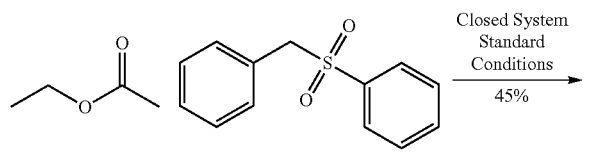

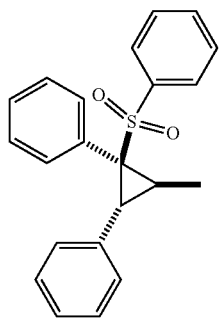

Physical state: Colorless crystals; Isolated Yield 60%. Isolated d. r. 99:1 crude d. r. 19:1. Identity of the major diastereomer determined from J coupling and crystal structures. Compound 2 was also purified by chiral HPLC in order to isolate each stereoisomer. The crystals of each stereoisomer and the original mixed crystals were analyzed by X-Ray (see below). Subsequent NMR of the crystals confirm them as the original compound. Thus, despite the large J coupling, the compound is assigned as trans. This cyclopropane and its related compound with couplings of—8 Hz, as far as the inventor is aware, hold the record for the largest trans coupling constants in a cyclopropane ring.

Figure 9:
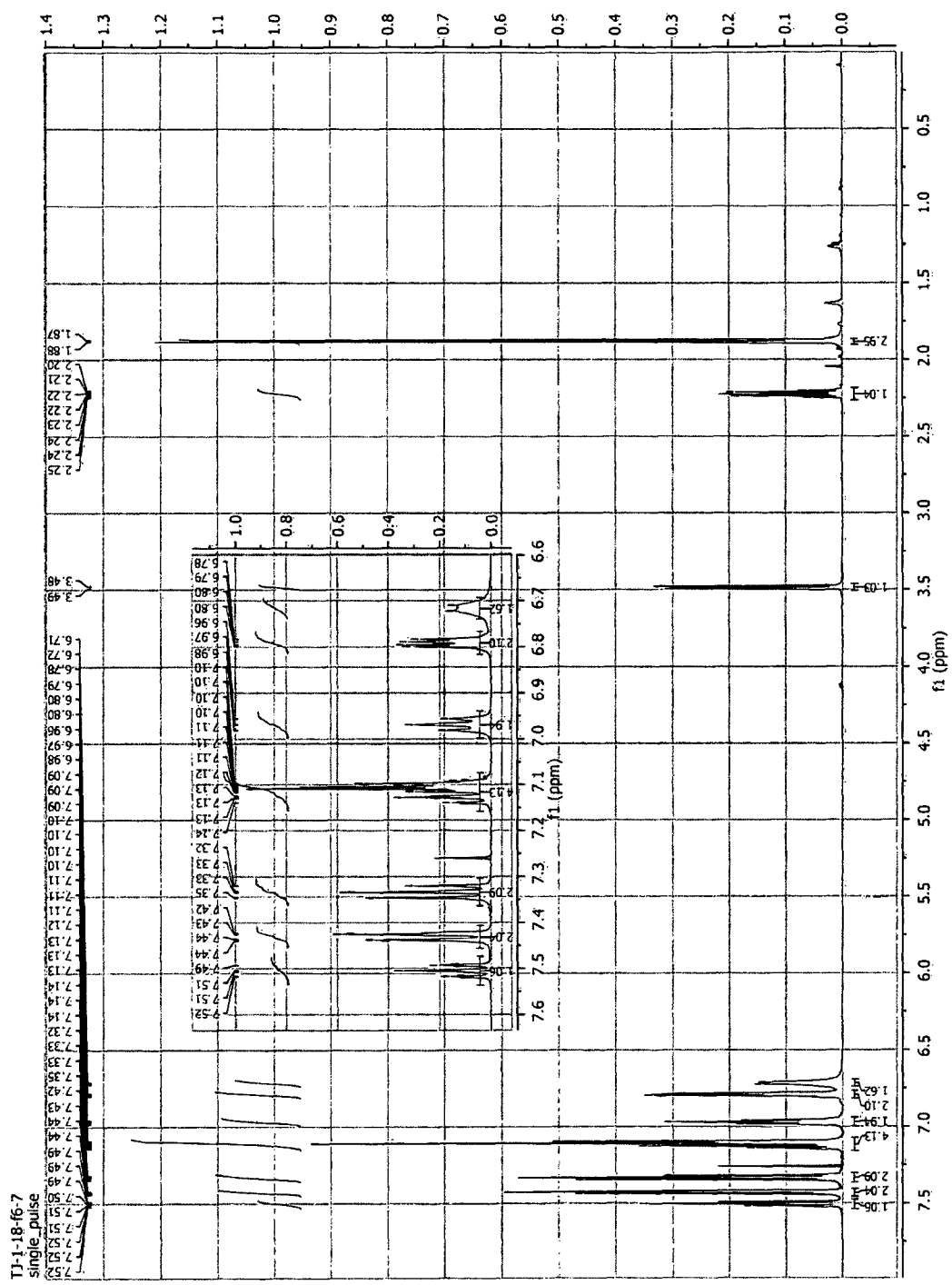
FIG. 9 illustrates $^1H$ NMR of Compound 2.

FIG. 9 illustrates $^1$H NMR (600 MHz, Chloroform-d) δ 7.51 (tt, J=7.3, 1.3 Hz, 1H), 7.43 (dd, J=8.5, 1.3 Hz, 2H), 7.36-7.30 (m, 2H), 7.16-7.07 (m, 4H), 6.97 (t, J=7.7 Hz. 2H). 6.79 (dd, J=6.9, 2.8 Hz, 2H), 6.72 (bd, J=7.6 Hz, 2H), 3.48 (d, J=7.8 Hz, 1H), 2.23 (dq, J=7.8, 6.5 Hz, 1H), 1.88 (d, J=6.5 Hz, 3H).

Figure 10:
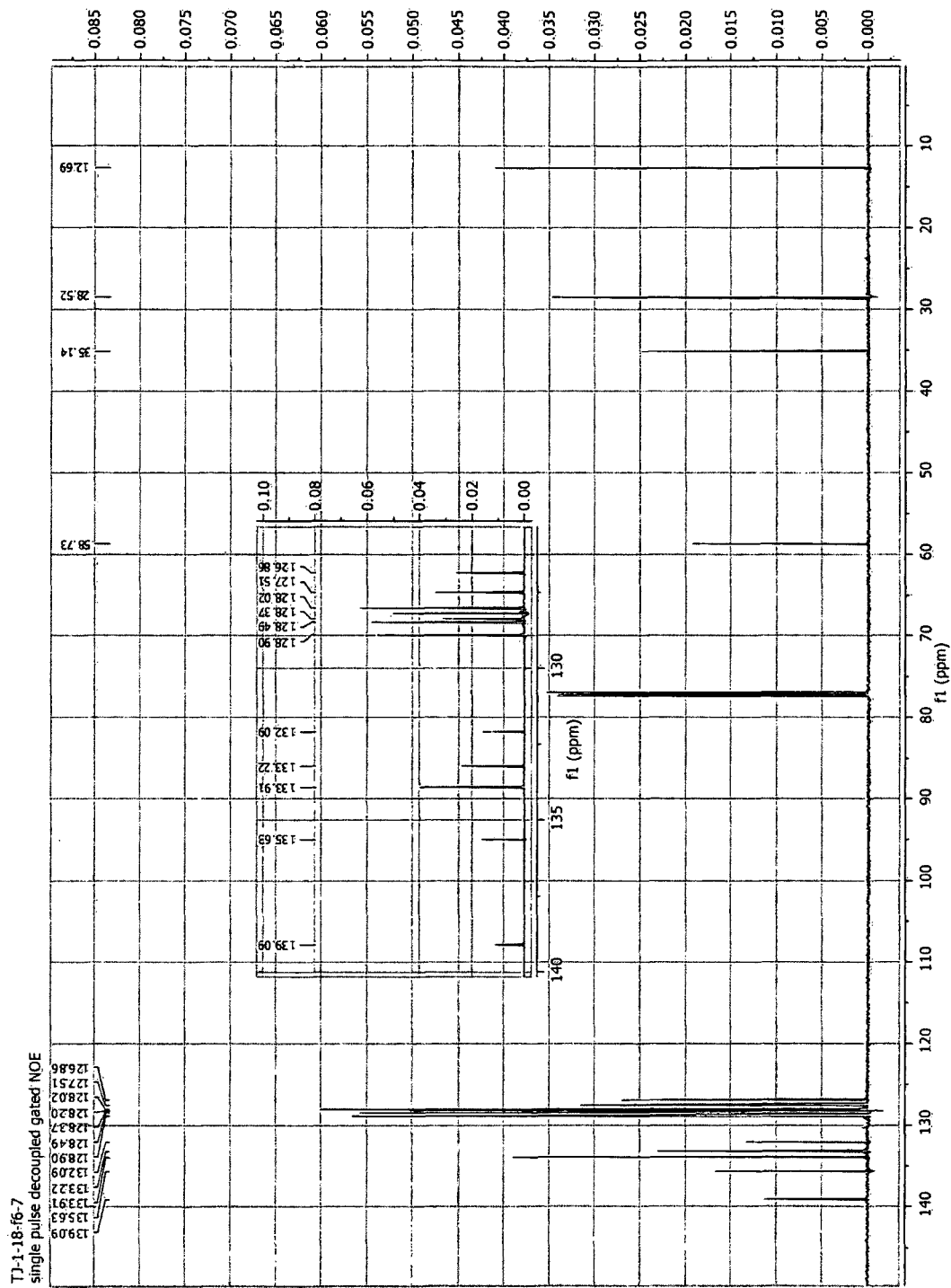
FIG. 10 illustrates $^{13}C$ NMR of Compound 2.
Figure 11:
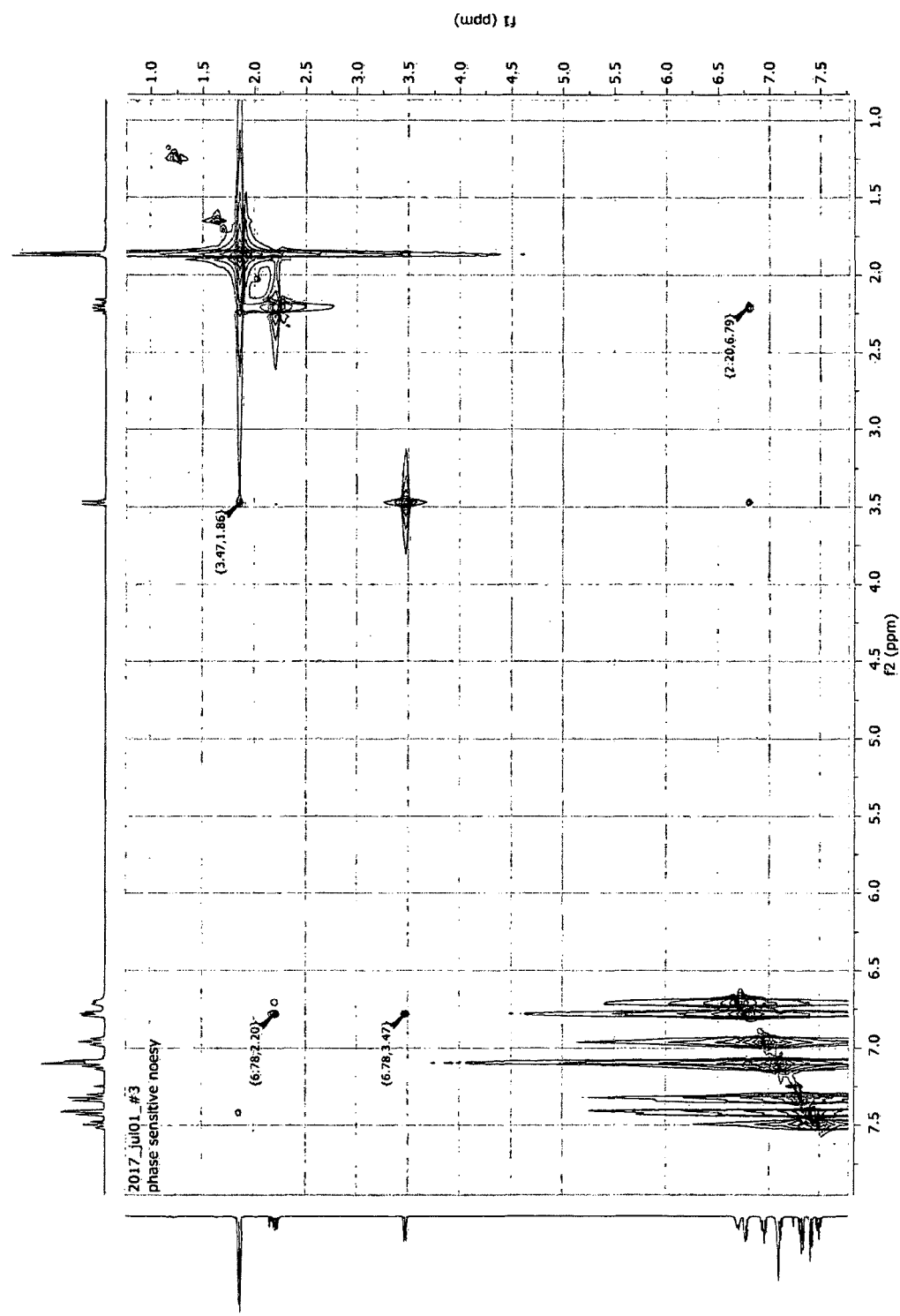
FIG. 11 illustrates NOESY of Compound 2.

FIG. 10 illustrates $^{13}$C NMR (151 MHz, Chloroform-d) δ 139.09, 135.63, 133.91, 133.22, 132.09, 128.90, 128.49, 128.37, 128.20, 128.02, 127.51, 126.86, 58.73, 35.14, 28.52, 12.69. FIG. 11 illustrates NOESY of Compound 2. HRMS: [M+H]+ Expected 349.1257; Obtained 349.1263

[Chem. 17]

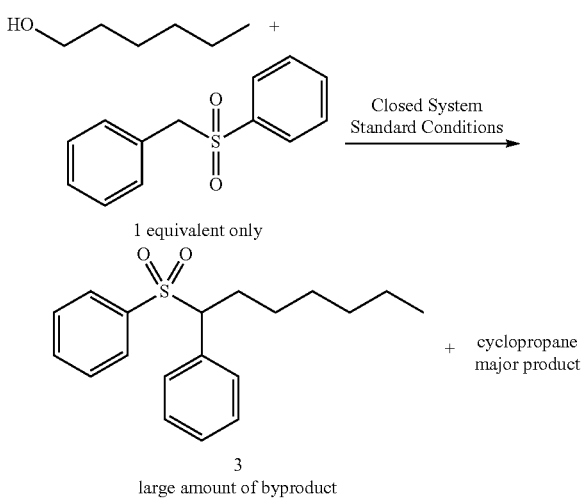

Physical state: white crystals

Since this is a byproduct in the reaction when only one equivalent of sulfone is used, the yield was not determined. It is slightly more polar than the cyclopropane and can be separated on the column at a slightly polar gradient (15% Et₂O to hexanes as opposed to 8% for the cyclopropane). The product contains a minor cyclopropane impurity (see doublets at ~3.45 ppm); despite the product being crystalline, it was very difficult to remove this impurity as the cyclopropane is a viscous liquid and its presence was taken into account when performing mechanistic experiments where it was tested as to whether this compound is an intermediate in the cyclopropanation reaction.

Figure 12:
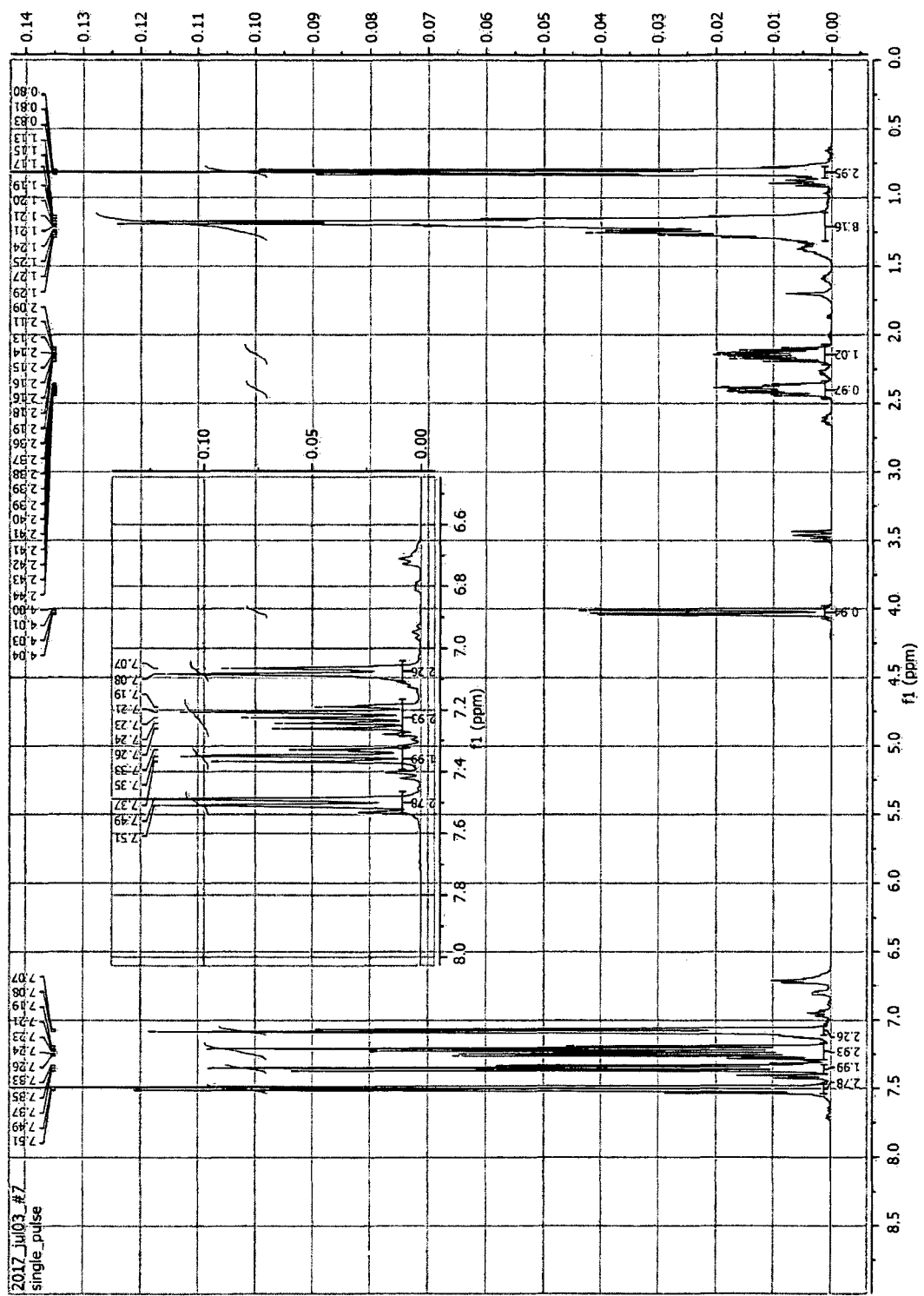
FIG. 12 illustrates $^1H$ NMR of Compound 3.

FIG. 12 illustrates ¹H NMR (400 MHz, Chloroform-d) δ 7.47-7.54 (m, 3H), 7.39-7.30 (m, 2H), 7.29-7.16 (m, 3H), 7.07 (d, J=7.0 Hz, 2H), 4.02 (dd, J=11.7, 3.6 Hz, 1H), 2.47-2.33 (m, 1H), 2.22-2.07 (m, 1H), 1.31-1.11 (m, 8H), 0.81 (t, J=6.9 Hz, 3H).

Figure 13:
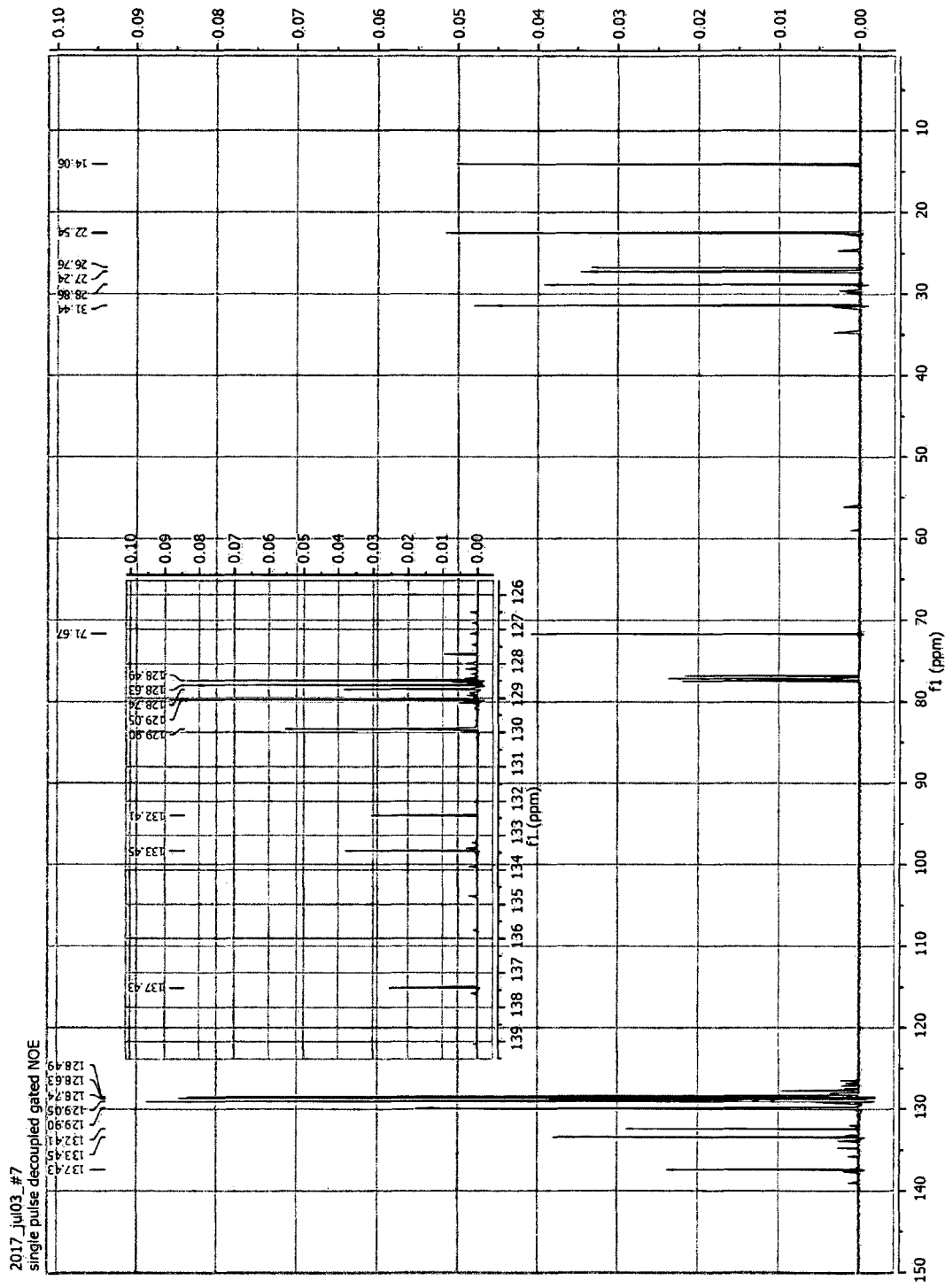
FIG. 13 illustrates $^{13}C$ NMR of Compound 3.

FIG. 13 illustrates ¹³C NMR (101 MHz, Chloroform-d) δ 137.43, 133.45, 132.41, 129.90, 129.05, 128.74, 128.63, 128.49, 71.67, 31.44, 28.86, 27.24, 26.76, 22.54, 14.06.

HRMS: [M+H]⁺ Expected 317.1570; Obtained 317.1574

[Chem. 18]

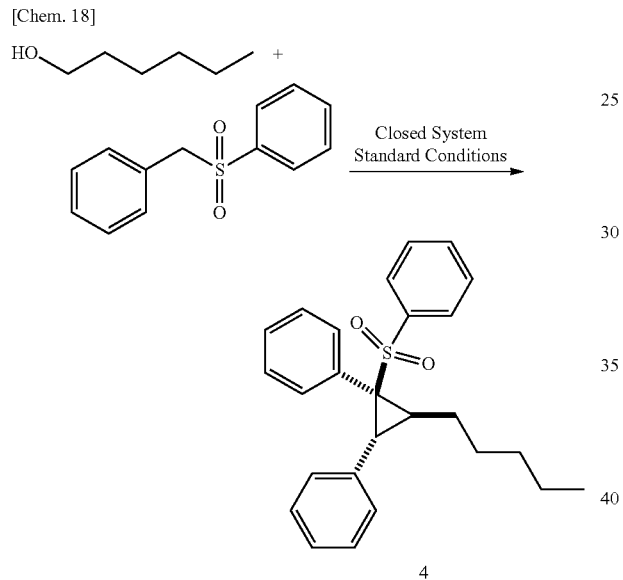

4

Physical state: colorless oil; isolated yield 64%

Isolated d. r. 3.6:1; Crude d. r. 3:1 The products are too close in polarity to separate cleanly by column chromatography. The major diastereomer is assigned as trans despite the large intensity of the J coupling, due to the similarity of the NMR spectrum in the aromatic region and cyclopropane region to compound 2, which was proven to be a trans compound by X-Ray crystallography and subsequent NMR of the crystals. The other diastereomer is likely cis, with the hexyl group facing away from the sulfone, based on its larger J coupling of ~11 Hz. It was decided that it would be too difficult to isolate the two diastereomers without significantly affecting the yield, thus the reported NMR data is only for the major diastereomer, with the NMR spectra showing a mixture of the two (see below). The close ratio of the diastereomers was convenient enough to use this compound as a model when testing the efficiency of different reaction conditions.

Figure 14:
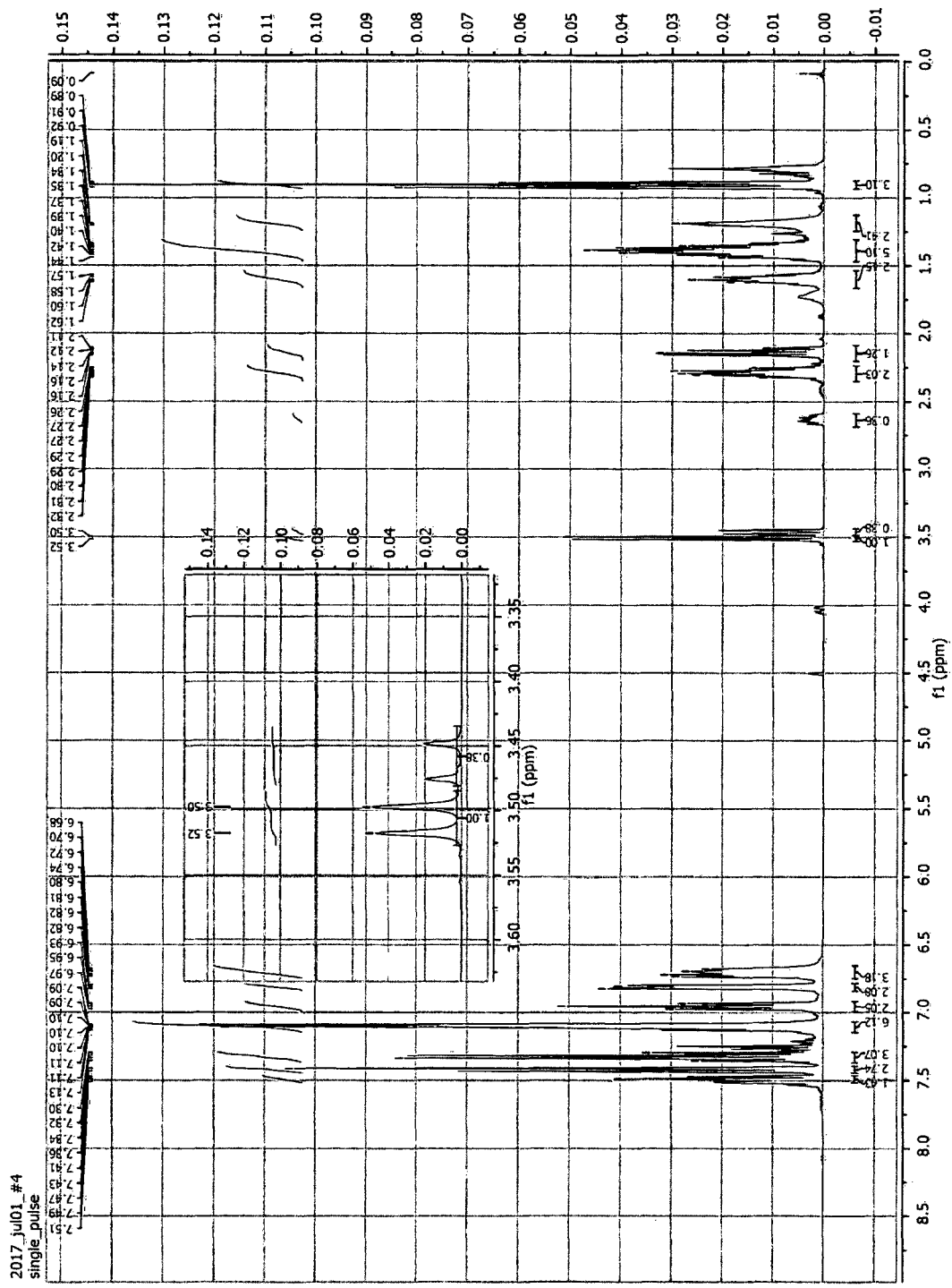
FIG. 14 illustrates $^1H$ NMR of Compound 4.

FIG. 14 illustrates ¹H NMR (400 MHz, Chloroform-d) δ 7.49 (t, J=7.4 Hz, 1H), 7.42 (d, J=7.2 Hz, 2H), 7.33 (q, J=8.0 Hz, 2H), 7.15-7.06 (m, 4H), 6.95 (t, J=7.7 Hz, 2H), 6.81 (dd, J=6.4, 3.2 Hz, 2H), 6.65-6.75 (m, 2H), 3.51 (d, J=8.1 Hz, 1H), 2.29 (ddt, J=11.7, 7.4, 3.9 Hz, 2H), 2.20-2.09 (m, 1H), 1.66-1.53 (m, 2H), 1.20-1.45 (m, 4H), 0.91 (t. J=7.1 Hz, 3H).

Figure 15:
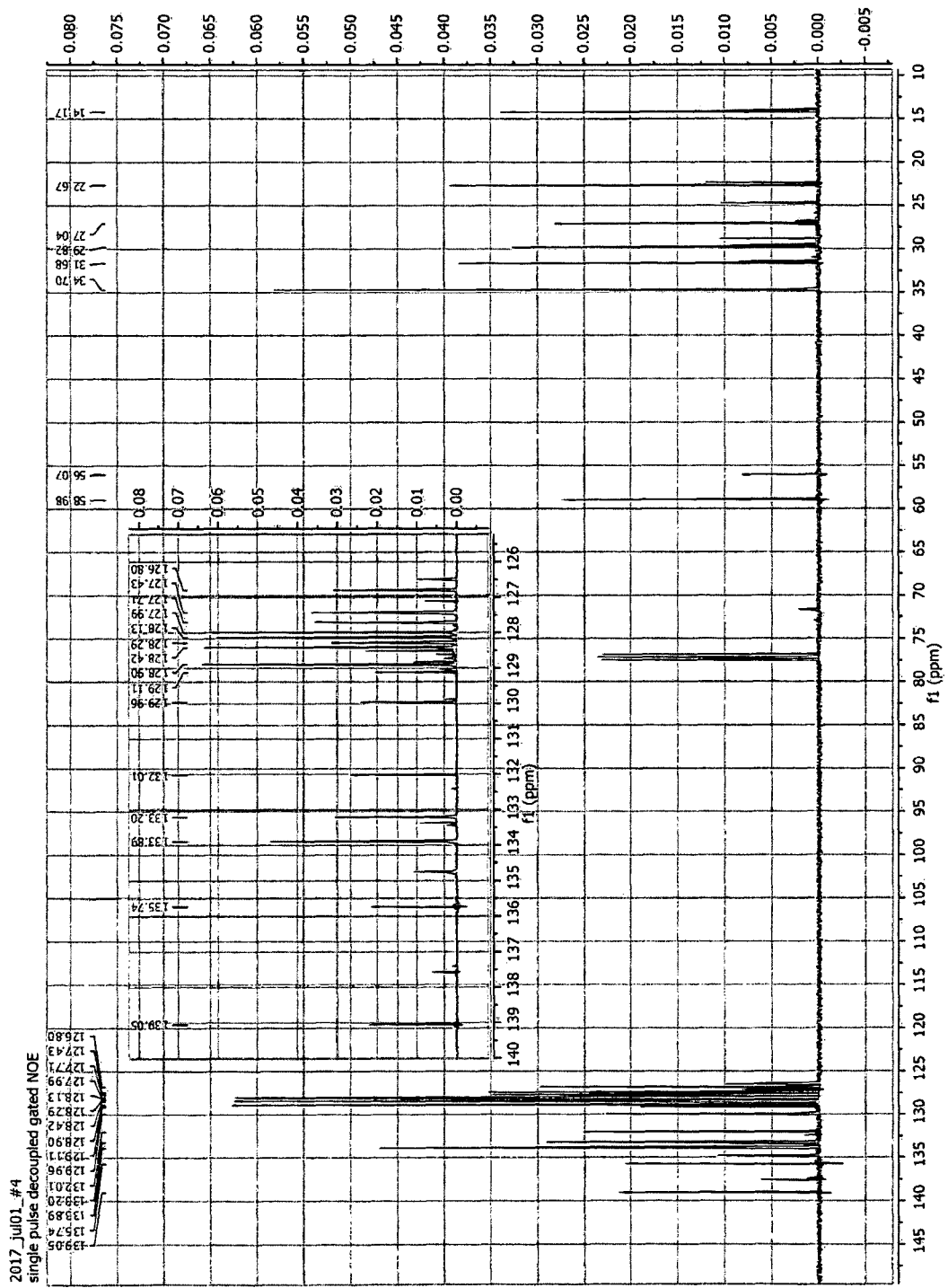
FIG. 15 illustrates $^{13}C$ NMR of Compound 4.

FIG. 15 illustrates ¹³C NMR (101 MHz, Chloroform-d) δ 139.05, 135.74, 133.89, 133.20, 132.01, 129.96, 129.11, 128.90, 128.42, 128.29, 128.13, 127.99, 127.71, 127.43, 126.80, 58.98, 56.07, 34.70, 31.68, 29.82, 27.04, 22.67, 14.17.

Figure 16:
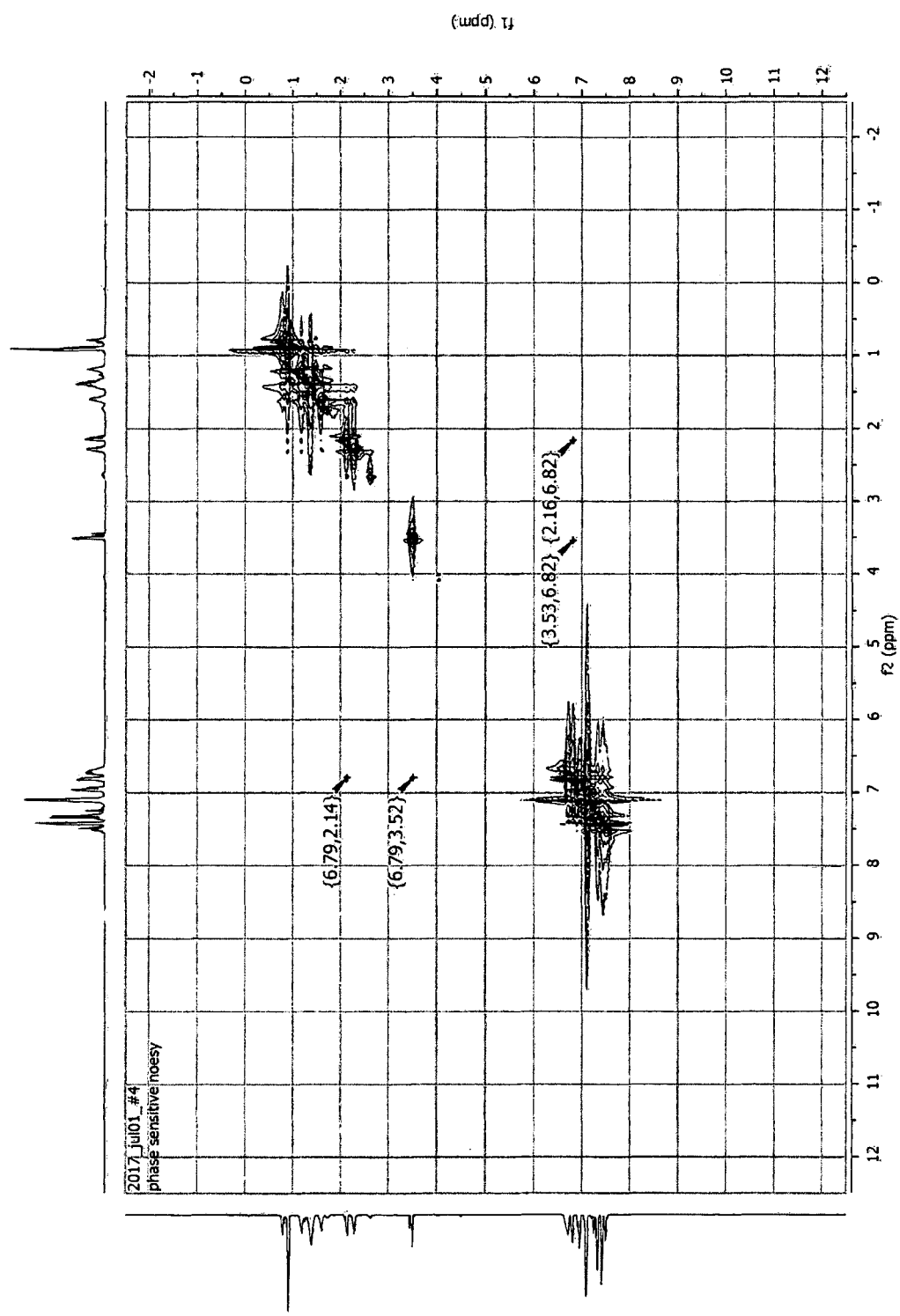
FIG. 16 illustrates NOESY of Compound 4.

FIG. 16 illustrates NOESY of Compound 4.

HRMS: [M+H]⁺ Expected 405.1883; Obtained 405.1889

[Chem. 19]

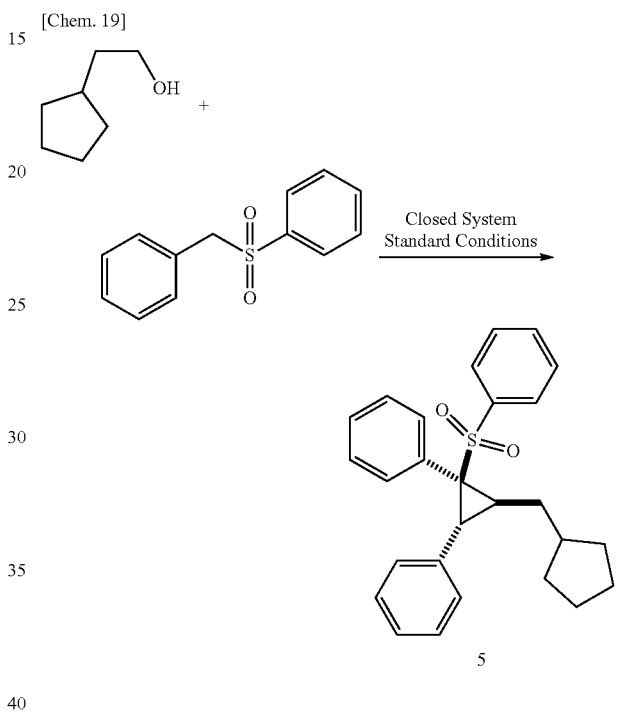

5

Physical state: colorless gel; yield 31%

Isolated d. r. 20:1; crude d. r. 20:1 Unlike the hexanol, this reaction was very stereospecific and the crude yield was ~70%, despite the low isolated yield. To get larger yields, a slower solvent gradient for the column will probably be required, as well as an Et₂O/hexane system as opposed to EtOAc/hexane. Assignment is made as trans despite the large~8 Hz J coupling of the ring protons due to similarity with compound 2, which is determined as trans by crystallography. The minor diastereometer has a J coupling of ~11 Hz and is likely cis.

Figure 17:
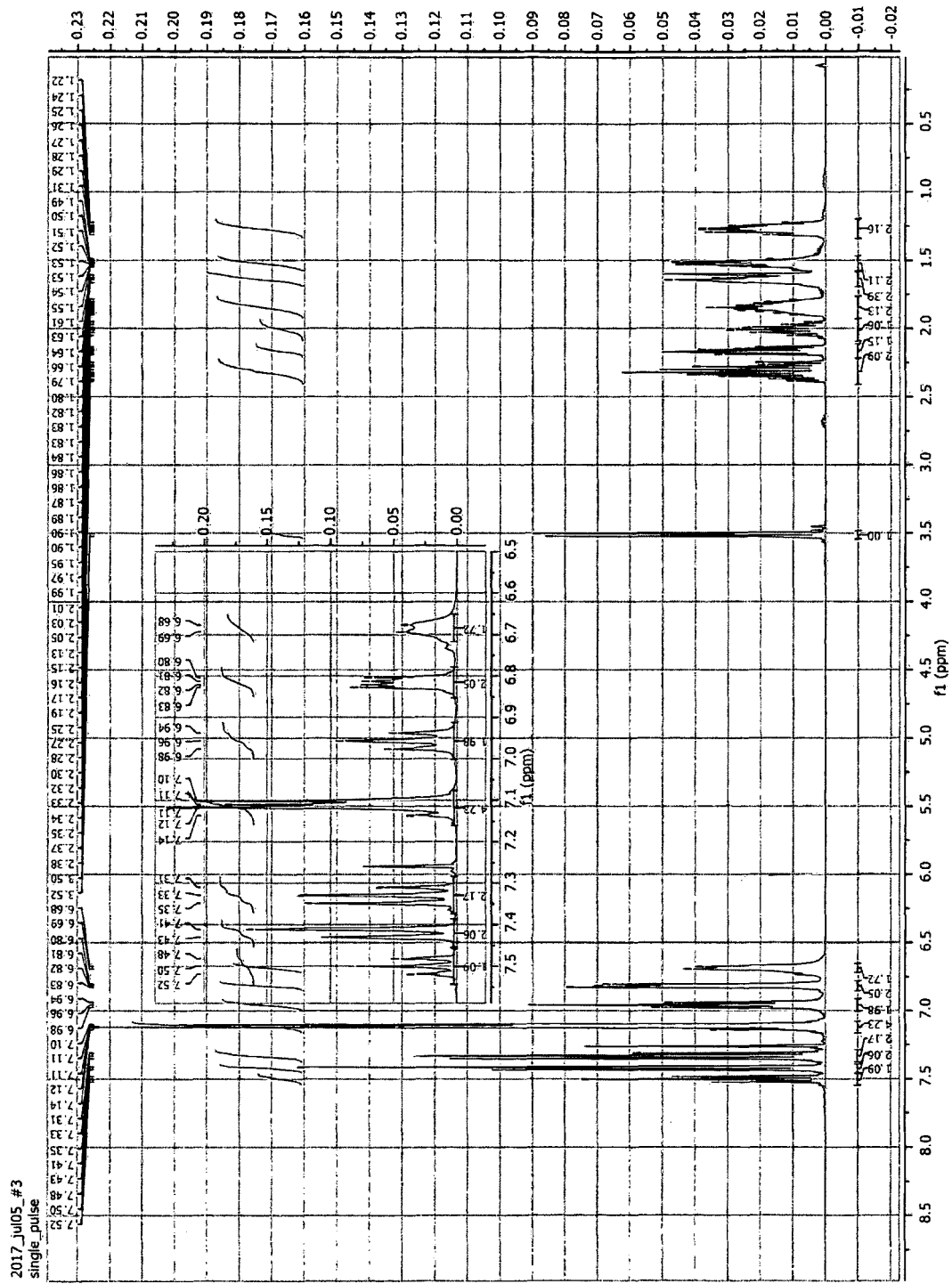
FIG. 17 illustrates ¹H NMR of Compound 5.

FIG. 17 illustrates ¹H NMR (400 MHz, Chloroform-d) δ 7.50 (t, J=7.4 Hz, 1H), 7.42 (d, J=7.4 Hz, 2H), 7.37-7.28 (m, 2H), 7.16-7.08 (m, 4H), 6.96 (t, J=7.8 Hz, 2H), 6.78-6.83 (m, 2H), 6.68 (bd, J=6.4 Hz, 2H), 3.51 (d, J=8.1 Hz, 1H), 2.41-2.22 (m, 2H), 2.21-2.11 (m, 1H), 2.01 (hept, J=7.7 Hz, 1H), 1.93-1.76 (m, 2H), 1.60-1.68 (m, 2H), 1.47-1.58 (m, 2H), 1.34-1.20 (m, 2H).

Figure 18:
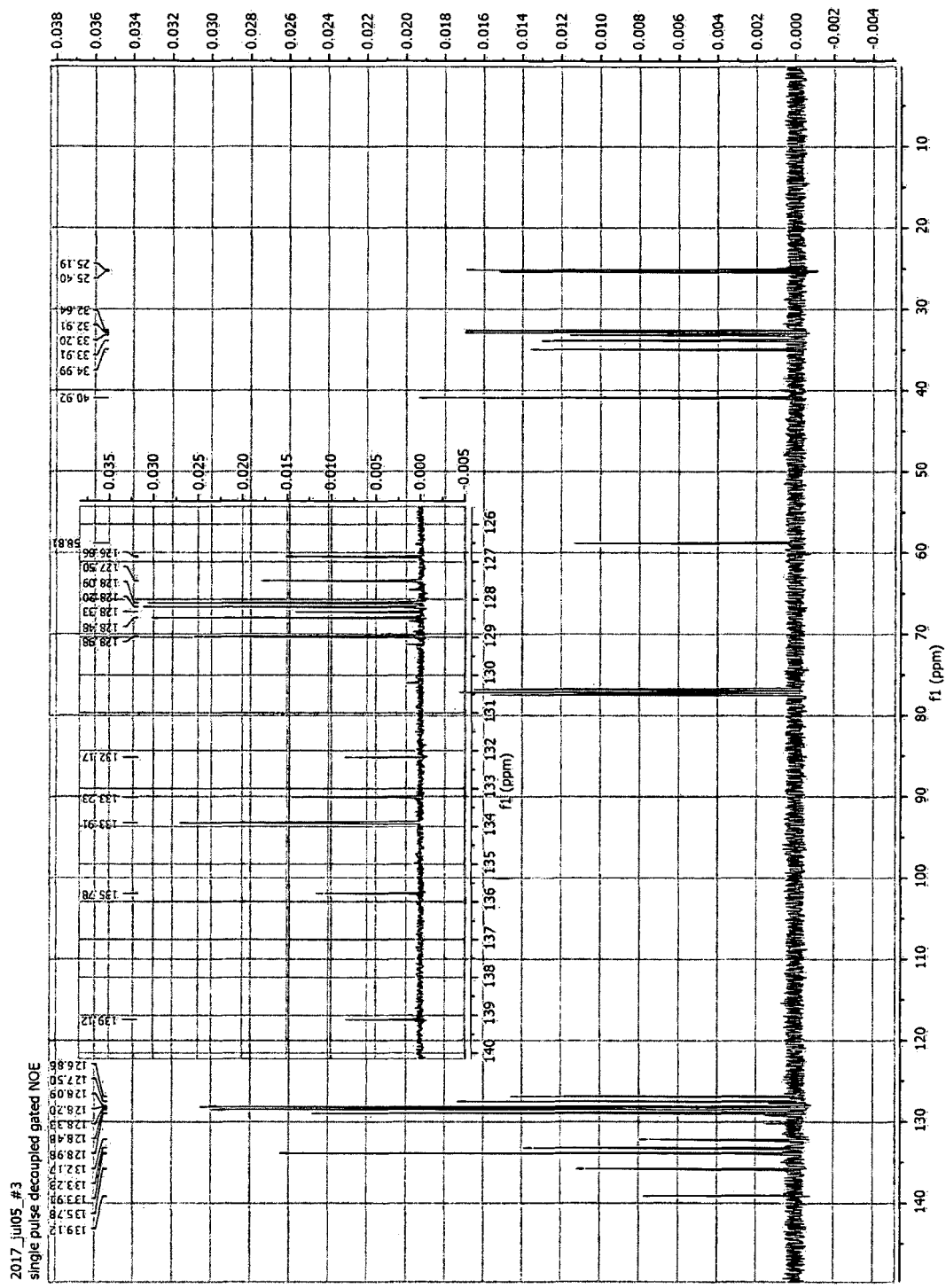
FIG. 18 illustrates ¹³C NMR of Compound 5.

FIG. 18 illustrates ¹³C NMR (101 MHz, Chloroform-d) δ 139.12, 135.78, 133.91, 133.23, 132.17, 128.98, 128.48, 128.33, 128.20, 128.09, 127.50, 126.86, 58.81, 40.92, 34.99, 33.91, 33.20, 32.91, 32.64, 25.40, 25.19.

Figure 19:
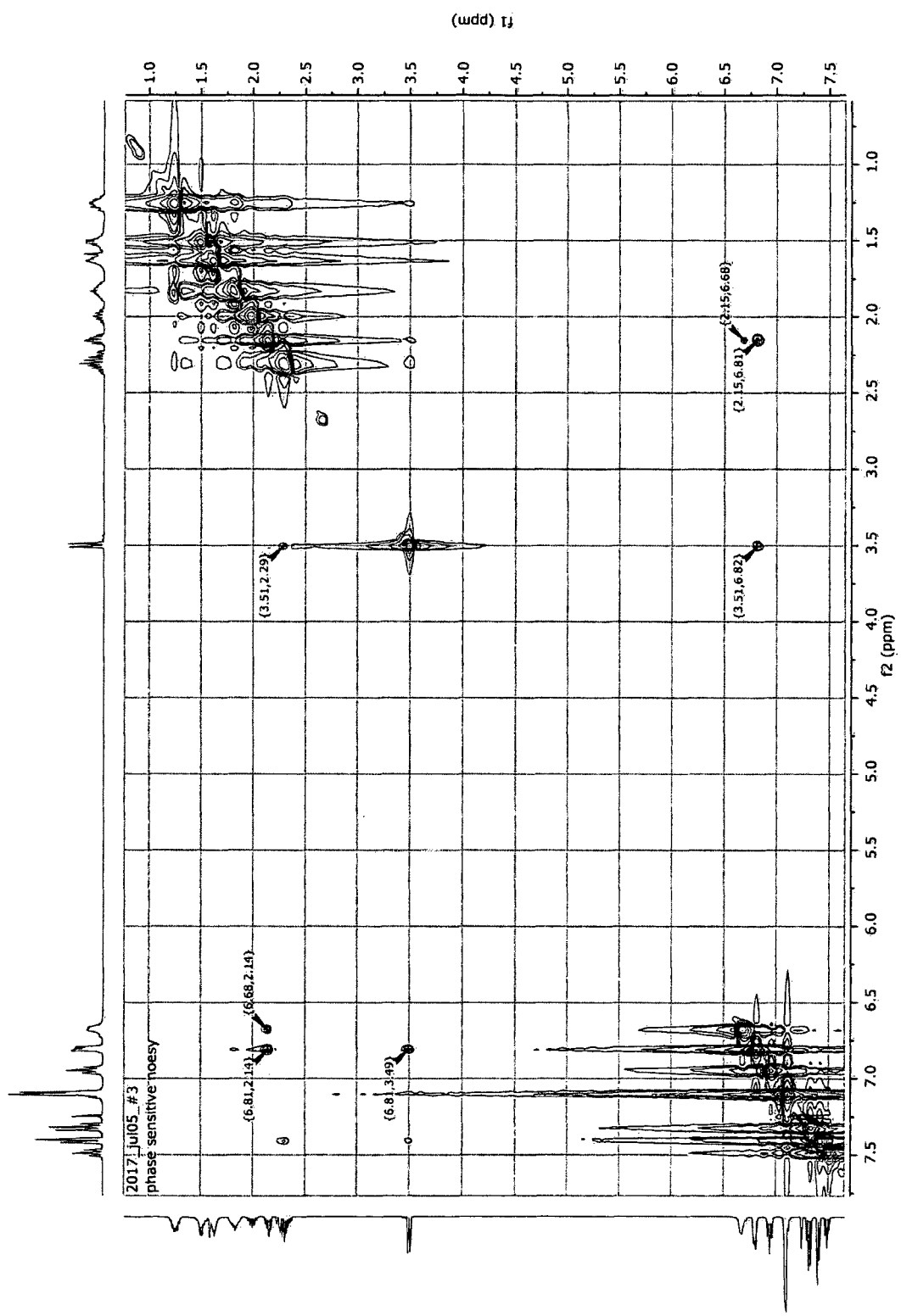
FIG. 19 illustrates NOESY of Compound 5.

FIG. 19 illustrates NOESY of Compound 5.

HRMS: [M+H]⁺ Expected 417.1883; Obtained 417.1887

[Chem. 20]

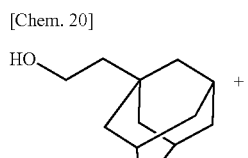
+

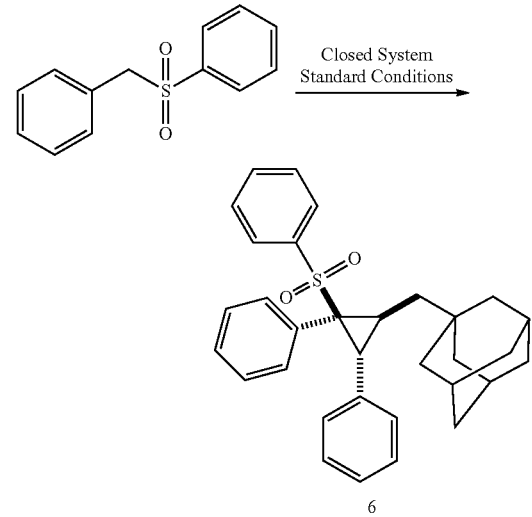

6

Physical state: Colourless crystal; isolated yield 10%

Significant quantities of what appears to be linear byproduct are obtained. Due to similar polarity, it is difficult to separate the product by column chromatography. However, with a gradient of Et₂O to hexanes, starting at 0% ether and increasing by 2% to 8%, it is possible to isolate cyclopropane from the byproduct containing fractions. Unlike the other cyclopropanes made from benzyl phenyl sulfone (2, 4, 5, etc. . . . ) the cyclopropane proton coupling of J=6.4 Hz is smaller than 8 Hz observed for those species and could be due to steric factors introduced by the adamantly group. d. r. 99:1

Figure 20:
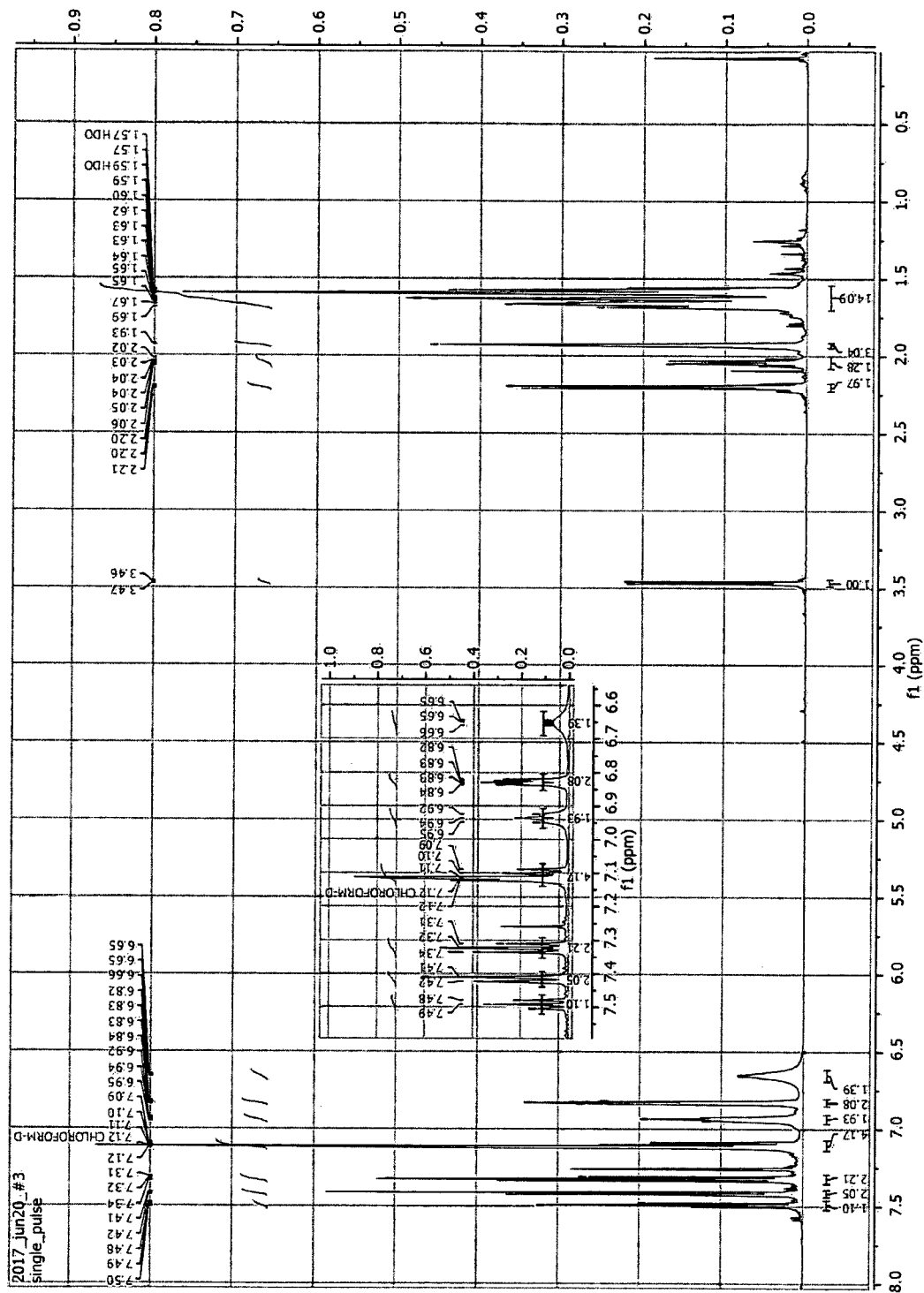
FIG. 20 illustrates ¹H NMR of Compound 6.

FIG. 20 illustrates $^1$H NMR (600 MHz, Chloroform-d) δ 7.49 (t, J=7.6 Hz, 1H), 7.42 (d, J=7.6 Hz, 2H), 7.32 (t, J=7.8 Hz, 2H), 7.14-7.07 (m, 3H), 6.94 (t, J=7.5 Hz, 2H), 6.83 (dd, J=6.5, 3.1 Hz, 2H), 6.68-6.63 (m, 2H), 6.65 (bs, 1H), 3.47 (d, J=6.4 Hz, 1H), 2.23-2.18 (m, 2H), 2.04 (m, 1H), 1.93 (s, 3H), 1.70-1.56 (m, 12H).

Figure 21:
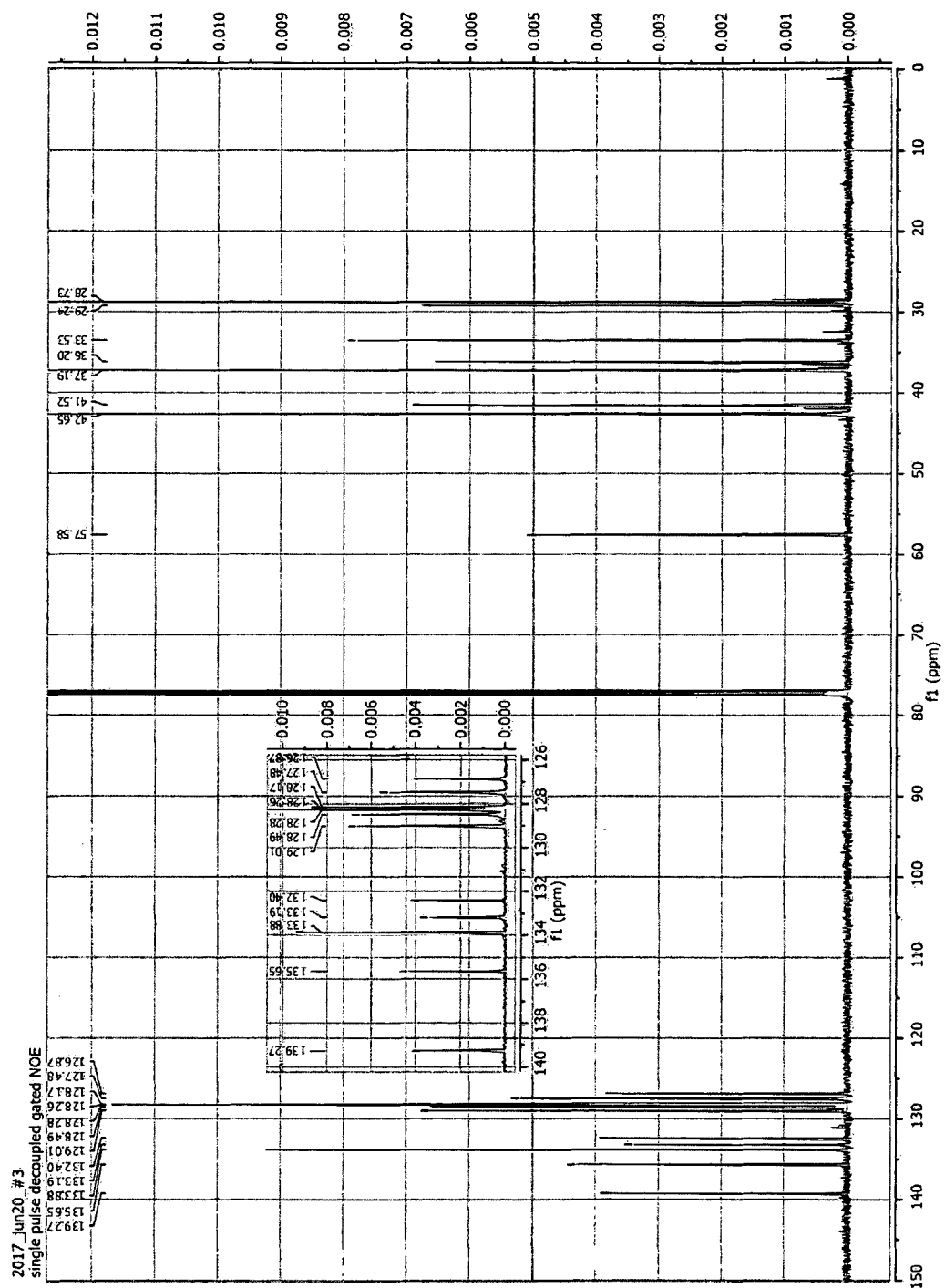
FIG. 21 illustrates ¹³C NMR of Compound 6.

FIG. 21 illustrates $^{13}$C NMR (151 MHz, Chloroform-d) δ 139.27, 135.65, 133.88, 133.19, 132.40, 129.01, 128.49, 128.28, 128.26, 128.17, 127.48, 126.87, 57.58, 42.65, 41.52, 37.19, 36.20, 33.53, 29.24, 28.73.

Figure 22:
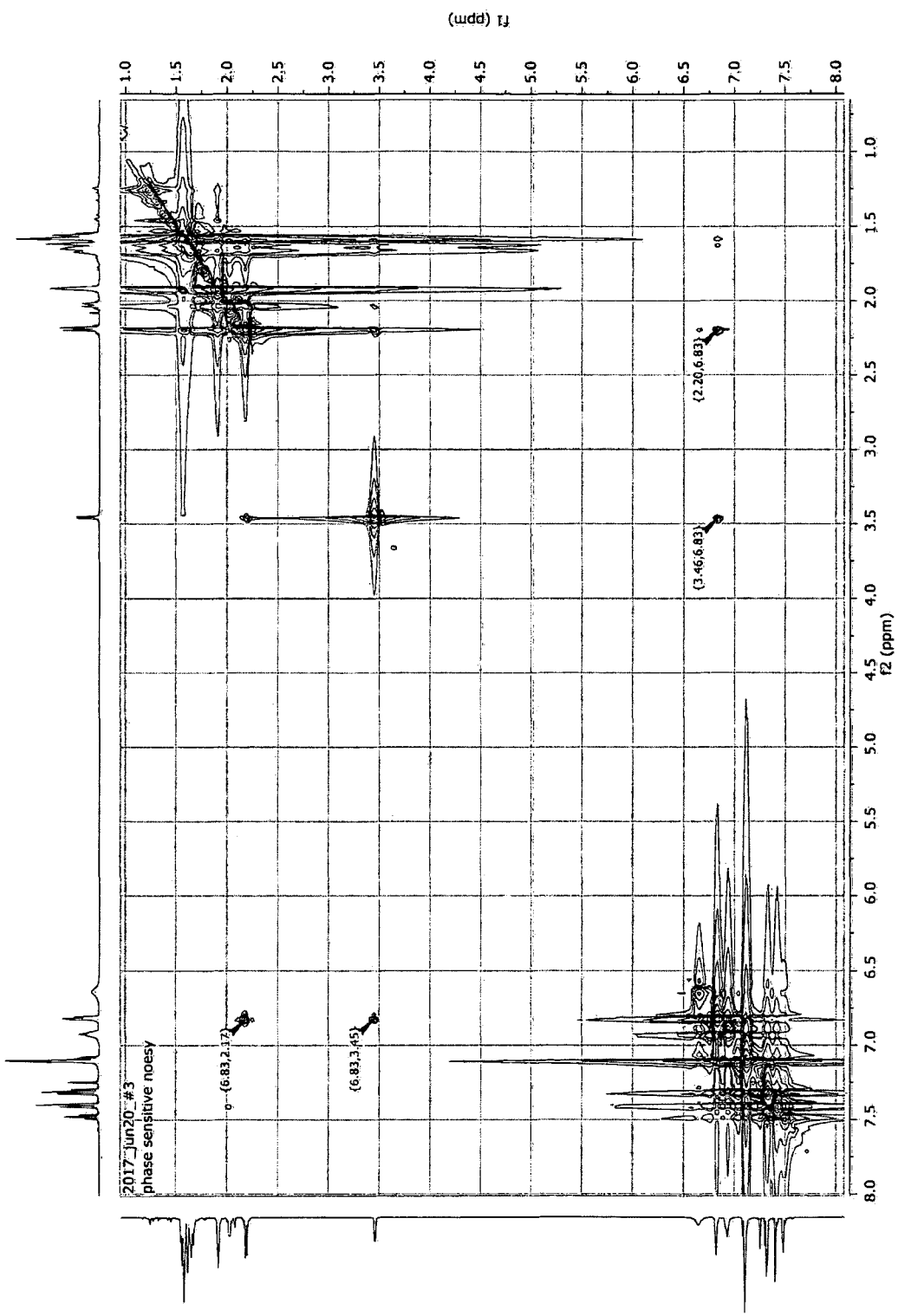
FIG. 22 illustrates NOESY of Compound 6.

FIG. 22 illustrates NOESY of Compound 6.

HRMS: [M+H]⁺ Expected 483.2352; Obtained 483.2356

[Chem. 20]

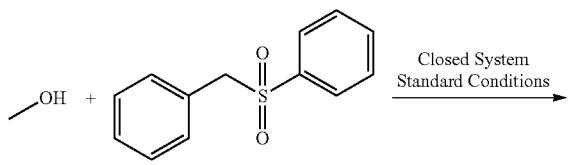

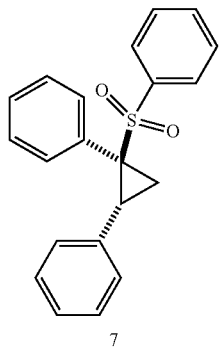

7

Physical state: Colorless crystal; isolated yield 41%

Crude d. r. 9:1; Isolated d. r. 15:1. Interestingly, the coupling of benzylic proton can be observed in relation both to the cis (J=10.0 Hz) and the trans (J=7.2 Hz) protons of the unsubstituted ring carbon. The trans coupling is elevated significantly above accepted literature values for trans coupling in cyclopropanes, although it is slightly less than the −8 Hz found in other trans compounds (2, 4, 5). This compound was synthesized earlier and reported in the literature, with the NMR spectrum corresponding to the published one; however, the J couplings were not reported.[53]

Figure 23:
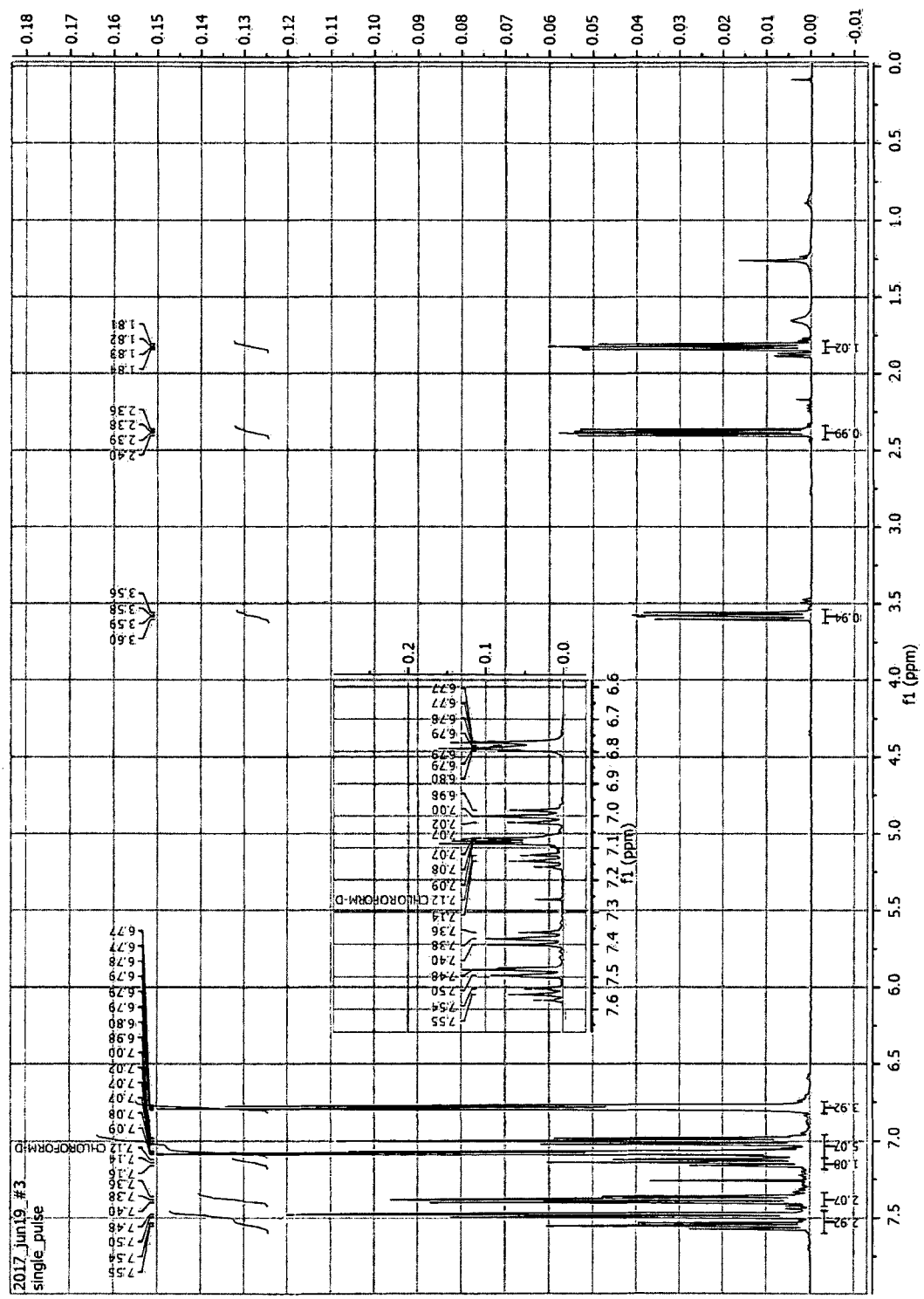
FIG. 23 illustrates ¹H NMR of Compound 7.

FIG. 23 illustrates $^1$H NMR (400 MHz, Chloroform-d) δ 7.55 (t, J=7.4 Hz, 1H), 7.49 (d, J=7.1 Hz, 2H), 7.43-7.34 (m, 2H), 7.15 (d, J=7.4 Hz, 1H), 7.11-6.96 (m, 5H), 6.82-6.74 (m, 4H), 3.58 (dd, J=10.0, 7.2 Hz, 1H), 2.38 (dd, J=10.0, 5.8 Hz, 1H), 1.83 (dd, J=7.2, 5.8 Hz, 1H).

Figure 24:
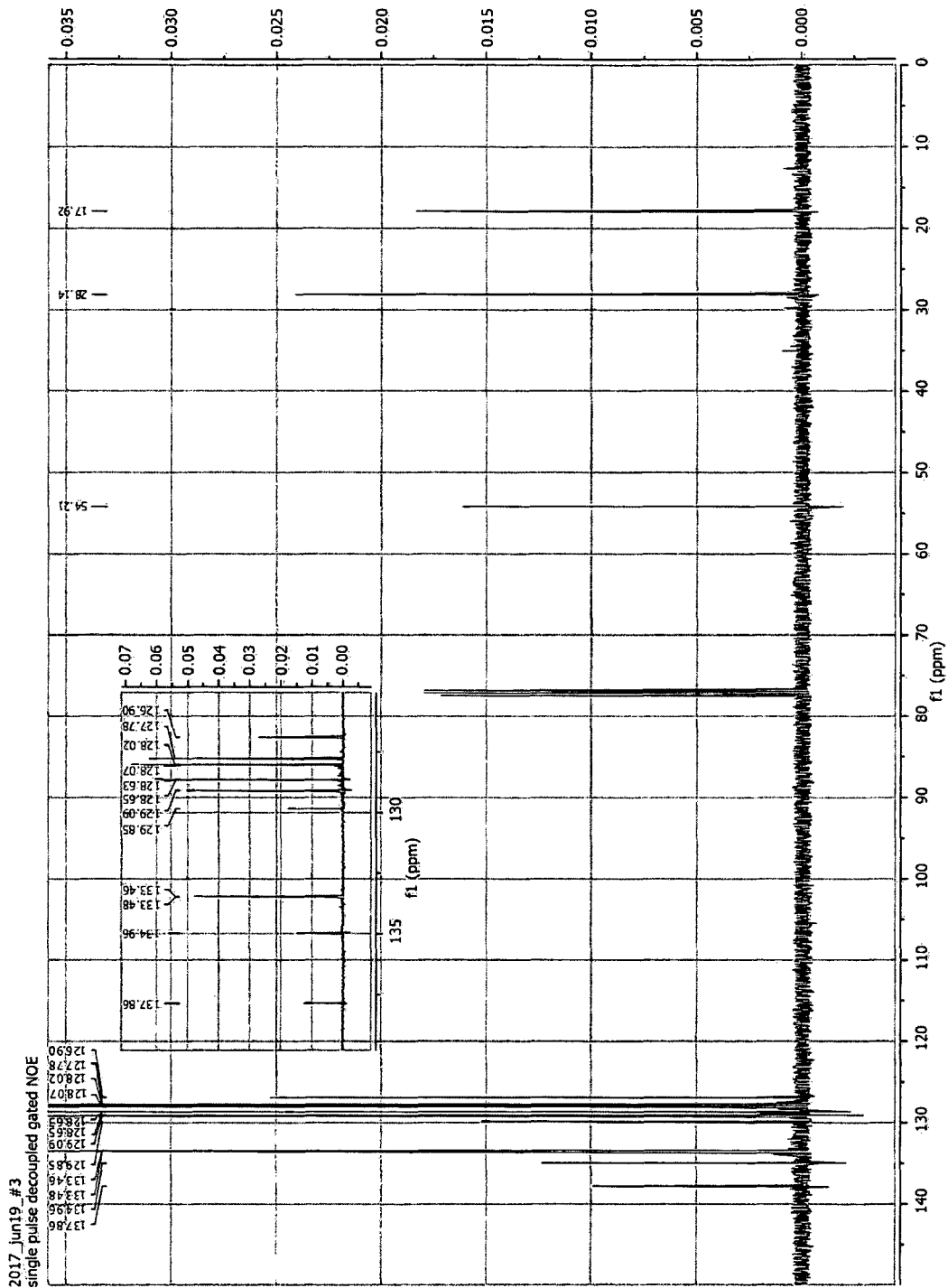
FIG. 24 illustrates ¹³C NMR of Compound 7.

FIG. 24 illustrates $^{13}$C NMR (101 MHz, Chloroform-d) δ 137.86, 134.96, 133.48, 133.46, 129.85, 129.09, 128.65, 128.63, 128.07, 128.02, 127.78, 126.90, 54.21, 28.14, 17.92.

Figure 25:
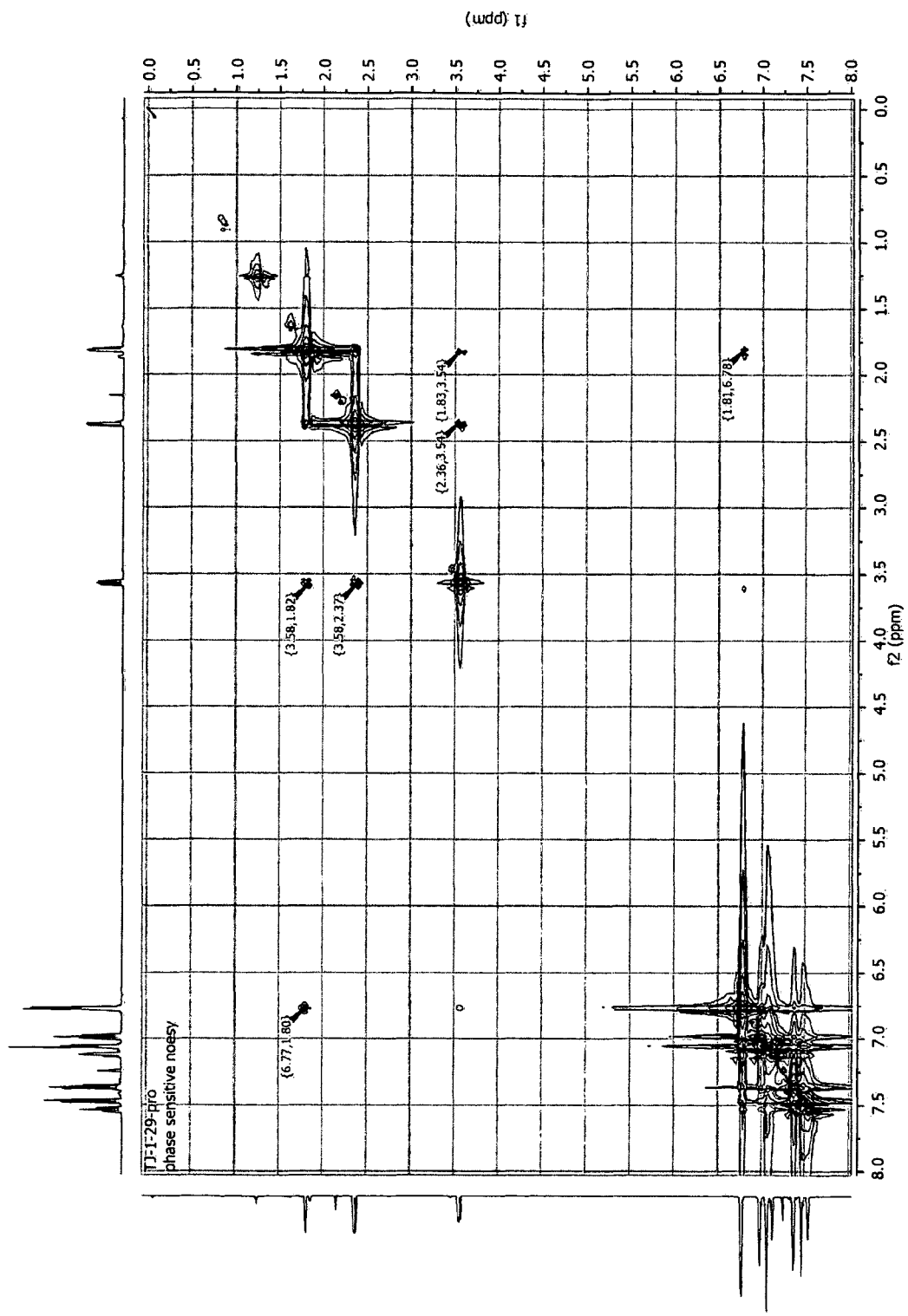
FIG. 25 illustrates NOESY of Compound 7.

FIG. 25 illustrates NOESY of Compound 7.

HRMS: [M+H]⁺ Expected 335.1100; Obtained 335.1108

[Chem. 22]

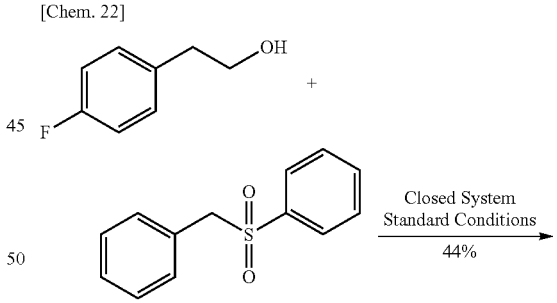

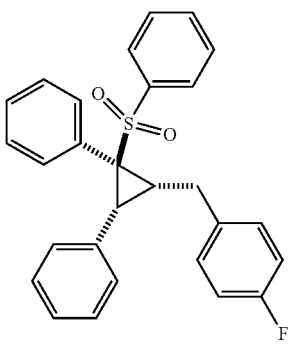

8

Physical state: White powder (can crystallize by slow hexane evaporation); isolated yield 44%

Isolated d. r. 50:1; Crude d. r. 3.4:1

Figure 26:
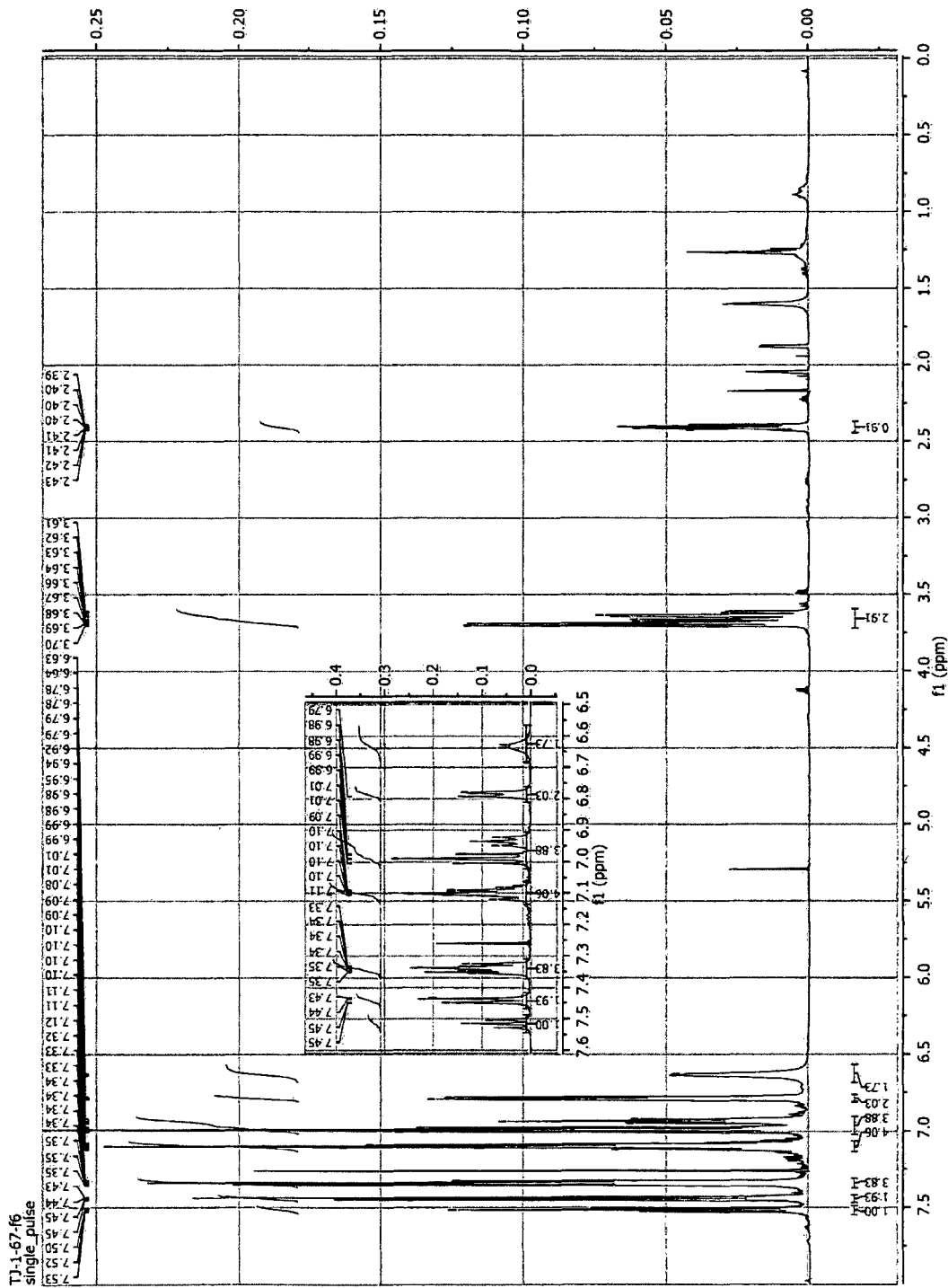
FIG. 26 illustrates ¹H NMR of Compound 8.

FIG. 26 illustrates $^1$H NMR (600 MHz, Chloroform-d) δ 7.52 (t, J=7.4 Hz, 1H), 7.44 (dd, J=8.4, 1.3 Hz, 2H), 7.37-7.31 (m, 4H), 7.14-7.06 (m, 4H), 6.99 (t, J=8.8 Hz, 2H), 6.94 (t, J=7.8 Hz, 2H), 6.79 (dd, J=7.6, 2.0 Hz, 2H), 6.55-6.67 (bd, 2H), 3.72-3.59 (m, 3H), 2.41 (ddd, J=8.7, 8.1, 5.6 Hz, 1H).

Figure 27:
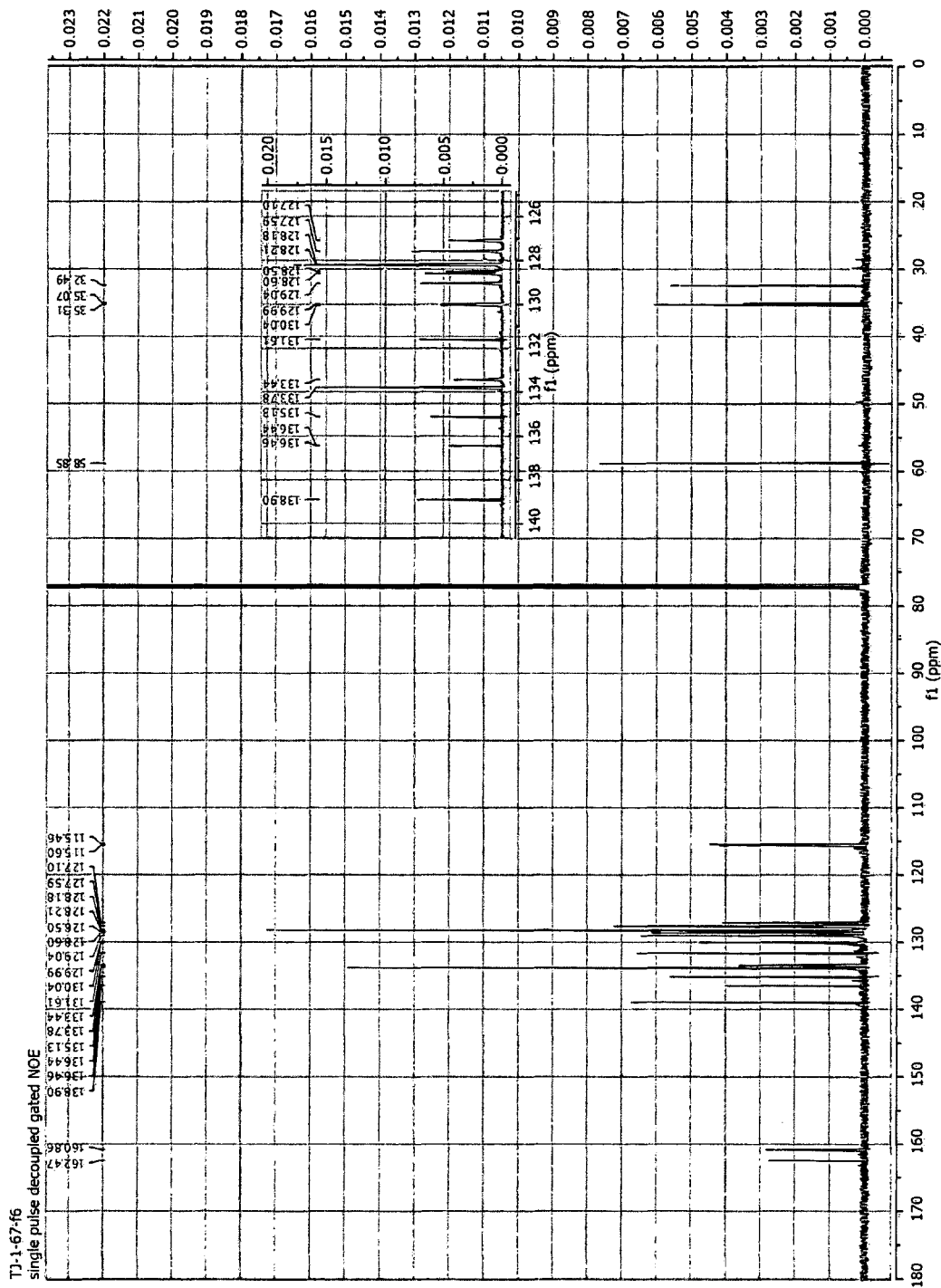
FIG. 27 illustrates ¹³C NMR of Compound 8.

FIG. 27 illustrates $^{13}$C NMR (151 MHz, Chloroform-d) δ 161.67 (d, $J_{CF}$=244.2 Hz), 138.90, 136.45 (d, $J_{CF}$=2.9 Hz), 135.13, 133.78, 133.44, 131.61, 130.01 (d, $J_{CF}$=7.9 Hz), 129.04, 128.60, 128.50, 128.21, 128.18, 127.59, 127.10, 115.53 (d, $J_{CF}$=21.3 Hz), 58.85, 35.31, 35.07, 32.49.

Figure 28:
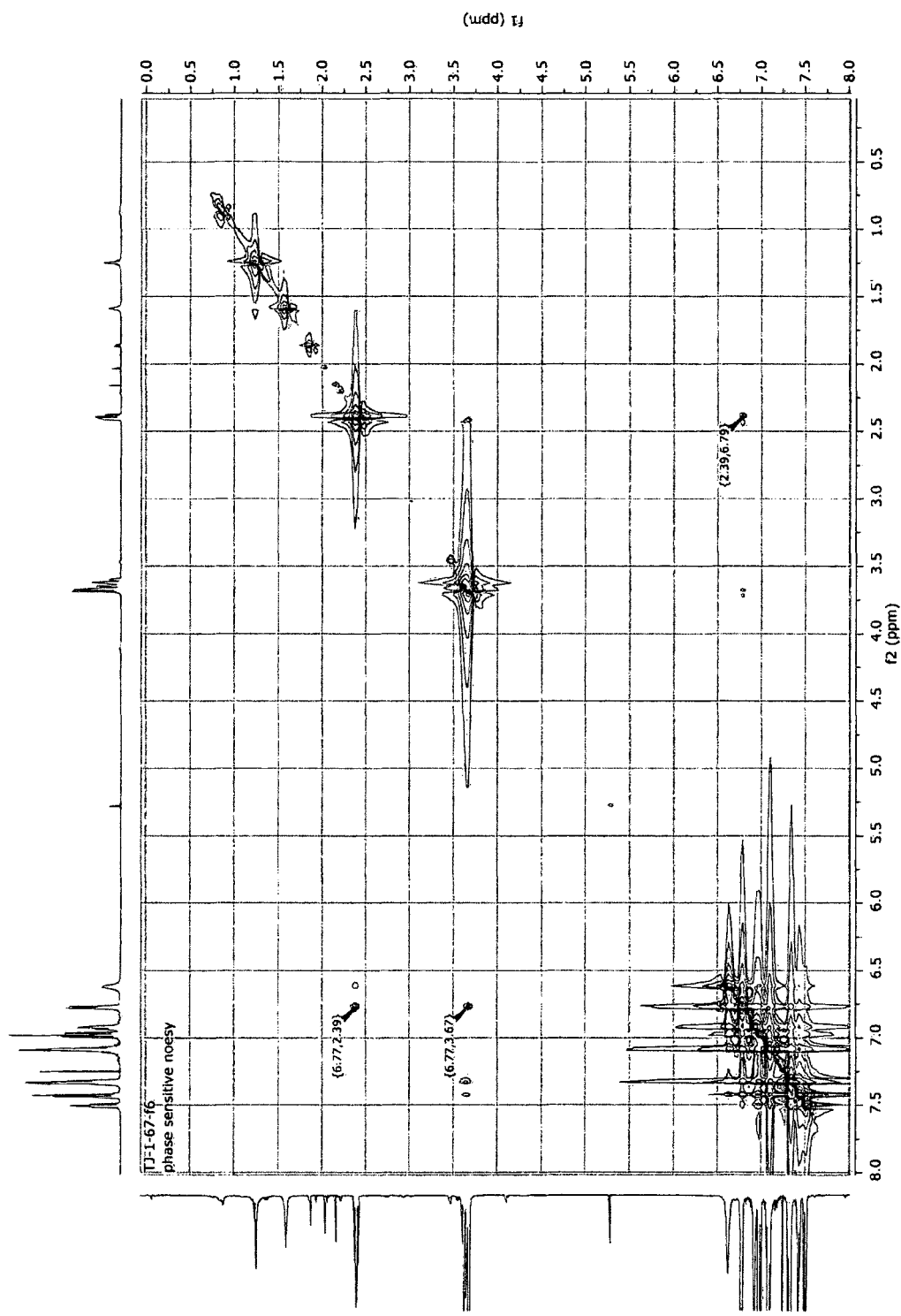
FIG. 28 illustrates NOESY of Compound 8.

FIG. 28 illustrates NOESY of Compound 8.

Figure 29:
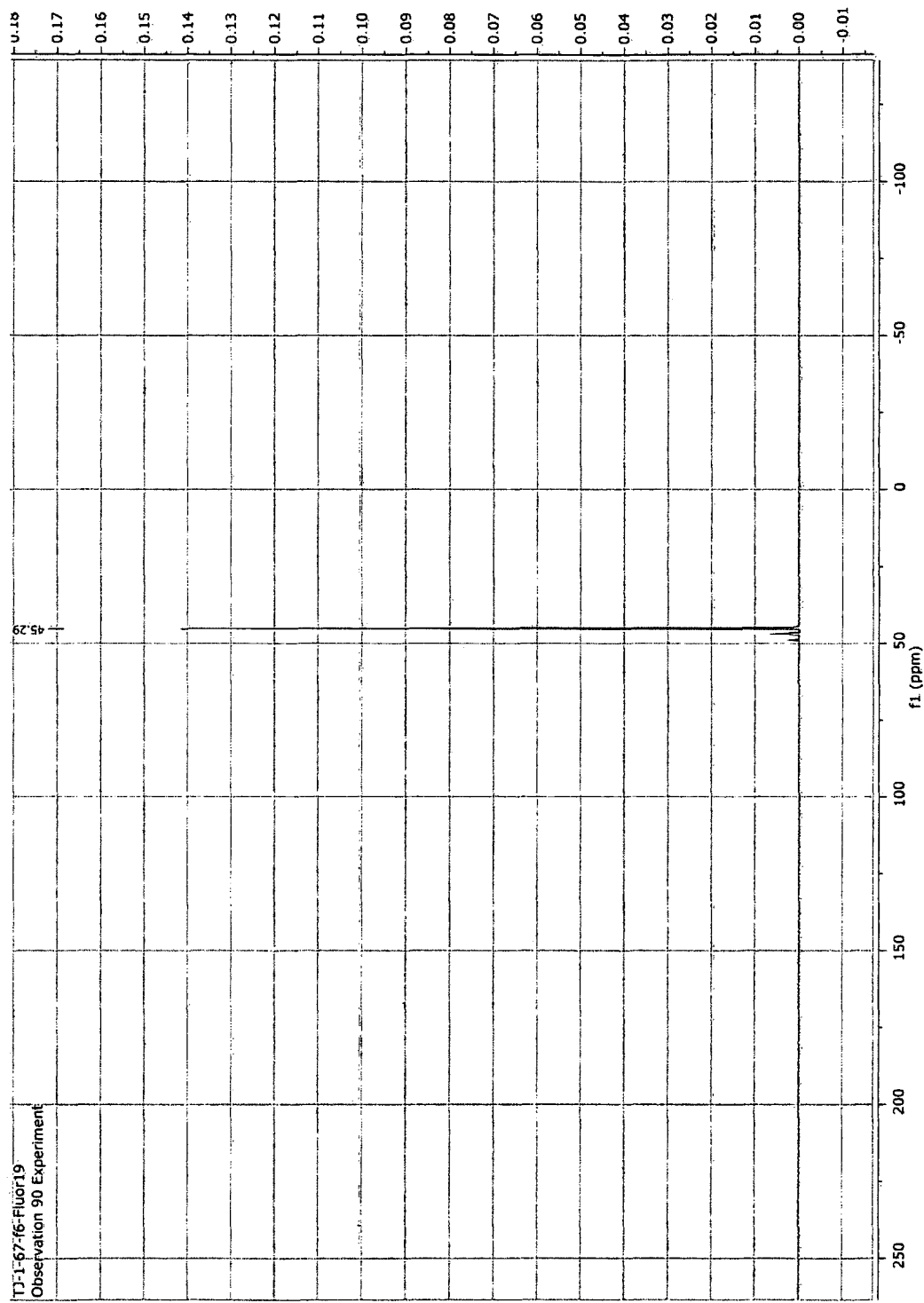
FIG. 29 illustrates ¹⁹F NMR of Compound 8.

FIG. 29 illustrates $^{19}$F NMR (376 MHz, CHLOROFORM-D) δ 45.3.

HRMS: [M+H]$^+$ Expected 443.1476; Obtained 443.1478

[Chem. 23]

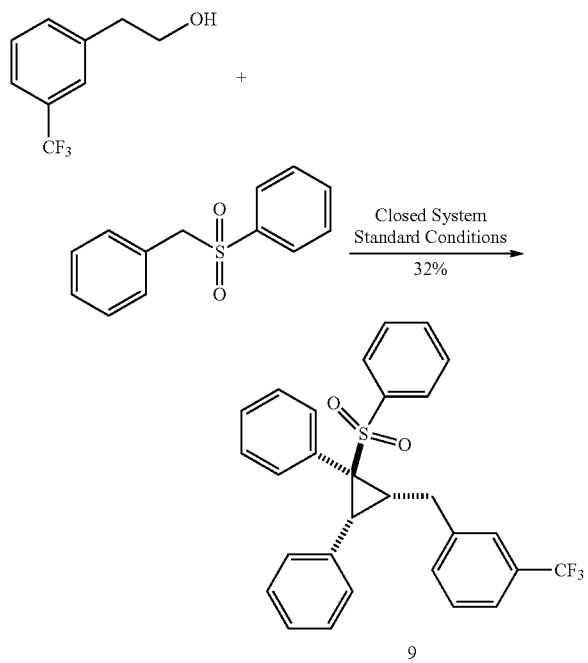

9

Physical state: White powder; isolated yield 32%

Isolated d. r. 18:1:1 crude d. r. 5.7:1

Figure 30:
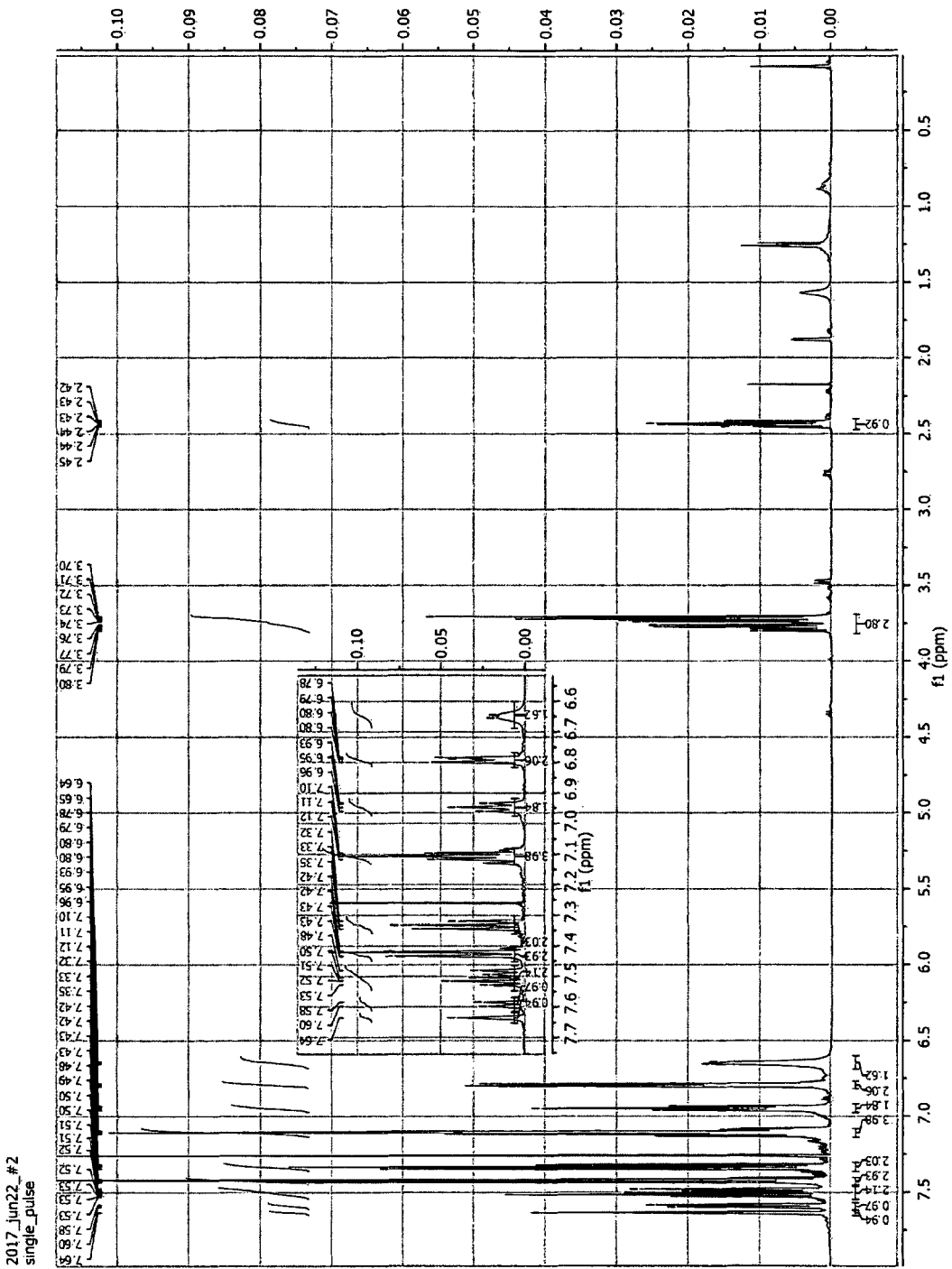
FIG. 30 illustrates ¹H NMR of Compound 9.

FIG. 30 illustrates $^1$H NMR (600 MHz, Chloroform-d) δ 7.64 (s, 1H), 7.59 (d, J=7.7 Hz, 1H), 7.55-7.46 (m, 2H), 7.43 (dd, J=8.4, 1.2 Hz, 3H), 7.36-7.30 (m, 1H), 7.11 (t, J=6.3 Hz, 2H), 6.95 (t, J=7.8 Hz, 2H), 6.79 (dd, J=7.6, 1.9 Hz, 2H), 6.65 (bd, J=6.0 Hz, 2H), 3.82-3.70 (m, 3H), 2.43 (td, J=8.5, 5.7 Hz, 1H).

Figure 31:
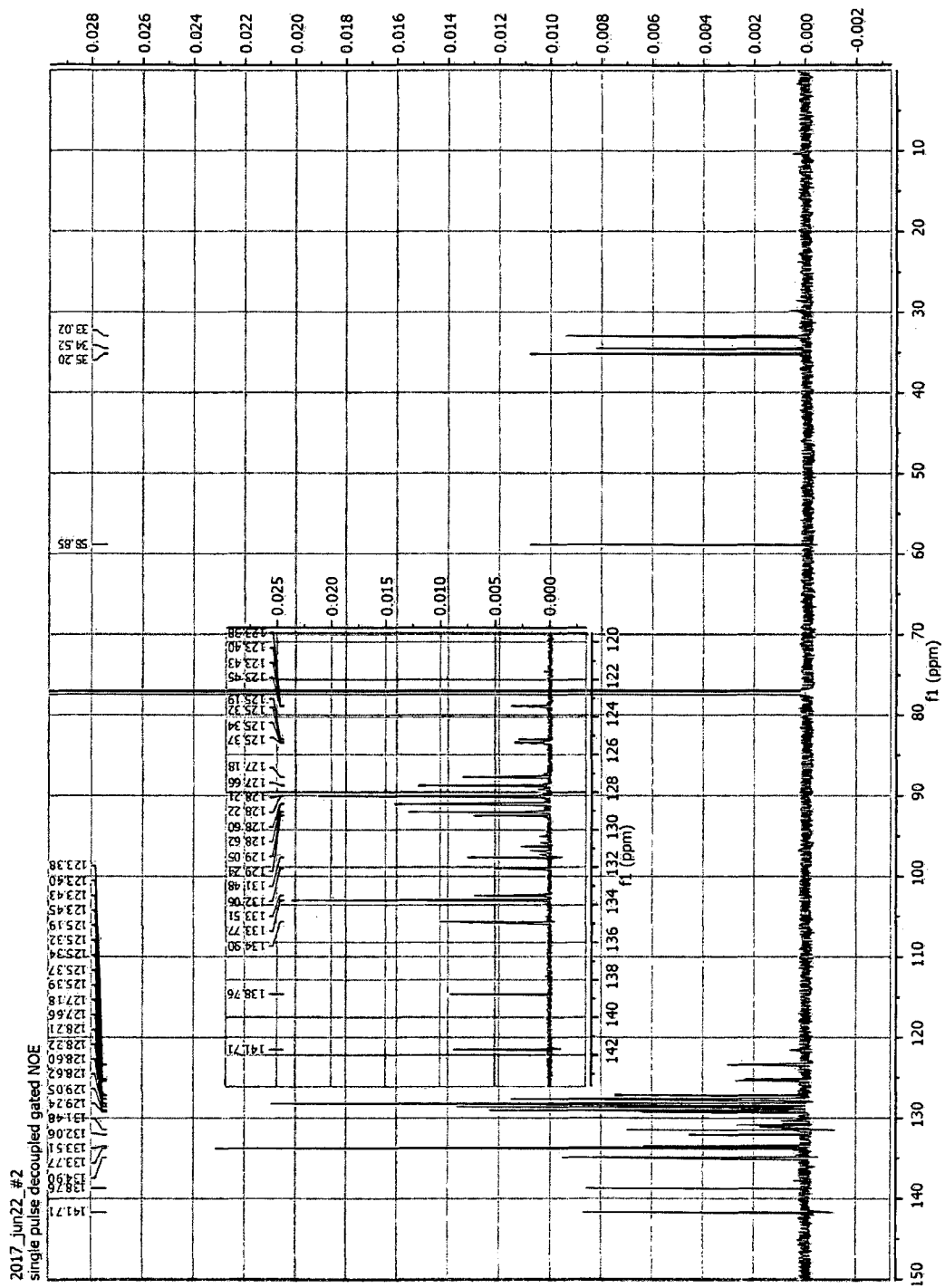
FIG. 31 illustrates ¹³C NMR of Compound 9.

FIG. 31 illustrates $^{13}$C NMR (151 MHz, Chloroform-d) δ 141.71, 138.76, 134.90, 133.77, 133.51, 132.06, 131.48, 129.24, 129.05, 128.62, 128.60, 128.22, 128.21, 127.66, 127.18, 125.35 (q, $J_{CF}$=3.4 Hz), 125.19, 123.42 (q, $J_{CF}$=3.9 Hz, CF$_3$), 123.38, 58.85, 35.20, 34.52, 33.02.

Figure 32:
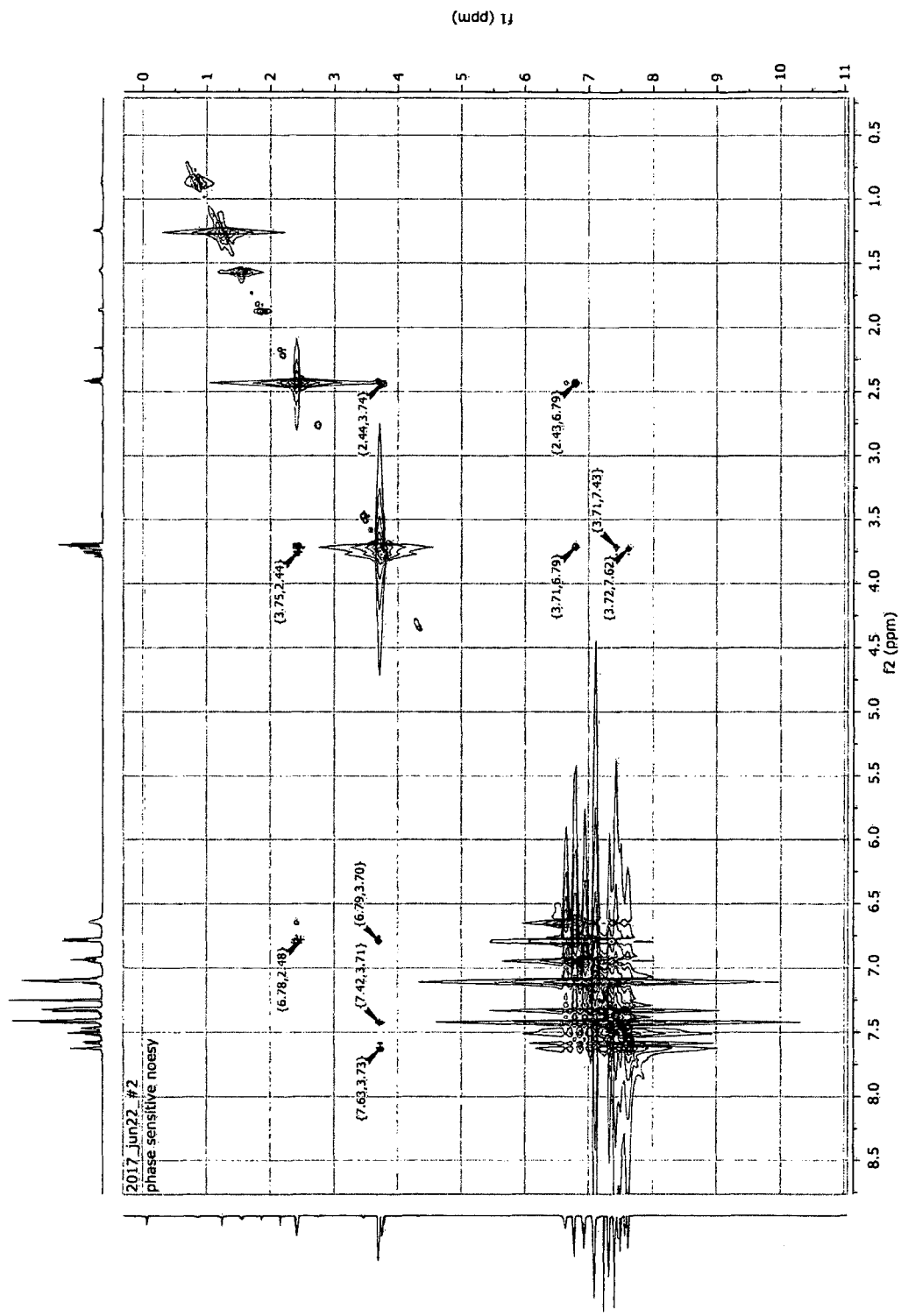
FIG. 32 illustrates NOESY of Compound 9.

FIG. 32 illustrates NOESY of Compound 9.

Figure 33:
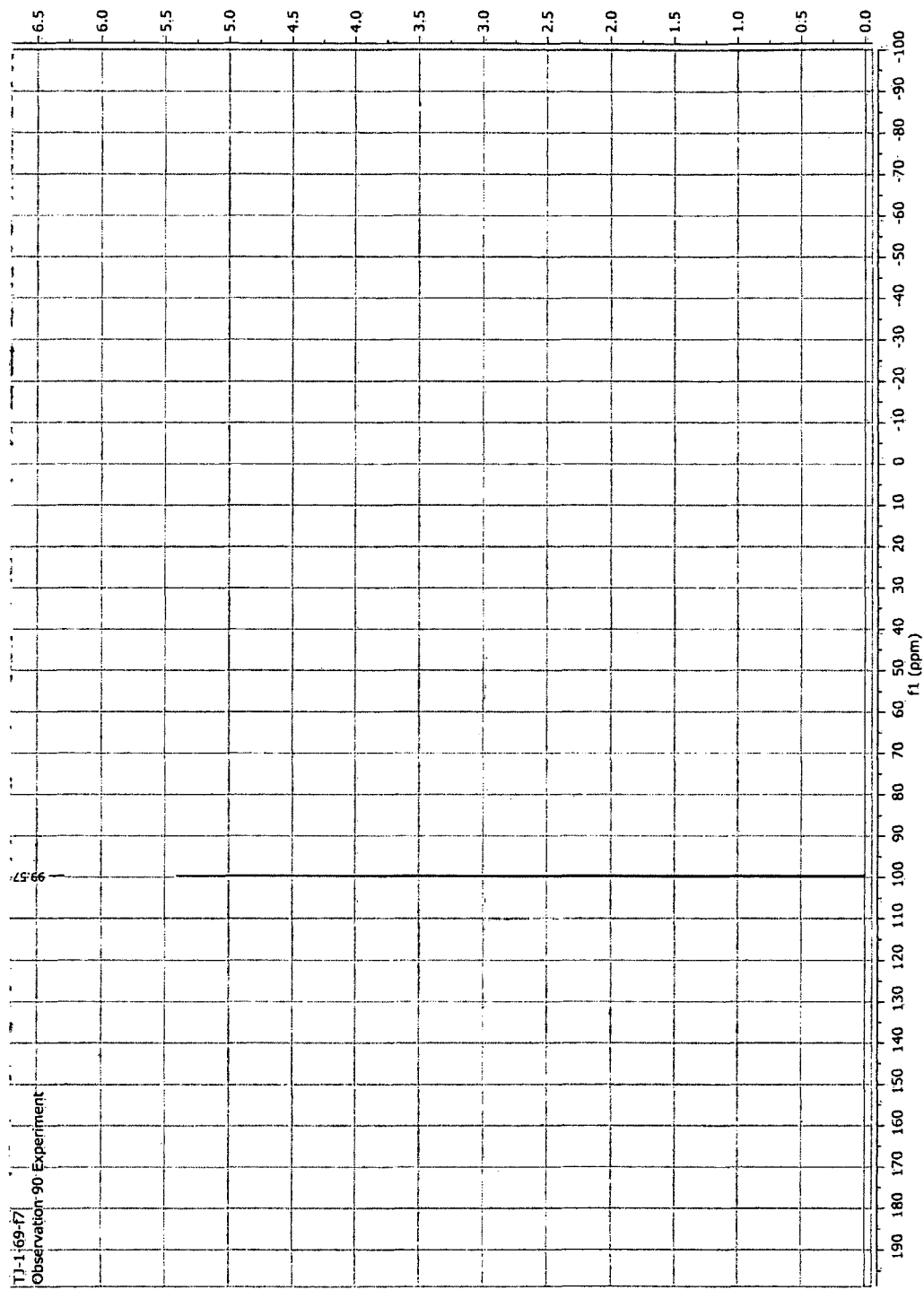
FIG. 33 illustrates ¹⁹F NMR of Compound 9.

FIG. 33 illustrates $^{19}$F NMR (565 MHz, Chloroform-d) δ 99.57.

HRMS: [M+H]$^+$ Expected 493.1444; Obtained 493.1447

[Chem. 24]

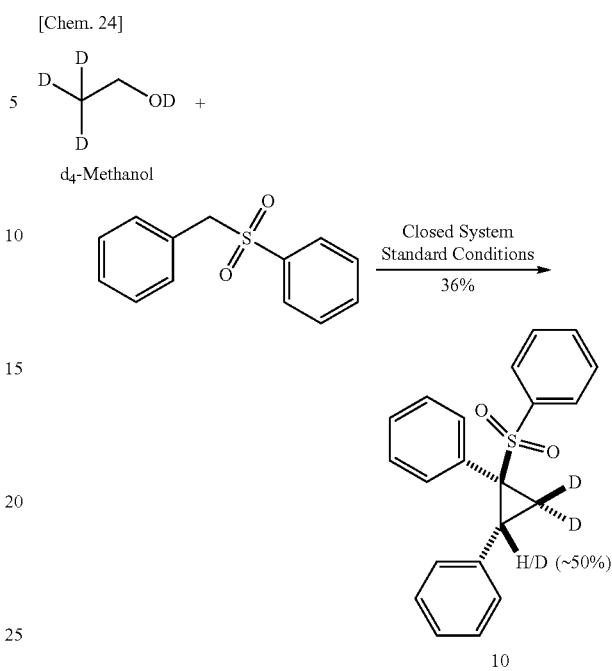

10

Physical state: colorless crystals; isolate yield 36%

Isolated d. r.~20:1 crude d. r. 9:1. Deuteration of the benzylic proton of the product occurs due to initial exchange with OD of methanol. Extent of this deuteration is only~33% due to 2:1 ratio of deprotonated sulfonate to methanol, assuming statistical scrambling after initial deprotonation. Subsequent exchange, if it occurs, should result in greater deuteration and presence of hydrogen on the aliphatic carbon atom, and accordingly much greater residual signals for the remaining two protons. This is not the case.

Figure 34:
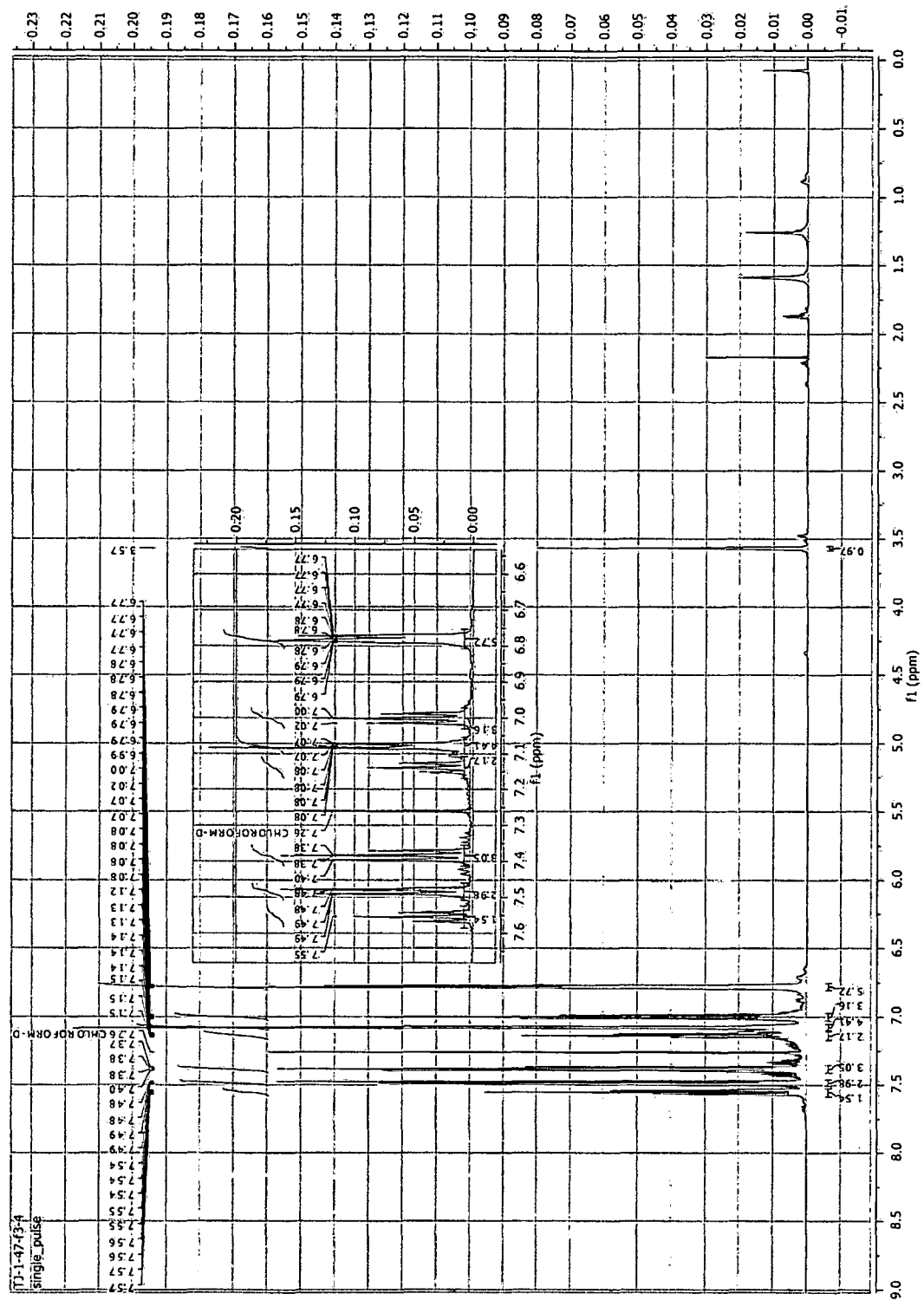
FIG. 34 illustrates ¹H NMR of Compound 10.

FIG. 34 illustrates NMR (600 MHz, Chloroform-d) δ 7.55 (tt, J=7.7, 1.3 Hz, 1H), 7.48 (dd, J=8.4, 1.3 Hz, 2H), 7.38 (dd, J=8.4, 7.4 Hz, 2H), 7.14 (tt, J=7.9, 1.2 Hz, 1H), 7.10-7.06 (m, 3H), 7.00 (t, J=7.9 Hz, 2H), 6.81-6.75 (m, 4H), 3.57 (s, 0.5H).

Figure 35:
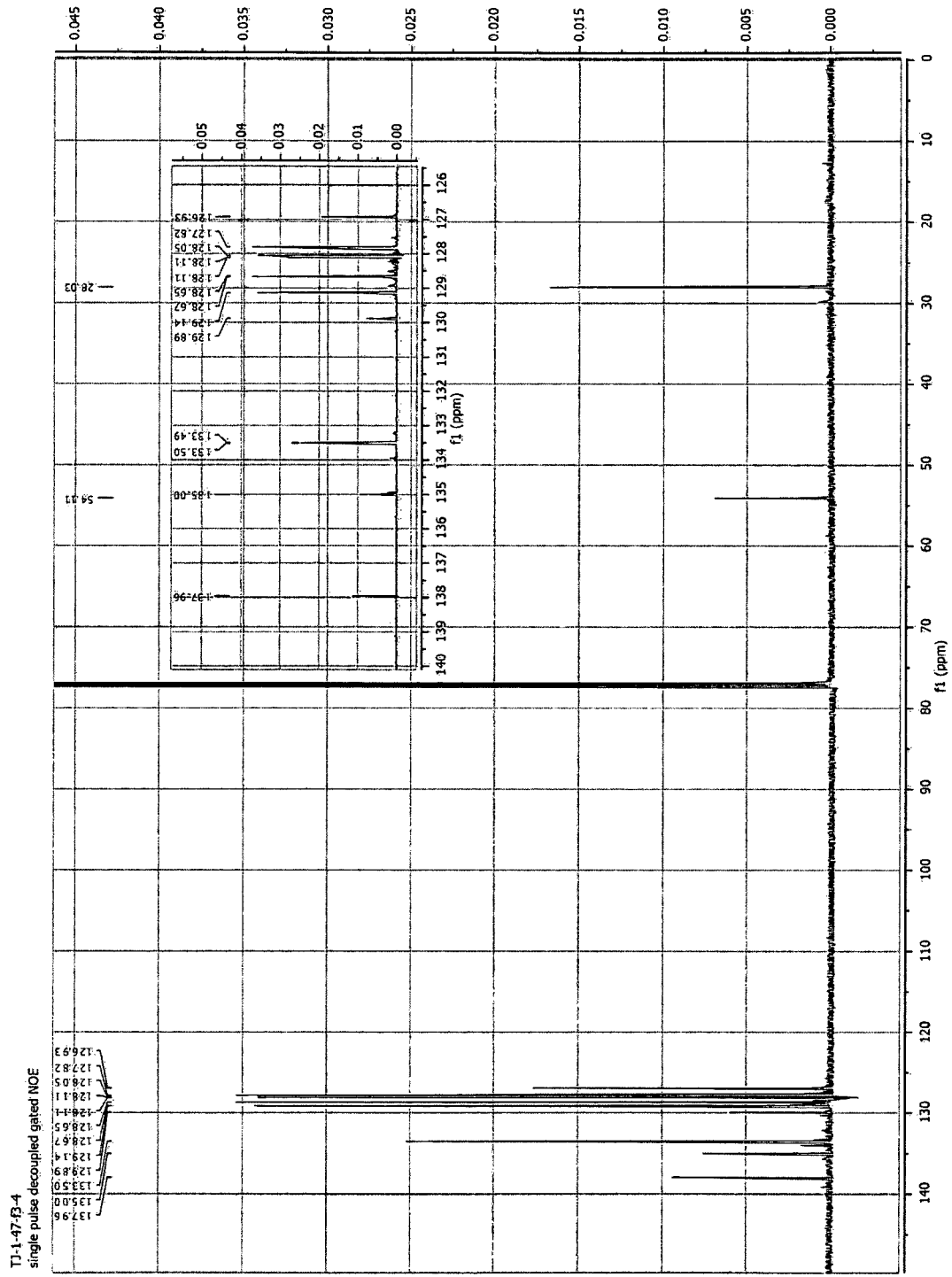
FIG. 35 illustrates ¹³C NMR of Compound 10.

FIG. 35 illustrates $^{13}$C NMR (151 MHz, Chloroform-d) δ 137.96, 135.00, 133.50, 129.89, 129.14, 128.67, 128.65, 128.11, 128.11, 128.05, 127.82, 126.93, 54.11, 28.03.

Figure 36:
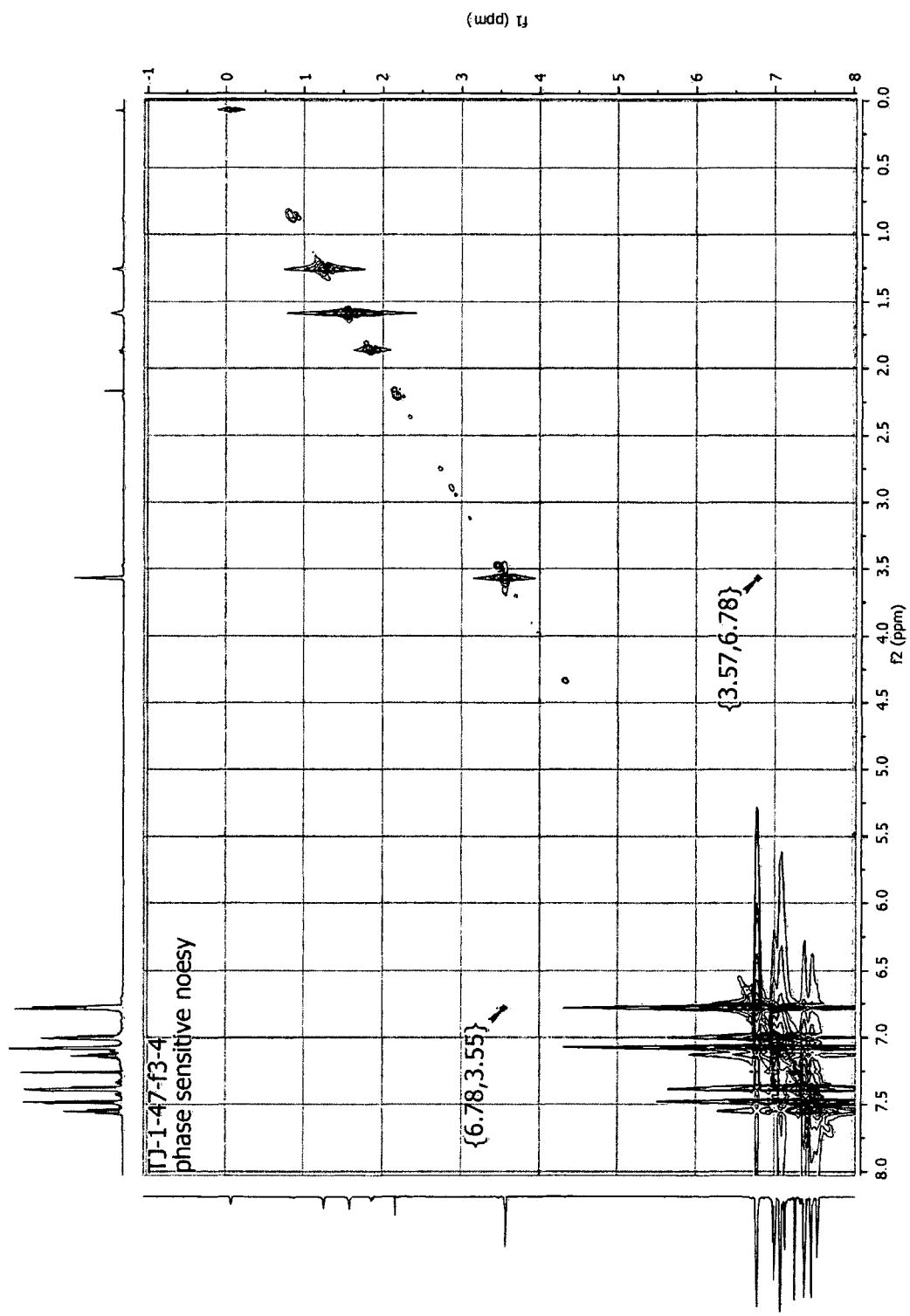
FIG. 36 illustrates NOESY of Compound 10.

FIG. 36 illustrates NOESY of Compound 10.

Assignment using just NOESY spectrum without J coupling values for cyclopropane protons is more difficult than the non-deuterated analogue 7 where the benzylic proton had very weak coupling as opposed to strong coupling of one of the aliphatic protons. Here, strength of coupling cannot be compared except by considering amplitude and comparing to 7. Based on this, diastereoselectivity was assigned to be the same as compound 7.

[Chem. 25]

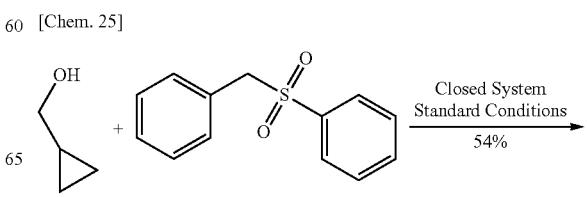

-continued

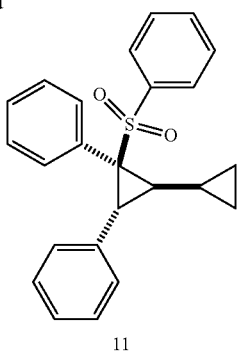

11

Physical state: White solid; isolated yield 54%

Isolated d. r. 50:1 crude d. r. 3:1. For diastereochemical assignment see compound 2 and comments on related compounds.

Figure 37:
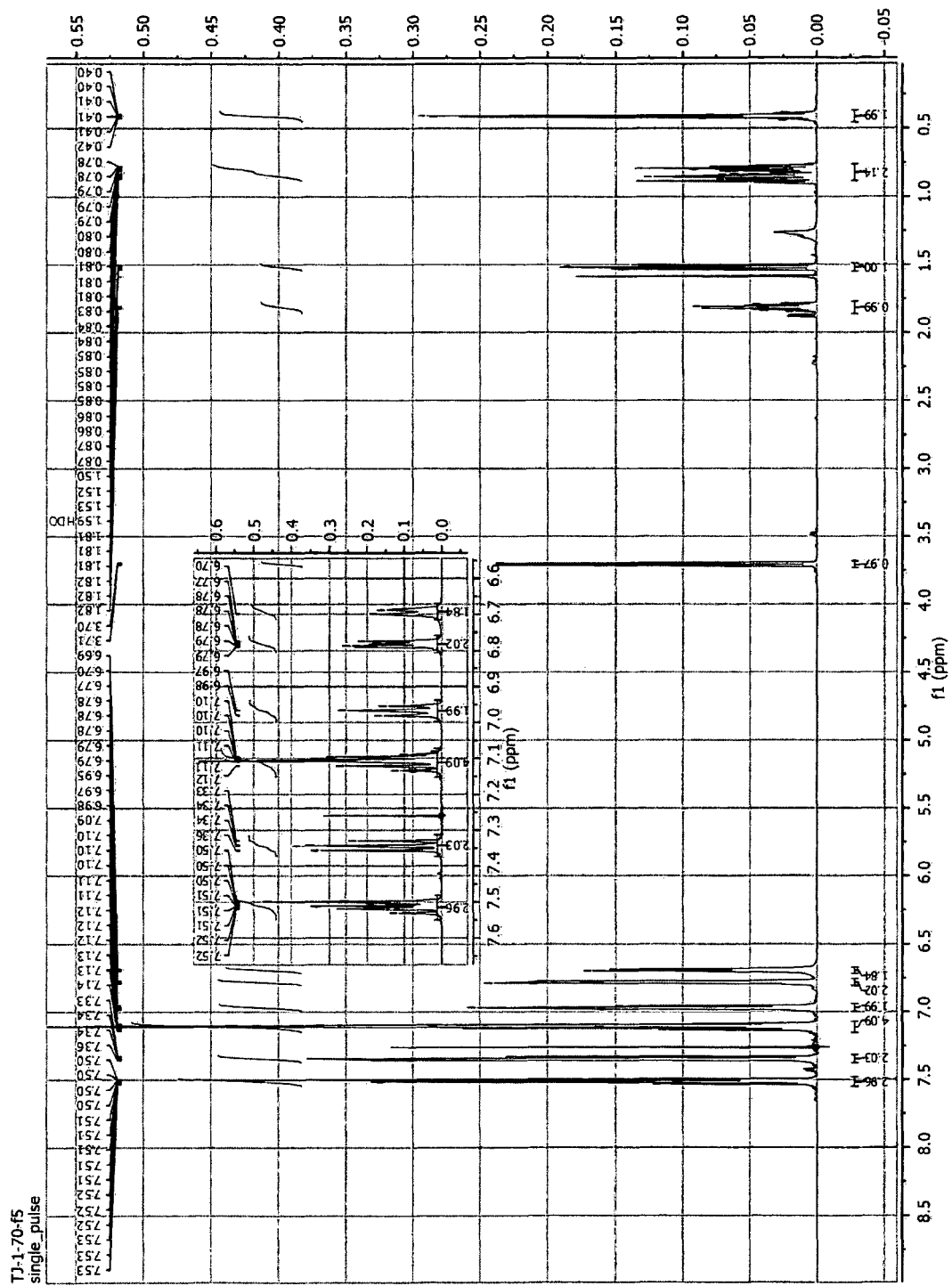
FIG. 37 illustrates ¹H NMR of Compound 11.

FIG. 37 illustrates NMR (600 MHz, Chloroform-d) δ 7.55-7.48 (m, 3H), 7.34 (dd, J=8.5, 7.4 Hz, 2H), 7.15-7.07 (m, 4H), 6.97 (t, J=7.8 Hz, 2H), 6.81-6.76 (m, 2H), 6.69 (bd, J=7.1 Hz, 2H), 3.70 (d, J=8.1 Hz, 1H), 1.86-1.77 (m, 1H), 1.55–1.49 (vt, 1H), 0.89-0.76 (m, 2H), 0.45-0.37 (m, 2H). Minor n-hexane and water impurities from $CDCl_3$ bottle observed.

Figure 38:
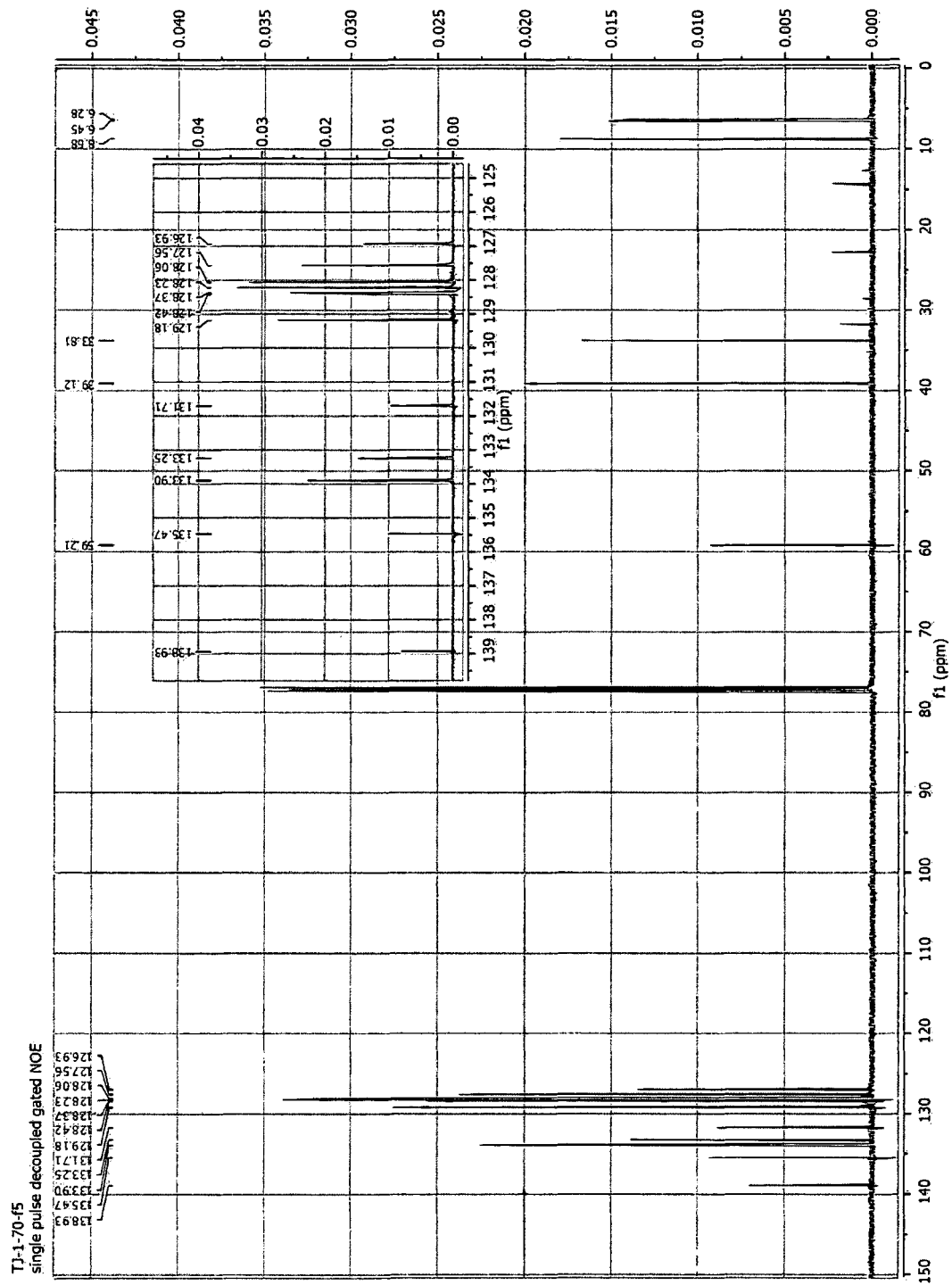
FIG. 38 illustrates ¹³C NMR of Compound 11.

FIG. 38 illustrates $^{13}$C NMR (151 MHz, Chloroform-d) δ 138.93, 135.47, 133.90, 133.25, 131.71, 129.18, 128.42, 128.37, 128.23, 128.06, 127.56, 126.93, 59.21, 39.12, 33.81, 8.68, 6.45, 6.28. Three minor aliphatic peaks (~14,23,32) are from n-hexane.

Figure 39:
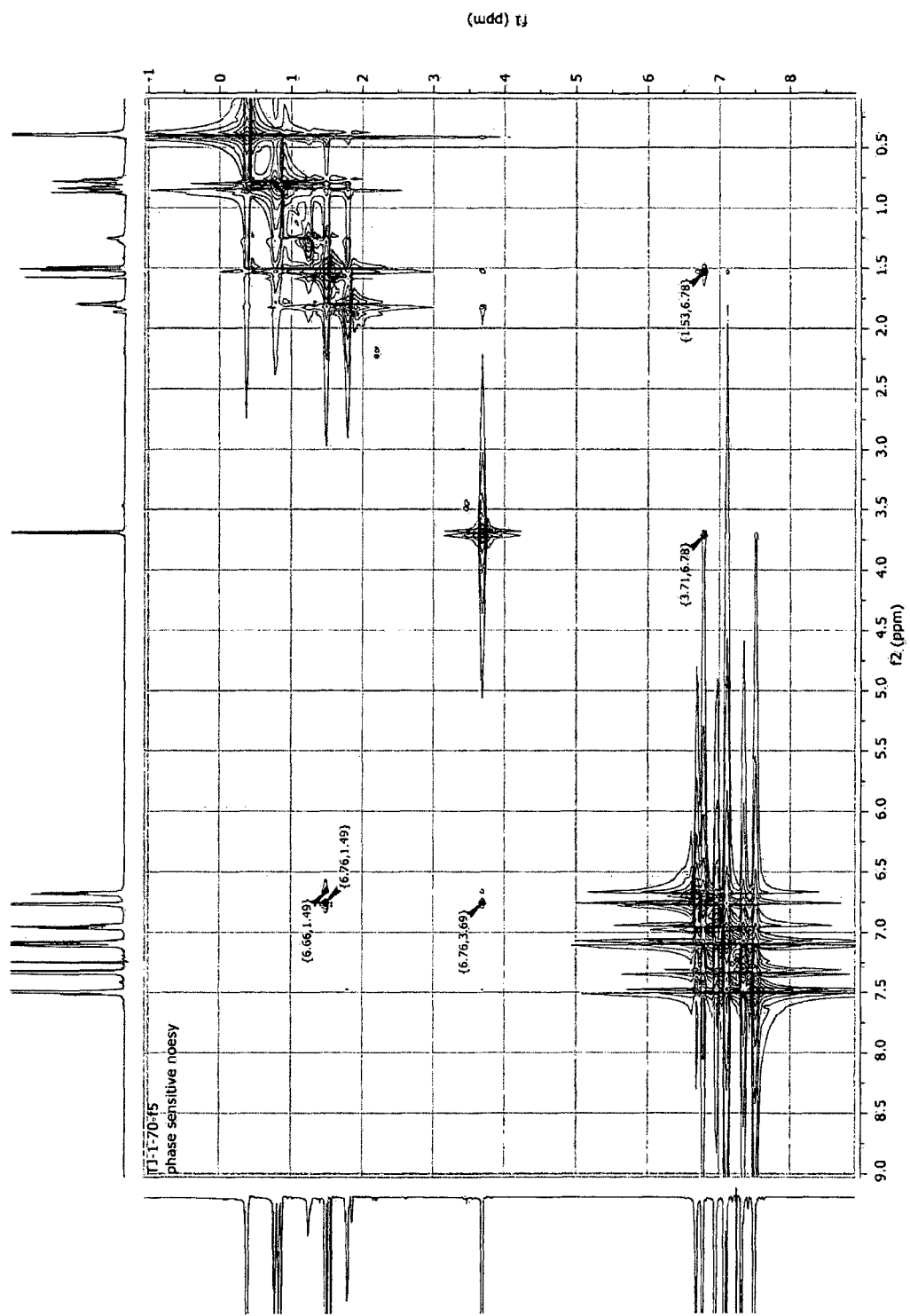
FIG. 39 illustrates NOESY of Compound 11.

FIG. 39 illustrates NOESY of Compound 11.

HRMS: [M+H]$^+$ Expected 375.1413; Obtained 375.1416

[Chem. 26]

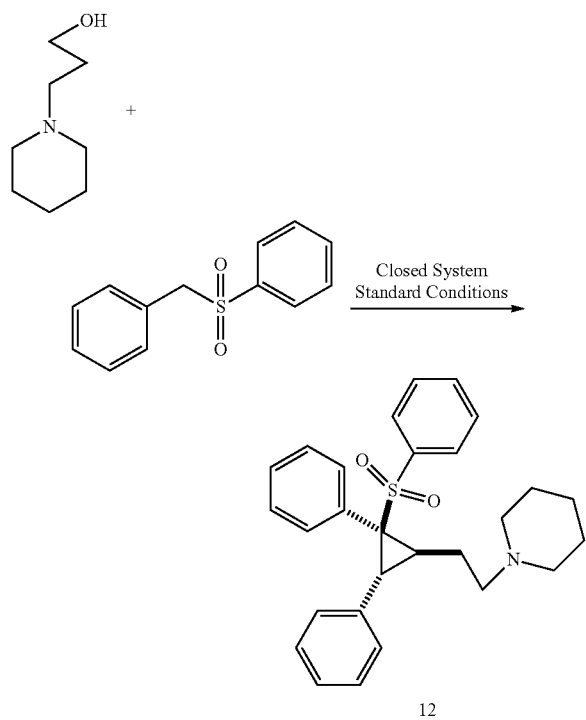

12

Physical state: white solid/white crystals; isolated yield 27%

Isolated d. r. 99:1; crude d. r. 20:1

The crystals were obtained when the reaction was done on small scale (2.0E-4 mol alcohol). The product is slightly soluble in hexanes and letting pure product stand in ~50 mL, of hexanes leads to crystallization after two days. The yield of the reaction is quantitative according to GC/MS vs. internal standard mesitylene and complete consumption of sulfonate is observed. However, the isolated yield is heavily compromised by the product sticking to silica, even after deactivation with $NEt_3$. The product is isolated at 60%-80% $Et_2O$ to hexanes elution gradient. For diastereochemical assignment see discussion on compound 2 and other related compounds above.

Figure 40:
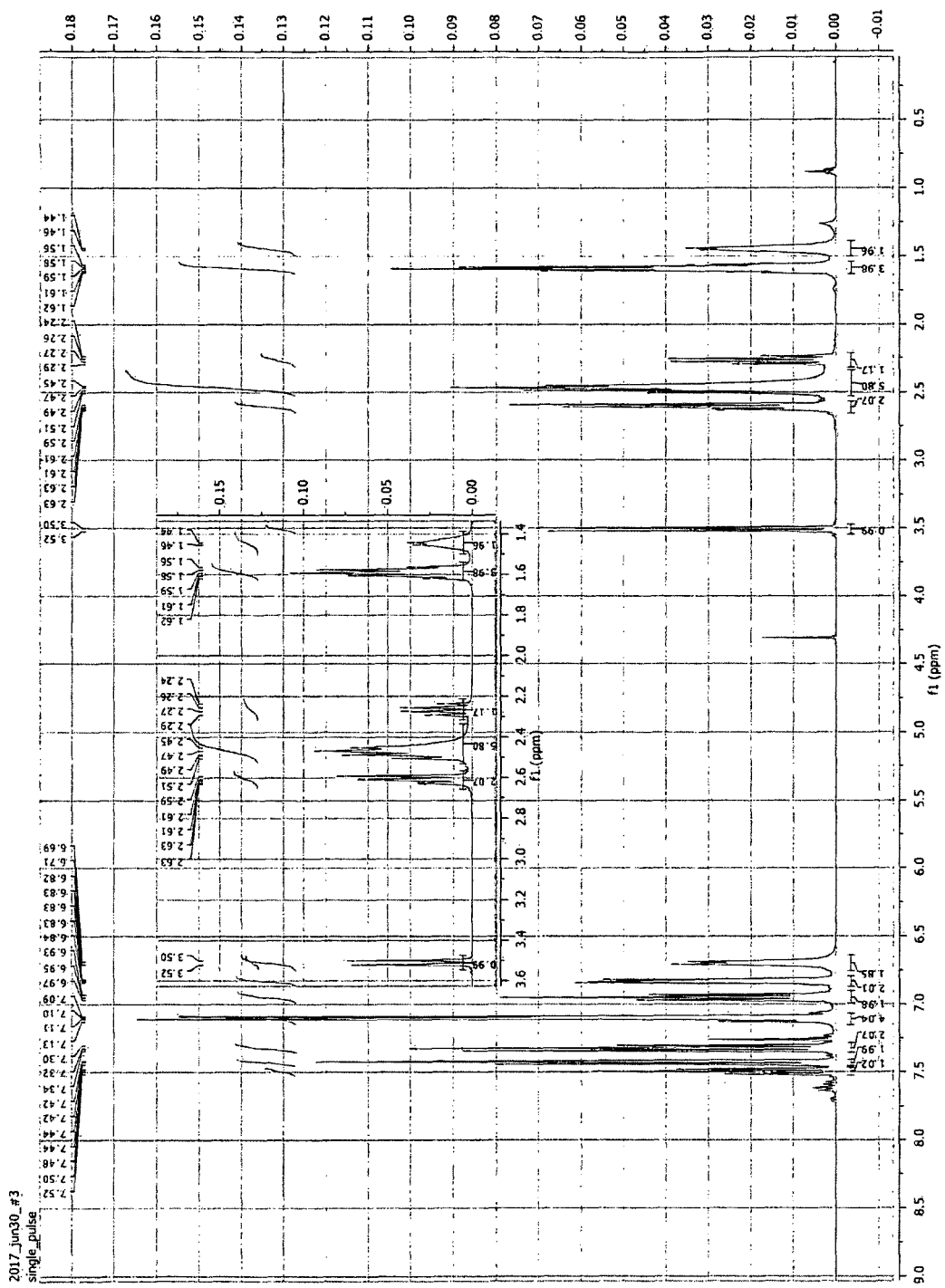
FIG. 40 illustrates ¹H NMR of Compound 12.

FIG. 40 illustrates $^1$H NMR (400 MHz, Chloroform-d) δ 7.50 (tt, J=7.4 Hz, 1.3 Hz, 1H), 7.43 (dd, J=8.3, 1.3 Hz, 2H), 7.32 (d, J=8.3 Hz, 2H), 7.15-7.07 (m, 4H), 6.95 (t, J=7.8 Hz, 2H), 6.87-6.79 (m, 2H), 6.70 (bd, J=6.9 Hz, 2H), 3.51 (d, J=8.2 Hz, 1H). 2.66-2.57 (m, 2H), 2.53-2.43 (m, 6H), 2.26 (vq, 1H), 1.59 (p, J=5.6 Hz. 4H), 1.48-1.42 (m, 2H).

Figure 41:
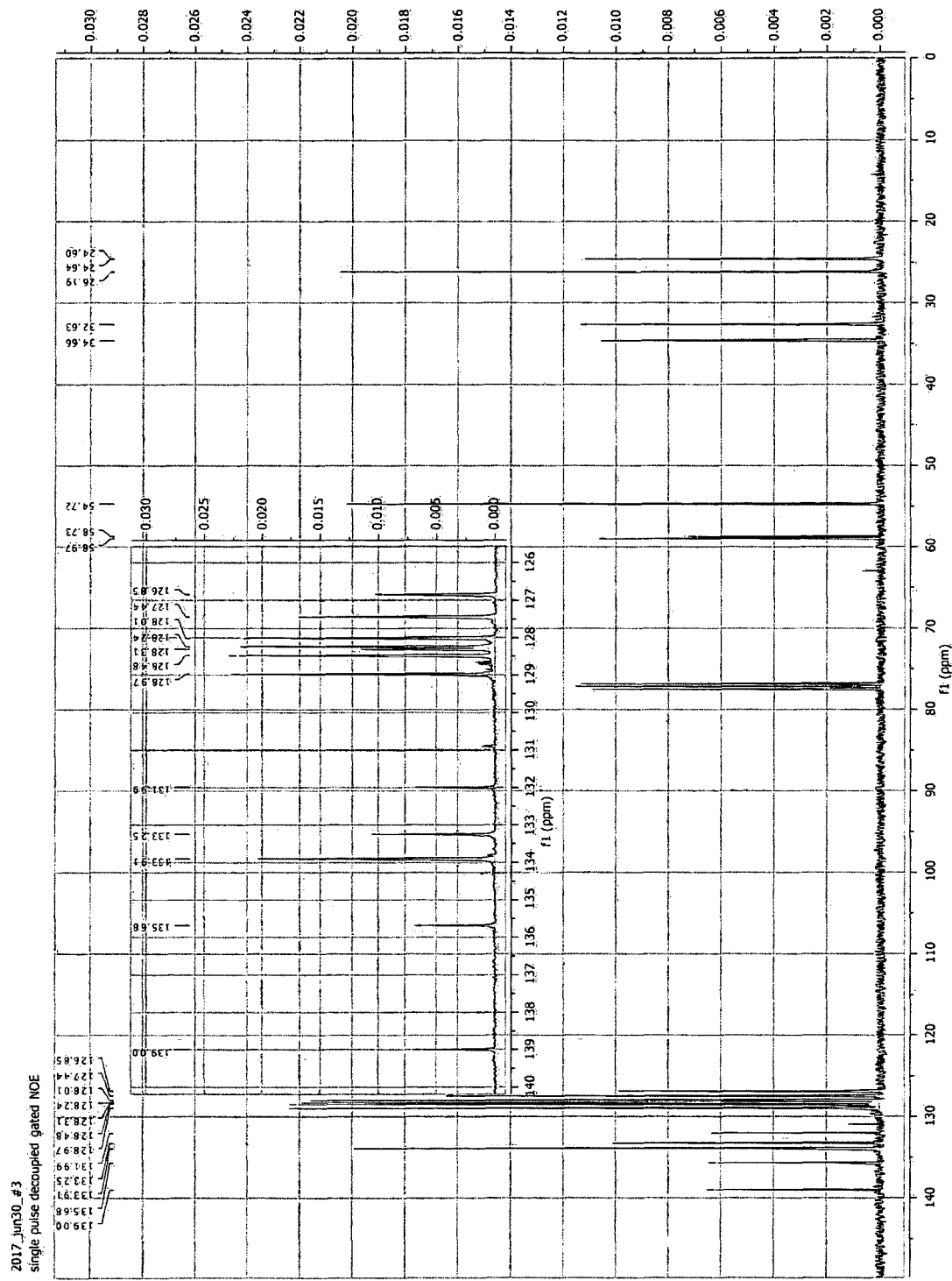
FIG. 41 illustrates ¹³C NMR of Compound 12.

FIG. 41 illustrates $^{13}$C NMR (101 MHz, Chloroform-d) δ 139.00, 135.68, 133.91, 133.25, 131.99, 128.97, 128.48, 128.31, 128.24, 128.01, 127.44, 126.85, 58.97, 58.73, 54.72, 34.66, 32.63, 26.19, 24.64, 24.60.

Figure 42:
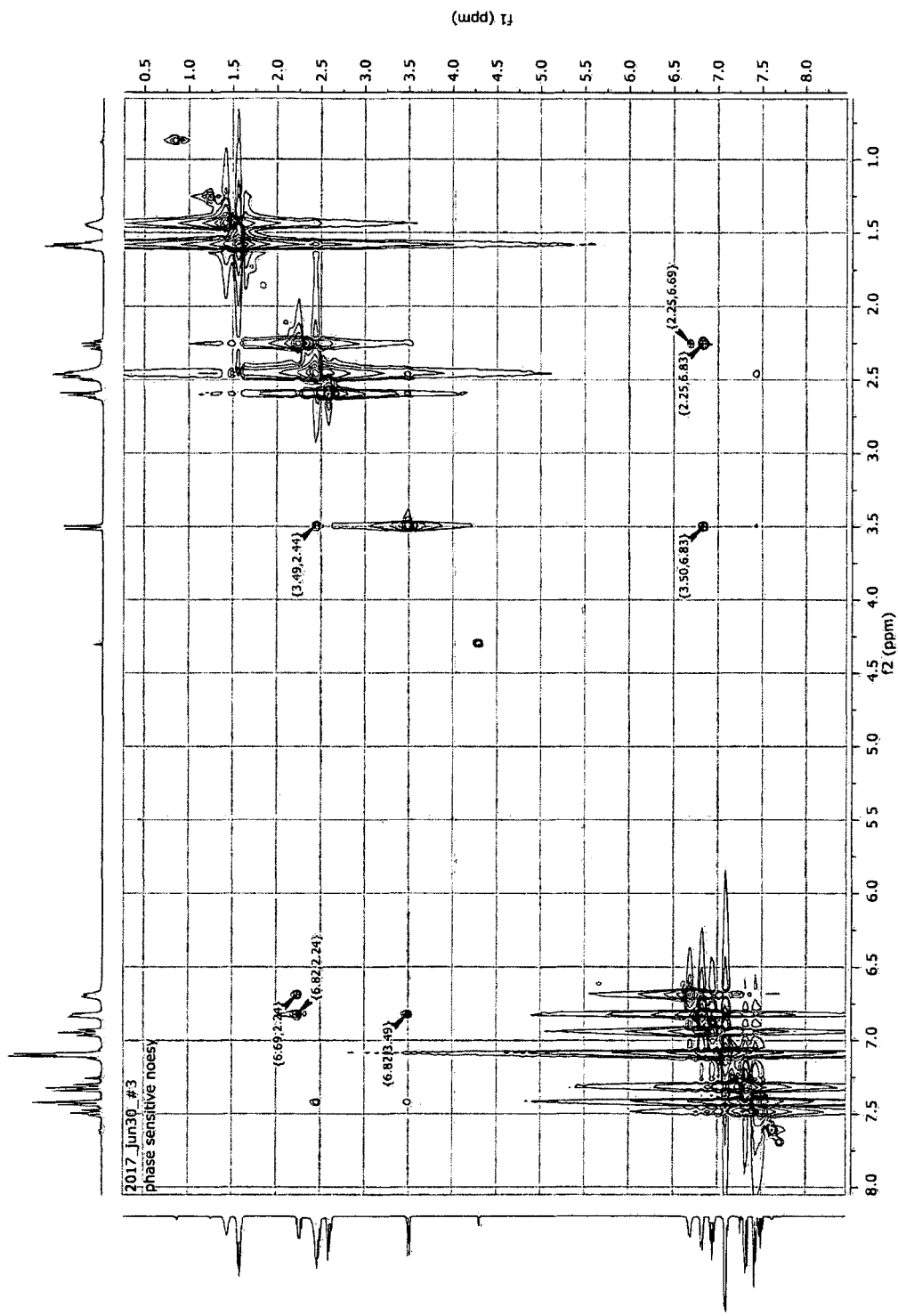
FIG. 42 illustrates NOESY of Compound 12.

FIG. 42 illustrates NOESY of Compound 12.

HRMS: [M+H]$^+$ Expected 446.2148; Obtained 446.2149

[Chem.27]

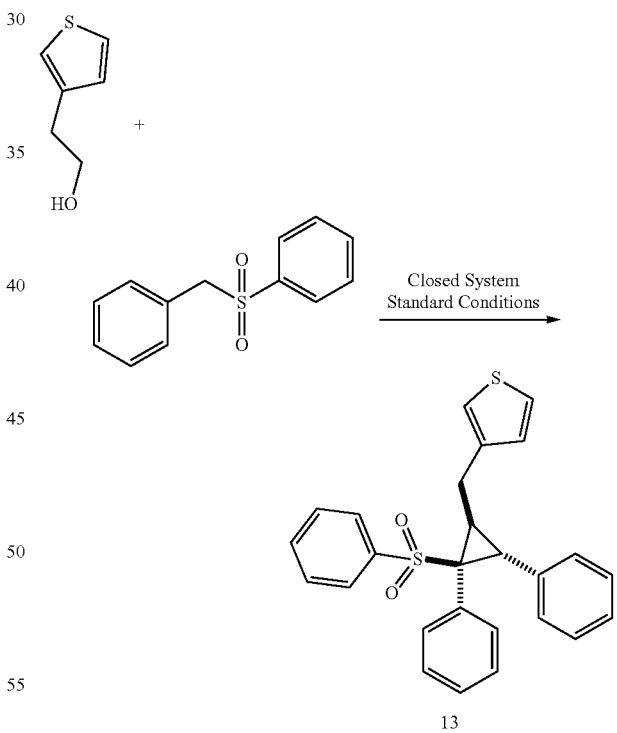

13

Physical state: White crystal; isolated yield 41%

Isolated d. r. 99:1 Crude d. r. 6.1:1

Figure 43:
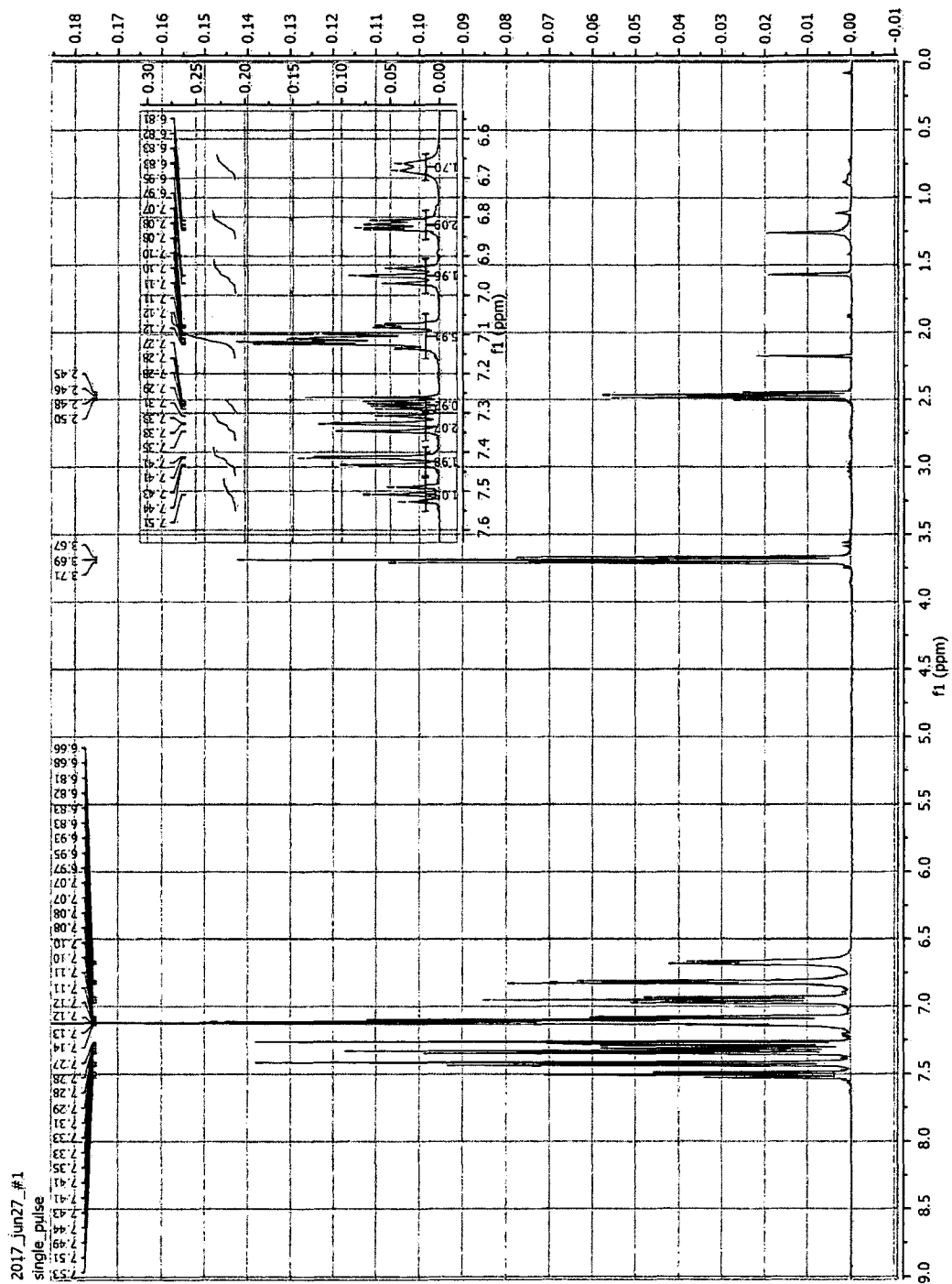
FIG. 43 illustrates ¹H NMR of Compound 13.

FIG. 43 illustrates $^1$H NMR (400 MHz, Chloroform-d) δ 7.51 (t, J=7.4 Hz, 1H), 7.42 (dd, J=8.5, 1.3 Hz, 2H), 7.37-7.30 (m, 2H), 7.28 (dd, J=4.9, 2.9 Hz. 1H), 7.16-7.05 (m, 6H), 6.95 (t, J=7.8 Hz, 2H), 6.86-6.78 (m, 2H), 6.67 (d, J=7.0 Hz, 2H), 3.73-3.64 (m, 3H), 2.53-2.42 (m, 1H).

Figure 44:
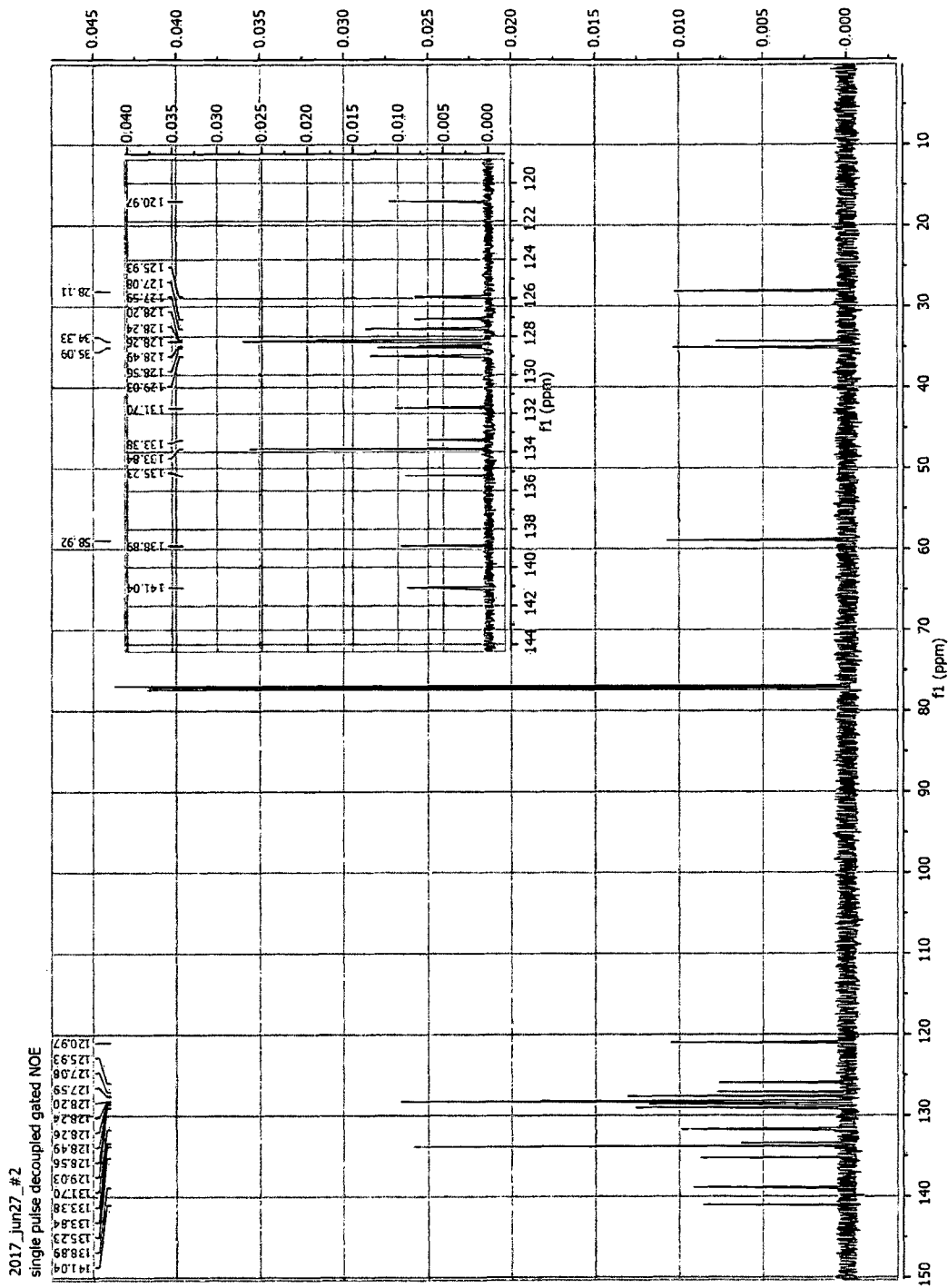
FIG. 44 illustrates ¹³C NMR of Compound 13.

FIG. 44 illustrates $^{13}$C NMR (151 MHz, Chloroform-d) δ 141.04, 138.89, 135.23, 133.84, 133.38, 131.70, 129.03, 128.56, 128.49, 128.26, 128.24, 128.20, 127.59, 127.08, 125.93, 120.97, 58.92, 35.09, 34.33, 28.11.

Figure 45:
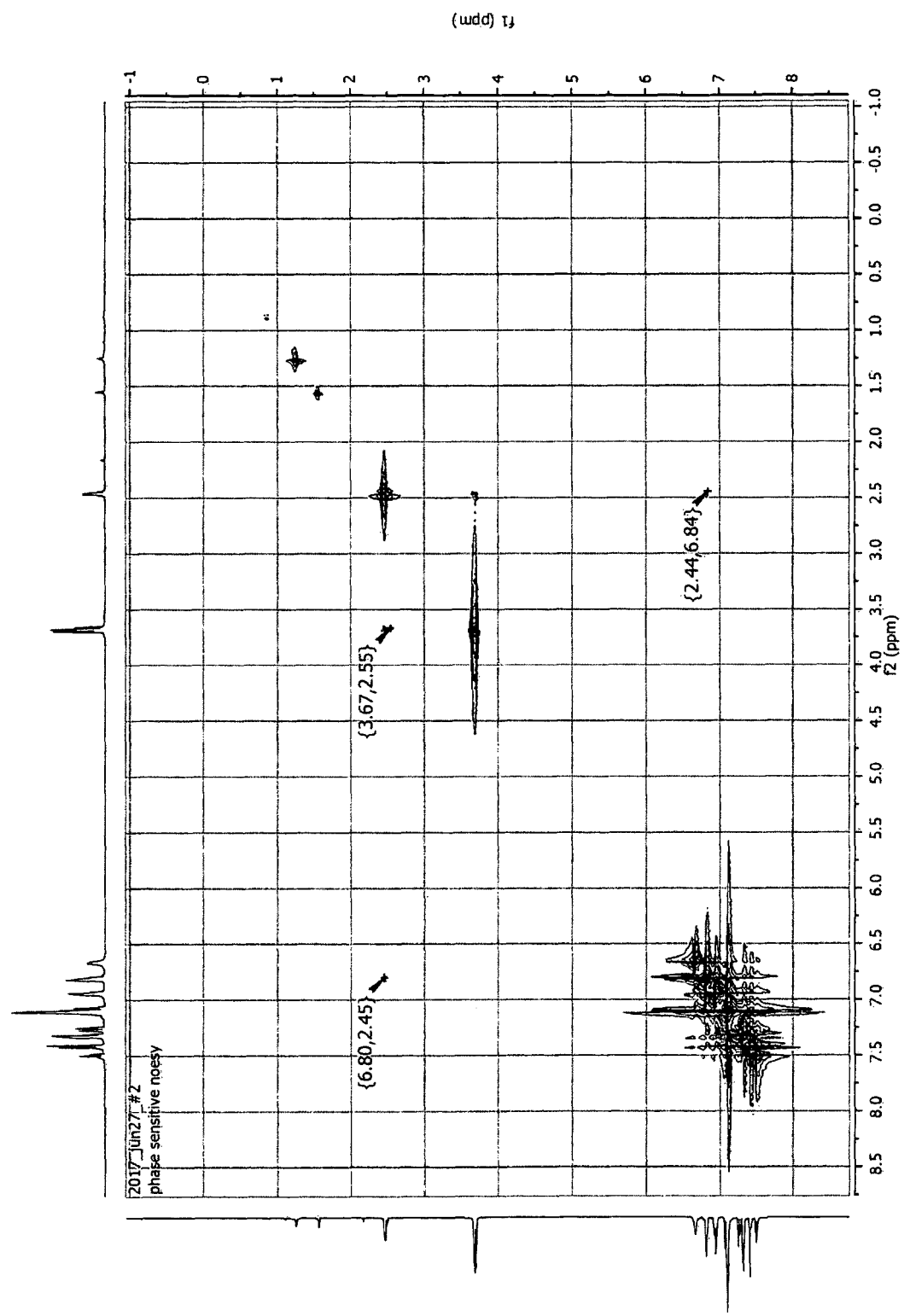
FIG. 45 illustrates NOESY of Compound 13.

FIG. 45 illustrates NOESY of Compound 13.

HRMS: [M+H]⁺ Expected 431.1134; Obtained 431.1139

[Chem.28]

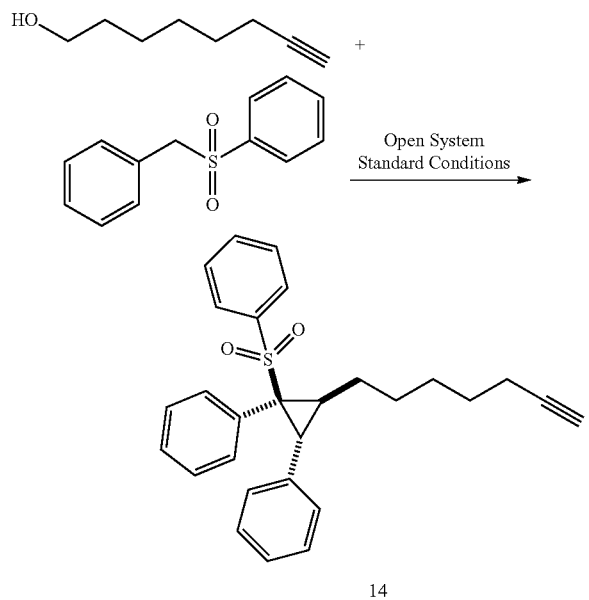

14

Physical state: Colorless oil; isolated yield 41%

Isolated d. r. 9:1; crude d. r. 9:1 The final product also contains trace impurities (2-3% of hydrogenated products). For diastereoselective assignment of the major isomer, see compound 2 above and discussion on related compounds. The minor isomer has a larger J coupling of ~11 Hz and is assigned as cis.

Figure 46:
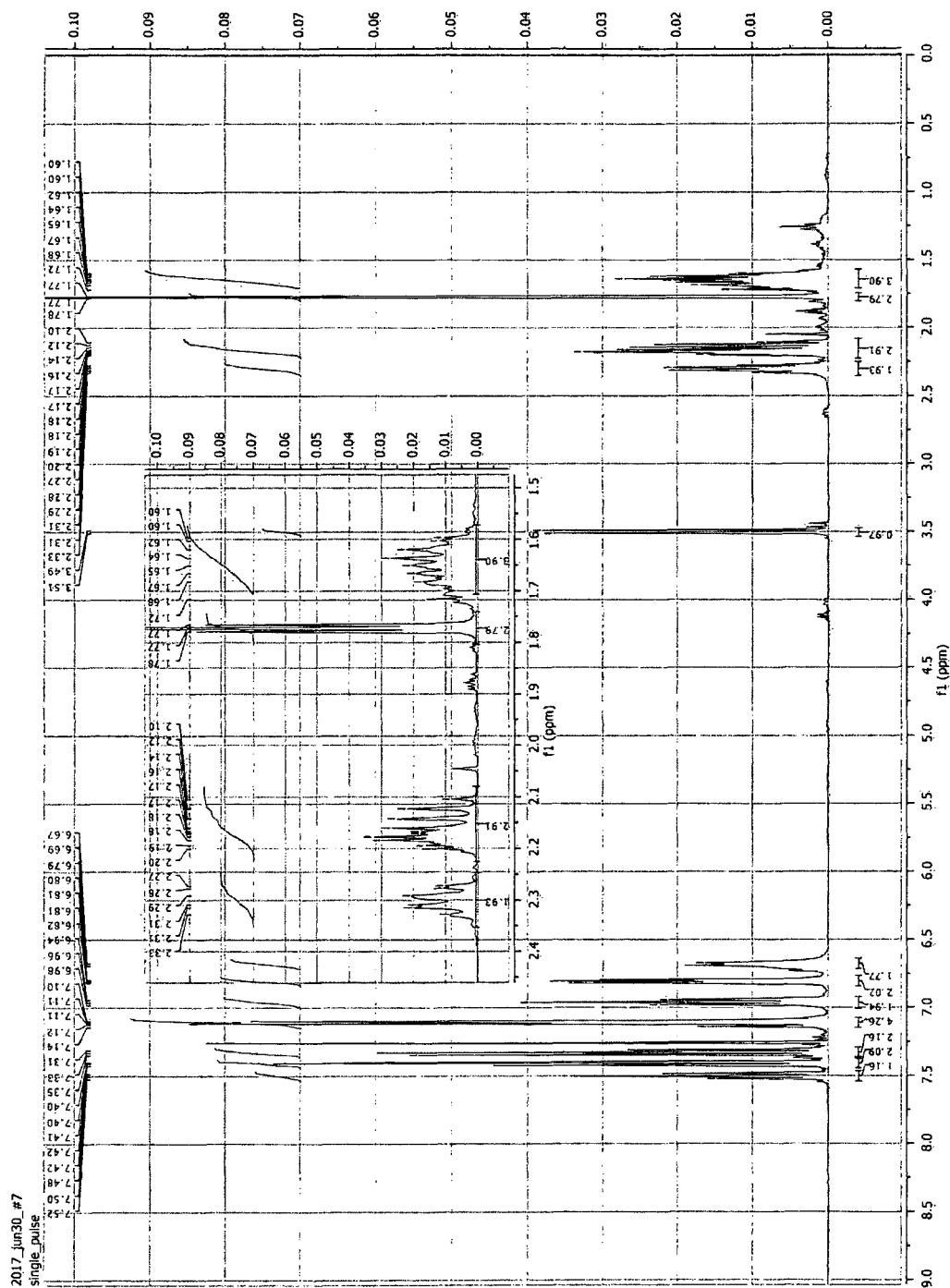
FIG. 46 illustrates ¹H NMR of Compound 14.

FIG. 46 illustrates $^1$H NMR (400 MHz, Chloroform-d) δ 7.50 (t, J=7.4 Hz, 1H), 7.41 (dd, J=8.3, 1.2 Hz, 2H), 7.37-7.28 (m, 2H), 7.15-7.07 (m, 4H), 6.96 (t, J=7.8 Hz, 2H), 6.84-6.77 (m, 2H), 6.68 (d, J=6.9 Hz, 2H), 3.50 (d, J=8.1 Hz, 1H), 2.35-2.25 (m, 2H), 2.23-2.08 (m, 3H), 1.77 (t, J=2.5 Hz, 3H), 1.73-1.57 (m, 4H).

Figure 47:
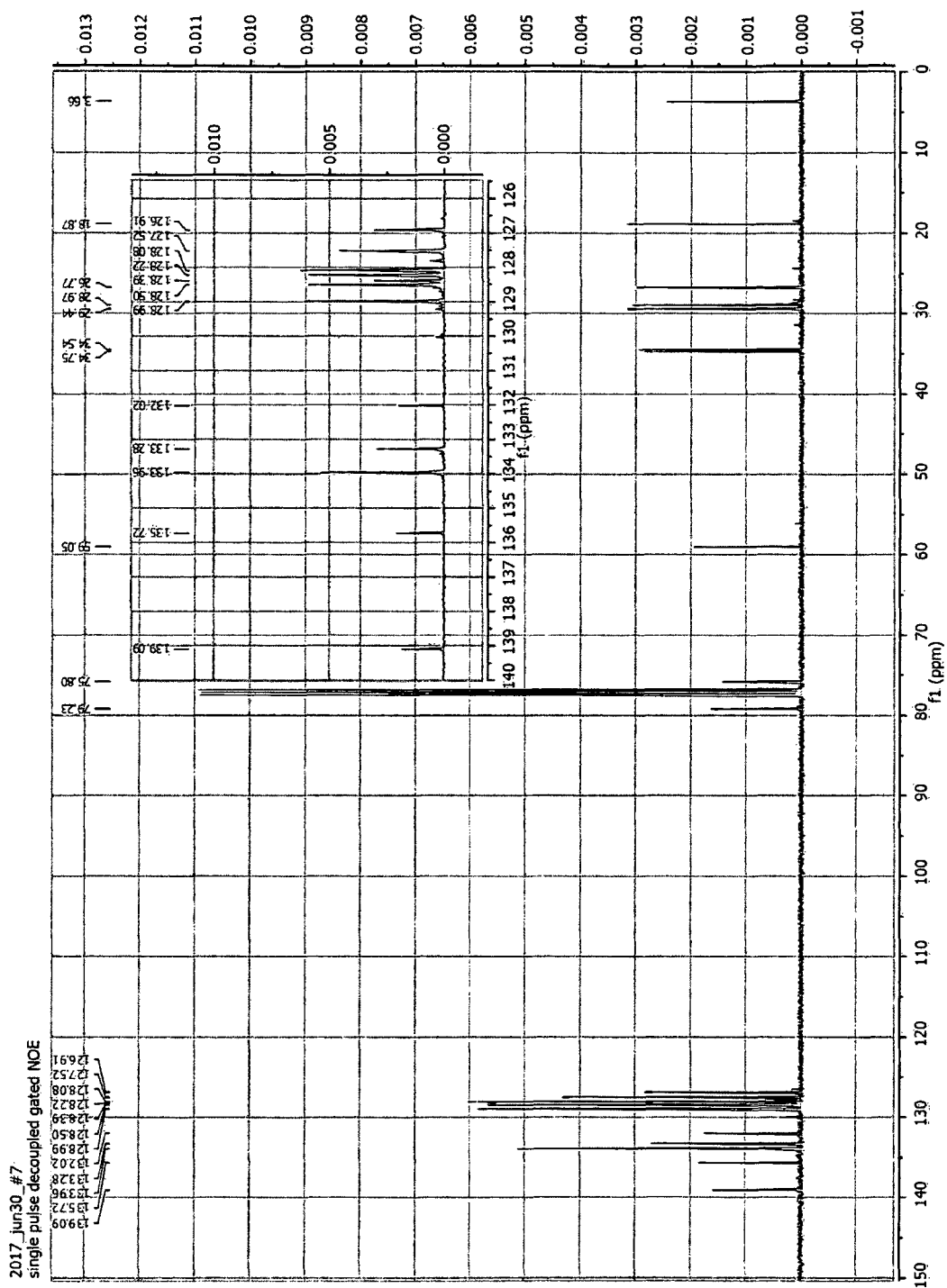
FIG. 47 illustrates ¹³C NMR of Compound 14.

FIG. 47 illustrates $^{13}$C NMR (101 MHz, Chloroform-d) δ 139.09, 135.72, 133.96, 133.28, 132.02, 128.99, 128.50, 128.39, 128.22, 128.08, 127.52, 126.91, 79.23, 75.80, 59.05, 34.75, 34.54, 29.44, 28.97, 26.77, 18.87, 3.66.

Figure 48:
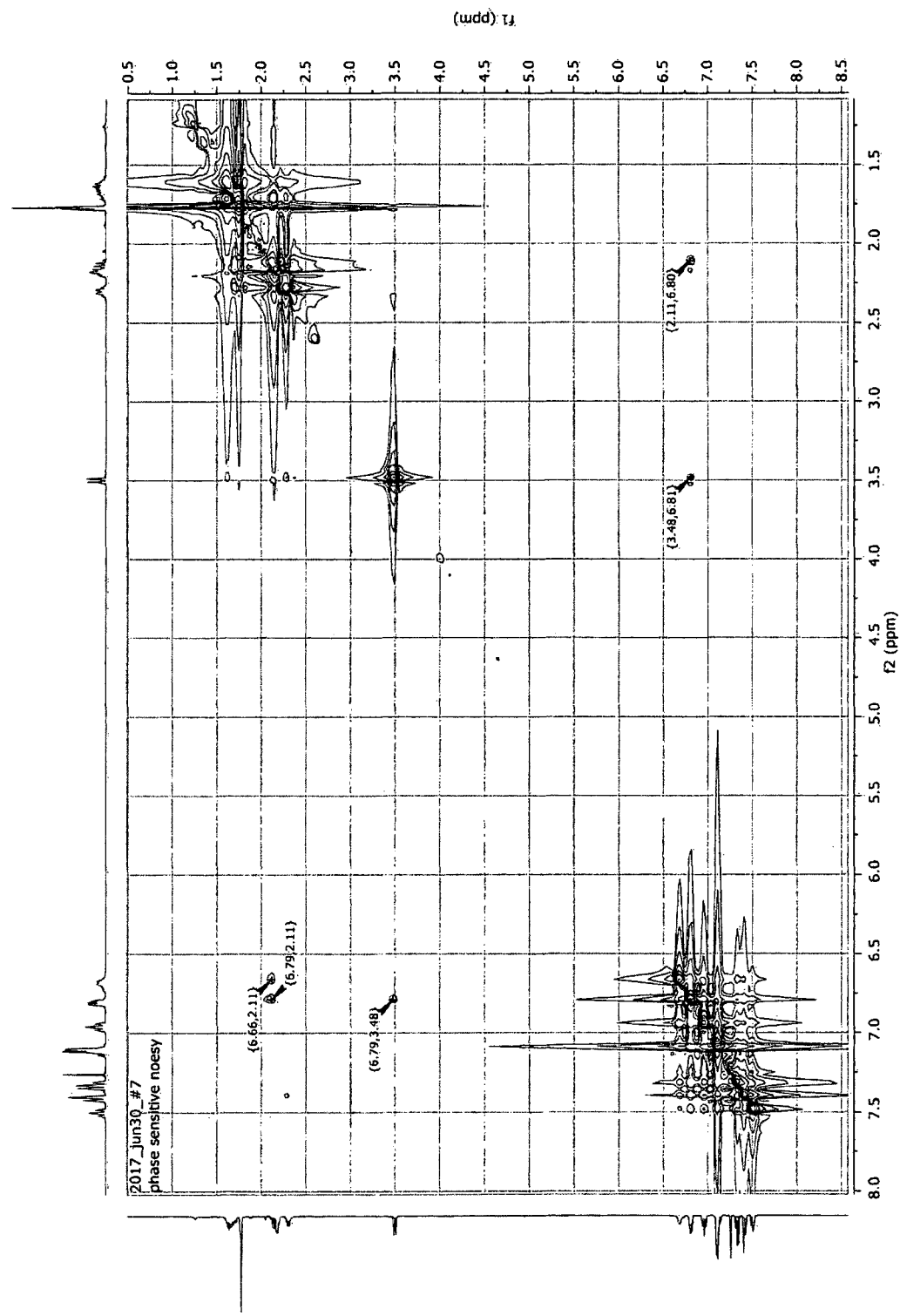
FIG. 48 illustrates NOESY of Compound 14.

FIG. 48 illustrates NOESY of Compound 14.

HRMS: [M+NH₄]⁺ Expected 446.2148; Obtained 446.2147 For all other substrates, both the M+H⁺ and M+NH₄⁺ ions are visible, but substrate 14 could only be seen as the M+NH₄⁺

[Chem.29]

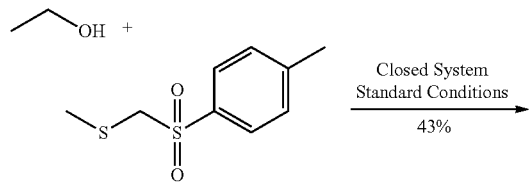

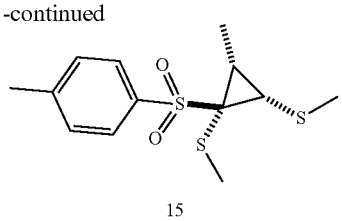

15

Physical state: White solid; isolated yield 43% d. r. 15.7:1. Model HSQC and HMBC are given for this compound, where a crystal structure is also available; however it was determined that these spectra are not necessary to establish identity and connectivity in the products.

Figure 49:
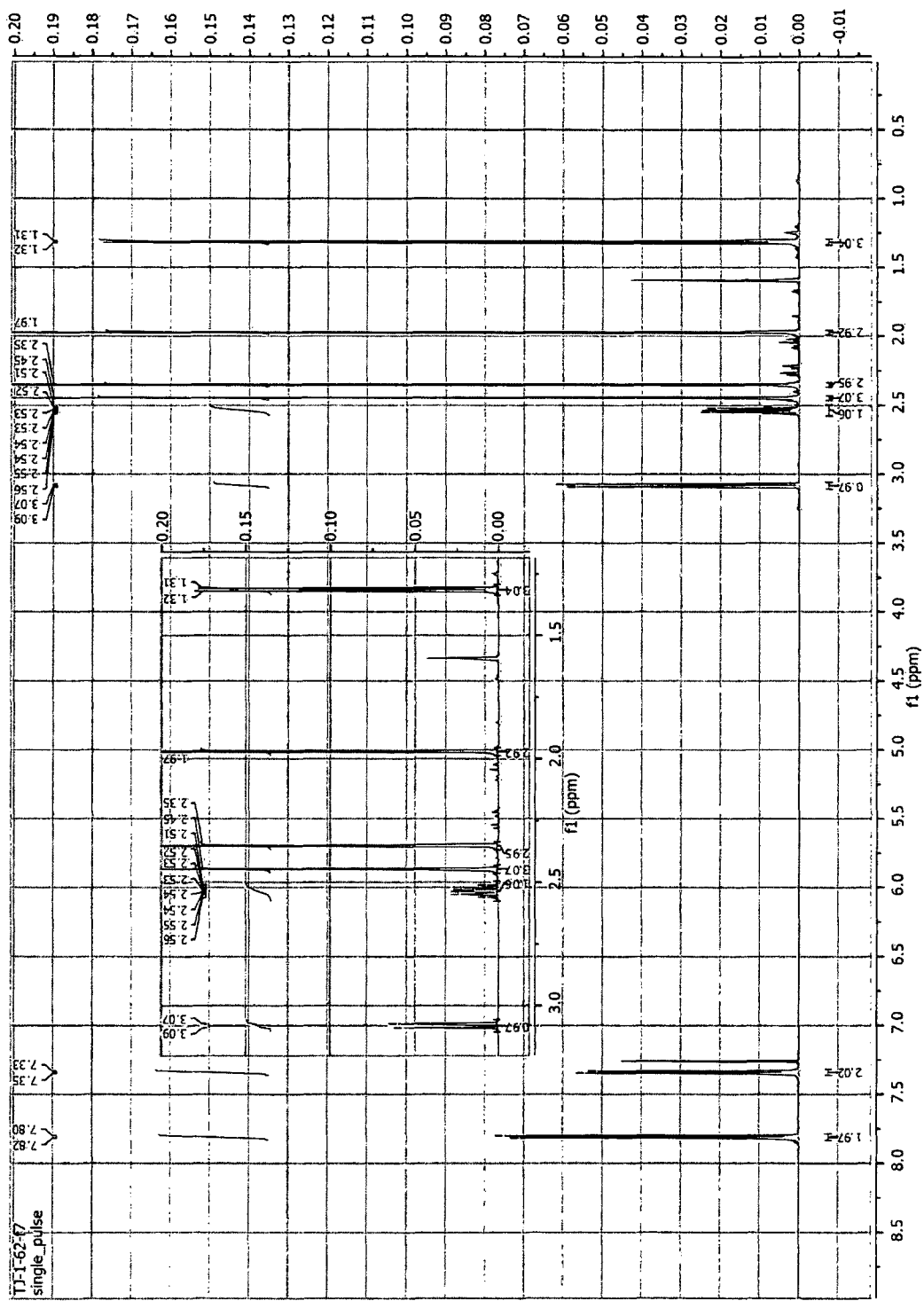
FIG. 49 illustrates ¹H NMR of Compound 15.

FIG. 49 illustrates $^1$H NMR (600 MHz) δ 7.81 (d, J=8.0 Hz, 2H), 7.34 (d, J=8.0 Hz, 2H), 3.08 (d, J=9.8 Hz, 1H), 2.53 (dq, J=9.8, 6.5 Hz, 1H). 2.45 (s, 3H), 2.35 (s, 3H), 1.97 (s, 3H), 1.31 (d, J=6.5 Hz, 3H).

Figure 50:
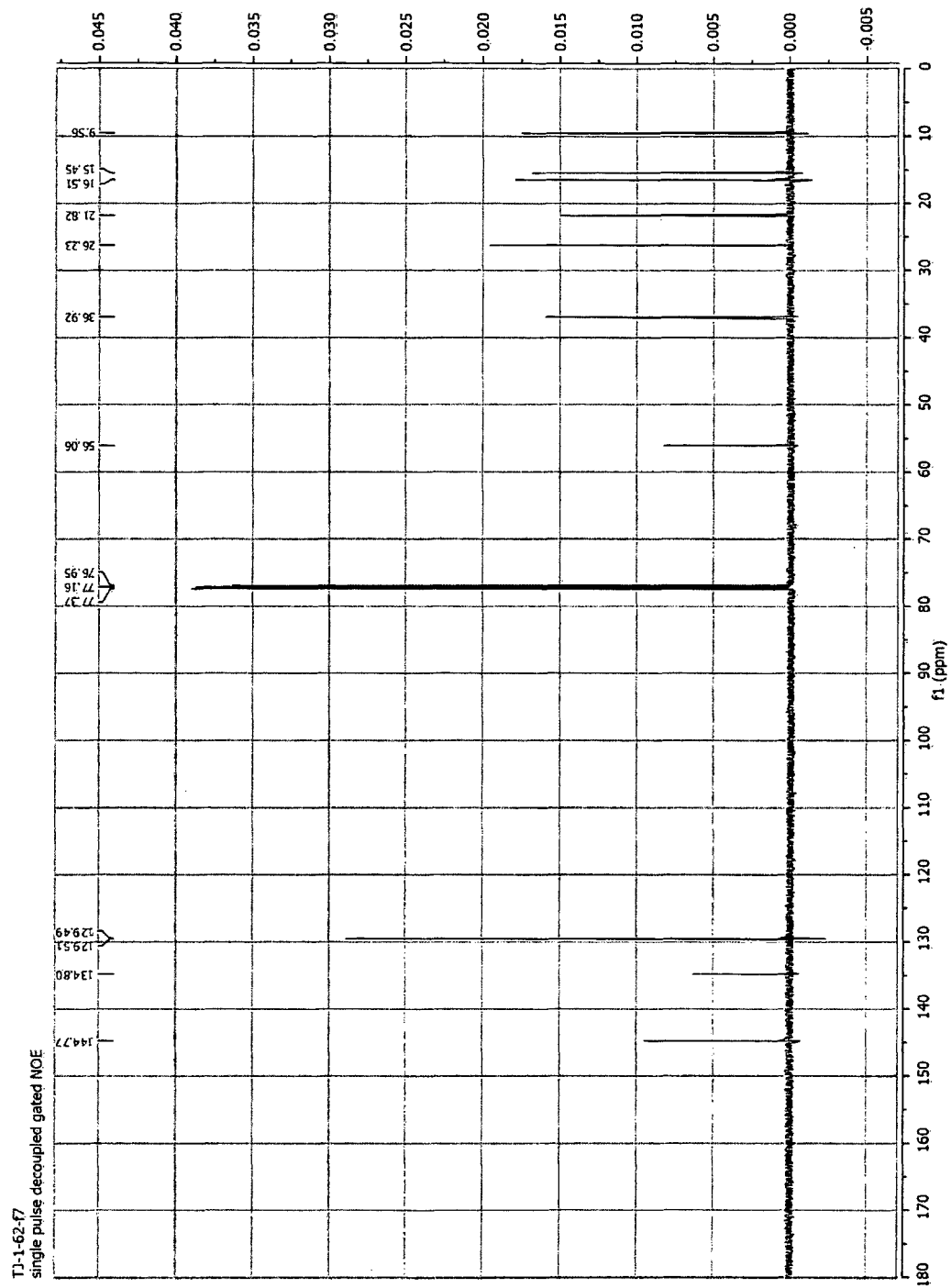
FIG. 50 illustrates ¹³C NMR of Compound 15.

FIG. 50 illustrates $^{13}$C NMR (151 MHz, CDCl₃) δ 144.77, 134.80, 129.51, 129.49, 56.06, 36.92, 26.23, 21.82, 16.51, 15.45, 9.56.

Figure 51:
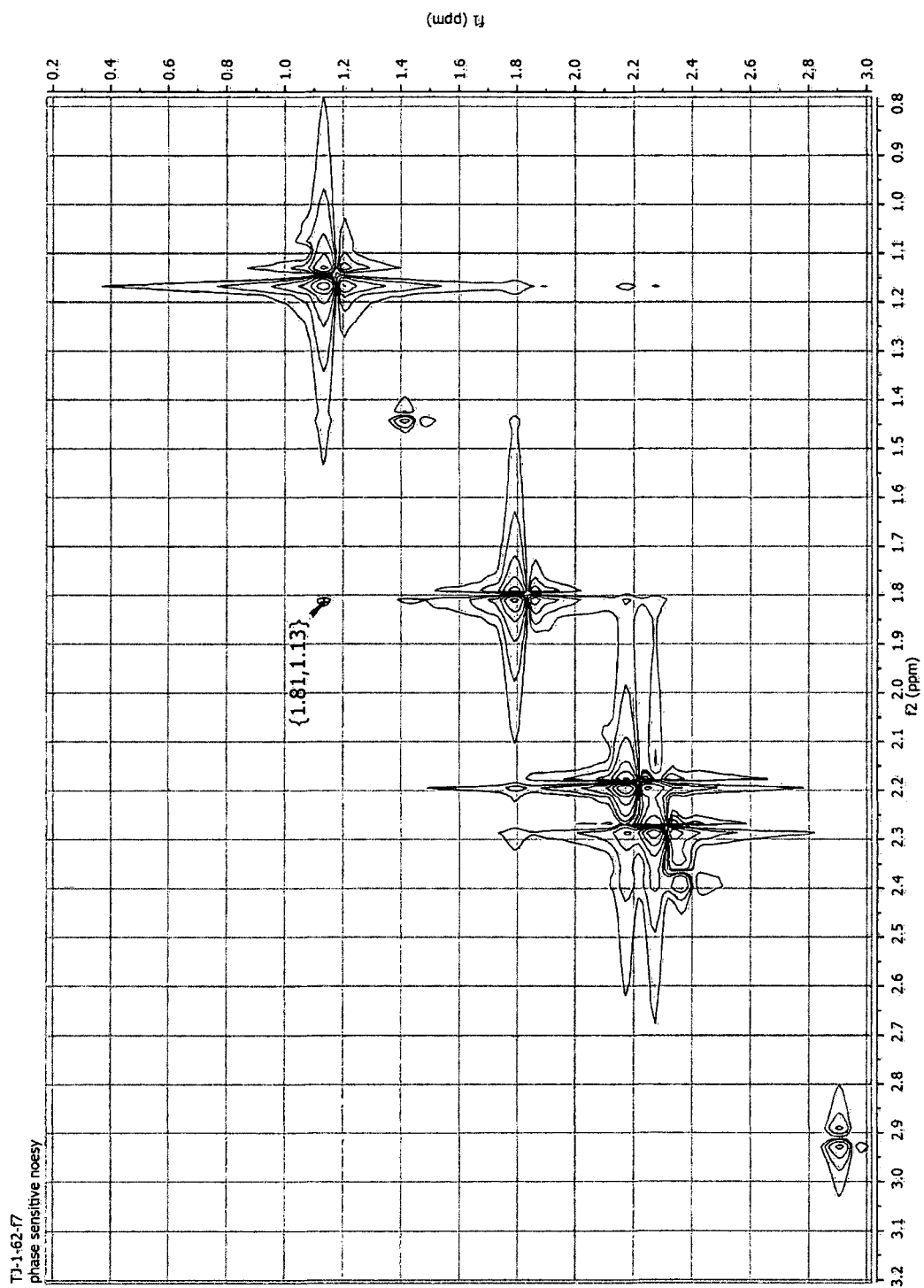
FIG. 51 illustrates NOESY of Compound 15.
Figure 52:
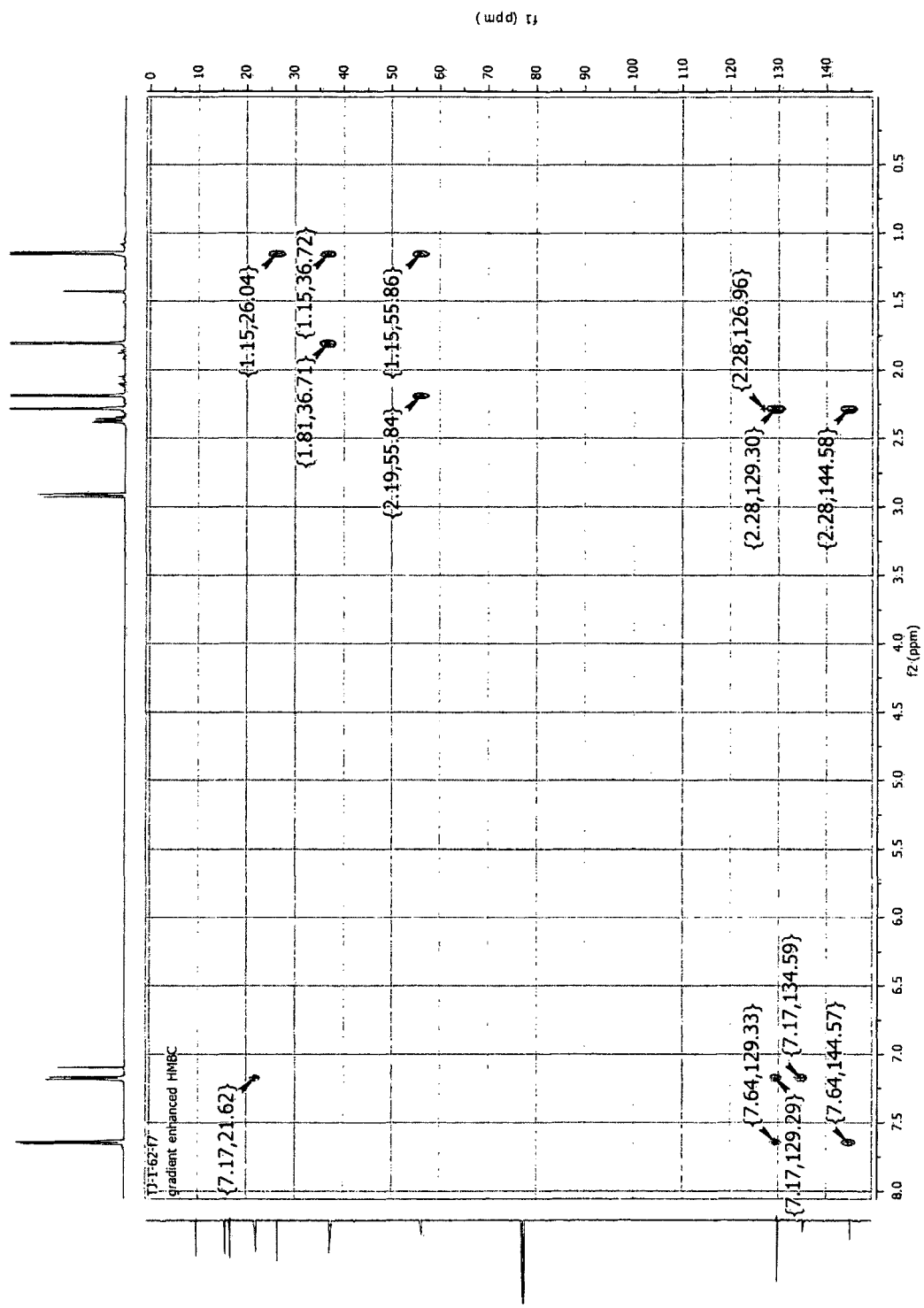
FIG. 52 illustrates HMBC of Compound 15.
Figure 53:
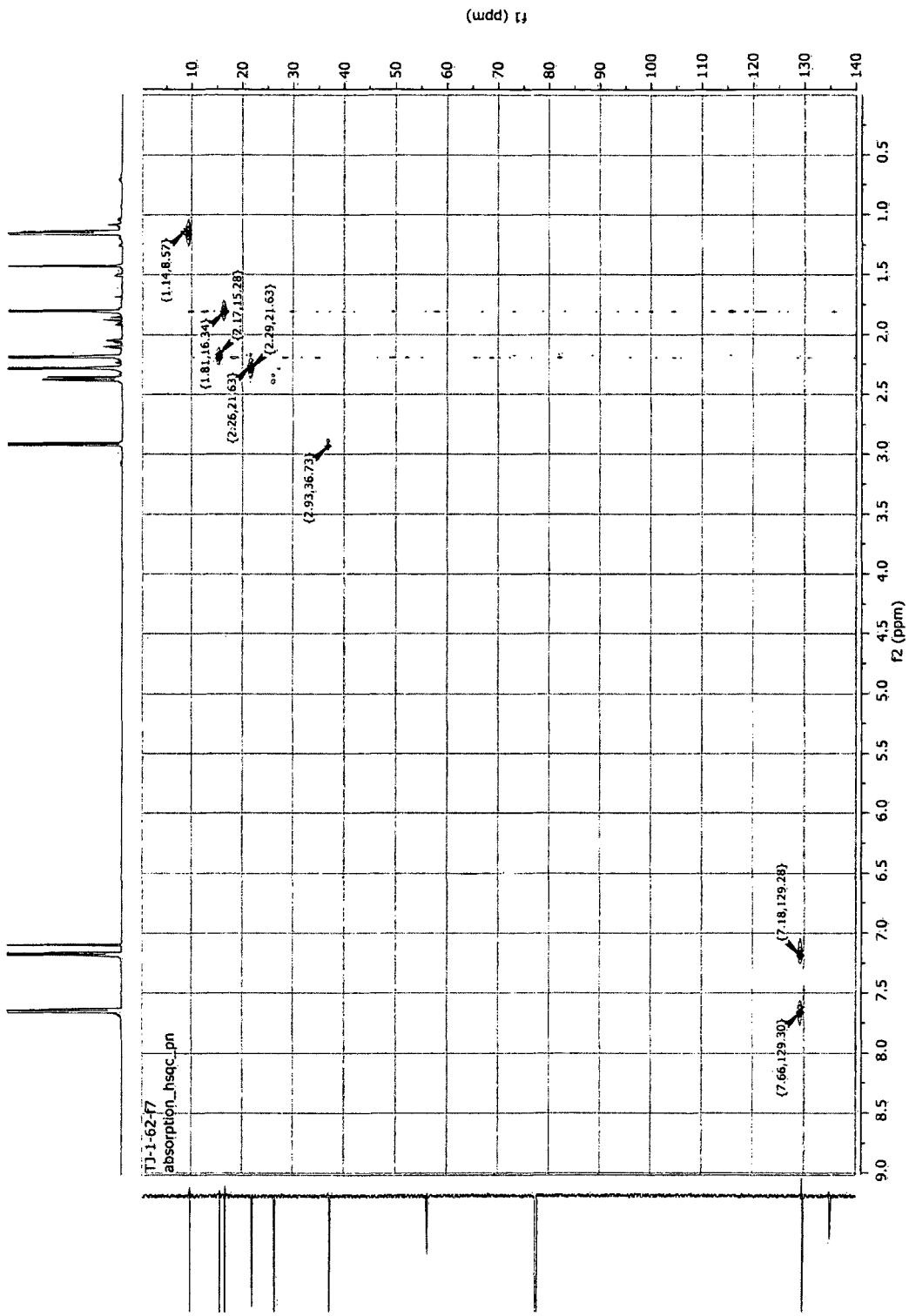
FIG. 53 illustrates HSQC of Compound 15.

FIG. 51 illustrates NOESY of Compound 15.
FIG. 52 illustrates HMBC of Compound 15.
FIG. 53 illustrates HSQC of Compound 15.

HRMS: [M+H]⁺ Expected 303.0542; Obtained 303.0547

[Chem.30]

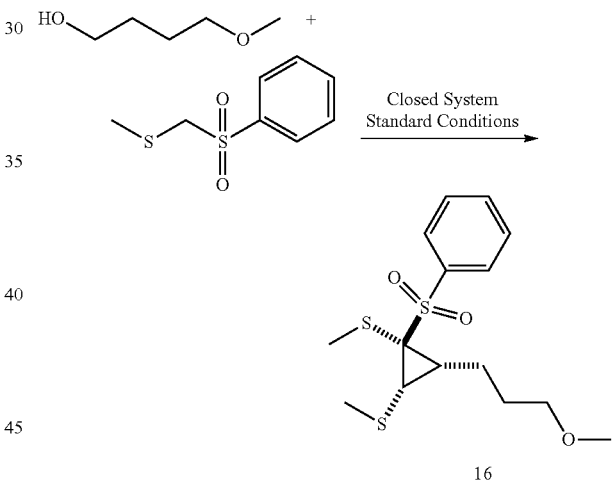

16

Physical state: colorless, viscous liquid; isolated yield 10%

Isolated d. r. 20:1; crude d. r. 20:1 Although the product peak was small when compared to internal standard mesitylene when the reaction was carried out on the 2.0E-4 mol scale, the reaction was repeated on larger scale. The yield is likely small due to O—C bond cleavage under the reaction conditions. Purification can be carried out carefully with Et₂O/hexanes gradient due to the large number of decomposition byproducts. Stereochemical assignment was based on the non-overlapping ring proton possing a coupling constant of ~10 Hz, ruling out a trans assignment. The two ring protons also show a NOESY coupling signal with each other.

Figure 54:
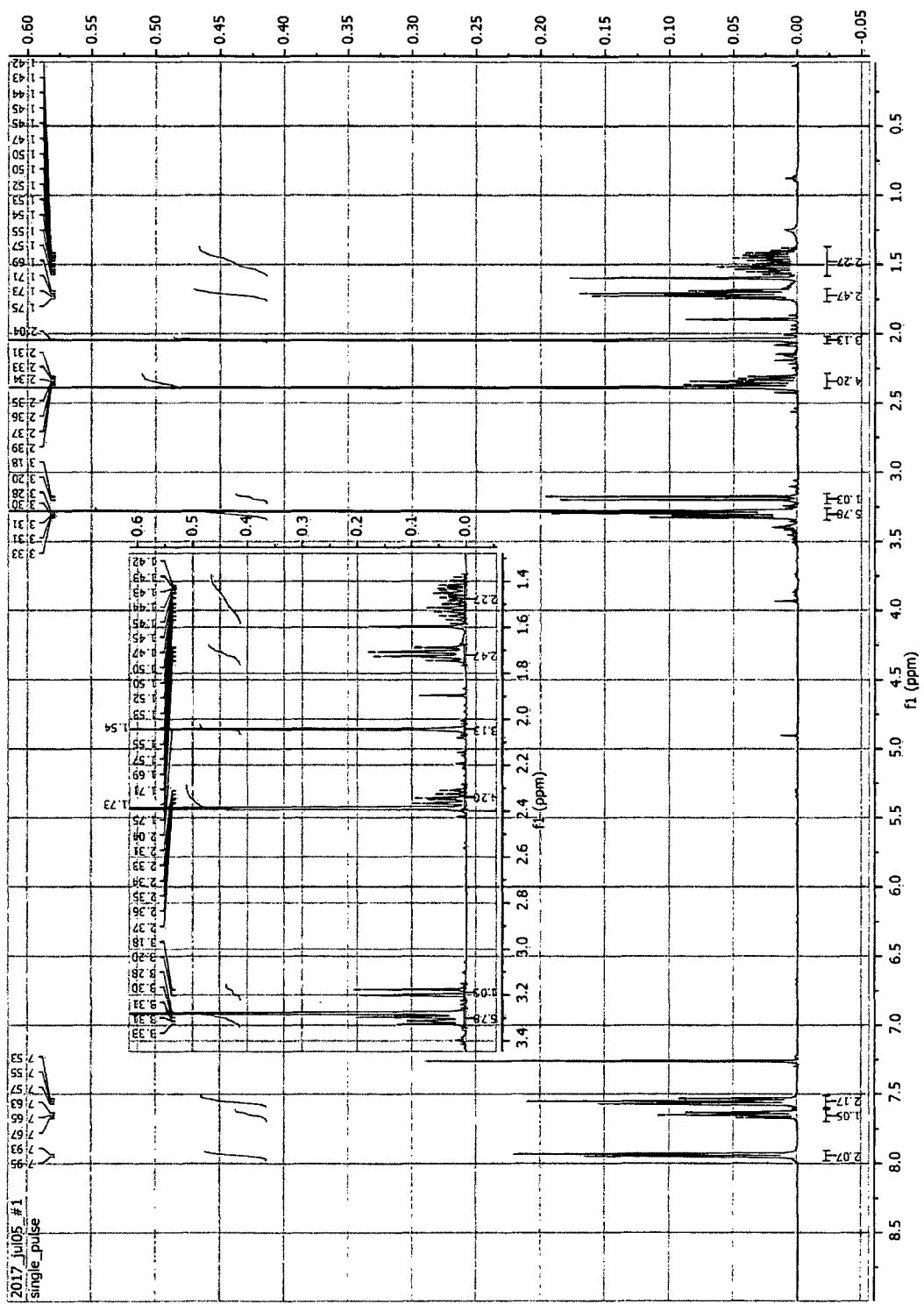
FIG. 54 illustrates ¹H NMR of Compound 16.

FIG. 54 illustrates NMR (400 MHz, Chloroform-d) δ 7.94 (d, J=8.2 Hz, 2H), 7.65 (t, J=7.6 Hz, 1H), 7.55 (t, J=7.6 Hz, 2H), 3.35-3.25 (m, 5H), 3.19 (d, J=9.9 Hz, 1H). 2.41-2.28 (m, 4H), 2.04 (s, 3H), 1.72 (q, J=7.6 Hz, 2H), 1.36-1.59 (m, 2H).

Figure 55:
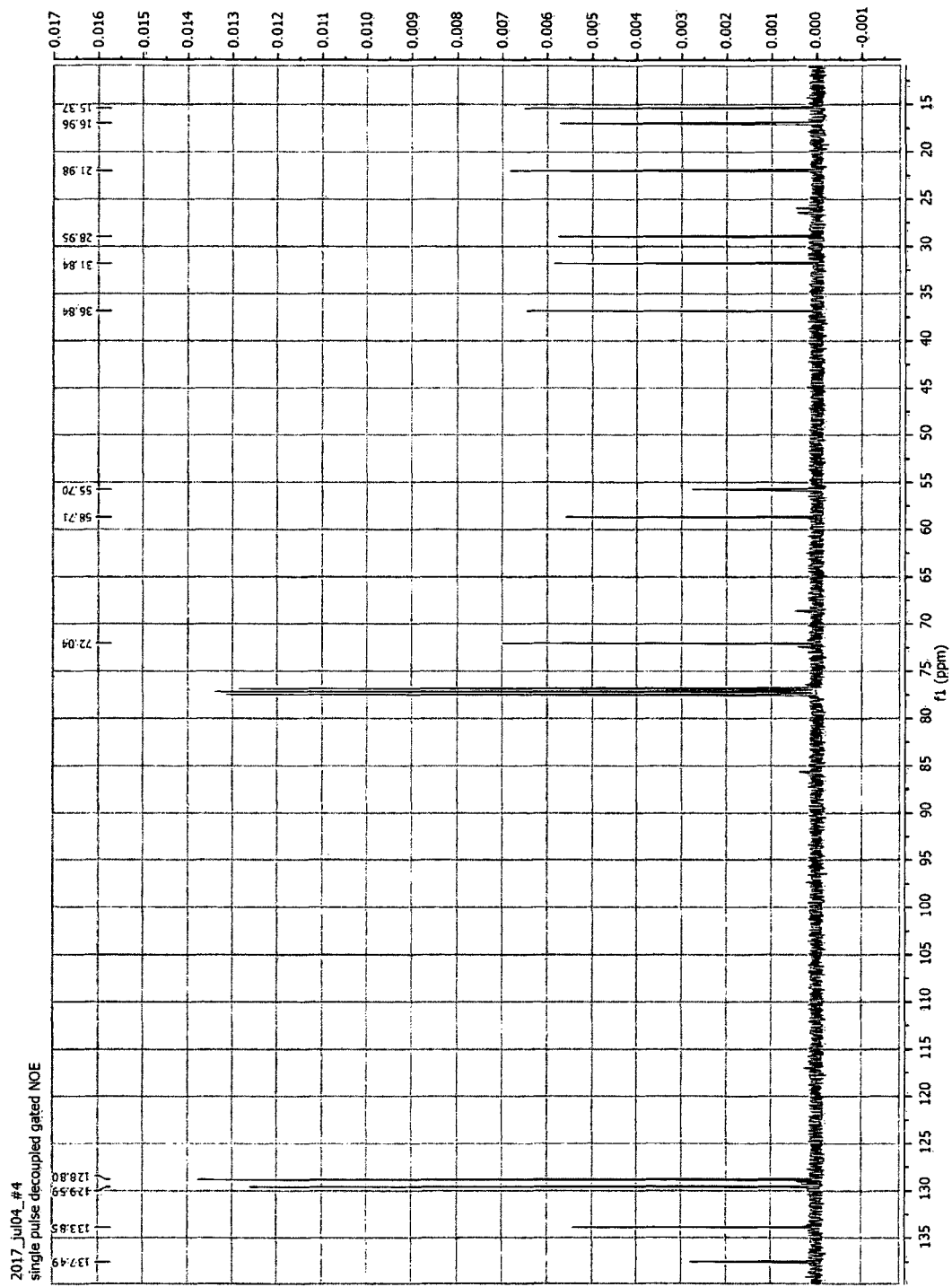
FIG. 55 illustrates ¹³C NMR of Compound 16.

FIG. 55 illustrates $^{13}$C NMR (101 MHz, Chloroform-d) δ 137.49, 133.85, 129.59, 128.80, 72.04, 58.71, 55.70, 36.84, 31.84, 28.95, 21.98, 16.96, 15.37.

Figure 56:
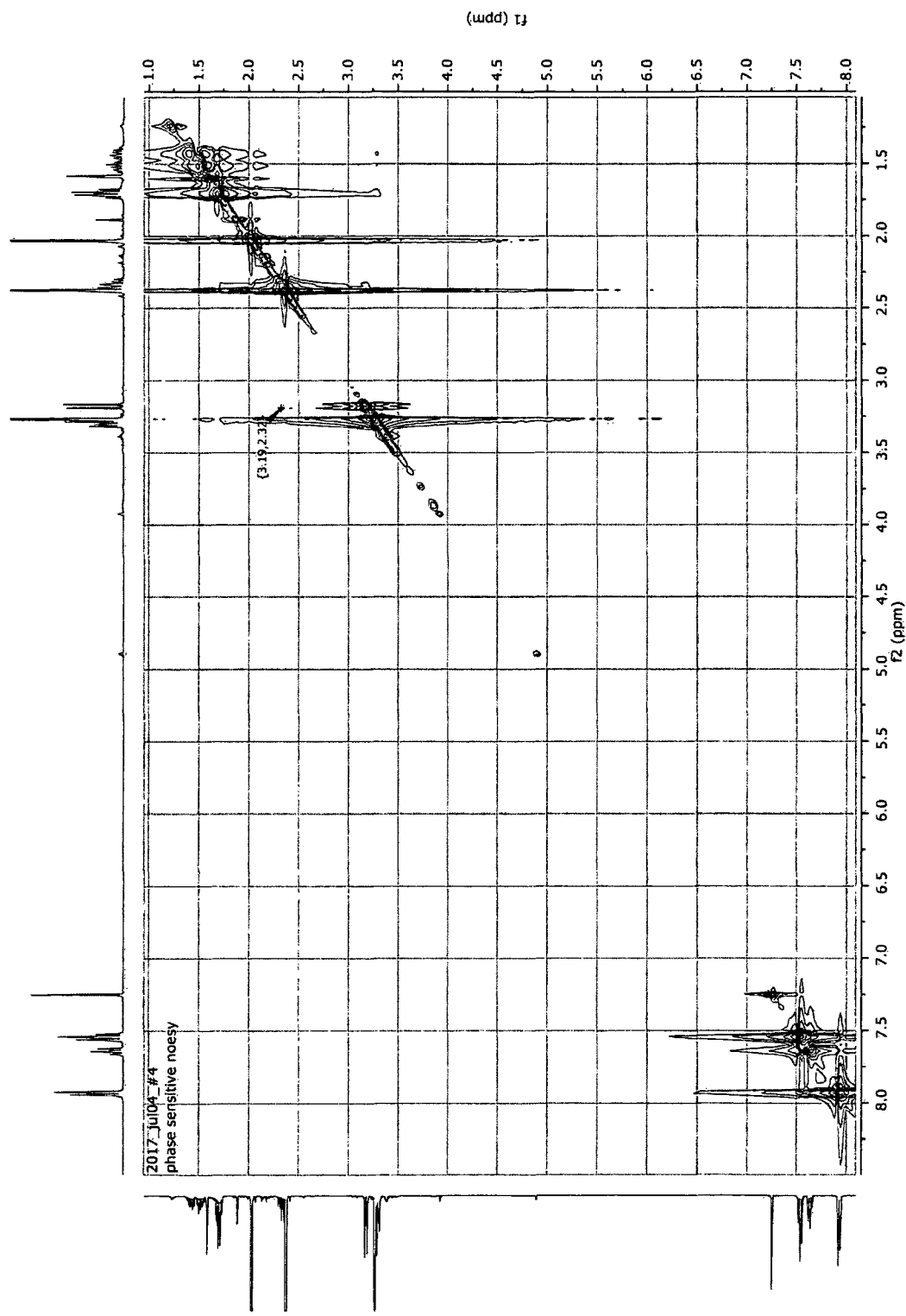
FIG. 56 illustrates NOESY of Compound 16.

FIG. 56 illustrates NOESY of Compound 16.

HRMS: [M+H]$^+$ Expected 347.0804; Obtained 347.0813

[Chem.31]

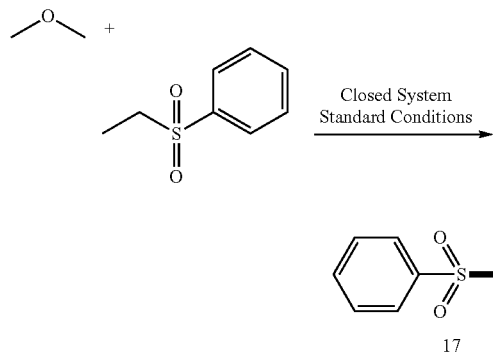

Physical state: colorless oil; isolated yield 53%

Isolated d. r. 99:1; Crude d. r. 49:1 NOESY spectrum was ambiguous, so assignment is based on reactivity precedent with substituents of both sulfonates appearing trans to the remaining sulfonate in the final product, and compound 17 being meso.

Figure 57:
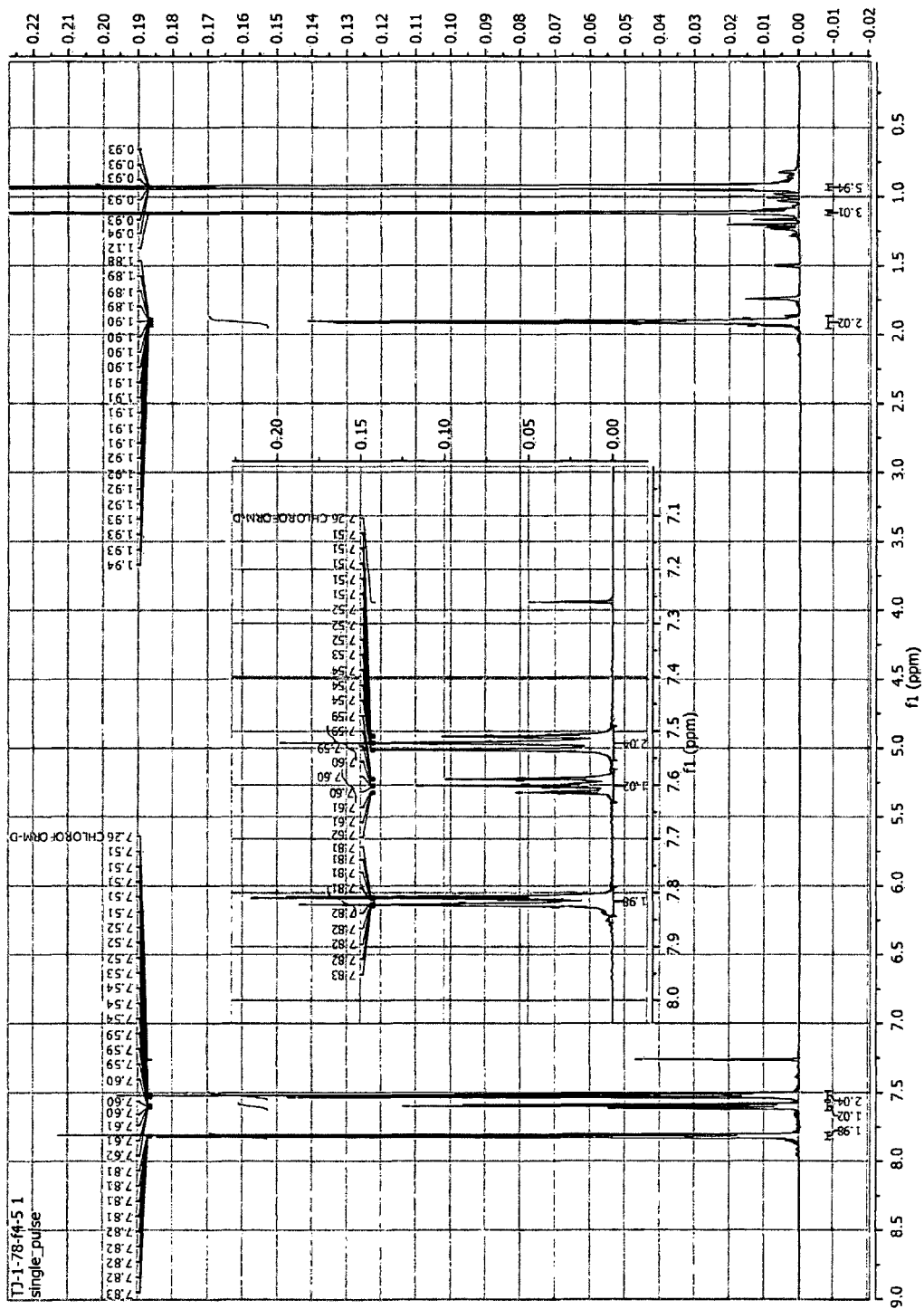
FIG. 57 illustrates NMR of Compound 17.

FIG. 57 illustrates $^1$H NMR (600 MHz, Chloroform-d) δ 7.84-7.79 (m, 2H), 7.63-7.57 (m, 1H), 7.55-7.49 (m, 2H), 1.96-1.87 (m, 2H), 1.12 (s, 3H), 0.95-0.91 (m, 6H).

Figure 58:
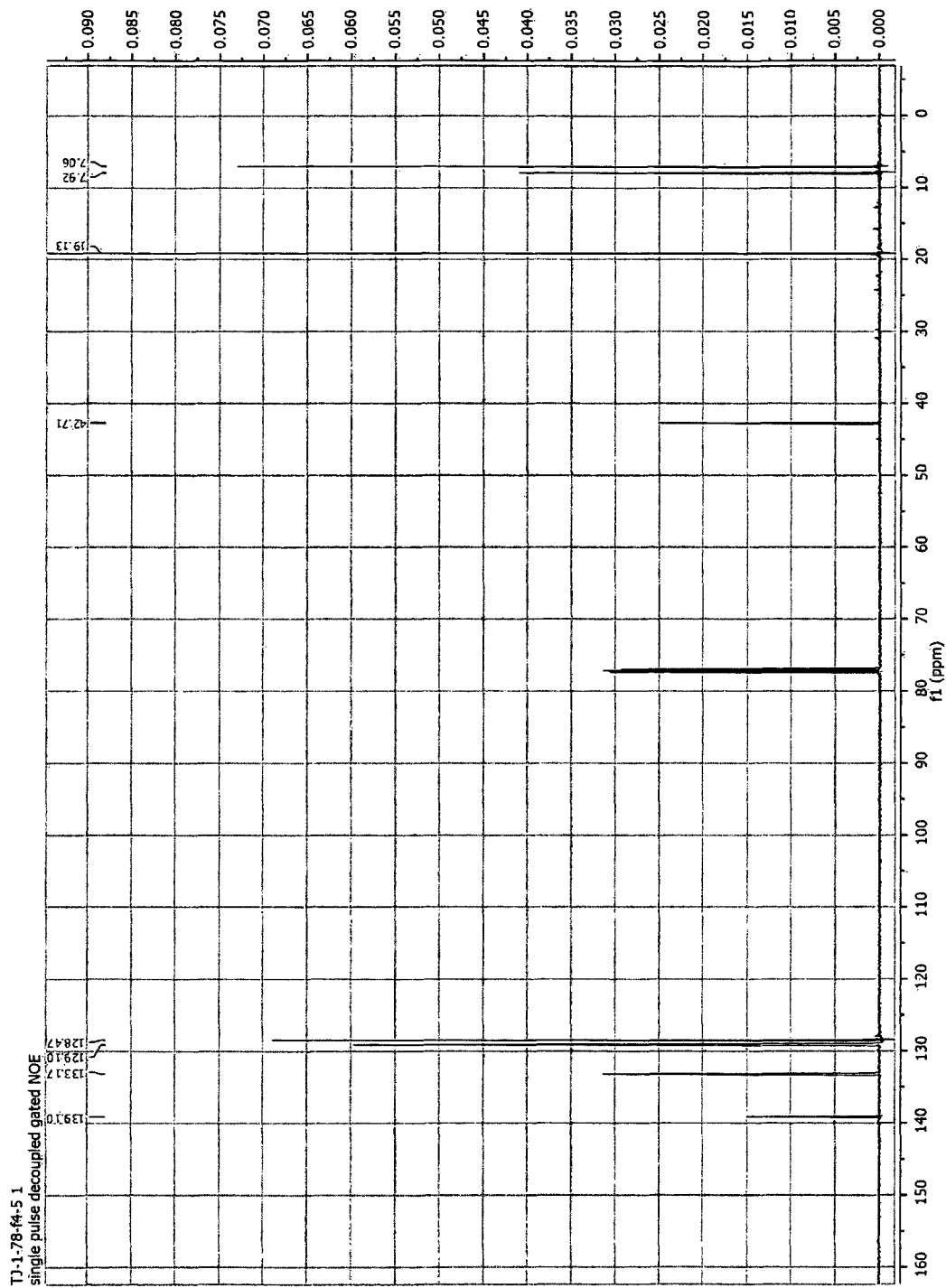
FIG. 58 illustrates ¹³C NMR of Compound 17.

FIG. 58 illustrates $^{13}$C NMR (151 MHz, Chloroform-d) δ 139.10, 133.17, 129.10, 128.47, 42.71, 19.13, 7.92, 7.06.

Figure 59:
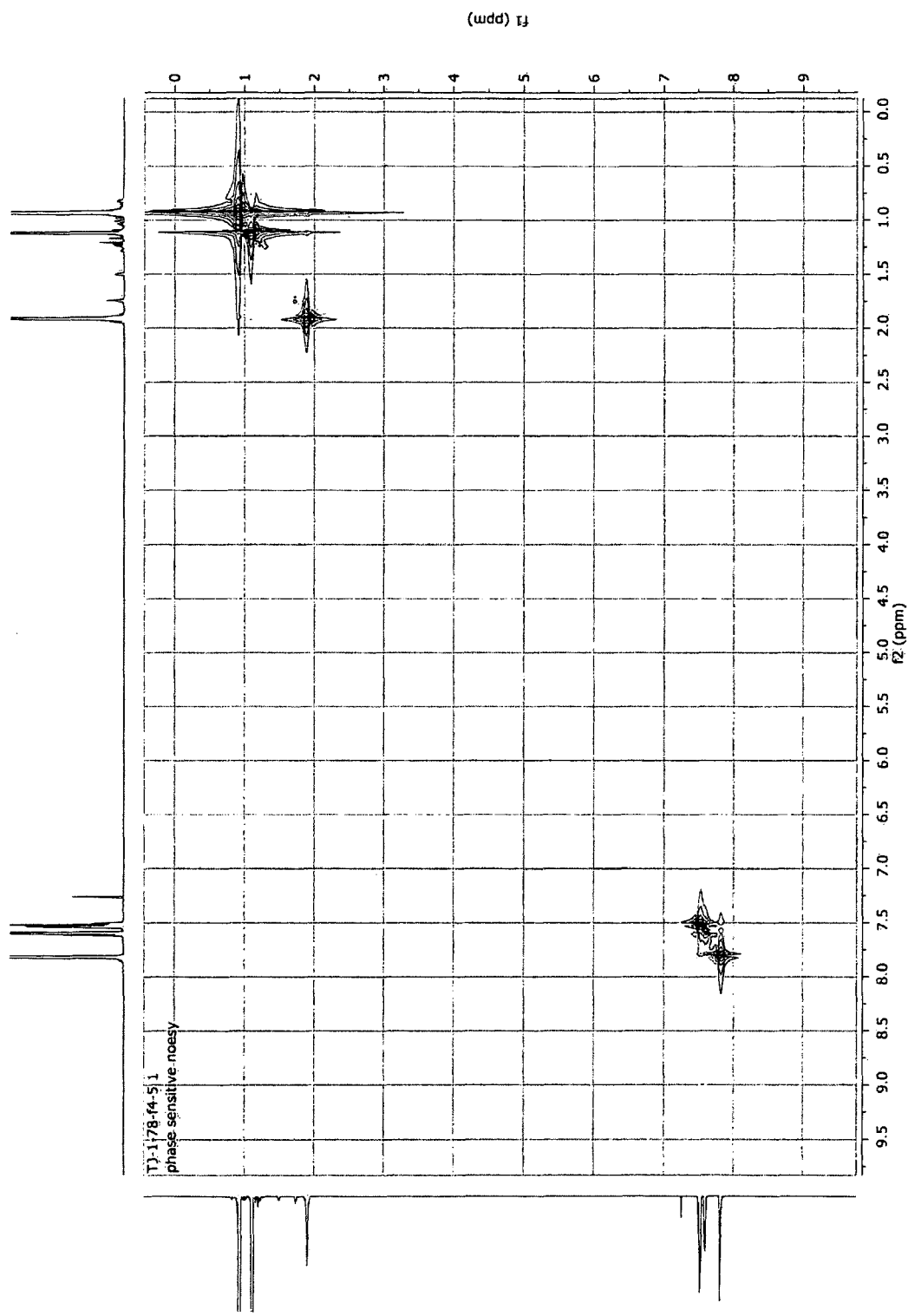
FIG. 59 illustrates NOESY of Compound 17.

FIG. 59 illustrates NOESY of Compound 17.

HRMS: [M+H]$^+$ Expected 225.0944; Obtained 225.0945

[Chem.32]

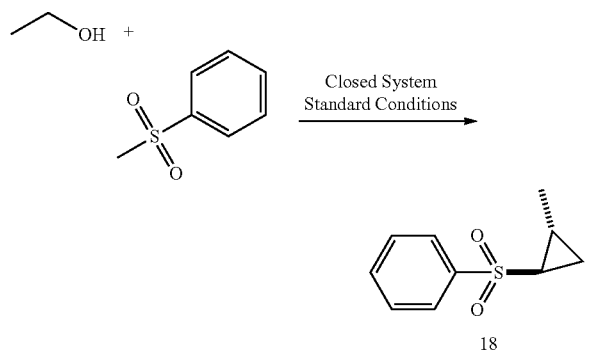

Physical state: colourless oil; isolated yield 72%

Isolated d. r. 12:1; crude d. r. 10:1. Isolated d. r. is very similar to crude d. r. due to the small differences in dipole moment between the diastereomers and thus difficulty in separation by flash chromatography. The isolated/crude d. r. are calculated from integrating aliphatic peaks in $^{13}$CNMR and GC/MS data. Assignment made based on no NOESY coupling between sulfonate and methyl substituted protons and only one NOESY coupling of the sulfonate proton to other protons.

Figure 60:
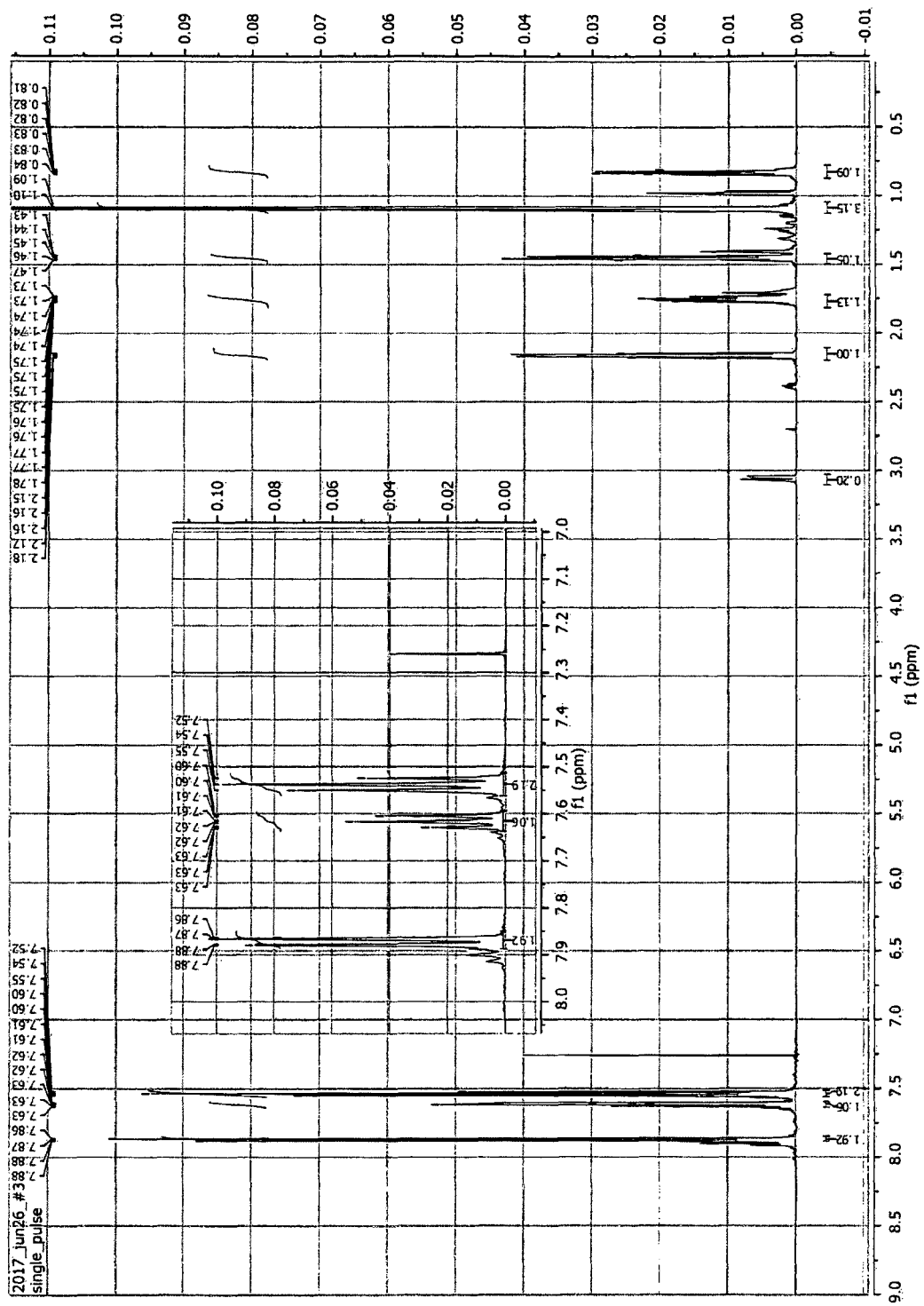
FIG. 60 illustrates ¹H NMR of Compound 18.

FIG. 60 illustrates $^1$H NMR (600 MHz, Chloroform-d) δ 7.87 (dd, J=8.4, 1.3 Hz, 2H), 7.64-7.59 (m, 1H), 7.54 (t, J=7.7 Hz, 2H), 2.20-2.11 (m, 1H), 1.82-1.72 (m, 1H), 1.45 (dt, J=10.1, 5.0 Hz, 1H), 1.09 (d, J=6.2 Hz, 3H), 0.83 (dt, J=8.0, 5.9 Hz, 1H).

Figure 61:
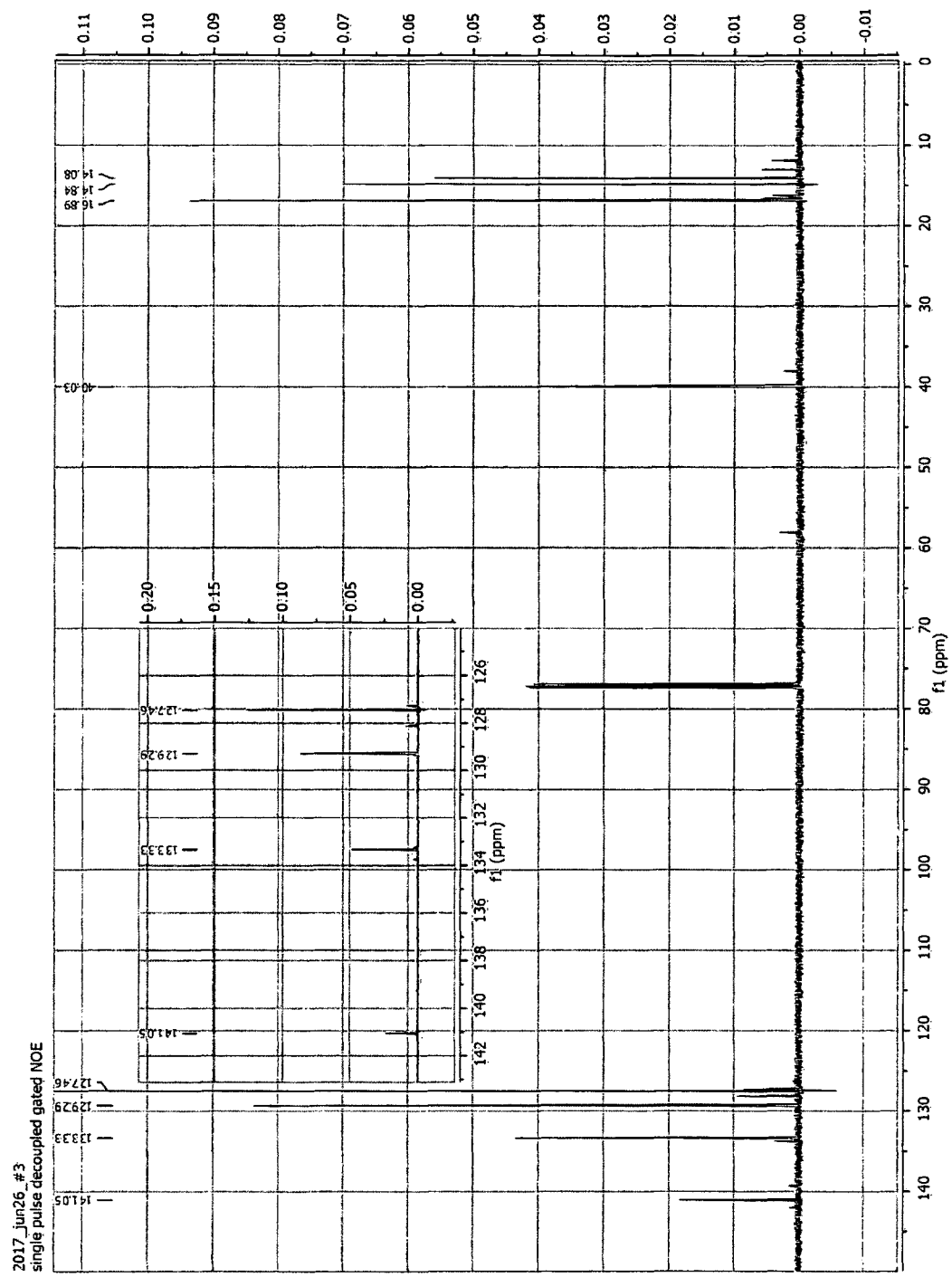
FIG. 61 illustrates ¹³C NMR of Compound 18.

FIG. 61 illustrates $^{13}$C NMR (151 MHz, Chloroform-d) δ 141.05, 133.33, 129.29, 127.46, 40.03, 16.89, 14.84, 14.08.

Figure 62:
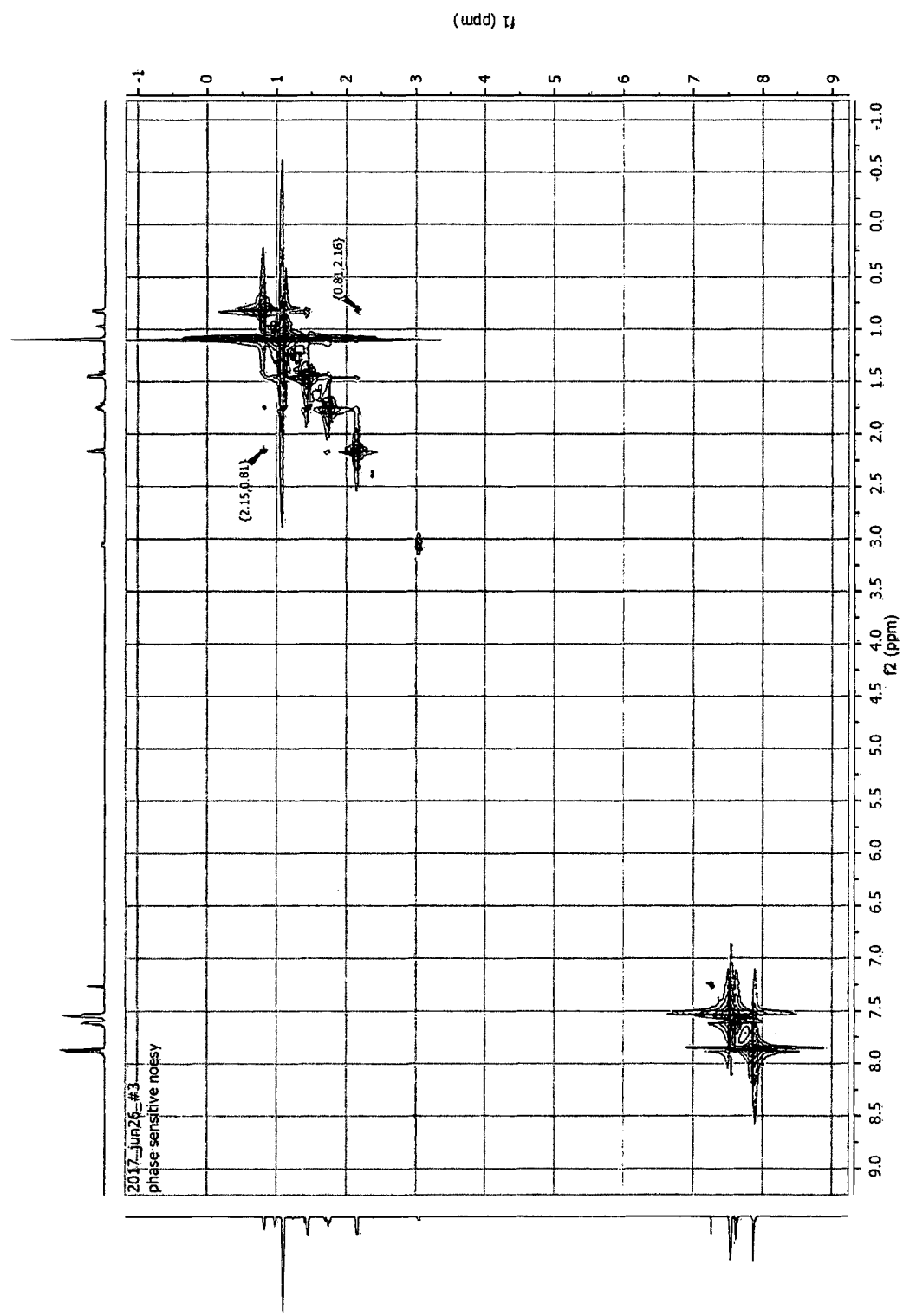
FIG. 62 illustrates NOESY of Compound 18.
Figure 63:
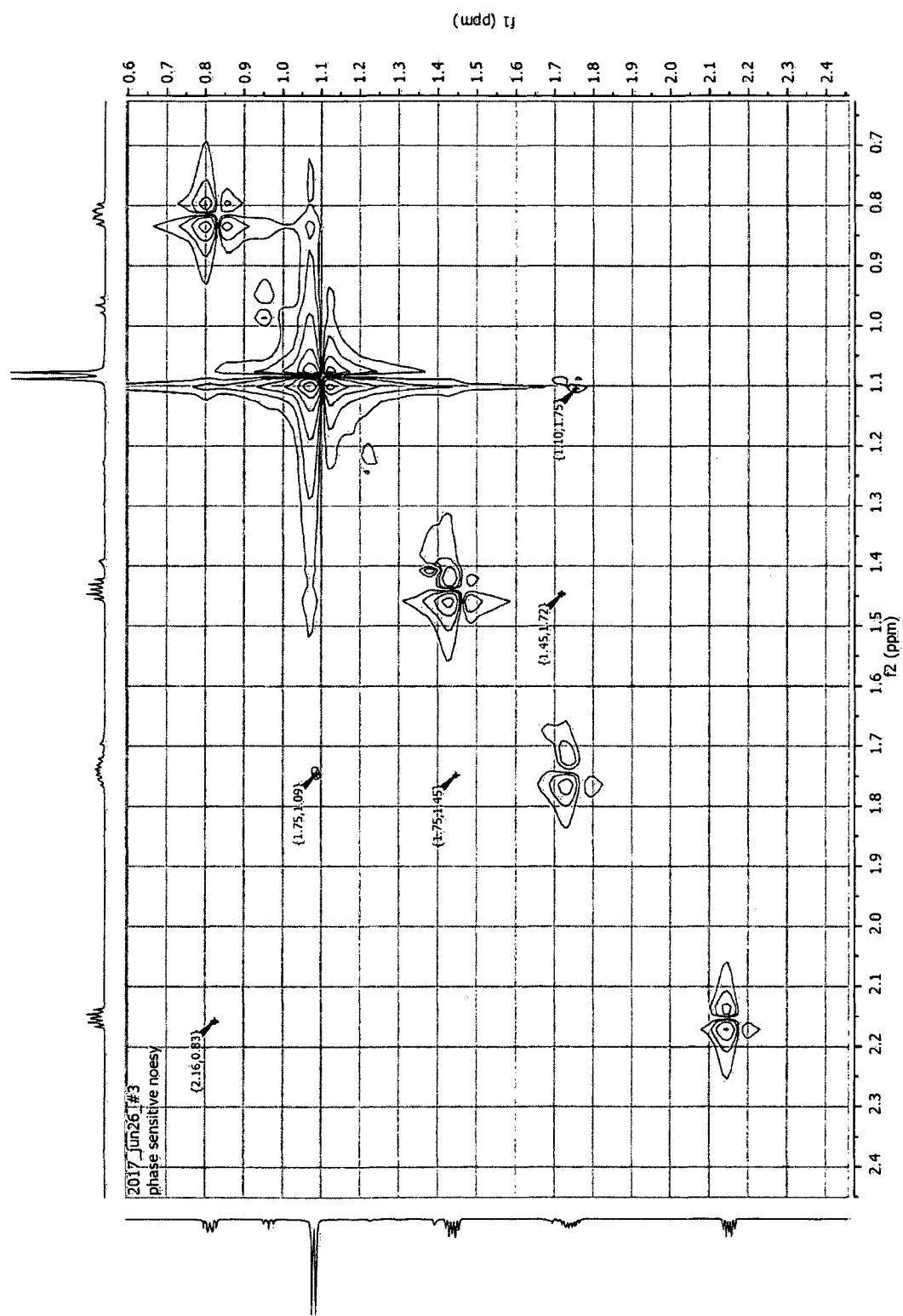
FIG. 63 illustrates NOESY of Compound 18 aliphatic region close-up.

FIG. 62 illustrates NOESY of Compound 18. FIG. 63 illustrates NOESY of Compound 18 aliphatic region close-up.

HRMS: [M+H]$^+$ Expected 197.0631; Obtained 197.0633

[Chem.33]

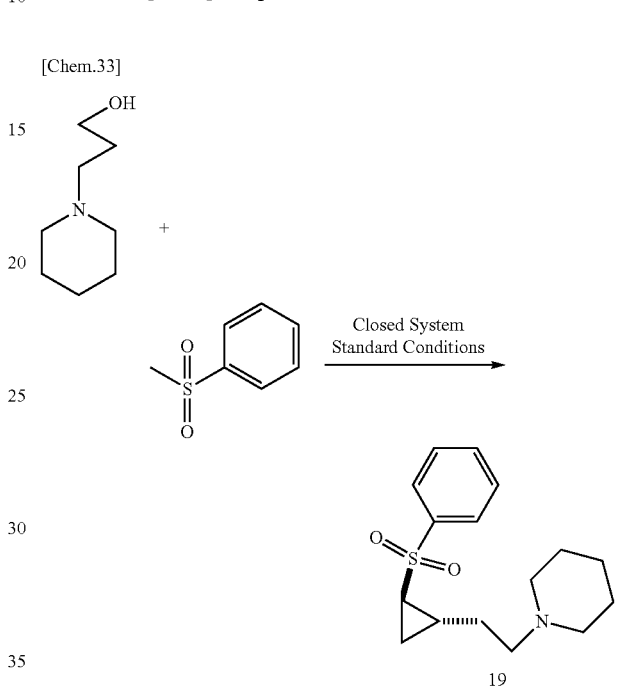

Physical state: white solid; isolated yield 28%

Isolated d. r. 15:1; crude d. r. 15:1 NOESY spectrum was not helpful, so assignment was made based on compound 18.

Figure 64:
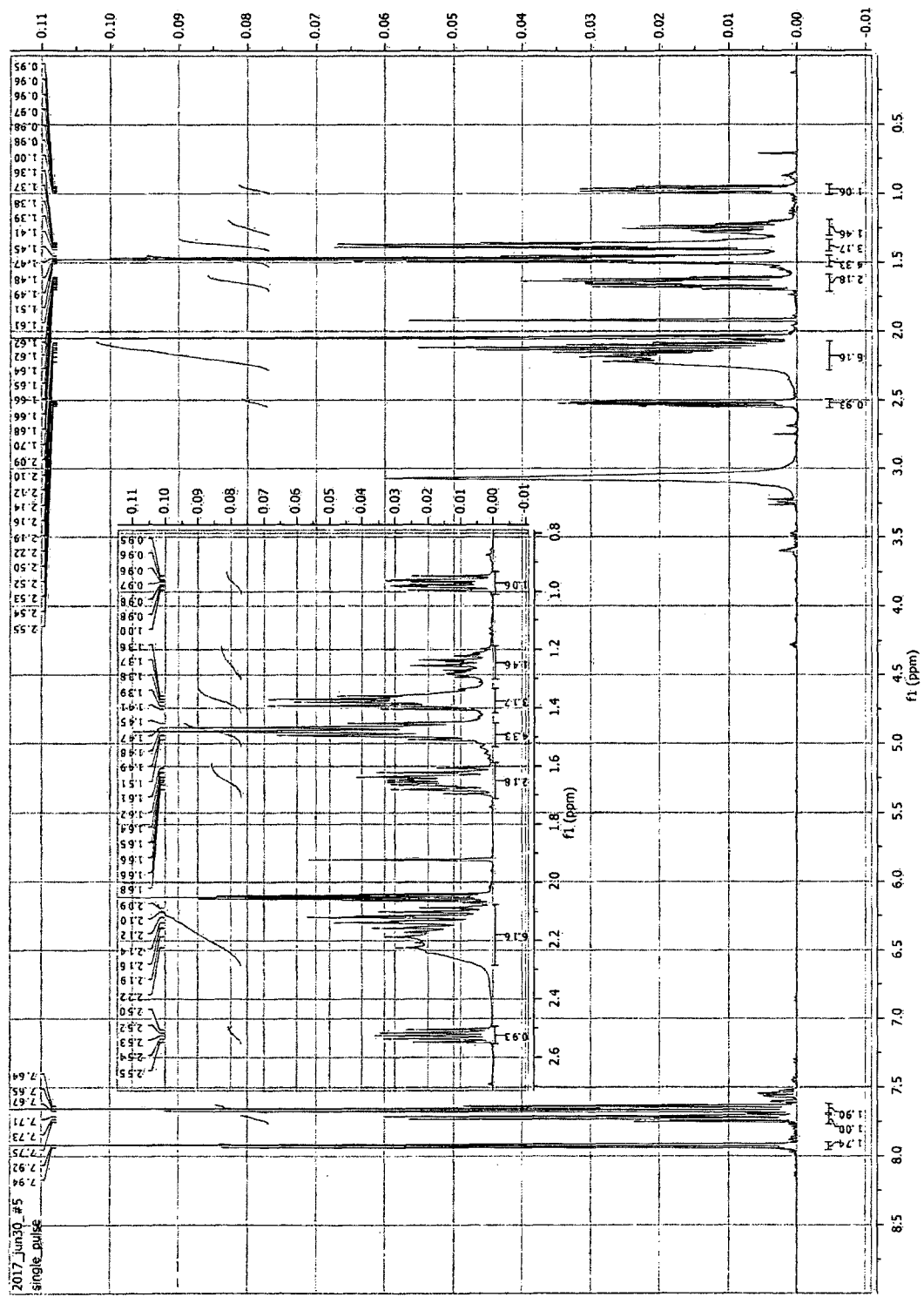
FIG. 64 illustrates ¹H NMR of Compound 19.
Figure 65:
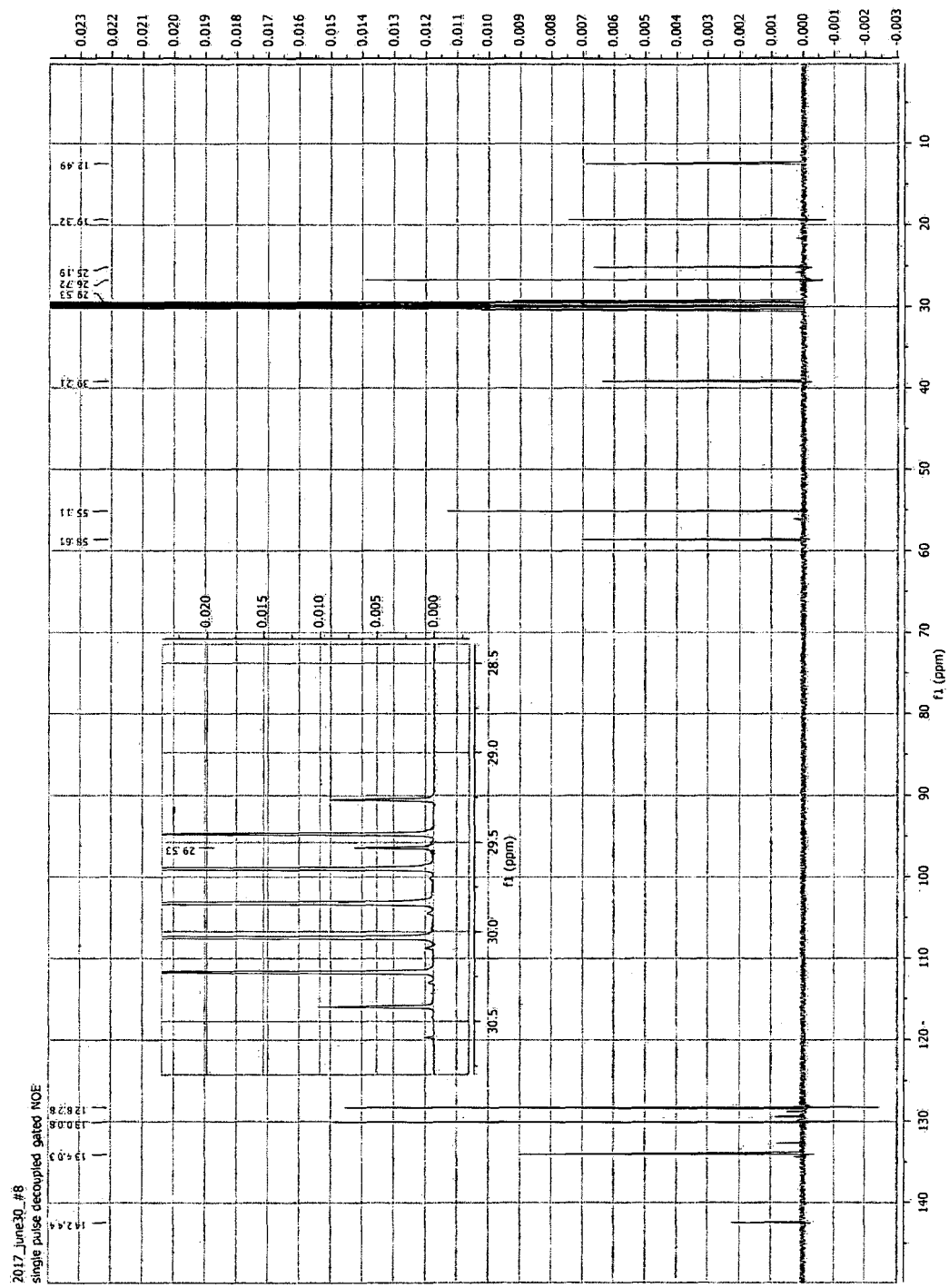
FIG. 65 illustrates ¹³C NMR of Compound 19.

FIG. 64 illustrates $^1$H NMR (400 MHz, Acetone-d$_6$) δ 7.93 (d, J=7.0 Hz, 2H), 7.76-7.70 (m, 1H), 7.65 (t, J=7.4 Hz, 2H), 2.57-2.48 (m, 1H), 2.28-2.08 (m, 6H), 1.72-1.58 (m, 2H), 1.48 (p, J=5.6 Hz, 4H), 1.43-1.33 (m, 3H), 1.21-1.29 (m, 1H), 1.02-0.92 (m, 1H). Water peak (HOD) at 3.05 ppm FIG. 65 illustrates $^{13}$C NMR (101 MHz, Acetone-d$_6$) δ 142.44, 134.03, 130.08, 128.28, 58.61, 55.11, 39.21, 29.53, 26.72, 35.19, 19.32, 12.49.

Figure 66:
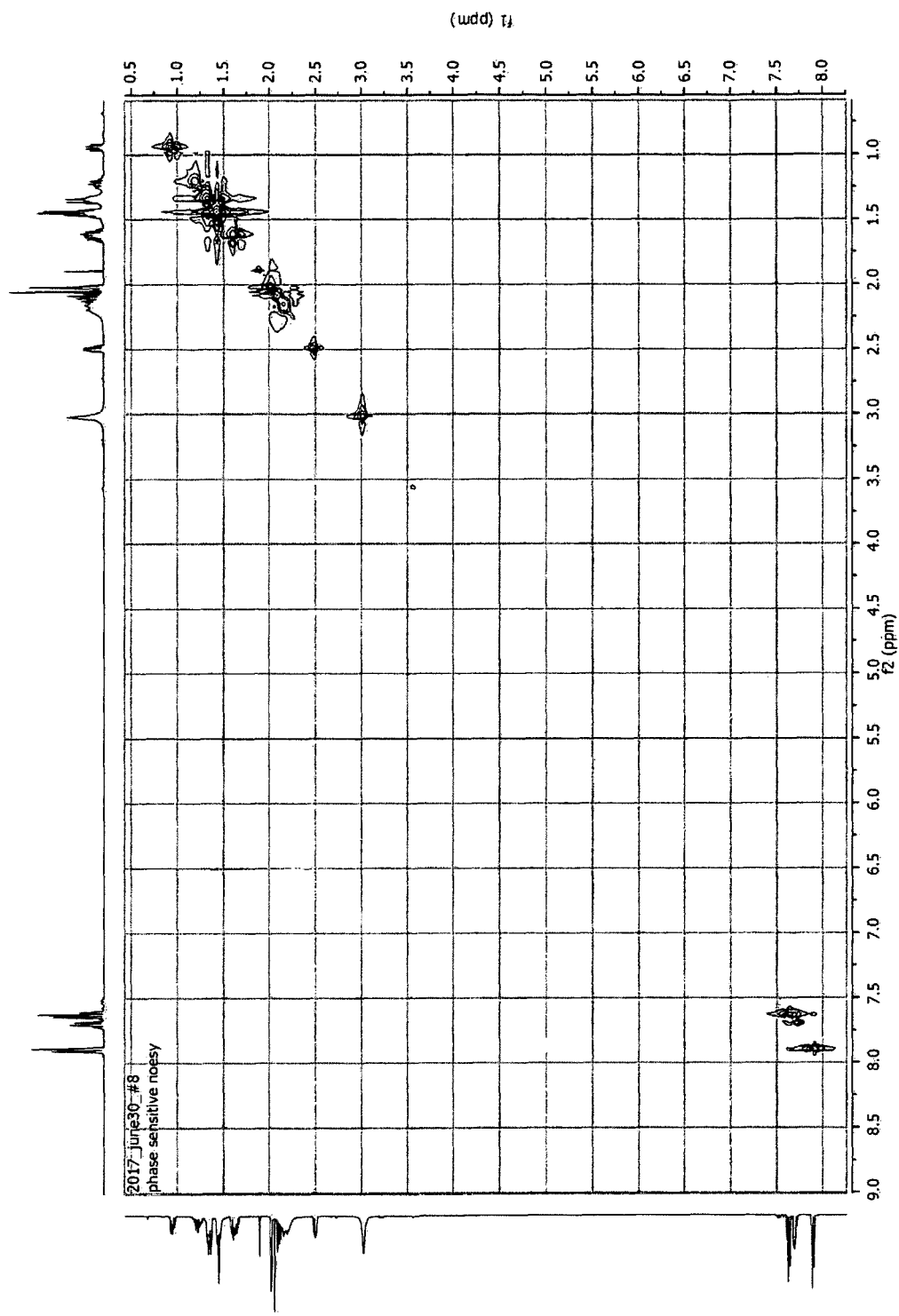
FIG. 66 illustrates NOESY of Compound 19.
Figure 67:
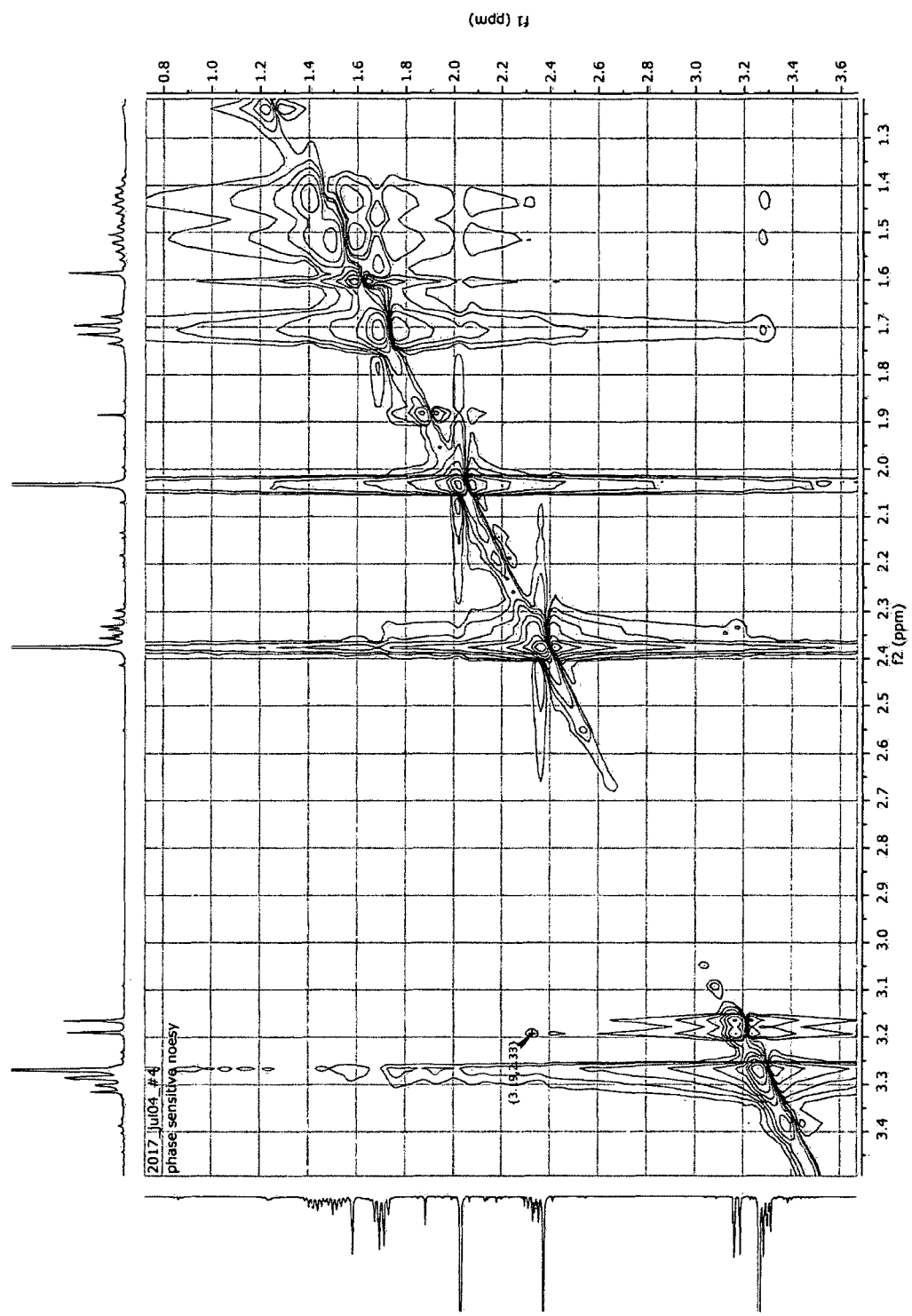
FIG. 67 illustrates NOESY aliphatic expansion of Compound 19.

FIG. 66 illustrates NOESY of Compound 19. FIG. 67 illustrates NOESY aliphatic expansion of Compound 19.

HRMS: [M+H]$^+$ Expected 294.1522; Obtained 294.1527

[Chem.34]

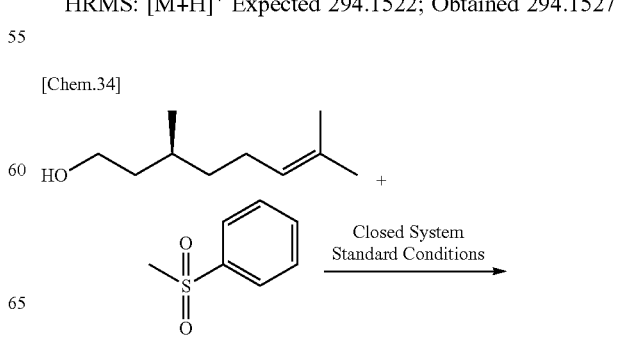

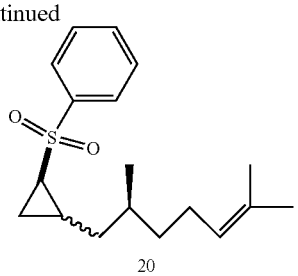

20

Physical state: colorless gel; isolated yield 50%

Isolated d. r. 1.6:1; crude d. r. 1.6:1 The reaction proceeds with full conversion and high yield according to GC/MS of the crude mixture. Due to very similar polarity, the two diastereomers were not separated by column chromatography. A small impurity at 3.05 ppm is from a minor product that fully comes out at a more polar gradient. Its identity has not been determined, but it is a cyclopropane derivative that does contain a CC double bond according to its $^{13}$CNMR. For the carbon NMR, peaks are given for both diastereomers if there is no overlap. It was impossible for the inventor to tell which diastereomer is the major one, as they are present in almost equal proportions and the NOESY spectrum cannot give useful information.

Figure 68:
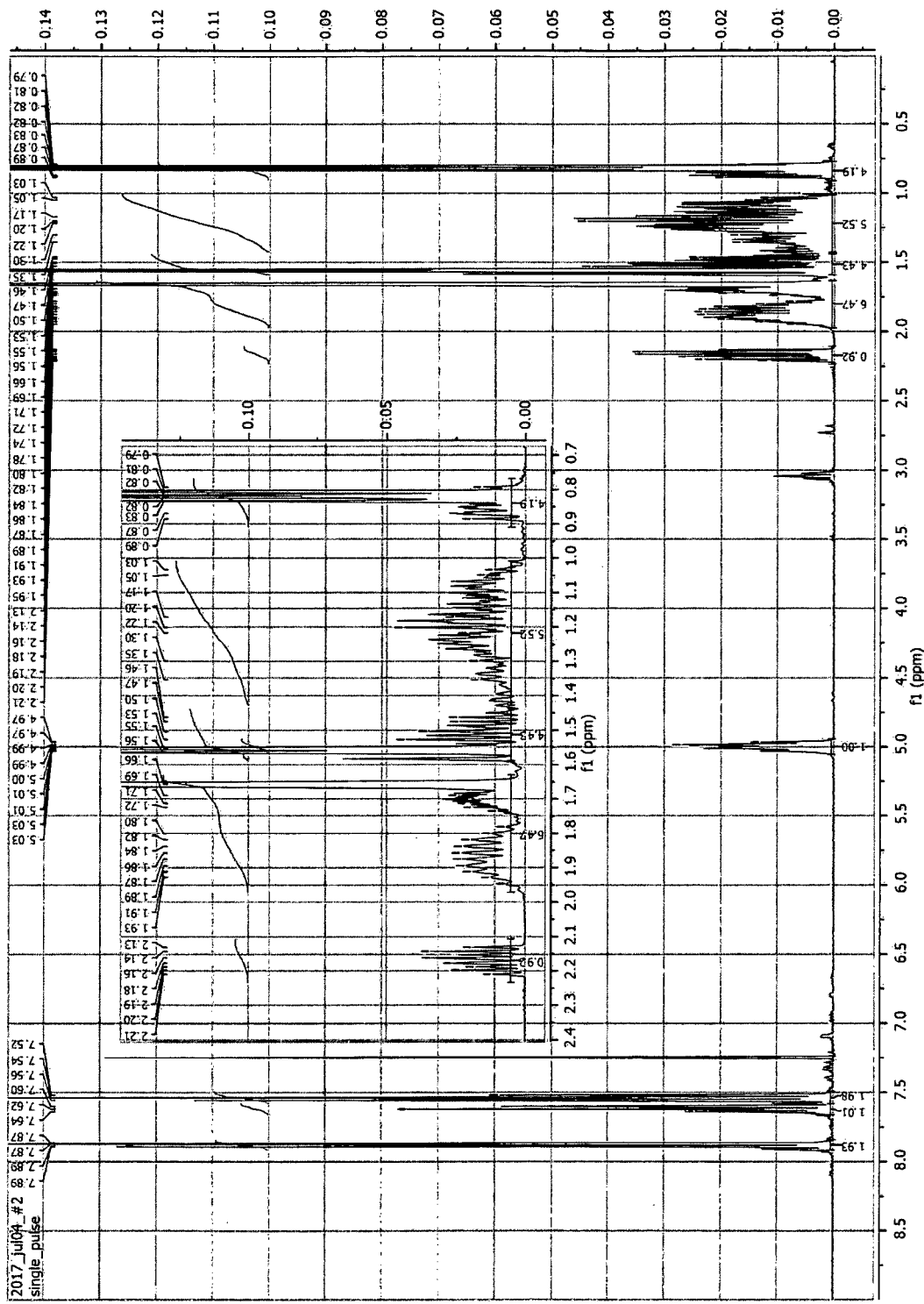
FIG. 68 illustrates ¹H NMR of Compound 20.

FIG. 68 illustrates $^1$H NMR (400 MHz, Chloroform-d) δ 7.88 (dd, J=8.4, 1.1 Hz, 2H), 7.62 (t, J=7.4 Hz, 1H), 7.54 (t, J=7.6 Hz, 2H), 5.06-4.94 (m, 1H), 2.23-2.11 (m, 1H), 1.97-1.64 (m, 6H), 1.59-1.44 (m, 4H), 1.40-1.00 (m, 5H), 0.91-0.77 (m, 4H).

Figure 69:
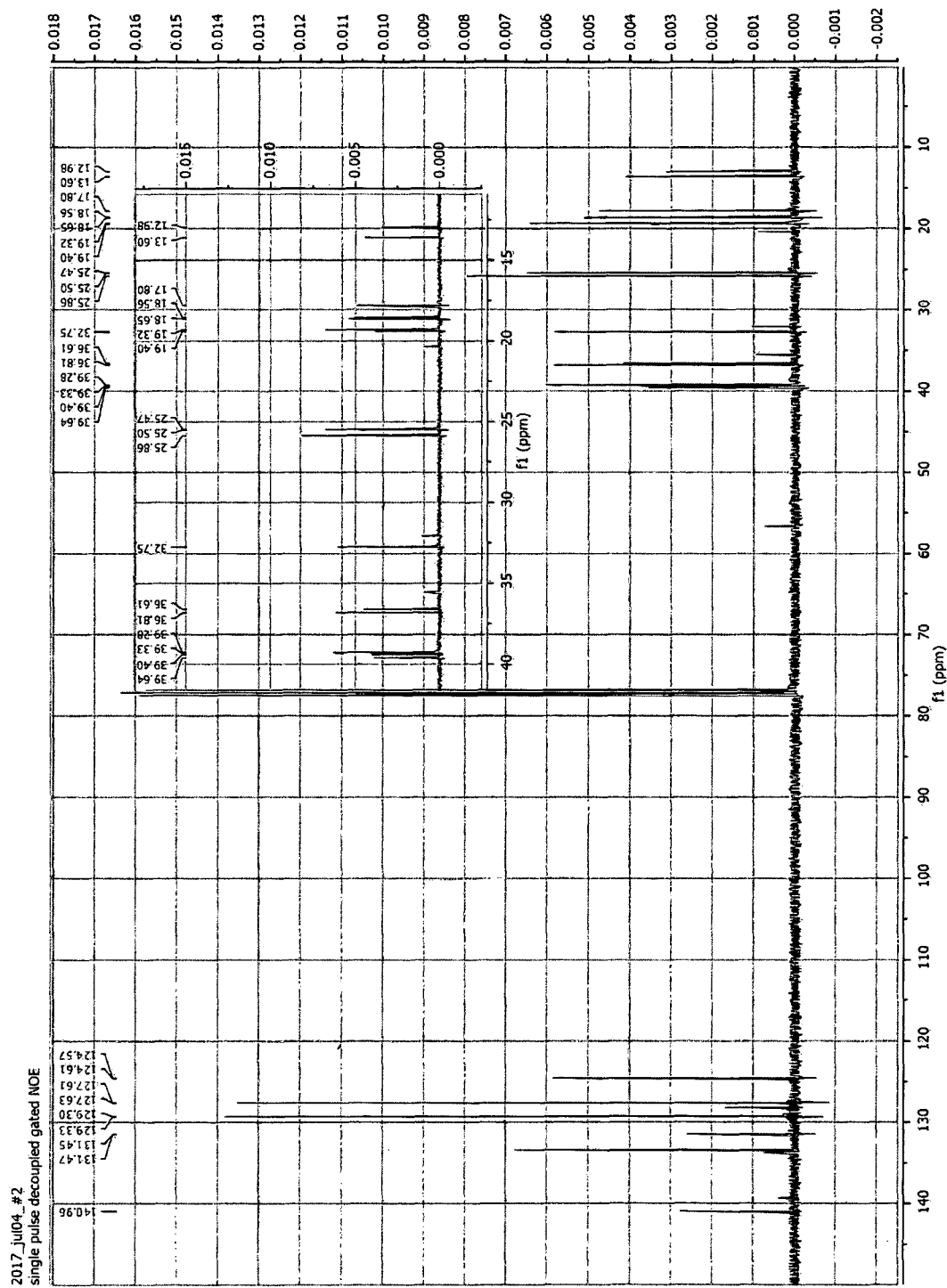
FIG. 69 illustrates ¹³C NMR of Compound 20.

FIG. 69 illustrates $^{13}$C NMR (101 MHz, Chloroform-d) δ 140.96, 131.47, 131.45, 129.33, 129.30, 127.63, 127.61, 124.61, 124.57, 39.64, 39.40, 39.33, 39.28, 36.81, 36.61, 32.75, 25.86, 25.50, 25.47, 19.40, 19.32, 18.65, 18.56, 17.80, 13.60, 12.98.

HRMS: [M+H]$^+$ Expected 307.1726; Obtained 307.1731

[Chem.35]

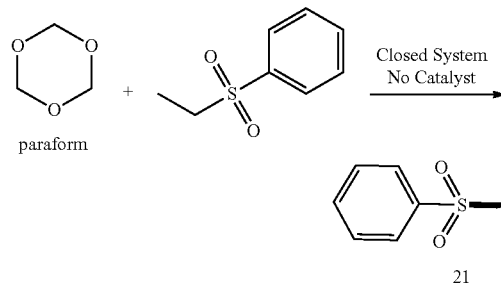

21

Physical state: Colorless Oil; isolated yield 38%

Isolated d. r. 50:1; crude d. r. 50:1 Assignment is made on the basis that the methyl substituted ring proton at 1.96 ppm only has one NOESY coupling to its methyl group while its trans partner has a very slight coupling to the Me on the sulfone substituted carbon. According to reactivity precedent with all other products, substituents from both sulfonates should be trans to the remaining sulfonate.

Figure 70:
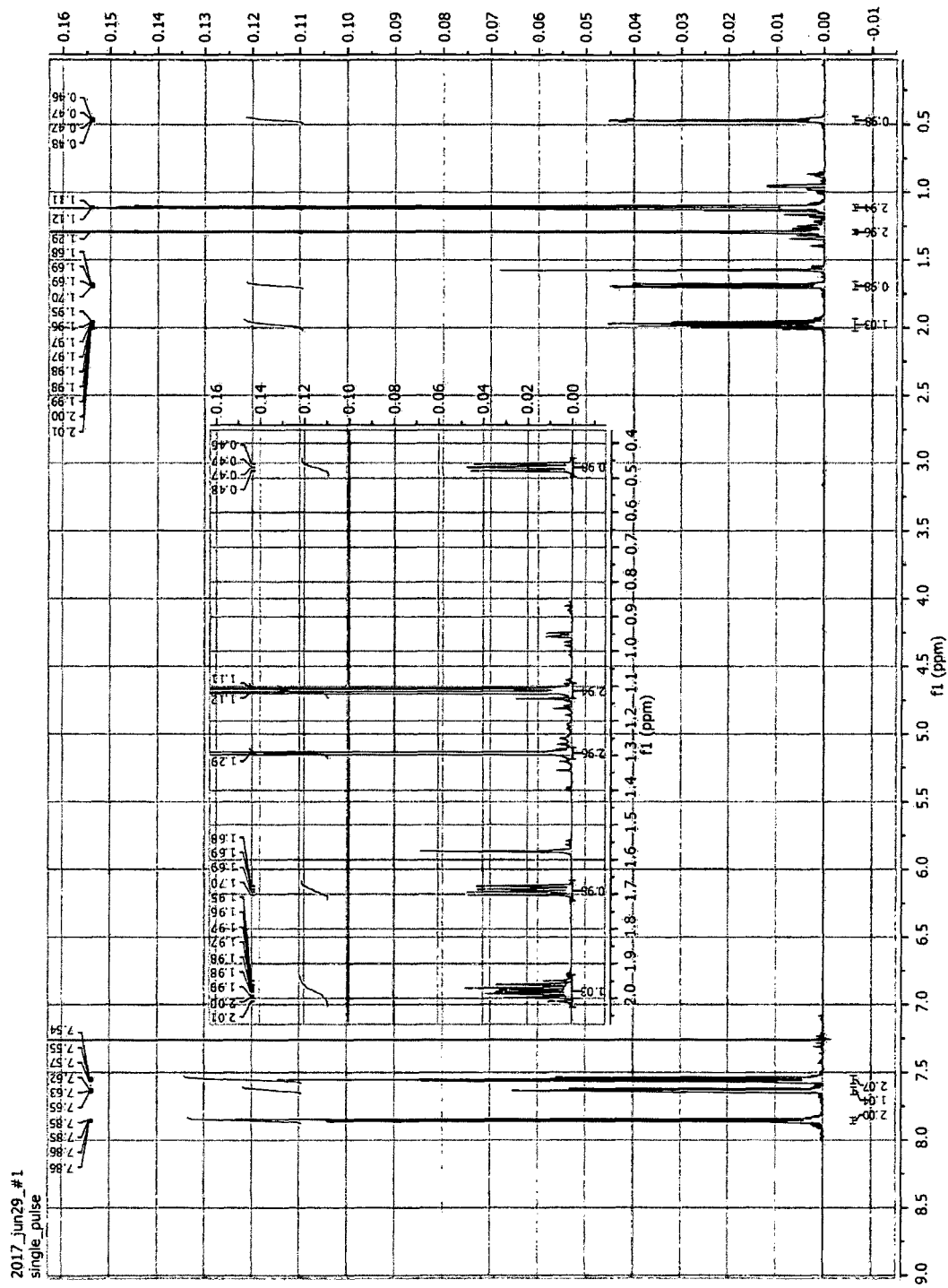
FIG. 70 illustrates ¹H NMR of Compound 21.

FIG. 70 illustrates NMR (600 MHz, Chloroform-d) δ 7.85 (dd, J=7.7, 2.0 Hz, 2H), 7.63 (t, J=7.4 Hz, 1H), 7.55 (t, J=7.7 Hz, 2H), 2.03-1.93 (m, 1H), 1.69 (dd, J=9.9, 5.2 Hz, 1H), 1.29 (s, 3H), 1.11 (d, J=6.4 Hz, 3H), 0.47 (dd, J=6.7, 5.2 Hz, 1H).

Figure 71:
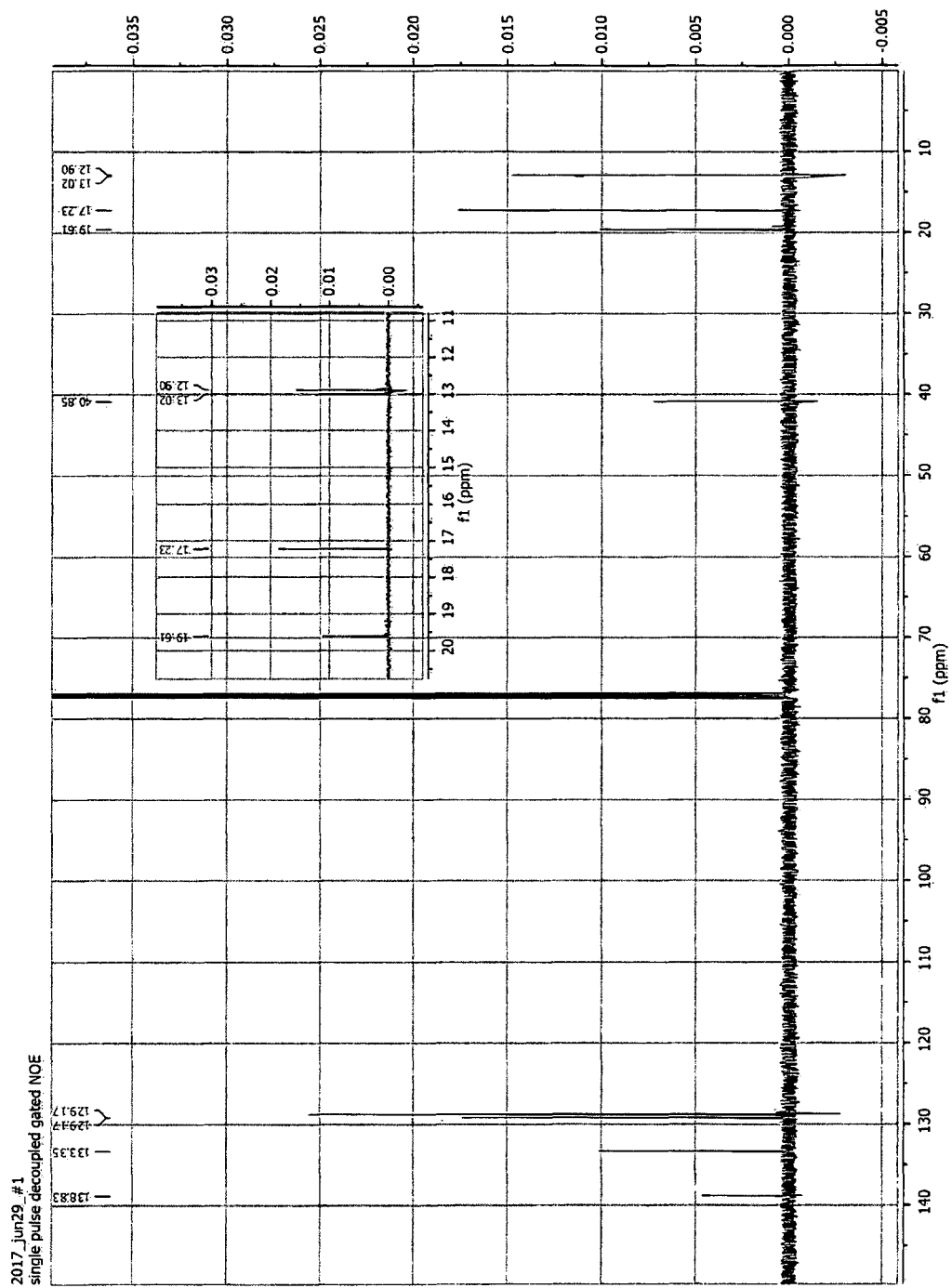
FIG. 71 illustrates ¹³C NMR of Compound 21.

FIG. 71 illustrates $^{13}$C NMR (151 MHz, Chloroform-d) δ 138.83, 133.35, 129.17, 129.17, 40.85, 19.61, 17.23, 13.02, 12.90.

Figure 72:
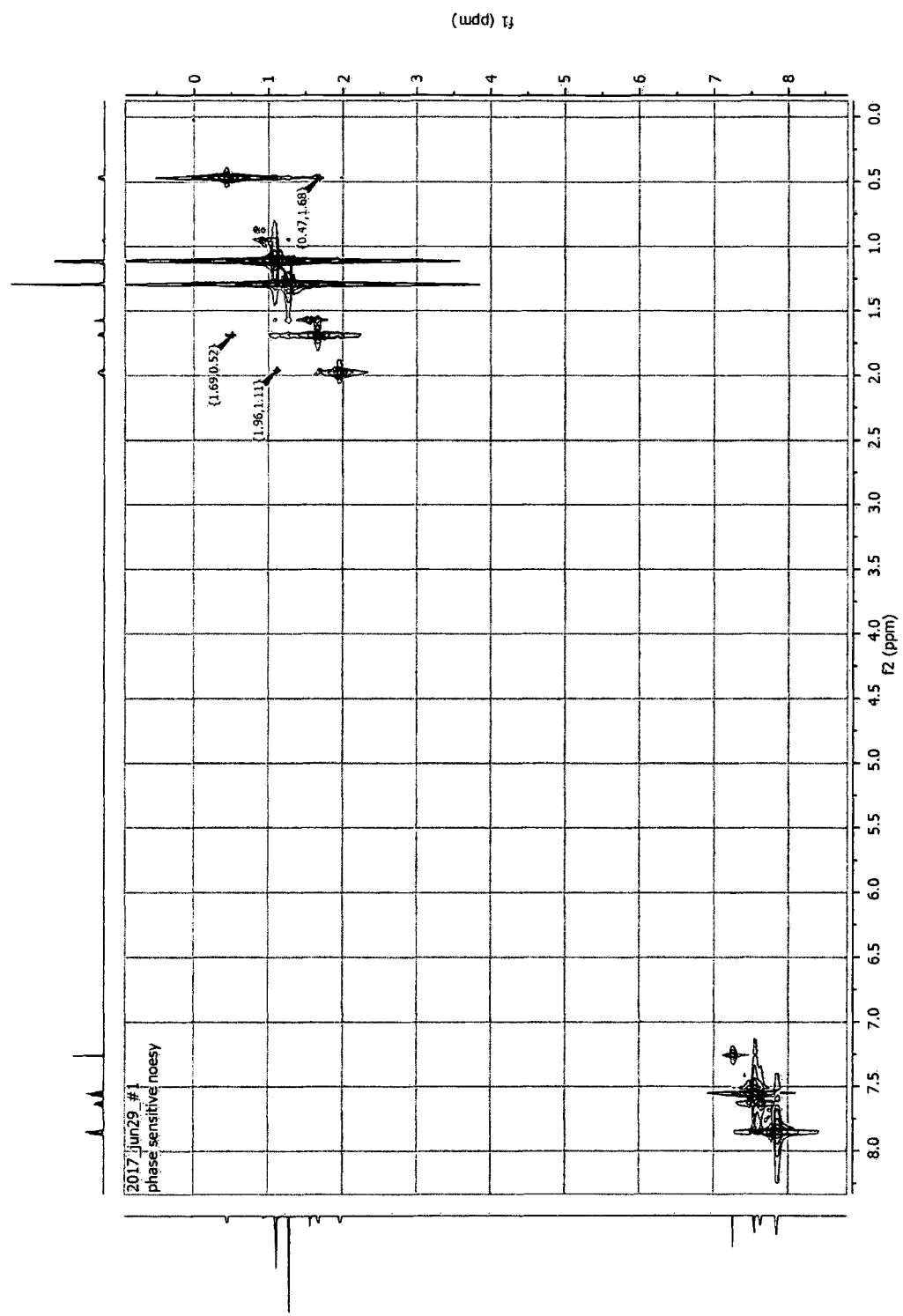
FIG. 72 illustrates NOESY of Compound 21.

FIG. 72 illustrates NOESY of Compound 21.

HRMS: [M+H]$^+$ Expected 211.0787; Obtained 211.0789

[Chem.36]

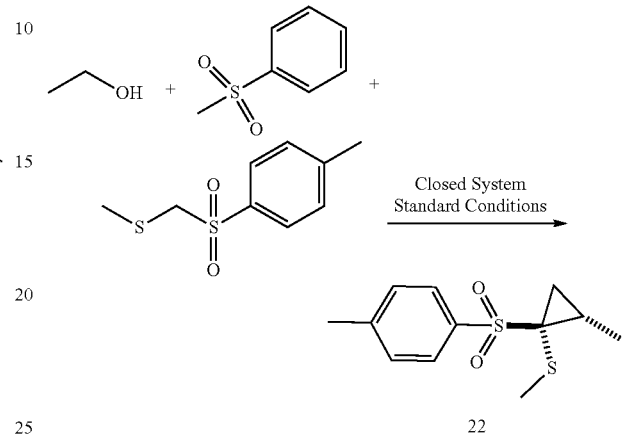

22

Solid state: White powder; isolated yield 35%

Isolated d. r. 50:1; Crude d. r. 50:1 Stereochemical assignment is based on the most downfield proton (methyl substituted) having NOESY coupling to the next downfield proton, which is assumed to be cis to the sulfonate, with the most upfield proton being trans to the sulfonate.

Figure 73:
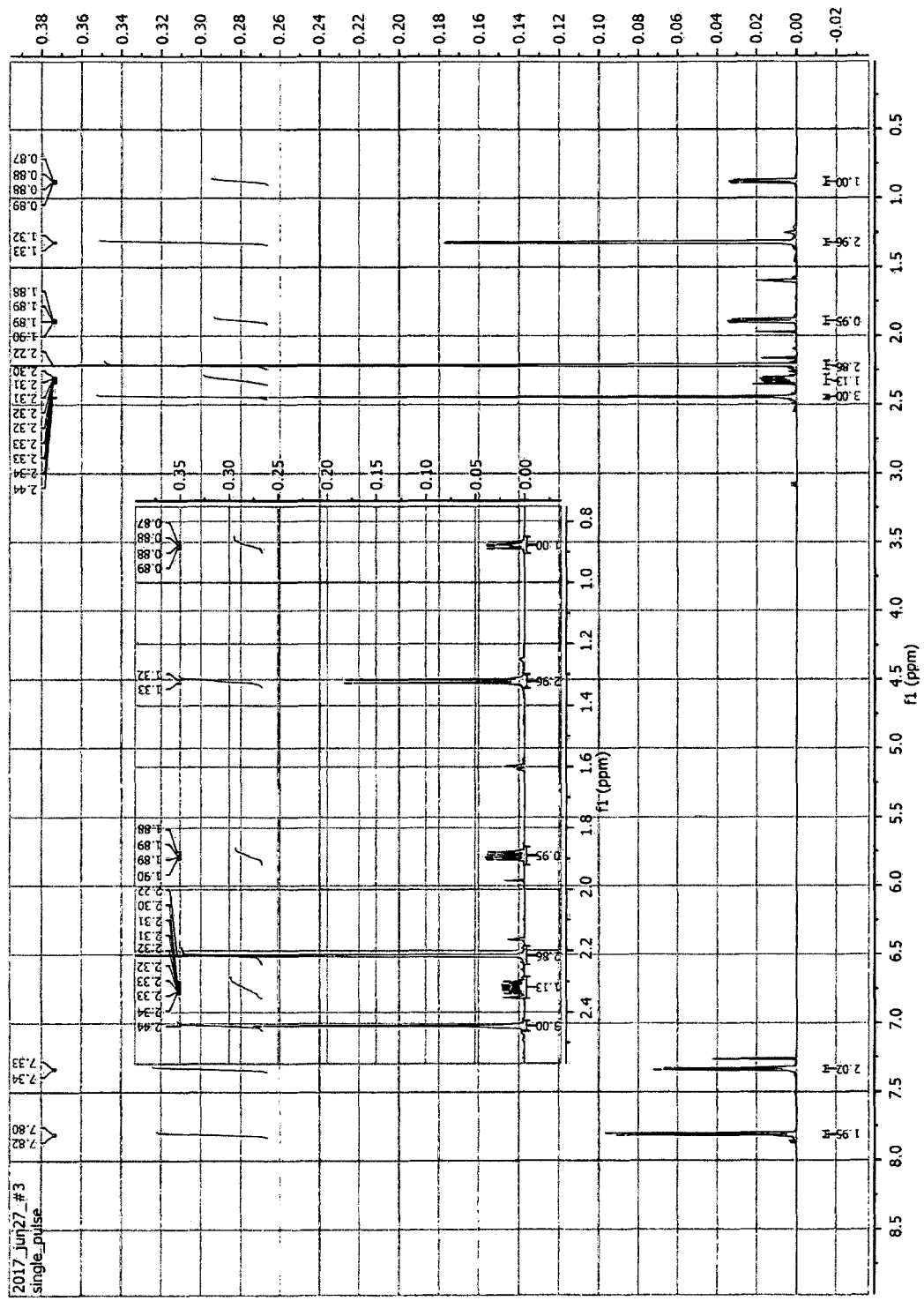
FIG. 73 illustrates ¹H NMR of Compound 22.

FIG. 73 illustrates $^1$H NMR (600 MHz, Chloroform-d) δ 7.81 (d, J=8.3 Hz, 1H), 7.33 (d, J=8.3 Hz, 2H), 2.44 (s, 3H), 2.30-2.34 (m, 1H), 2.22 (s, 3H), 1.89 (dd, J=9.7, 5.2 Hz, 1H), 1.32 (d, J=6.3 Hz, 3H), 0.88 (dd, J=7.4, 5.2 Hz, 1H).

Figure 74:
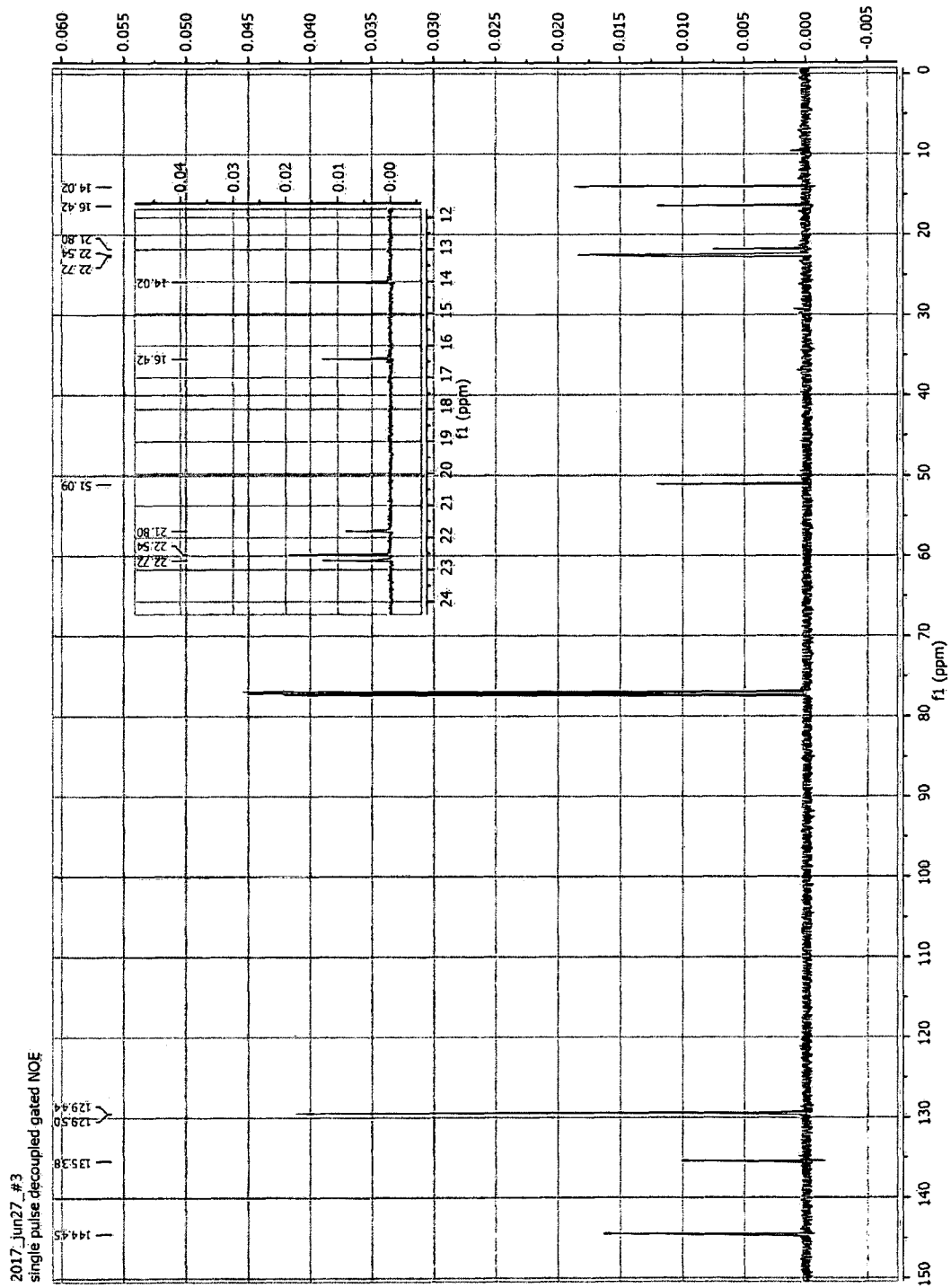
FIG. 74 illustrates ¹³C NMR of Compound 22.

FIG. 74 illustrates $^{13}$C NMR (151 MHz, Chloroform-d) δ 144.45, 135.38, 129.50, 129.44, 51.09, 22.72, 22.54, 21.80, 16.42, 14.02.

Figure 75:
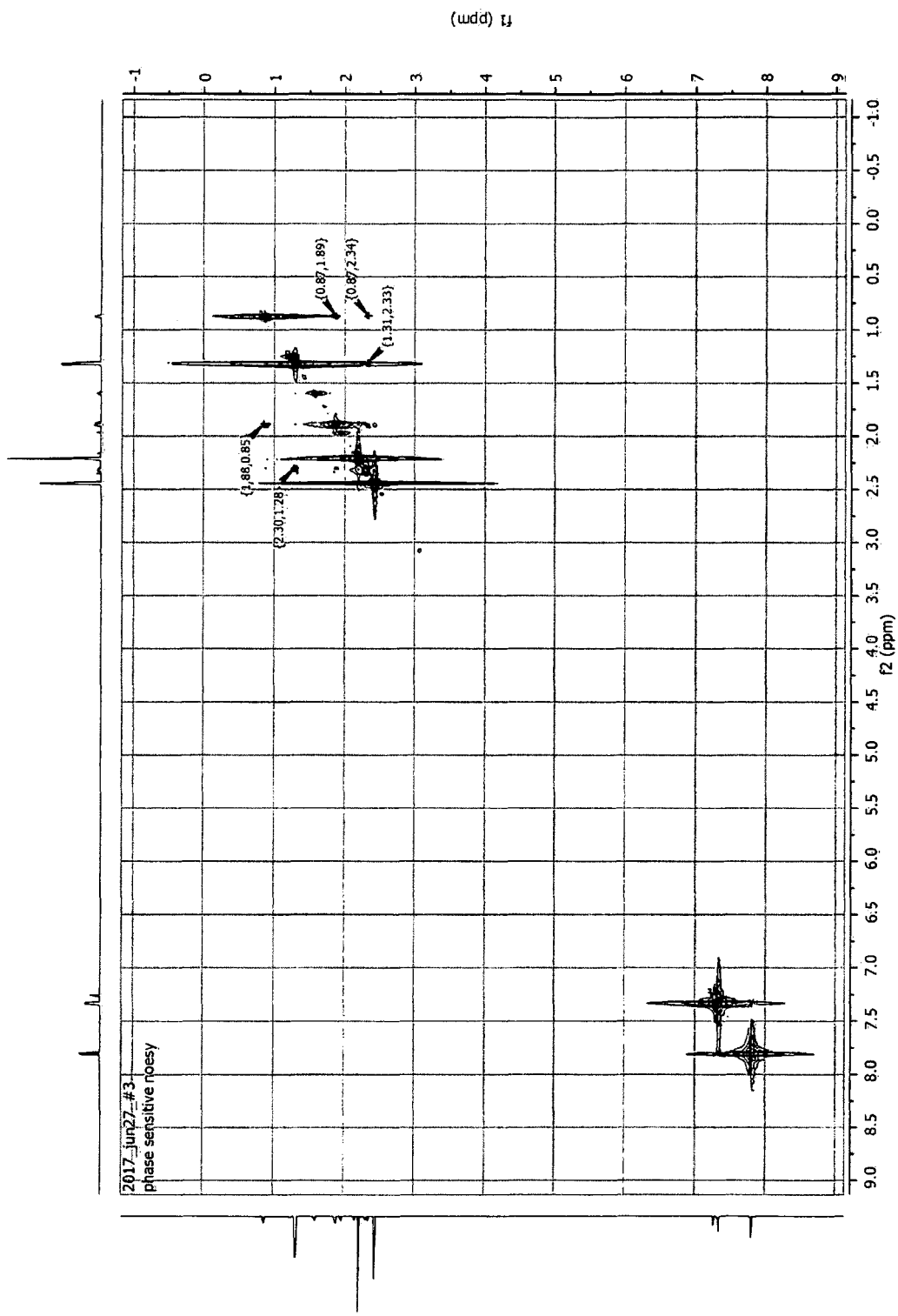
FIG. 75 illustrates NOESY of Compound 22.
Figure 76:
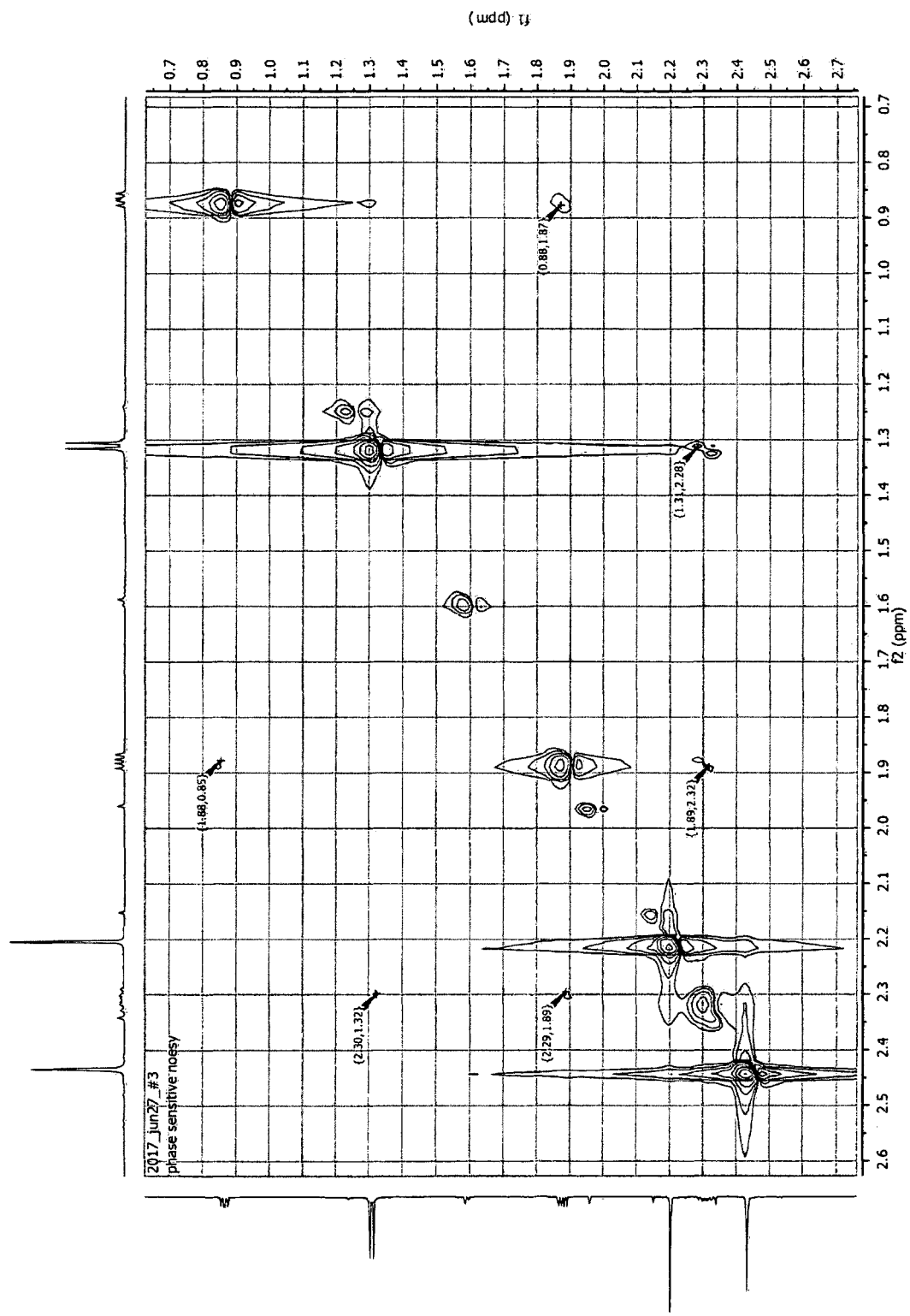
FIG. 76 illustrates NOESY aliphatic expansion of Compound 22.

FIG. 75 illustrates NOESY of Compound 22. FIG. 76 illustrates NOESY aliphatic expansion of Compound 22.

HRMS: [M+H]$^+$ Expected 257.0664; Obtained 257.0672

[Chem.37]

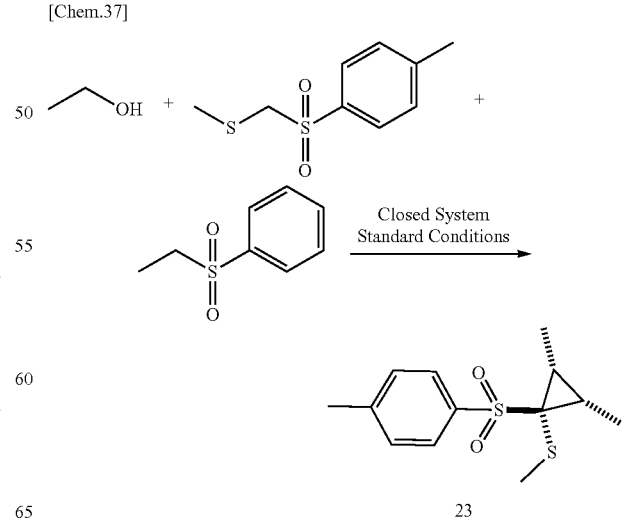

23

Physical state: Colorless oil; isolated yield 35%

Isolated d. r. 99:1; crude d. r. 99:1

Sample is 80% pure, with 20% impurity of the homo coupling product 15. Yield is given for just the heterocoupling product. Stacked NMR is included for clarification. Reported peaks are only those from the target compound.

Figure 77:
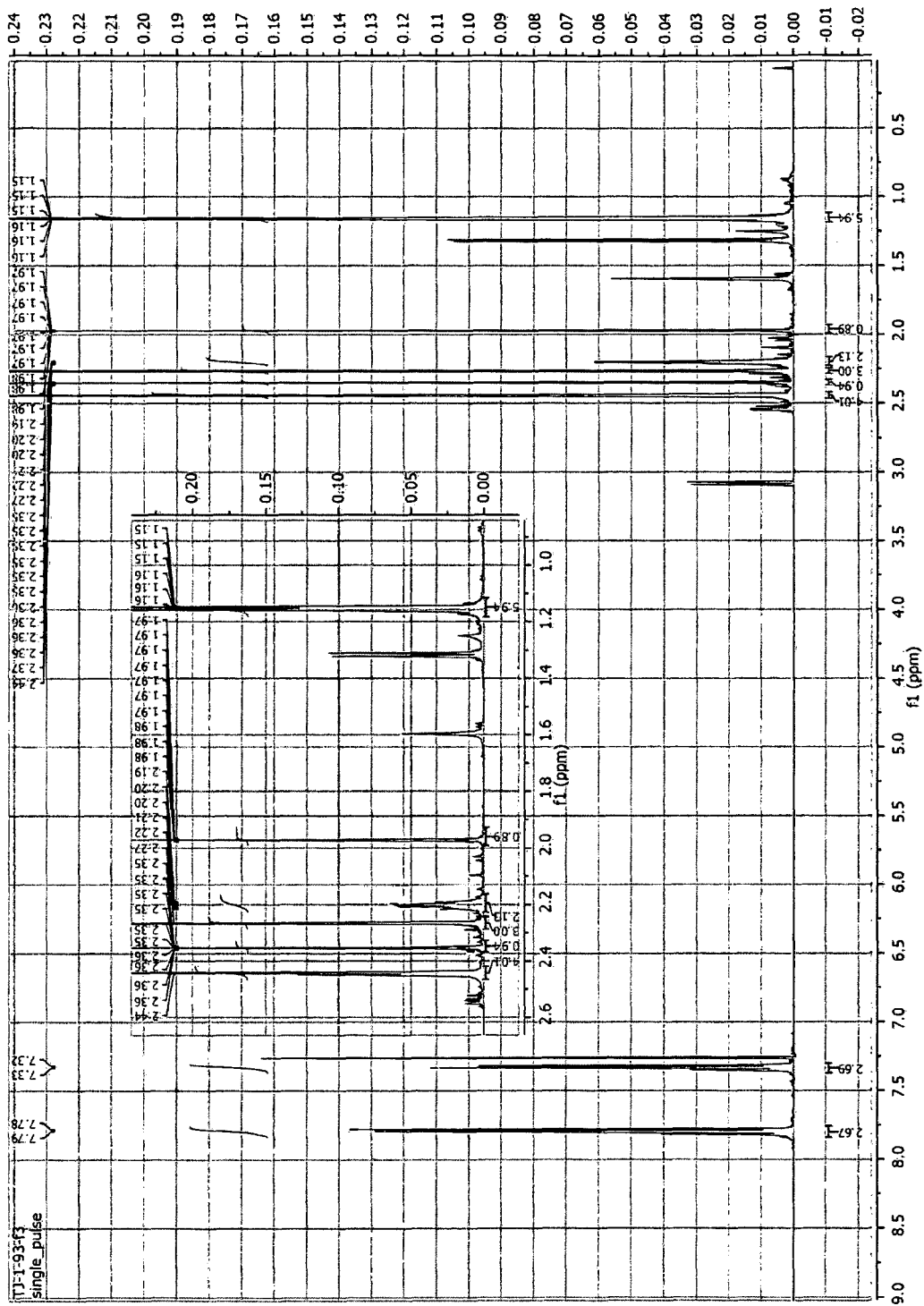
FIG. 77 illustrates ¹H NMR of Compound 23.

FIG. 77 illustrates $^1$H NMR (600 MHz, Chloroform-d) δ 7.79 (d, J=8.3 Hz, 2H), 7.32 (d, J=7.8 Hz, 2H), 2.44 (s, 3H), 2.27 (s, 3H), 2.23-2.16 (m, 2H), 1.18-1.12 (m, 6H).

Figure 78:
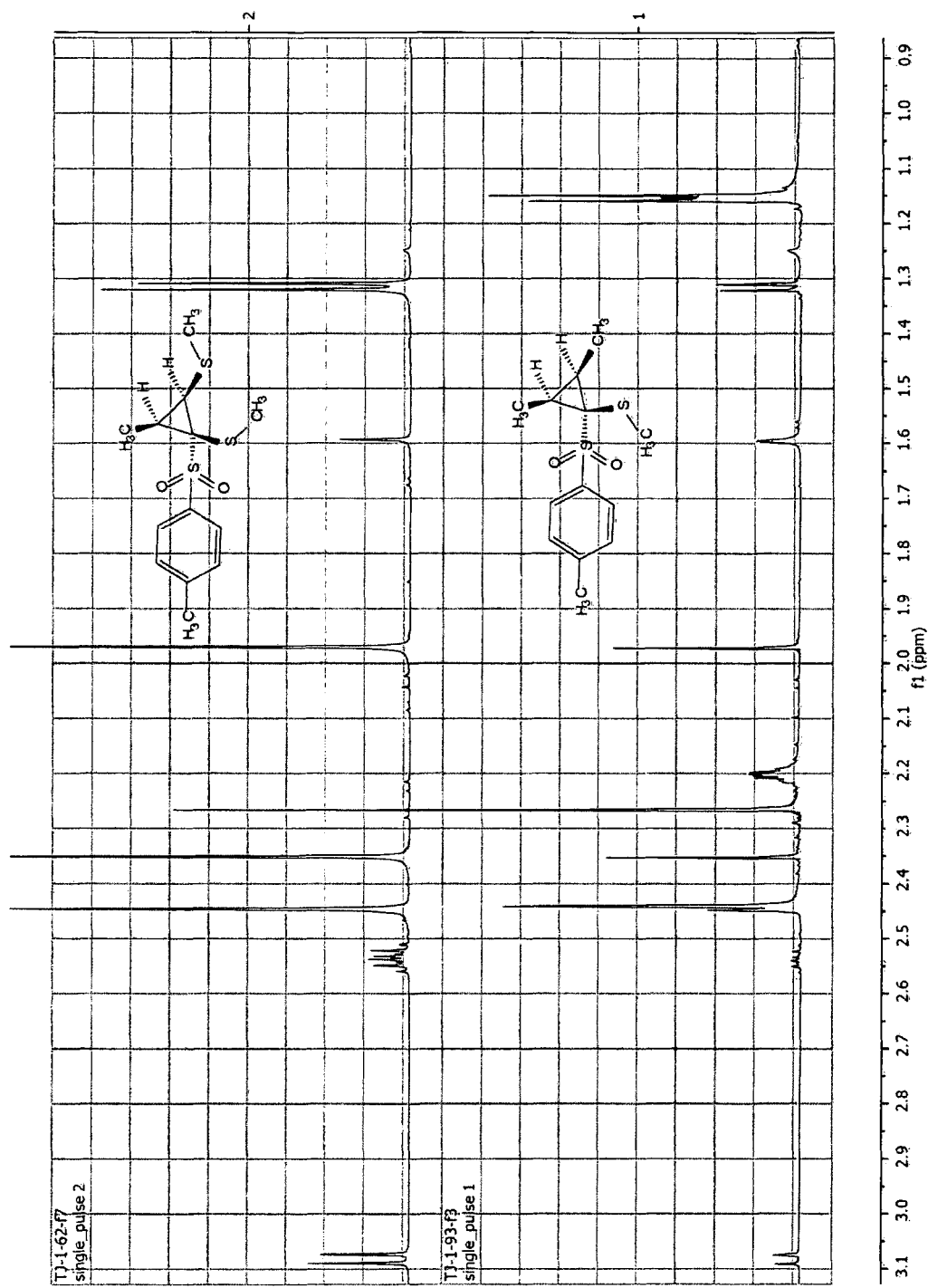
FIG. 78 illustrates ¹H NMR of Compound 23 stacked with Compound 15.

FIG. 78 illustrates $^1$HNMR of Compound 23 stacked with Compound 15.

Figure 79:
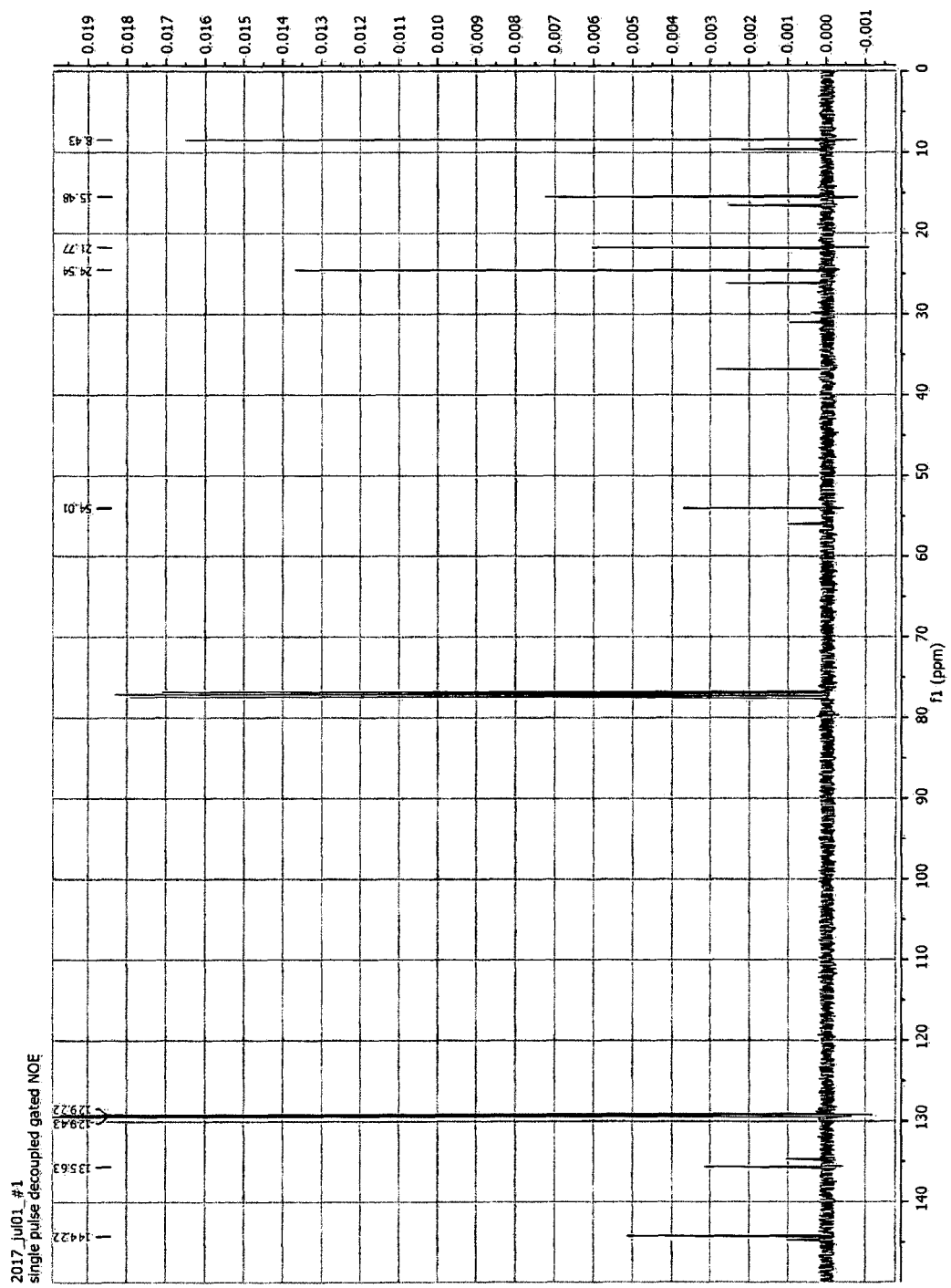
FIG. 79 illustrates ¹³C NMR of Compound 23.

FIG. 79 illustrates $^{13}$C NMR (101 MHz, Chloroform-d) δ 144.22, 135.63, 129.43, 129.22, 54.01, 24.54, 21.77, 15.48, 8.43.

Figure 80:
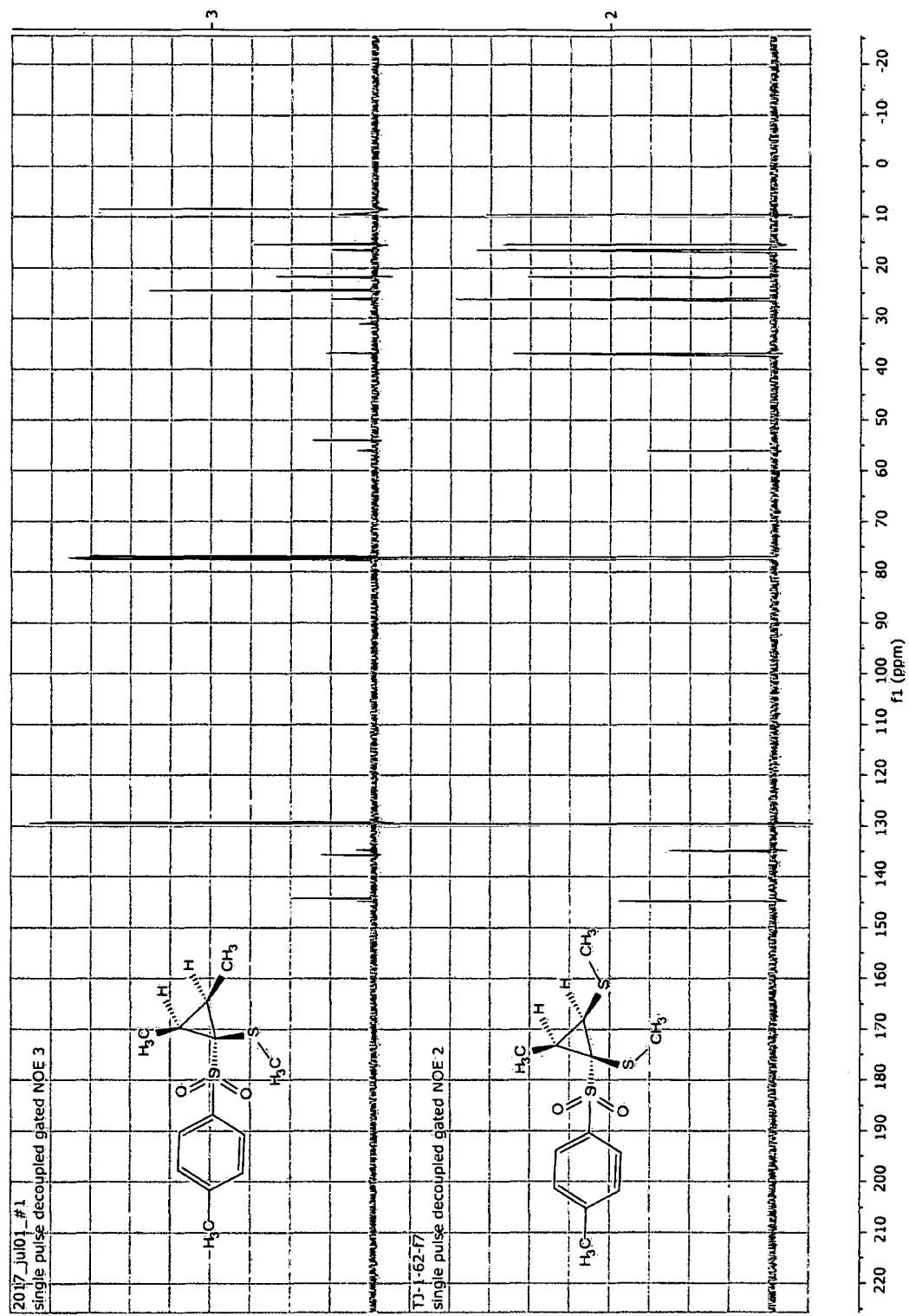
FIG. 80 illustrates ¹³C NMR of Compound 23 stacked with Compound 15.

FIG. 80 illustrates $^{13}$C NMR of Compound 23 stacked with Compound 15.

Figure 81:
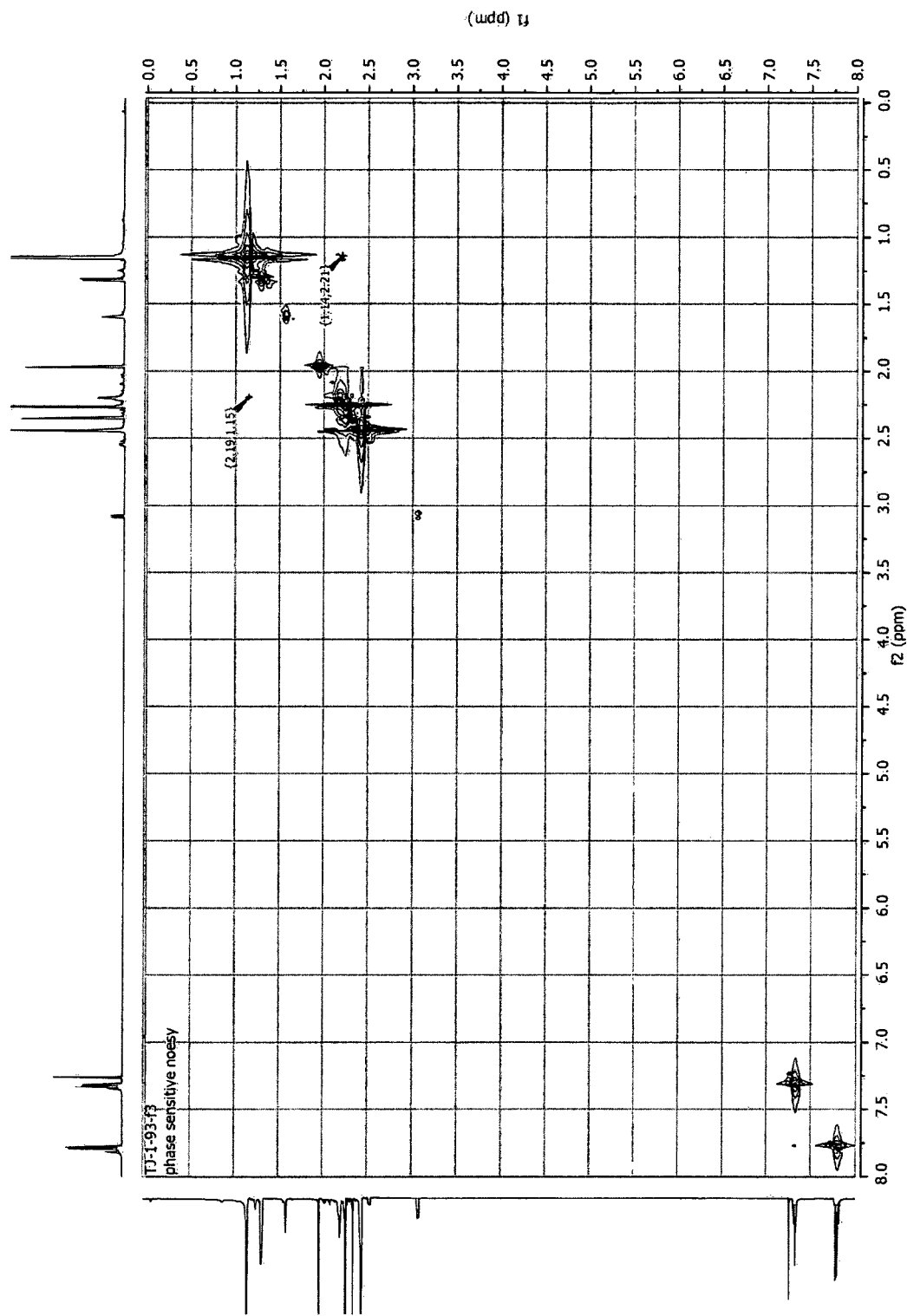
FIG. 81 illustrates NOESY of Compound 23.

FIG. 81 illustrates NOESY of Compound 23.

HRMS: [M+H]$^+$ Expected 271.0821; Obtained 271.0829

[Chem.38]

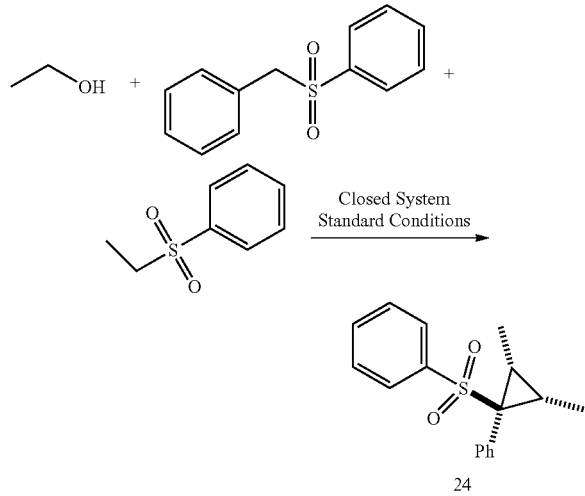

Physical state: white, crystalline powder; isolated yield 50%

Isolated d. r. 50:1 d. r. 8.1:1. Despite the crystalline nature of the sample, it contains 20% of homocoupling product 2. Both products are crystalline and have similar polarity, so they are difficult to separate by column chromatography. Product 2 has bigger crystals of different morphology, so it's possible to pick out crystals of the desired material for X-Ray analysis. Side by side NMRs are given below and assignment is only given for the desired product.

Figure 82:
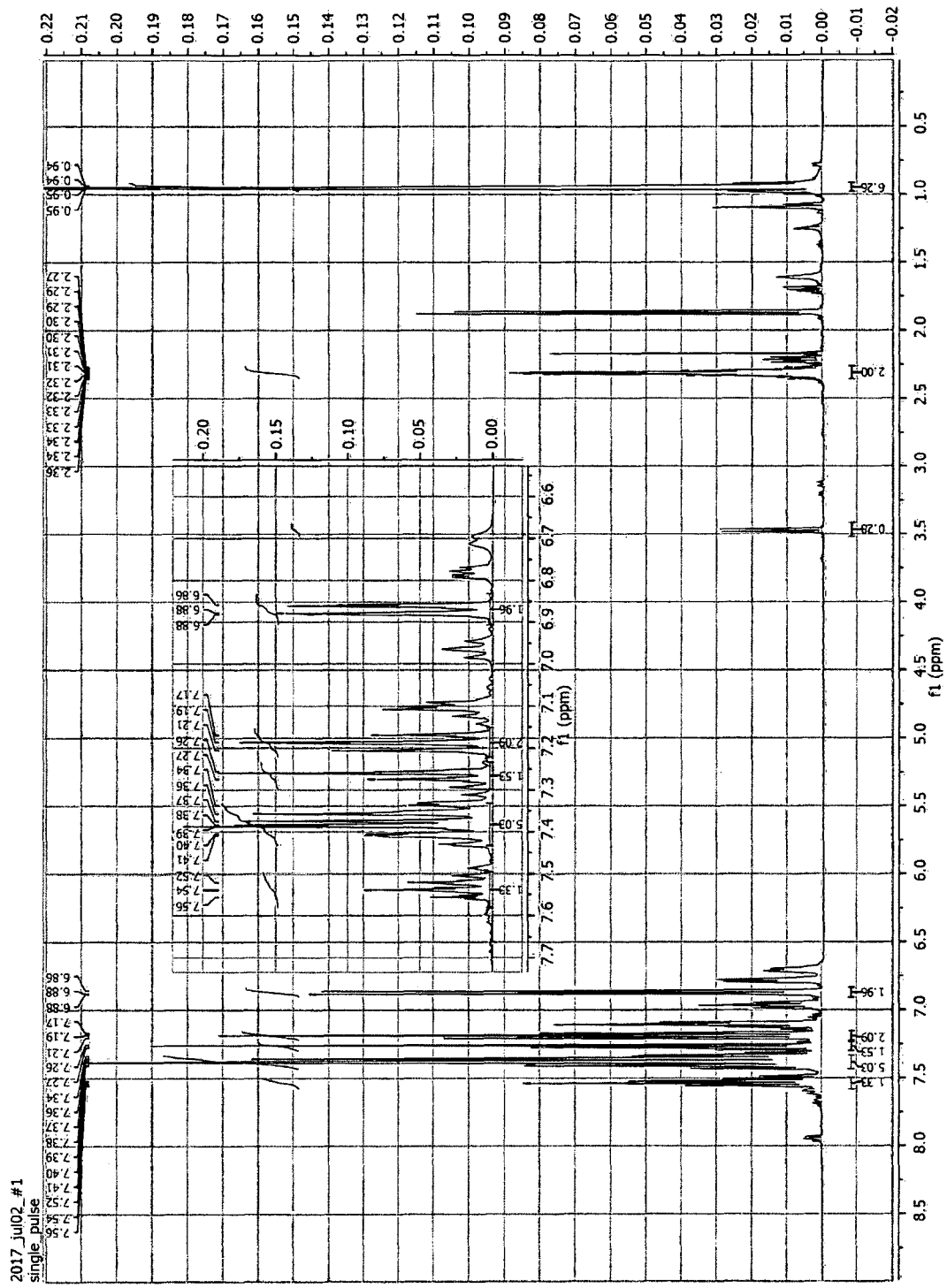
FIG. 82 illustrates ¹H NMR of Compound 24.

FIG. 82 illustrates NMR (400 MHz, Chloroform-d) δ 7.54 (t, J=7.0 Hz, 1H), 7.43-7.33 (m, 6H), 7.27 (d, J=7.3 Hz, 1H), 7.19 (t, J=7.5 Hz, 3H), 6.91-6.83 (m, 3H), 2.38-2.25 (m, 2H), 0.98-0.91 (m, 6H).

Figure 83:
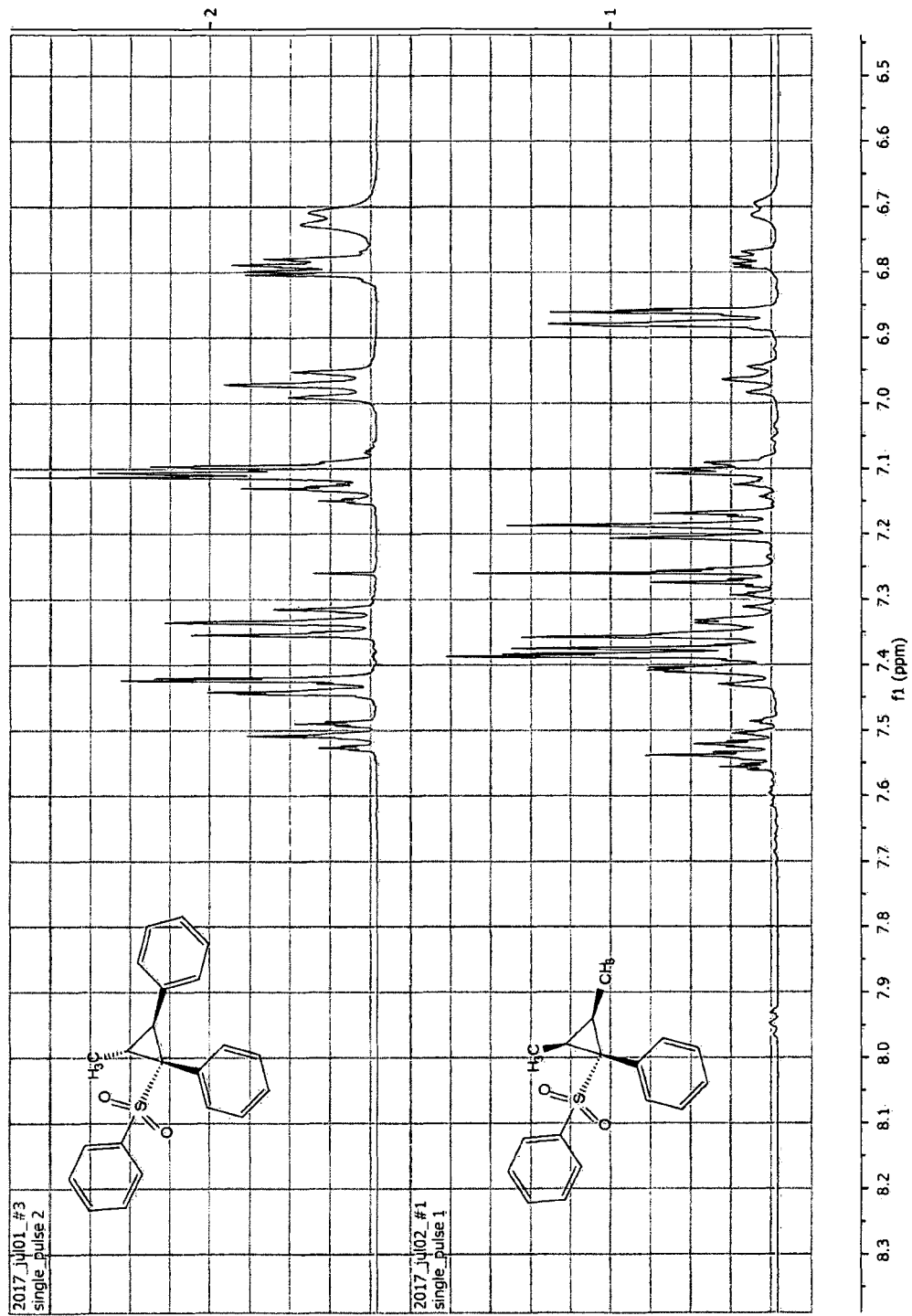
FIG. 83 illustrates ¹H NMR side by side aromatic regions of Compound 24 and pure Compound 2.

FIG. 83 illustrates $^1$HNMR side by side aromatic regions of Compound 24 and pure Compound 2.

Figure 84:
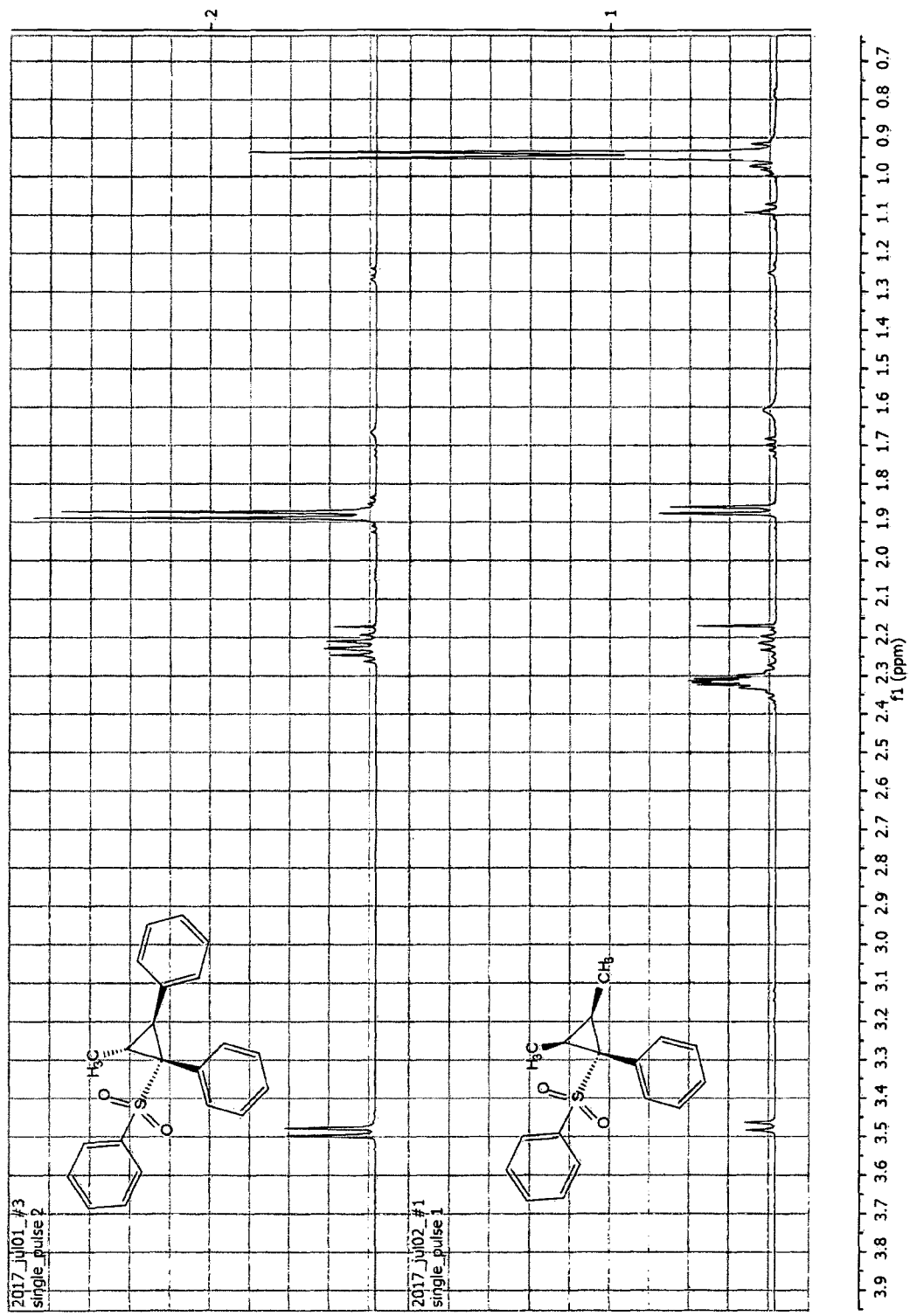
FIG. 84 illustrates ¹H NMR side by side aliphatic regions of Compound 24 and pure Compound 2.

FIG. 84 illustrates $^1$HNMR side by side aliphatic regions of Compound 24 and pure Compound 2.

Figure 85:
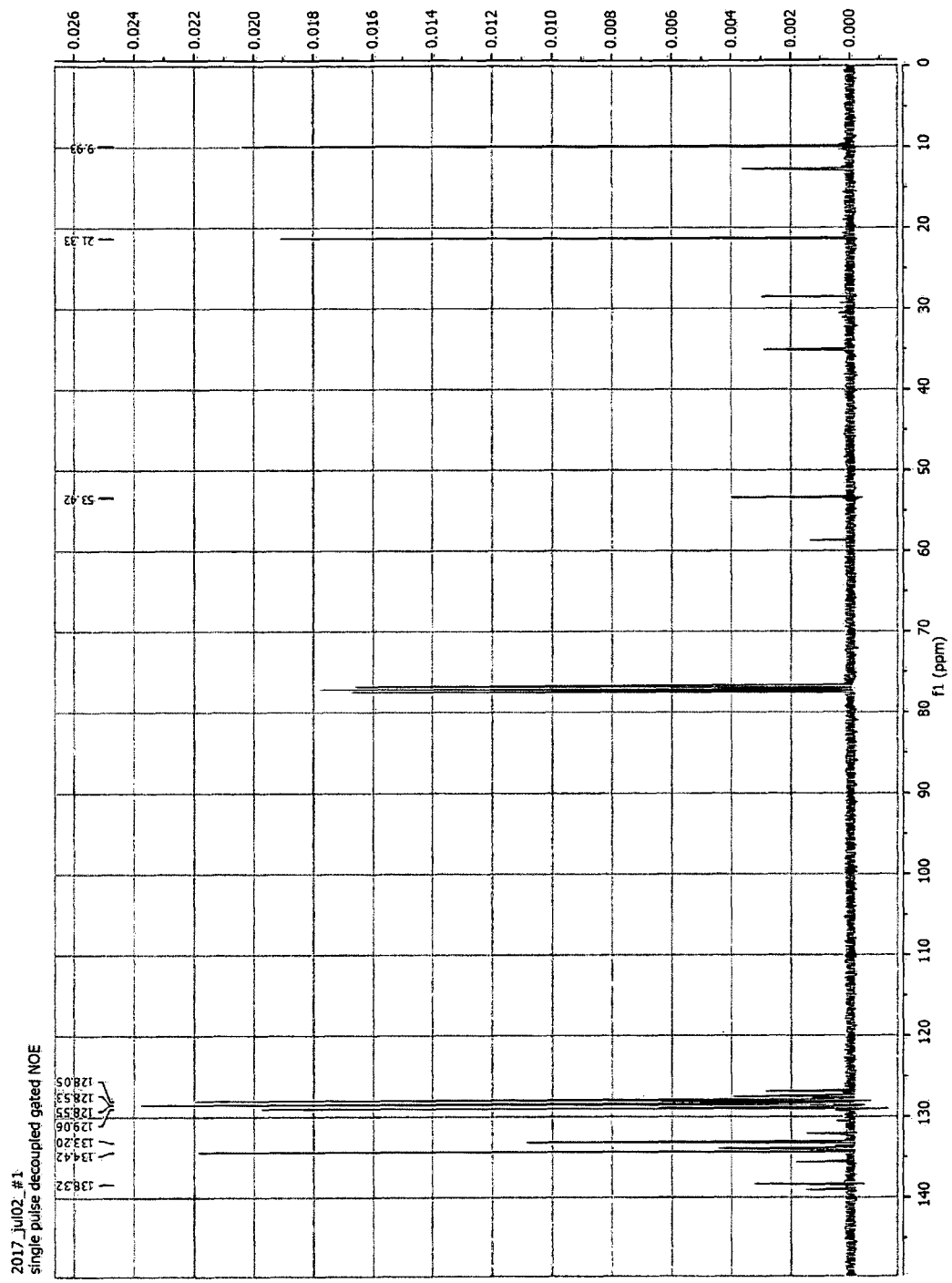
FIG. 85 illustrates ¹³C NMR of Compound 24.

FIG. 85 illustrates $^{13}$C NMR (101 MHz, Chloroform-d) δ 138.32, 134.42, 133.20, 129.06, 128.55, 128.53, 128.05, 53.42, 21.33, 9.93. Note: (one of the carbons could not be located due to overlap)

Figure 86:
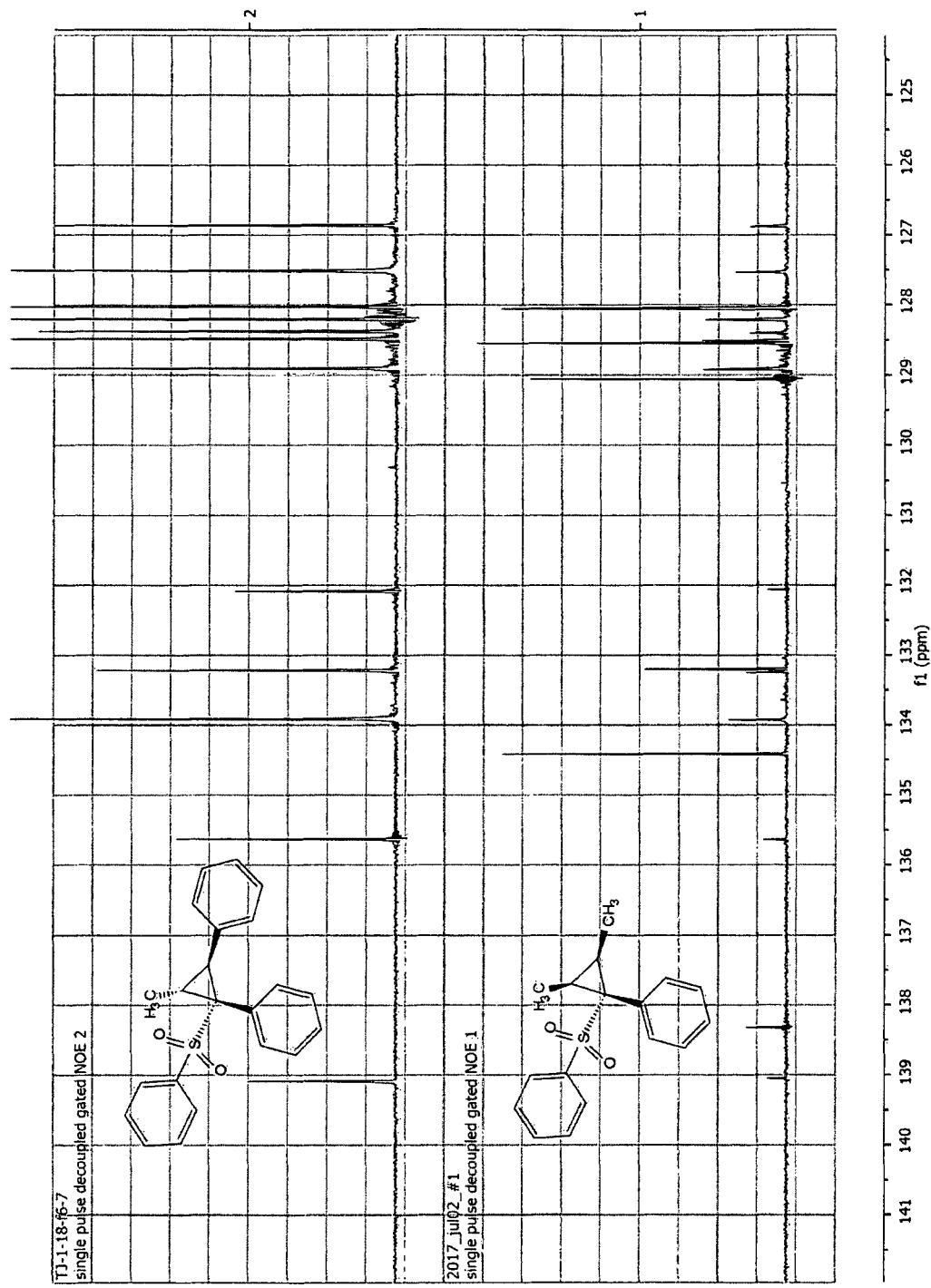
FIG. 86 illustrates ¹³C NMR side by side aromatic regions of Compound 24 and pure Compound 2.

FIG. 86 illustrates $^{13}$CNMR side by side aromatic regions of Compound 24 and pure Compound 2.

Figure 87:
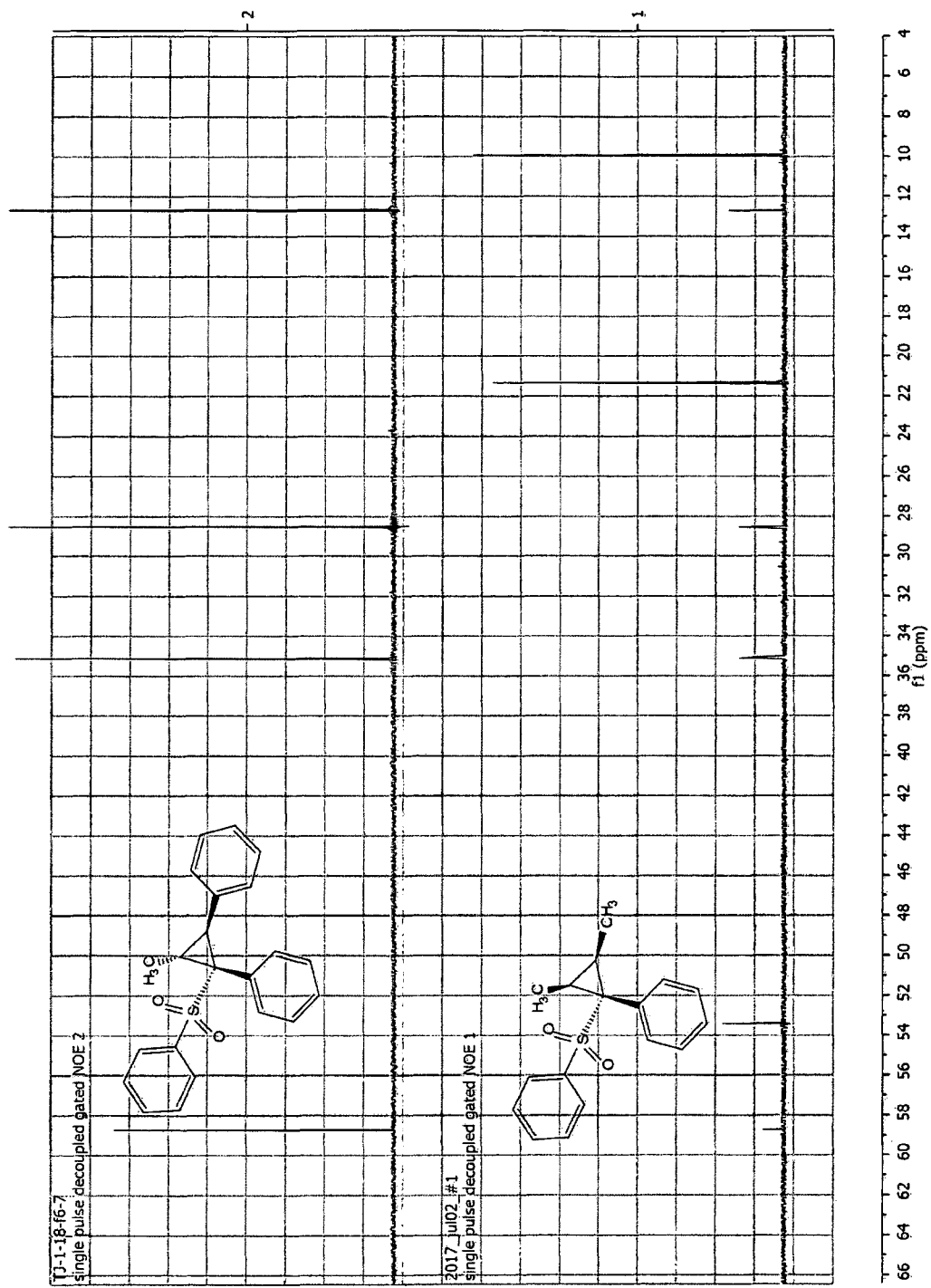
FIG. 87 illustrates ¹³C NMR side by side aliphatic regions of Compound 24 and pure Compound 2.

FIG. 87 illustrates $^{13}$CNMR side by side aliphatic regions of Compound 24 and pure Compound 2.

Figure 88:
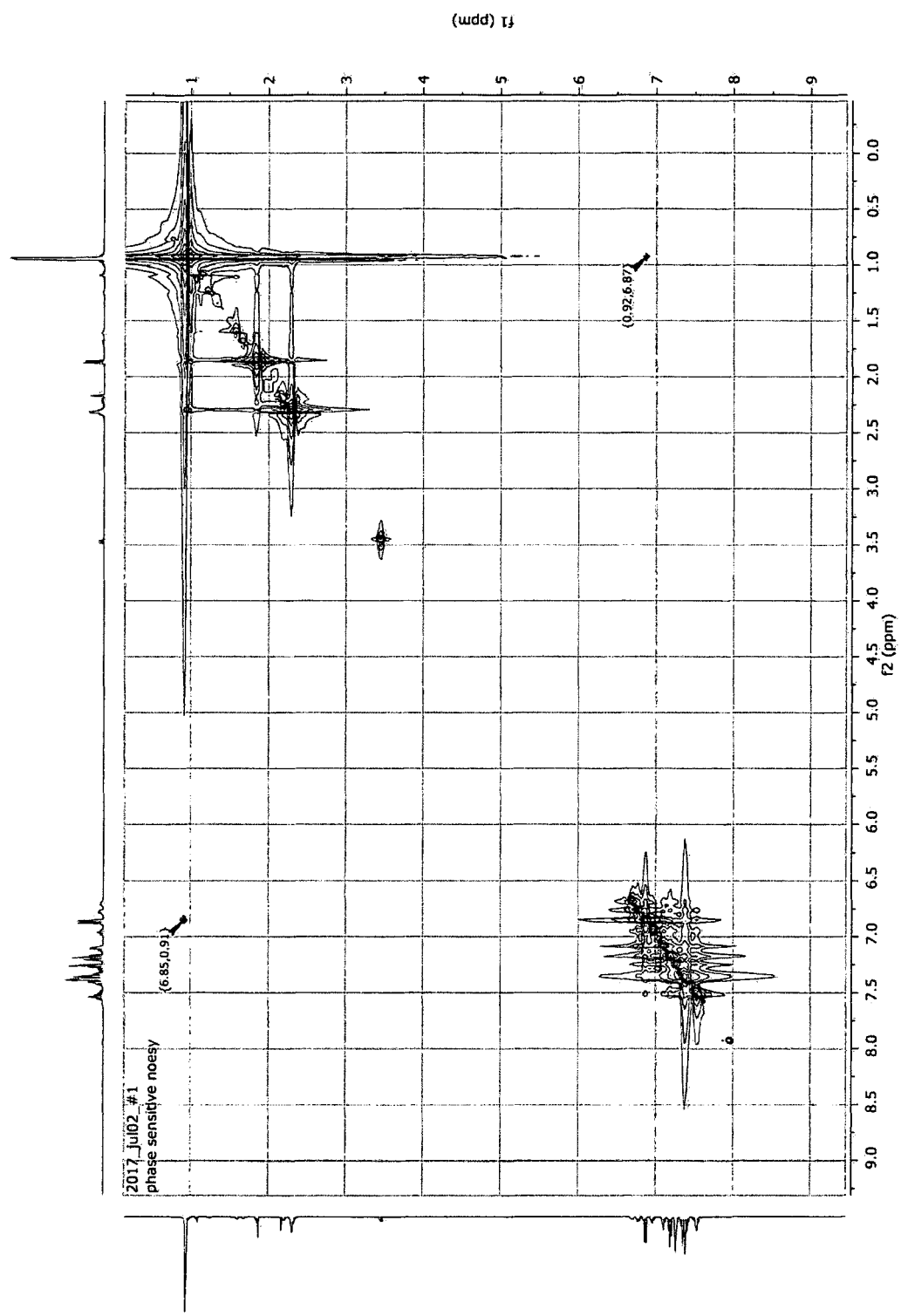
FIG. 88 illustrates NOESY of Compound 24.
Figure 89:
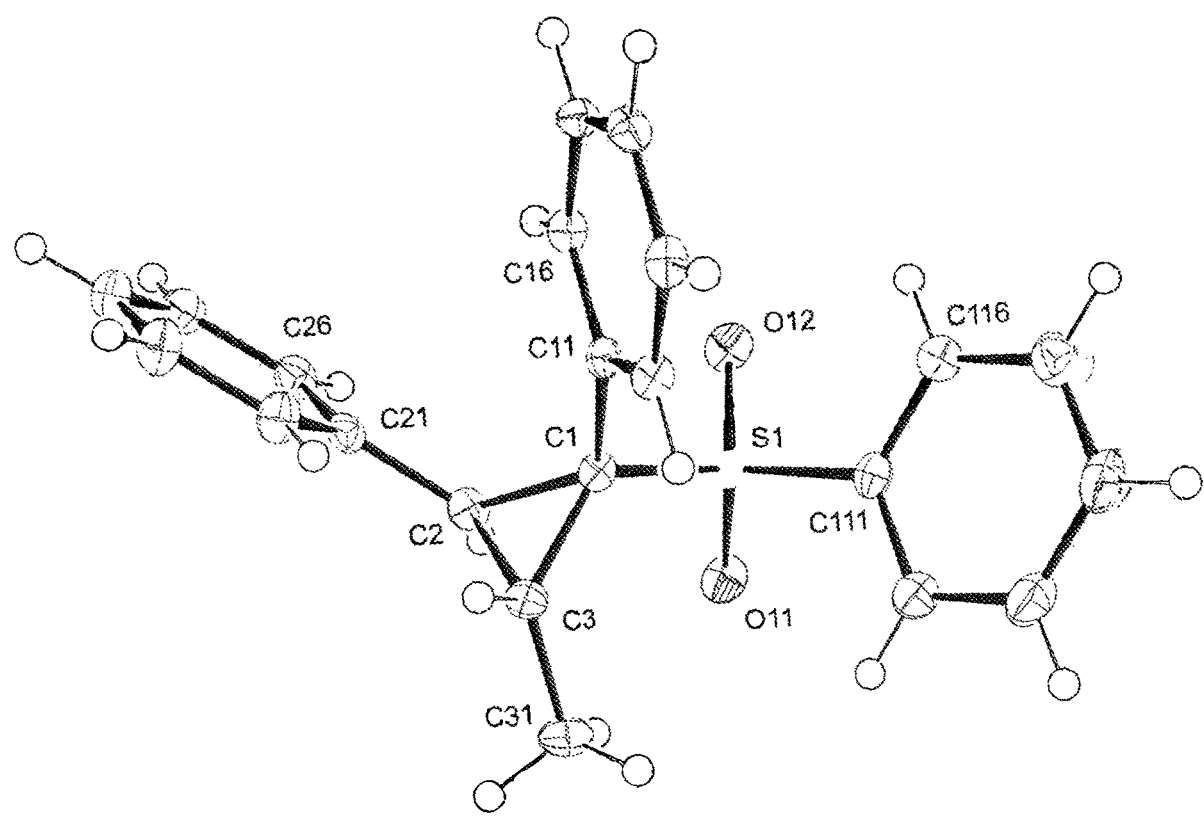
FIG. 89 illustrates ORTEP diagram showing 50% probability anisotropic displacement ellipsoids of non-hydrogen atoms for compound 2 (racemic sample) according to single crystal X-ray diffraction data. Selected interatomic distances [Å], valence and dihedral angles [°]: C1-C2 1.540(3), C2-C3 1.510(3), C1-C3 1.519(3), C1-S1 1.783(2), C1-C11 1.503 (3), C2-C21 1.489(3), C3-C31 1.515(3), C2-C1-C3 59.15 (13), C1-C2-C3 59.75(13), C2-C3-C1 61.11(13), S1-C1-C11 111.36(15), C116-C111-S1-C1-99.00(19), C111-S1-C1-C3−94.32(18), C16-C11-C1-C3−129.5(2), C26-C21-C2-C3−167.74(19).
Figure 90:
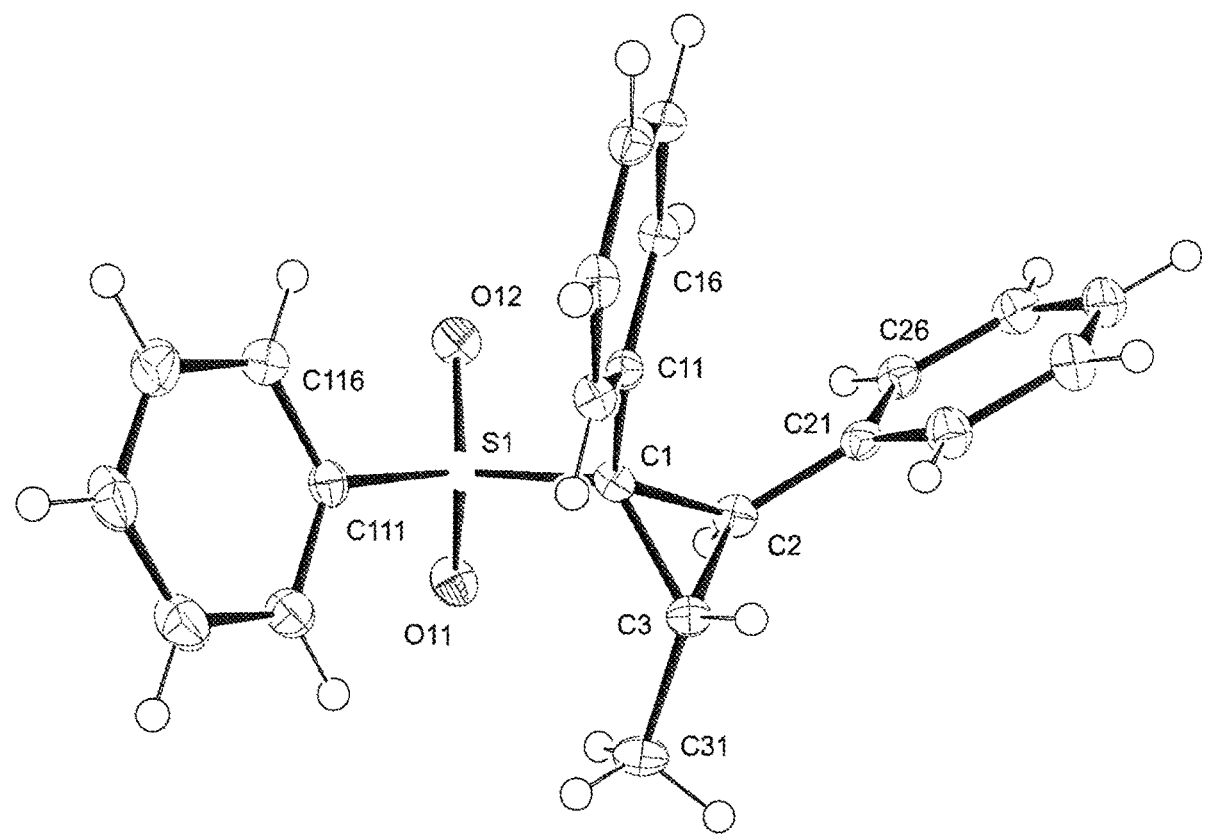
FIG. 90 illustrates ORTEP diagram showing 50% probability anisotropic displacement ellipsoids of non-hydrogen atoms for compound (1S,2R,3S)-2 according to single crystal X-ray diffraction data. Selected interatomic distances [Å], valence and dihedral angles [°]: C1-C2 1.538(3), C2-C3 1.510(3), C1-C3 1.517(3), C1-S1 1.785(2), C1-C11 1.503 (3), C2-C21 1.488(3), C3-C31 1.512(3), C2-C1-C3 59.25 (14), C1-C2-C3 59.66(13), C2-C3-C1 61.09(14), S1-C1-C11 111.19(15), C116-C111-S1-C1 99.14(19), C111-S1-C1-C3 94.20(18), C16-C11-C1-C3 129.5(2), C26-C21-C2-C3 167.81(19).
Figure 91:
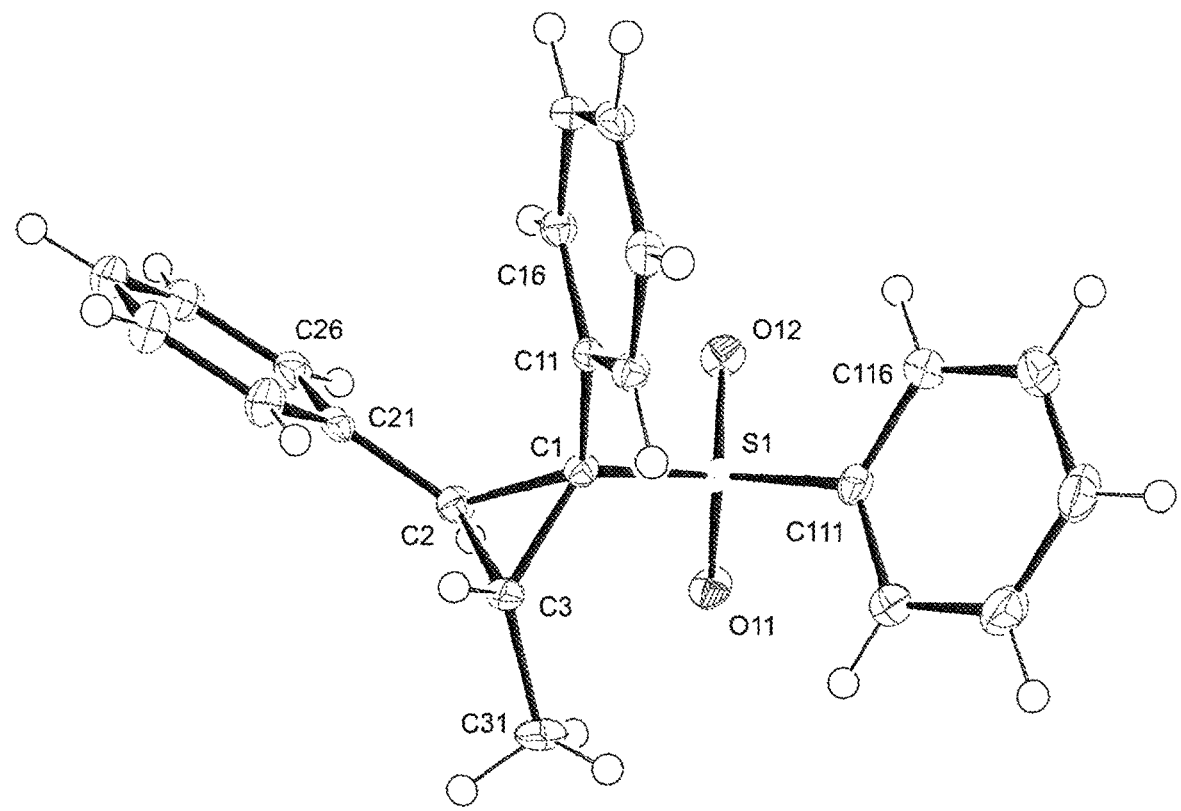
FIG. 91 illustrates ORTEP diagram showing 50% probability anisotropic displacement ellipsoids of non-hydrogen atoms for compound (1R,2S,3R)-2 according to single crystal X-ray diffraction data. Selected interatomic distances [Å], valence and dihedral angles [°]: C1-C2 1.541(3), C2-C3 1.508(3), C1-C3 1.519(3), C1-S1 1.781(2), C1-C11 1.503 (2), C2-C21 1.486(3), C3-C31 1.512(3), C2-C1-C3 59.07 (12), C1-C2-C3 59.76(12), C2-C3-C1 61.18(12), S1-C1-C11 111.41(13), C116-C111-S1-C1−98.85(17), C111-S1-C1-C3−94.33(17), C16-C11-C1-C3−129.5(2), C26-C21-C2-C3−167.79(18).
Figure 92:
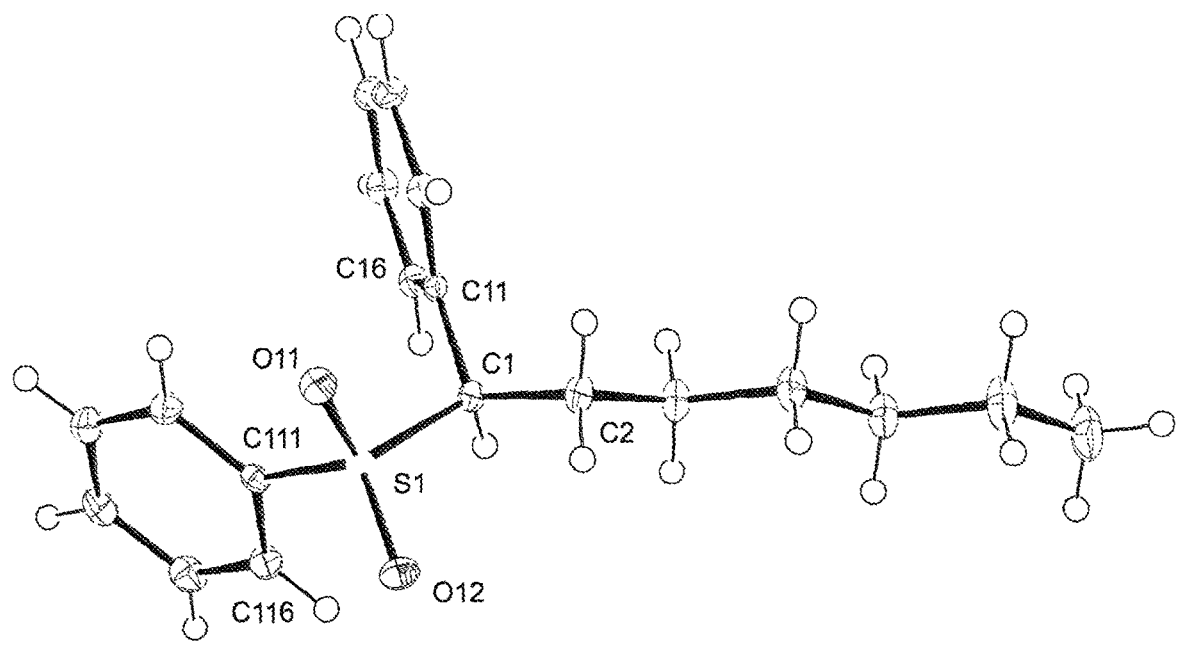
FIG. 92 illustrates ORTEP diagram showing 50% probability anisotropic displacement ellipsoids of non-hydrogen atoms for compound 3 according to single crystal X-ray diffraction data. Selected interatomic distances [Å], valence and dihedral angles [°]: C1-C2 1.5408(15), C1-C11 1.5132 (14). S1-C1 1.8036(11), S1-C111 1.7677(11), S1-C1-C2 109.82(7), C1-S1-C111 103.88(5), C111-S1-C1-C2−169.95 (8), C111-S1-C1-C11 61.36(8), C116-C111-S1-C1 76.89 (10).
Figure 93:
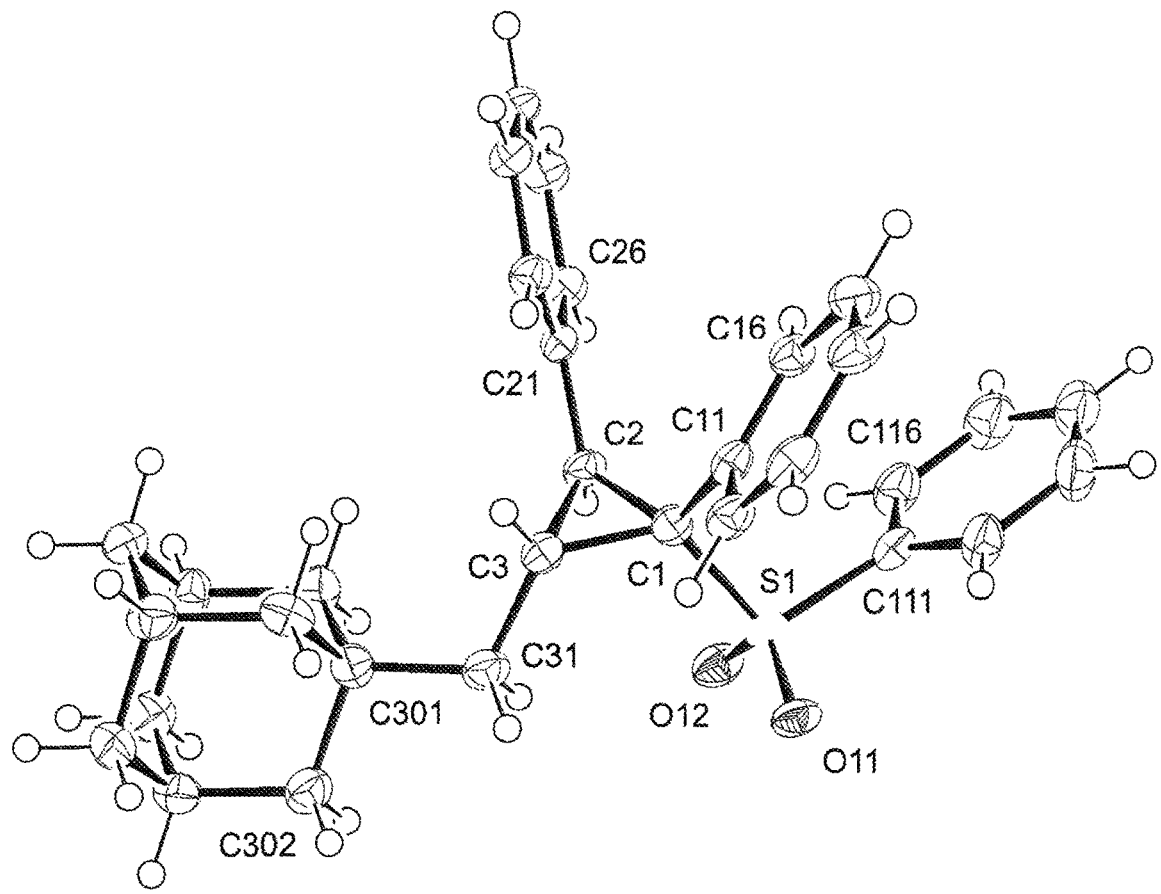
FIG. 93 illustrates ORTEP diagram showing 50% probability anisotropic displacement ellipsoids of non-hydrogen atoms for compound 6 (racemic sample) according to single crystal X-ray diffraction data. Selected interatomic distances [Å], valence and dihedral angles [°]: C1-C2 1.532(4), C2-C3 1.524(4), C1-C3 1.525(4), S1-C1 1.786(3), C1-C11 1.501 (4), C2-C21 1.485(4), C3-C31 1.507(4), C2-C1-C3 59.84 (19), C1-C2-C3 59.86(19), C2-C3-C1 60.30(19), S1-C1-C11 111.2(2), C116-C111-S1-C1−86.3(3), C111-S1-C1-C3

FIG. 88 illustrates NOESY of Compound 24.

HRMS: [M+H]$^+$ Expected 287.1100; Obtained 287.1100

X-Ray Diffraction Data and Molecular Structure List

The X-ray diffraction data for the single crystals were collected on a Rigaku XtaLab PRO instrument (K-goniometer) with a PILATUS3R 200K hybrid pixel array detector using MoKα, 0.71073 Å, (3) or CuKα, 1.54184 Å, (in all other cases) radiation. The performance mode of Micro-Max™-003 microfocus sealed X-ray tubes was 50 kV, 0.60 mA. The diffractometer was equipped with a Rigaku GN2 low temperature system for low temperature experiments. Suitable crystals of appropriate dimensions were mounted on loops in random orientations. Preliminary unit cell parameters were determined with three sets of total 10 narrow frame scans in the case of a Mo-source and six sets of total 10 narrow frame scans at two different 2Θ positions in the case of a Cu-source. The data were collected according to recommended strategies in ω or ω/φ scan mode. Final cell constants were determined by global refinement of reflections from the complete data sets using the Lattice wizard module. Images were indexed and integrated (with "smart" background evaluation) using the CrysAlis$^{Pro}$ data reduction package (version 1.171.39.7b or 1.171.39.20a, Rigaku Oxford Diffraction, 2015). Analysis of the integrated data did not show any decay. Data were corrected for systematic errors and absorption using the ABSPACK module: Numerical absorption correction based on Gaussian integration over a multifaceted crystal model and empirical absorption correction based on spherical harmonics (according to the Laue symmetry using equivalent reflections). The GRAL module and the ASSIGN SPACEGROUP routine of the WinGX suite were used for analysis of systematic absences and space group determination.

The structures were solved by the direct intrinsic phasing method using SHELXT-2014/5[S5] and refined by the full matrix least-squares on F$^2$ using SHELXL-2016/6 or SHELXL-2017/1,[S6] which uses a model of atomic scattering based on spherical atom. Calculations were mainly performed using WinGX-2014.1 suite of programs.[S7] Nonhydrogen atoms were refined anisotropically. The hydrogen atoms were inserted at the calculated positions and refined as riding atoms. The positions of the hydrogen atoms of methyl groups were found using a rotating group refinement with idealized tetrahedral angles. All the compounds studied have no unusual bond lengths and angles. The absolute structure of the crystals and absolute configuration were determined on the basis of the Flack parameter.[S8,S9]

Interestingly, racemic samples of cyclopropanes 2 and 6 crystallize in the Sohncke space group P2$_1$ of the monoclinic crystal system as conglomerates of enantiomer crystals. In the case of 2 the crystals are complicated by racemic twinning. The other substances studied form racemic compounds.

Chiral high performance liquid chromatography of racemic 2 allowed for the isolation of (1S,2R,3S)-2 and (1R,2S,3R)-2 isomers, which were analyzed by X-ray diffraction. HPLC was performed on a Nexera Liquid Chromatography machine (LC-10AD, Shimadzu) equipped with an autosampler (SIL-30AC), a column oven (CTO-20AC), and a diode array detector (SPD-M20A): $t_R$=8.15 min [(1S,2R,3S)-2], $t_R$=9.18 min [(1R,2S,3R)-2] {ChiralPak IA-3 (250×4.6 mm) column; column oven temperature: 25° C.; eluent: i-PrOH-n-hexane, 5:95; flow rate: 1 ml min$^{-1}$; λ=254 nm, cell temperature: 40° C.}.

The studied crystal of rac-2 turned out to be an inversion twin with the fractional volume contribution of 0.281(16) for the minor component. The investigated crystal of 7 demonstrated non-merohedral twinning: orientation matrices of four components were found by using the Lattice wizard routine and the final model was refined against a combined set of diffraction indices. The second component with fractional volume contribution of 0.2860(28) rotated from the first one by 5.4032° around reciprocal axis [0.03-1.00 0.05] and real axis [0.00-1.00 0.01]. The third component with fractional contribution of 0.2724(28) rotated by 179.9947° around reciprocal axis [0.00 0.00 1.00] and real axis [0.05 0.00 1.00]. The fourth component with fractional contribution of 0.1996(25) rotated from the first one by −179.9640° around reciprocal axis [1.00 0.00 0.00] and real axis [1.00 0.00 0.05].

In the case of 9, it was found that the trifluoromethyl group was disordered on two components {C38(F311)(F312)-F313 with relative occupancy of 0.871(4) and C38(F321)(F322)-F323}. The thiophene moiety of 13 was disordered over two positions with relative occupancy of 0.802(3) for the main component. The disorder was resolved using free variables and reasonable restraints on geometry and anisotropic displacement parameters.

The crystal data, data collection and structure refinement details for the investigated crystals are summarized in Tables 5 to 16. Molecular structures and the mutual arrangement of substituents of the investigated complexes in the crystalline phase as well as accepted partial numbering can be presented as ORTEP diagrams of FIGS. 89 to 100.

TABLE 5

Table 5: Crystallographic data summary for 2 (the crystal was selected from racemic sample).

| | |
|---|---|
| Compound | 2 |
| File name | jk248 |
| CCDC number | 1562834 |
| Empirical formula | $C_{22}H_{20}O_2S$ |
| Formula weight | 348.44 |
| Temperature | 103(2) K |
| Radiation, wavelength | CuKα, 1.54184 Å |
| Crystal system | Monoclinic |
| Space group | $P2_1$ (No. 4) |
| Unit cell dimensions | a = 5.95663(4) Å    α = 90° |
| | b = 16.32660(12) Å  β = 101.3720(6)° |
| | c = 9.34629(6) Å    γ = 90° |
| Volume | 891.096(11) Å$^3$ |
| Z and Z' | 2 and 1 |
| Calculated density | 1.299 g cm$^{-3}$ |
| Absorption coefficient | 1.699 mm$^{-1}$ |
| F(000) | 368 |
| Crystal size | 0.271 × 0.172 × 0.131 mm$^3$ |
| Colour | Colourless |
| Theta range for data collection | 4.826 to 75.153 |
| Index ranges | −7 ≤ h ≤ 7, −20 ≤ k ≤ 20, −11 ≤ l ≤ 11 |
| Reflections collected | 35000 |
| Independent reflections | 3649 [R(int) = 0.0327] |
| Observed Data [I > 2σ(I)] | 3648 |
| Completeness to theta = 67.684° | 100.0% |
| Absorption correction | Gaussian |
| Max. and min. transmission | 1.000 and 0.420 |
| Data/restraints/parameters | 3649/1/229 |
| Goodness-of-fit on F$^2$ | 1.028 |
| Final R indices [I > 2σ(I)] | R1 = 0.0280, wR2 = 0.0738 |
| R indices (all data) | R1 = 0.0280, wR2 = 0.0738 |
| Flack parameter | 0.281(16) |
| Extinction coefficient | 0.0139(11) |
| Largest diff. peak and hole | 0.277 and −0.302 e Å$^{-3}$ |

TABLE 6-1

Table 6: Crystallographic data summary for (1S,2R,3S)-2.

| | |
|---|---|
| Compound | (1S,2R,3S)-2 |
| File name | jk243 |
| CCDC number | 1562864 |
| Empirical formula | $C_{22}H_{20}O_2S$ |
| Formula weight | 348.44 |
| Temperature | 103(2) K |
| Radiation, wavelength | CuKα, 1.54184 Å |
| Crystal system | Monoclinic |
| Space group | $P2_1$ (No. 4) |
| Unit cell dimensions | a = 5.95677(4) Å    α = 90° |
| | b = 16.33181(11) Å  β = 101.3471(7)° |
| | c = 9.34432(7) Å    γ = 90° |
| Volume | 891.292(11) Å$^3$ |
| Z and Z' | 2 and 1 |
| Calculated density | 1.298 g cm$^{-3}$ |
| Absorption coefficient | 1.698 mm$^{-1}$ |
| F(000) | 368 |
| Crystal size | 0.242 × 0.140 × 0.100 mm$^3$ |
| Colour | Colourless |

TABLE 6-2

| | |
|---|---|
| Theta range for data collection | 4.827 to 75.807° |
| Index ranges | −7 ≤ h ≤ 7, −20 ≤ k ≤ 20, −11 ≤ l ≤ 11 |
| Reflections collected | 24679 |
| Independent reflections | 3677 [R(int) = 0.0305] |
| Observed Data [I > 2σ(I)] | 3671 |
| Completeness to theta = 67.684° | 100.0% |
| Absorption correction | Gaussian |
| Max. and min. transmission | 1.000 and 0.449 |
| Data/restraints/parameters | 3677/1/227 |
| Goodness-of-fit on F$^2$ | 1.064 |
| Final R indices [I > 2σ(I)] | R1 = 0.0279, wR2 = 0.0715 |
| R indices (all data) | R1 = 0.0279, wR2 = 0.0715 |
| Flack parameter | 0.004(5) |
| Extinction coefficient | n/a |
| Largest diff. peak and hole | 0.149 and −0.409 e Å$^{-3}$ |

TABLE 7-1

Table 7: Crystallographic data summary for (1R,2S,3R)-2.

| | |
|---|---|
| Compound | (1R,2S,3R)-2 |
| File name | jk247 |
| CCDC number | 1562865 |
| Empirical formula | $C_{22}H_{20}O_2S$ |
| Formula weight | 348.44 |
| Temperature | 103(2) K |
| Radiation, wavelength | CuKα, 1.54184 Å |
| Crystal system | Monoclinic |
| Space group | $P2_1$ (No. 4) |
| Unit cell dimensions | a = 5.95282(3) Å    α = 90° |
| | b = 16.32754(10) Å  β = 101.3599(6)° |
| | c = 9.34466(6) Å    γ = 90° |
| Volume | 890.459(9) Å$^3$ |
| Z and Z' | 2 and 1 |
| Calculated density | 1.300 g cm$^{-3}$ |
| Absorption coefficient | 1.700 mm$^{-1}$ |
| F(000) | 368 |
| Crystal size | 0.259 × 0.194 × 0.185 mm$^3$ |
| Colour | Colourless |

TABLE 7-2

| | |
|---|---|
| Theta range for data collection | 4.827 to 75.041° |
| Index ranges | −7 ≤ h ≤ 7, −19 ≤ k ≤ 20, −11 ≤ l ≤ 11 |
| Reflections collected | 21963 |
| Independent reflections | 3620 [R(int) = 0.0299] |
| Observed Data [I > 2σ(I)] | 3620 |

TABLE 7-2-continued

| | |
|---|---|
| Completeness to theta = 67.684° | 100.0% |
| Absorption correction | Gaussian |
| Max. and min. transmission | 1.000 and 0.343 |
| Data/restraints/parameters | 3620/1/228 |
| Goodness-of-fit on $F^2$ | 1.055 |
| Final R indices [I > 2σ(I)] | R1 = 0.0271, wR2 = 0.0722 |
| R indices (all data) | R1 = 0.0271, wR2 = 0.0722 |
| Flack parameter | 0.013(10) |
| Extinction coefficient | 0.0195(13) |
| Largest diff. peak and hole | 0.232 and −0.263 e Å$^{-3}$ |

TABLE 8-1

Table 8: Crystallographic data summary for 3.

| | | |
|---|---|---|
| Compound | 3 | |
| File name | jk146 | |
| CCDC number | 1562835 | |
| Empirical formula | $C_{19}H_{24}O_2S$ | |
| Formula weight | 316.44 | |
| Temperature | 105(2) K | |
| Radiation, wavelength | MoKα, 0.71073 Å | |
| Crystal system | Monoclinic | |
| Space group | P2$_1$/c (No. 14) | |
| Unit cell dimensions | a = 19.2122(5) Å | α = 90° |
| | b = 5.60896(14) Å | β = 106.458(3)° |
| | c = 16.8447(4) Å | γ = 90° |
| Volume | 1740.81(8) Å$^3$ | |
| Z and Z' | 4 and 1 | |
| Calculated density | 1.207 g cm$^{-3}$ | |
| Absorption coefficient | 0.191 mm$^{-1}$ | |
| F(000) | 680 | |
| Crystal size | 0.308 × 0.158 × 0.054 mm$^3$ | |
| Colour | Colourless | |

TABLE 8-2

| | |
|---|---|
| Theta range for data collection | 2.522 to 28.949° |
| Index ranges | −26 ≤ h ≤ 26, −7 ≤ k ≤ 7, −22 ≤ l ≤ 22 |
| Reflections collected | 36122 |
| Independent reflections | 4627 [R(int) = 0.0436] |
| Observed Data [I > 2σ(I)] | 4219 |
| Completeness to theta = 25.242° | 99.9% |
| Absorption correction | Gaussian |
| Max. and min. transmission | 1.000 and 0.544 |
| Data/restraints/parameters | 4627/0/200 |
| Goodness-of-fit on $F^2$ | 1.064 |
| Final R indices [I > 2σ(I)] | R1 = 0.0354, wR2 = 0.0901 |
| R indices (all data) | R1 = 0.0392, wR2 = 0.0922 |
| Extinction coefficient | n/a |
| Largest diff. peak and hole | 0.524 and 0.382 e Å$^{-3}$ |

TABLE 9-1

Table 9: Crystallographic data summary for 6 (the crystal was selected from racemic sample).

| | | |
|---|---|---|
| Compound | 6 | |
| File name | jk256 | |
| CCDC number | 1562836 | |
| Empirical formula | $C_{32}H_{34}O_2S$ | |
| Formula weight | 482.65 | |
| Temperature | 99(2) K | |
| Radiation, wavelength | CuKα, 1.54184 Å | |
| Crystal system | Monoclinic | |
| Space group | P2$_1$ (No. 4) | |
| Unit cell dimensions | a = 9.94302(9) Å | α = 90° |
| | b = 13.85818(10) Å | β = 116.1465(12)° |
| | c = 10.36258(10) Å | γ = 90° |

TABLE 9-1-continued

Table 9: Crystallographic data summary for 6 (the crystal was selected from racemic sample).

| | |
|---|---|
| Volume | 1281.77(2) Å$^3$ |
| Z and Z' | 2 and 1 |
| Calculated density | 1.251 g cm$^{-3}$ |
| Absorption coefficient | 1.323 mm$^{-1}$ |
| F(000) | 516 |
| Crystal size | 0.142 × 0.042 × 0.023 mm$^3$ |
| Colour | Colourless |

TABLE 9-2

| | |
|---|---|
| Theta range for data collection | 4.754 to 76.066° |
| Index ranges | −12 ≤ h ≤ 12, −17 ≤ k ≤ 17, −12 ≤ l ≤ 12 |
| Reflections collected | 40731 |
| Independent reflections | 5270 [R(int) = 0.0568] |
| Observed Data [I > 2σ(I)] | 5188 |
| Completeness to theta = 67.684° | 100.0% |
| Absorption correction | Gaussian |
| Max. and min. transmission | 1.000 and 0.835 |
| Data/restraints/parameters | 5270/1/316 |
| Goodness-of-fit on $F^2$ | 1.078 |
| Final R indices [I > 2σ(I)] | R1 = 0.0423, wR2 = 0.1143 |
| R indices (all data) | R1 = 0.0427, wR2 = 0.1146 |
| Flack parameter | −0.004(11) |
| Extinction coefficient | n/a |
| Largest diff. peak and hole | 0.443 and −0.315 e Å$^{-3}$ |

TABLE 10-1

Table 10: Crystallographic data summary for 7.

| | | |
|---|---|---|
| Compound | 7 | |
| File name | jk197 | |
| CCDC number | 1562838 | |
| Empirical formula | $C_{21}H_{18}O_2S$ | |
| Formula weight | 334.41 | |
| Temperature | 105(2) K | |
| Radiation, wavelength | CuKα, 1.54184 Å | |
| Crystal system | Monoclinic | |
| Space group | P2$_1$/c (No. 14) | |
| Unit cell dimensions | a = 16.4622(15) Å | α = 90° |
| | b = 5.8724(7) Å | β = 93.026(11)° |
| | c = 16.929(3) Å | γ = 90° |
| Volume | 1634.3(4) Å$^3$ | |
| Z and Z' | 4 and 1 | |
| Calculated density | 1.359 g cm$^{-3}$ | |
| Absorption coefficient | 1.830 mm$^{-1}$ | |
| F(000) | 704 | |
| Crystal size | 0.093 × 0.033 × 0.013 mm$^3$ | |
| Colour | Colourless | |

TABLE 10-2

| | |
|---|---|
| Theta range for data collection | 5.758 to 73.010° |
| Index ranges | −20 ≤ h ≤ 20, −6 ≤ k ≤ 6, −20 ≤ l ≤ 20 |
| Reflections collected | 4834 |
| Independent reflections | 4834 |
| Observed Data [I > 2σ(I)] | 4215 |
| Completeness to theta = 67.684° | 99.4% |
| Absorption correction | Semi-empirical from equivalents |
| Max. and min. transmission | 1.00000 and 0.57149 |
| Data/restraints/parameters | 4834/0/220 |
| Goodness-of-fit on $F^2$ | 1.068 |
| Final R indices [I > 2σ(I)] | R1 = 0.0797, wR2 = 0.2260 |
| R indices (all data) | R1 = 0.0883, wR2 = 0.2367 |
| Extinction coefficient | n/a |
| Largest diff. peak and hole | 0.890 and −0.614 e Å$^{-3}$ |

TABLE 11-1

Table 11: Crystallographic data summary for 8.

| | |
|---|---|
| Compound | 8 |
| File name | jk244 |
| CCDC number | 1562839 |
| Empirical formula | $C_{28}H_{23}FO_2S$ |
| Formula weight | 442.52 |
| Temperature | 103(2) K |
| Radiation, wavelength | CuKα, 1.54184 Å |
| Crystal system | Orthorhombic |
| Space group | Pbca (No. 61) |
| Unit cell dimensions | a = 24.4556(5) Å    α = 90° |
| | b = 6.94795(10) Å    β = 90° |
| | c = 26.1114(6) Å    γ = 90° |
| Volume | 4436.75(14) Å$^3$ |
| Z and Z' | 8 and 1 |
| Calculated density | 1.325 g cm$^{-3}$ |
| Absorption coefficient | 1.552 mm$^{-1}$ |
| F(000) | 1856 |
| Crystal size | 0.112 × 0.02.1 × 0.009 mm$^3$ |
| Colour | Colourless |

TABLE 11-2

| | |
|---|---|
| Theta range for data collection | 3.385 to 69.989° |
| Index ranges | −23 ≤ h ≤ 29, −8 ≤ k ≤ 8, −31 ≤ l ≤ 31 |
| Reflections collected | 32203 |
| Independent reflections | 4197 [R(int) = 0.0559] |
| Observed Data [I > 2σ(I)] | 3567 |
| Completeness to theta = 67.684° | 99.6% |
| Absorption correction | Semi-empirical from equivalents |
| Max. and min. transmission | 1.00000 and 0.63087 |
| Data/restraints/parameters | 4197/0/289 |
| Goodness-of-fit on F$^2$ | 1.025 |
| Final R indices [I > 2σ(I)] | R1 = 0.0412, wR2 = 0.1052 |
| R indices (all data) | R1 = 0.0496, wR2 = 0.1106 |
| Extinction coefficient | n/a |
| Largest diff. peak and hole | 0.252 and −0.421 e Å$^{-3}$ |

TABLE 12-1

Table 12: Crystallographic data summary for 9.

| | |
|---|---|
| Compound | 9 |
| File name | jk245 |
| CCDC number | 1562840 |
| Empirical formula | $C_{29}H_{23}F_3O_2S$ |
| Formula weight | 492.53 |
| Temperature | 103(2) K |
| Radiation, wavelength | CuKα, 1.54184 Å |
| Crystal system | Orthorhombic |
| Space group | Pbca (No. 61) |
| Unit cell dimensions | a = 25.5323(4) Å    α = 90° |
| | b = 6.94016(11) Å    β = 90° |
| | c = 27.4879(5) Å    γ = 90° |
| Volume | 4870.81(14) Å$^3$ |
| Z and Z' | 8 and 1 |
| Calculated density | 1.343 g cm$^{-3}$ |
| Absorption coefficient | 1.592 mm$^{-1}$ |
| F(000) | 2048 |
| Crystal size | 0.121 × 0.024 × 0.013 mm$^3$ |
| Colour | Colourless |

TABLE 12-2

| | |
|---|---|
| Theta range for data collection | 3.216 to 75.676° |
| Index ranges | −32 ≤ h ≤ 30, −4 ≤ k ≤ 8, −30 ≤ l ≤ 34 |
| Reflections collected | 26932 |
| Independent reflections | 5008 [R(int) = 0.0622] |
| Observed Data [I > 2σ(I)] | 3997 |
| Completeness to theta 67.684° | 100.0% |
| Absorption correction | Gaussian |
| Max. and min. transmission | 1.000 and 0.799 |
| Data/restraints/parameters | 5008/42/344 |
| Goodness-of-fit on F$^2$ | 1.058 |
| Final R indices [I > 2σ(I)] | R1 = 0.0454, wR2 = 0.1171 |
| R indices (all data) | R1 = 0.0579, wR2 = 0.1252 |
| Extinction coefficient | n/a |
| Largest diff. peak and hole | 0.276 and −0.442 e Å$^{-3}$ |

TABLE 13-1

Table 13: Crystallographic data summary for 12.

| | |
|---|---|
| Compound | 12 |
| File name | jk282 |
| CCDC number | 1562841 |
| Empirical formula | $C_{28}H_{31}NO_2S$ |
| Formula weight | 445.60 |
| Temperature | 99(2) K |
| Radiation, wavelength | CuKα, 1.54184 Å |
| Crystal system | Monoclinic |
| Space group | P2$_1$/n (No. 14) |
| Unit cell dimensions | a = 13.8460(2) Å    α = 90° |
| | b = 9.95257(15) Å    β = 107.2106(15)° |
| | c = 18.1020(3) Å    γ = 90° |
| Volume | 2382.82(6) Å$^3$ |
| Z and Z' | 4 and 1 |
| Calculated density | 1.242 g cm$^{-3}$ |
| Absorption coefficient | 1.391 mm$^{-1}$ |
| F(000) | 952 |
| Crystal size | 0.397 × 0.262 × 0.069 mm$^3$ |
| Colour | Colourless |

TABLE 13-2

| | |
|---|---|
| Theta range for data collection | 4.773 to 75.094° |
| Index ranges | −16 ≤ h ≤ 17, −12 ≤ k ≤ 12, −21 ≤ l ≤ 21 |
| Reflections collected | 29536 |
| Independent reflections | 4806 [R(int) = 0.0502] |
| Observed Data [I > 2σ(I)] | 4605 |
| Completeness to theta = 67.684° | 99.3% |
| Absorption correction | Gaussian |
| Max. and min. transmission | 0.858 and 0.375 |
| Data/restraints/parameters | 4806/0/289 |
| Goodness-of-fit on F$^2$ | 1.041 |
| Final R indices [I > 2σ(I)] | R1 = 0.0394, wR2 = 0.1053 |
| R indices (all data) | R1 = 0.0405, wR2 = 0.1063 |
| Extinction coefficient | n/a |
| Largest diff. peak and hole | 0.238 and −0.593 e Å$^{-3}$ |

TABLE 14-1

Table 14: Crystallographic data summary for 13.

| | |
|---|---|
| Compound | 13 |
| File name | jk268 |
| CCDC number | 1562842 |
| Empirical formula | $C_{26}H_{22}O_2S_2$ |
| Formula weight | 430.55 |
| Temperature | 103(2) K |
| Radiation, wavelength | CuKα, 1.54184 Å |
| Crystal system | Monoclinic |
| Space group | C2/c (No. 15) |
| Unit cell dimensions | a = 33.0048(10) Å    α = 90° |
| | b = 6.06084(16) Å    β = 109.856(4)° |
| | c = 22.8814(8) Å    γ = 90° |
| Volume | 4305.0(2) Å$^3$ |
| Z and Z' | 8 and 1 |
| Calculated density | 1.329 g cm$^{-3}$ |
| Absorption coefficient | 2.397 mm$^{-1}$ |

TABLE 14-1-continued

Table 14: Crystallographic data summary for 13.

| | |
|---|---|
| F(000) | 1808 |
| Crystal size | 0.269 × 0.036 × 0.009 mm$^3$ |
| Colour | Colourless |

TABLE 14-2

| | |
|---|---|
| Theta range for data collection | 2.847 to 75.253° |
| Index ranges | −36 ≤ h ≤ 40, −7 ≤ k ≤ 7, −28 ≤ l ≤ 28 |
| Reflections collected | 21078 |
| Independent reflections | 4376 [R(int) = 0.0871] |
| Observed Data [I > 2σ(I)] | 3840 |
| Completeness to theta = 67.684° | 100.0% |
| Absorption correction | Gaussian |
| Max. and min. transmission | 1.000 and 0.373 |
| Data/restraints/parameters | 4376/178/317 |
| Goodness-of-fit on F$^2$ | 1.109 |
| Final R indices [I > 2σ(I)] | R1 = 0.0574, wR2 = 0.1601 |
| R indices (all data) | R1 = 0.0622, wR2 = 0.1656 |
| Extinction coefficient | n/a |
| Largest diff. peak and hole | 0.643 and −0.714 e Å$^{-3}$ |

TABLE 15-1

Table 15: Crystallographic data summary for 15.

| | | |
|---|---|---|
| Compound | 15 | |
| File name | jk271 | |
| CCDC number | 1562843 | |
| Empirical formula | C$_{13}$H$_{18}$O$_2$S$_3$ | |
| Formula weight | 302.45 | |
| Temperature | 99(2) K | |
| Radiation, wavelength | CuKα, 1.54184 Å | |
| Crystal system | Monoclinic | |
| Space group | P2$_1$/n (No. 14) | |
| Unit cell dimensions | a = 10.05017(8) Å | α = 90° |
| | b = 8.21067(7) Å | β = 90.5483(8)° |
| | c = 18.02926(18) Å | γ = 90° |
| Volume | 1487.68(2) Å$^3$ | |
| Z and Z' | 4 and 1 | |
| Calculated density | 1.350 g cm$^{-3}$ | |
| Absorption coefficient | 4.490 mm$^{-1}$ | |
| F(000) | 640 | |
| Crystal size | 0.232 × 0.177 × 0.066 mm$^3$ | |
| Colour | Colourless | |

TABLE 15-2

| | |
|---|---|
| Theta range for data collection | 4.906 to 75.215° |
| Index ranges | −12 ≤ h ≤ 12, −10 ≤ k ≤ 10, −22 ≤ l ≤ 22 |
| Reflections collected | 41069 |
| Independent reflections | 3059 [R(int) = 0.0598] |
| Observed Data [I > 2σ(I)] | 3056 |
| Completeness to theta = 67.684° | 100.0% |
| Absorption correction | Gaussian |
| Max. and min. transmission | 1.000 and 0.215 |
| Data/restraints/parameters | 3059/0/167 |
| Goodness-of-fit on F$^2$ | 1.098 |
| Final R indices [I > 2σ(I)] | R1 = 0.0562, wR2 = 0.1546 |
| R indices (all data) | R1 = 0.0562, wR2 = 0.1546 |
| Extinction coefficient | n/a |
| Largest diff. peak and hole | 1.768 and −0.904 e Å$^{-3}$ |

TABLE 16-1

Table 16: Crystallographic data summary for 24.

| | | |
|---|---|---|
| Compound | 24 | |
| File name | jk232 | |
| CCDC number | 1562844 | |
| Empirical formula | C$_{17}$H$_{18}$O$_2$S | |
| Formula weight | 286.37 | |
| Temperature | 1.05(2) K | |
| Radiation, wavelength | CuKα, 1.54184 Å | |
| Crystal system | Monoclinic | |
| Space group | P2$_1$/n (No. 14) | |
| Unit cell dimensions | a = 15.99520(12) Å | α = 90° |
| | b = 6.26635(3) Å | β = 118.0562(9)° |
| | c = 16.71842(11) Å | γ = 90° |
| Volume | 1478.79(2) Å$^3$ | |
| Z and Z' | 4 and 1 | |
| Calculated density | 1.286 g cm$^{-3}$ | |
| Absorption coefficient | 1.925 mm$^{-1}$ | |
| F(000) | 608 | |
| Crystal size | 0.183 × 0.081 × 0.070 mm$^3$ | |
| Colour | Colourless | |

TABLE 16-2

| | |
|---|---|
| Theta range for data collection | 3.155 to 75.092° |
| Index ranges | −19 ≤ h ≤ 20, −7 ≤ k ≤ 7, −20 ≤ l ≤ 20 |
| Reflections collected | 33649 |
| Independent reflections | 3042 [R(int) = 0.0396] |
| Observed Data [I > 2σ(I)] | 2969 |
| Completeness to theta = 67.684° | 100.0% |
| Absorption correction | Semi-empirical from equivalents |
| Max. and min. transmission | 1.00000 and 0.68790 |
| Data/restraints/parameters | 3042/0/183 |
| Goodness-of-fit on F$^2$ | 1.072 |
| Final R indices [I > 2σ(I)] | R1 = 0.0306, wR2 = 0.0839 |
| R indices (all data) | R1 = 0.0311, wR2 = 0.0843 |
| Extinction coefficient | n/a |
| Largest diff. peak and hole | 0.275 and −0.452 e Å$^{-3}$ |

In conclusion, the inventor has outlined a fundamentally new cyclopropanation reaction. Alcohols and sulfones can serve as diverse and cheap substrates that lead to a complex product with new carbon-carbon bonds, two or three new chiral centers, one new quaternary carbon center, and a good sulfone leaving group that also polarizes the resulting ring, thus enabling further push-pull ring opening reactivity. Due to this being a one-step, catalytic reaction, the resulting cyclopropanes can be obtained in high yields and with excellent diastereoselectivities when compared with alternative routes for the synthesis of these products. Control over all the ring substituents can be obtained by using two different sulfones in the reaction, with the most acidic one reacting first.

REFERENCES (1)(a) Chen, D. Y. K.; Pouwer, R. H.; Richard, J.-A., Chem. Soc. Rev. 2012, 41, 4631-4642; (b) Donaldson, W. A., Tetrahedron 2001, 57, 8589-8627.
(2)(a) Gharpure, S. J.; Nanda, L. N., Tetrahedron Lett. 2017, 58, 711-720; (b) Wang, Z., Synlett 2012, 23, 2311-2327; (c) Thibodeaux, C. J.; Chang, W.-c.; Liu, H.-w., Chem. Rev. 2012, 112, 1681-1709; (d) Tang, P.; Qin, Y., Synthesis 2012, 44, 2969-2984; (e) Carson, C. A.; Kerr, M. A., Chem. Soc. Rev. 2009, 38, 3051-3060.
(3)(a) shitama, H.; Katsuki, T., Angew. Chem., Int. Ed. 2008, 47, 2450-2453; (b) Charette, A. B.; Juteau, H., J. Am. Chem. Soc. 1994, 116, 2651-2; (c) Furukawa, J.; Kawabata, N., Advan. Organometal. Chem. 1974, 12, 83-134;

(d) Filliatre, C.; Gueraud, C., C. R. Acad. Sci., Ser. C 1971, 273, 1186-9; (e) Simmons, H. E.; Smith, R. D., J. Am. Chem. Soc. 1958, 80, 5323-4.

(4)(a) Volla, C. M. R.; Atodiresei, Rueping, M., Chem. Rev. 2014, 114, 2390-2431; (b) del Villar, I. S.; Gradillas, A.; Dominguez, G.; Perez-Castells, J., Tetrahedron Lett. 2010, 51, 3095-3098; (c) Ye, Y.; Zheng, C.; Fan, R., Org. Lett. 2009, 11, 3156-3159; (d) Sun, X.-L.; Tang, Y., Acc. Chem. Res. 2008, 41, 937-948; (e) Abramovitch, A.; Fensterbank, L.; Malacria, M.; Marek, I., Angew. Chem., Int. Ed. 2008, 47, 6865-6868; (f) Kakei. H.; Sone, T.; Sohtome, Y.; Matsunaga, S.; Shibasaki, M., J. Am. Chem. Soc. 2007, 129, 13410-13411; (g) Gaunt, M. J.; Johansson, C. C. C., Chem. Rev. 2007, 107, 5596-5605; (h) Johansson, C. C. C.; Bremeyer, N.; Ley, S. V.; Owen. D. R.; Smith, S. C.; Gaunt, M. J., Angew. Chem., Int. Ed. 2006, 45, 6024-6028; (i) Kunz, R. K.; MacMillan, D. W. C., J. Am. Chem. Soc. 2005, 127, 3240-3241; (j) Papageorgiou, C. D.; Cubillo de Dios, M. A.; Ley, S. V.; Gaunt, M. J., Angew. Chem., Int. Ed. 2004, 43, 4641-4644; (k) Aggarwal, V. K.; Alonso, E.; Fang, G.; Ferrara, M.; Hynd, G.; Porcelloni, M., Angew. Chem., Int. Ed. 2001, 40, 1433-1436.

(5)(a) Riches, S. L.; Saha. C.; Filgueira, N. F.; Grange, E.; McGarrigle, E. M.; Aggarwal, V. K., J. Am. Chem. Soc. 2010, 132, 7626-7630; (b) Appel, R.; Hartmann, N.; Mayr, H., J. Am. Chem. Soc. 2010, 132, 17894-17900; (c) Deng, X.-M.; Cai, P.; Ye, S.; Sun, X.-L.; Liao, W.-W.; Li, K.; Tang, Y.; Wu, Y.-D.; Dai, L.-X., J. Am. Chem. Soc. 2006, 128, 9730-9740; (d) Corey, E. J.; Chaykovsky, M., J. Am. Chem. Soc. 1965, 87, 1353-64.

(6)(a) Chanthamath, S.; Iwasa, S., Acc. Chem. Res. 2016, 49, 2080-2090; (b) Shen, J.-J.; Zhu, S.-F.; Cai, Y.; Xu, H.; Xie, X.-L.; Zhou. Q.-L., Angew. Chem., Int. Ed. 2014, 53, 13188-13191; (c) Levesque, E.; Goudreau, S. R.; Charette, A. B., Org. Lett. 2014, 16, 1490-1493; (d) Lindsay, V. N. G.; Fiset, D.; Gritsch, P. J.; Azzi, S.; Charette, A. B., J. Am. Chem. Soc. 2013, 135, 1463-1470; (e) Xu, X.; Lu, H.; Ruppel, J. V.; Cui, X.; Lopez de Mesa, S.; Wojtas, L.; Zhang, X. P., J. Am. Chem. Soc. 2011, 133, 15292-15295; (f) Gao, L.; Hwang, G.-S.; Ryu, D. H., J. Am. Chem. Soc. 2011, 133, 20708-20711; (g) Zhu, S.; Xu, X.; Perman, J. A.; Zhang, X. P., J. Am. Chem. Soc. 2010, 132, 12796-12799; (h) Emerzian, M. A.; Davenport, W.; Song, J.; Li, J.; Erden, I., Adv. Synth. Catal. 2009, 351, 999-1004; (i) Doyle, M. P., Angew. Chem., Int. Ed. 2009, 48, 850-852.

(7)(a) Wang, J.; Liu, X.; Dong, S.; Lin, L.; Feng, X., J. Org. Chem. 2013, 78, 6322-6327; (b) Rueping, M.; Sunden, H.; Hubener, L.; Sugiono, E., Chem. Commun. 2012, 48, 2201-2203; (c) Biswas, A.; De Sarkar, S.; Tebben, L.; Studer, A., Chem. Commun. 2012, 48, 5190-5192; (d) Cheng, Y.; An, J.; Lu, L.-Q.; Luo, L.; Wang, Z.-Y.; Chen, J.-R.; Xiao, W.-J., J. Org. Chem. 2011, 76, 281-284; (e) Raveendran, A. E.; Paul, R. R.; Suresh, E.; Nair, V., Org. Biomol. Chem. 2010, 8, 901-905; (f) Alba, A.-N.; Companyo, X.; Viciano, M.; Rios, R., Curr. Org. Chem. 2009, 13, 1432-1474.

(8)(a) Wu, W.; Jiang, H.; Gao, Y.; Huang, H.; Zeng, W.; Cao, D., Chem. Commun. 2012, 48, 10340-10342; (b) Welbes, L. L.; Lyons, T. W.; Cychosz, K. A.; Sanford, M. S., J. Am. Chem. Soc. 2007, 129, 5836-5837.

(9) Muller, D. S.; Marek, I., J. Am. Chem. Soc. 2015, 137, 15414-15417.

(10) Lucht, A.; Patalag, L. J.; Augustin, A. U.; Jones, P. G.; Werz, D. B., Angewandte Chemie International Edition, n/a-n/a.

(11)(a) Lopchuk, J. M.; Fjelbye, K.; Kawamata, Y.; Malins, L. R.; Pan, C.-M.; Gianatassio, R.; Wang, J.; Prieto, L.; Bradow, J.; Brandt, T. A.; Collins, M. R.; Elleraas, J.; Ewanicki, J.; Farrell, W.; Fadeyi, O. O.; Gallego, G. M.; Mousseau, J. J.; Oliver, R.; Sach, N. W.; Smith, J. K.; Spangler, J. E.; Zhu, H.; Zhu, J.; Baran, P. S., J. Am. Chem. Soc. 2017, 139, 3209-3226; (b) Gianatassio, R.; Lopchuk, J. M.; Wang, J.; Pan, C.-M.; Malins, L. R.; Prieto, L.; Brandt, T. A.; Collins, M. R.; Gallego, G. M.; Sach, N. W.; Spangler, J. E.; Zhu, H.; Zhu, J.; Baran, P. S., Science 2016, 351, 241-246.

(12)(a) Wang, L.; Tang, Y., Isr. J. Chem. 2016, 56, 463-475; (b) O'Connor, N. R.; Wood, J. L.; Stoltz, B. M., Isr. J. Chem. 2016, 56, 431-444; (c) Schneider, T. F.; Kaschel, J.; Werz, D. B., Angew. Chem., Int. Ed. 2014, 53, 5504-5523; (d) Cavitt, M. A.; Phun, L. H.; France, S., Chem. Soc. Rev. 2014, 43, 804-818.

(13)(a) Vasin, V. A.; Razin, V. V.; Bezrukova, E. V.; Korovin, D. Y.; Petrov, P. S.; Somov, N. V., Russ. J. Org. Chem. 2015, 51, 1144-1154; (b) Li, Y.; Huang, Z.; Wu, X.; Xu, P.-F.; Jin, J.; Zhang, Y.; Wang, J., Tetrahedron 2012, 68, 5234-5240; (c) Bernard, A. M.; Frongia, A.; Piras, P. P.; Secci, F.; Spiga, M., Org. Lett. 2005, 7, 4565-4568; (d) Skarzewski, J.; Siedlecka, R.; Wojaczynska, E.; Zielinska-Blajet, M., Tetrahedron: Asymmetry 2002, 13, 2105-2111; (e) Bailey, P. L.; Hewkin, C. T.; Clegg, W.; Jackson, R. F. W., J. Chem. Soc., Perkin Trans. 1 1993, 577-84; (f) Reddy, D. B.; Reddy, P. V. R.; Padmavathi, V.; Reddy, M. V. R., Sulfur Lett. 1991, 13, 83-90; (g) Reddy, D. B.; Balaji, T.; Reddy, B. V., Phosphorus Sulfur 1983, 17, 297-305; (h) Corbel, B.; Durst, T., J. Org. Chem. 1976, 41, 3648-50; (i) Nudelman, A.; Cram, D. J., J. Org. Chem. 1969, 34, 3659-61.

(14) Srimani, D.; Leitus, G.; Ben-David, Y.; Milstein, D., Angew. Chem., Int. Ed. 2014, 53, 11092-11095.

(15)(a) Balaraman, E.; Khaskin, E.; Leitus, G.; Milstein, D., Nat. Chem. 2013, 5, 122-125; (b) Bauer, J. O.; Leitus, G.; Ben-David, Y.; Milstein, D., ACS Catal. 2016, 6, 8415-8419; (c) Khaskin, E.; Milstein, D., ACS Catal. 2013, 3, 448-452; (d) Khaskin, E.; Milstein, D., Chem. Commun. 2015, 51, 9002-9005.

(16)(a) Aissa, C., Eur. J. Org. Chem. 2009, 1831-1844; (b) Babudri, F. In Silicon and sulfur reagents in carbonyl olefination, Societa Chimica Italiana: 2008; pp 173-198.

(17)(a) Baudin, J. B.; Hareau, G.; Julia, S. A.; Ruel, O., Tetrahedron Lett. 1991, 32, 1175-8; (b) Blakemore, P. R., J. Chem. Soc., Perkin Trans. 1 2002, 2563-2585.

(18) Dubey, A.; Khaskin, E., ACS Catal. 2016, 6, 3998-4002.

(19) Spasyuk, D.; Smith, S.; Gusev, D. G., Angew. Chem., Int. Ed. 2013, 52, 2538-2542.

(20) Jin, Z.; Xu, J.; Yang, S.; Song, B.-A.; Chi, Y. R., Angew. Chem., Int. Ed. 2013, 52, 12354-12358.

(21)(a) Zhang, J.; Leitus, G.; Ben-David, Y.; Milstein, D., Angew. Chem., Int. Ed. 2006, 45, 1113-1115; (b) Zhang, J.; Leitus, G.; Ben-David, Y.; Milstein, D., J. Am. Chem. Soc. 2005, 127, 10840-10841.

(22) Kuriyama, W.; Matsumoto, T.; Ogata, O.; Ino, Y.; Aoki, K.; Tanaka, S.; Ishida, K.; Kobayashi, T.; Sayo, N.; Saito, T., Org. Process Res. Dev. 2012, 16, 166-171.

(23) Spasyuk, D.; Gusev, D. G., Organometallics 2012, 31, 5239-5242.

(24) Spasyuk, D.; Vicent, C.; Gusev, D. G., J. Am. Chem. Soc. 2015, 137, 3743-3746.

(25) Gai, Y.; Julia, M.; Verpeaux, J. N., Synlett 1991, 56-7.

(26) Bailey, P. L.; Clegg, W.; Jackson, R. F. W.; Meth-Cohn, O., J. Chem. Soc., Perkin Trans. 1 1990, 200-2.

(27)(a) Agawa, T.; Yoshida, Y.; Komatsu, M.; Ohshiro, Y., J. Chem. Soc., Perkin Trans. 1 1981, 751-5; (b) Campbell, R. V. M.; Crombie, L.; Findley, D. A. R.; King, R. W.; Pattenden, G.; Whiting, D. A., J. Chem. Soc., Perkin Trans. 1 1975, 897-913.
(28) Kulinkovich, O. G., Cyclopropanes in Organic Synthesis. Wiley: 2015.
S1) http://evans.rc.fas.harvard.edu/pdf/evans_pKa_table.pdf
S2) http://www.chem.wisc.edu/areas/reich/pkatable/index.htm
S3) Skarzewski, J.; Siedlecka, R.; Wojaczynska, E.; Zielinska-Blajet, M., Tetrahedron: Asymmetry 2002, 13 (19), 2105-2111
S4) Srimani, D.; Leitus, G.; Ben-David, Y.; Milstein, D., Angew. Chem., Int. Ed. 2014, 53 (41), 11092-11095.
S5) Sheldrick, G. M. Acta Cryst. A 2015, 71, 3-8.
S6) Sheldrick, G. M. Acta Cryst. C 2015, 71, 3-8.
S7) Farrugia, L. J. J. Appl. Cryst. 2012, 45, 849-854.
S8) Flack, H. D.; Bernardinelli, G. J. Appl. Cryst. 2000, 33, 1143-1148.
S9) Parsons, S.; Flack, H. D.; Wagner T. Acta Cryst. B 2013, 69, 249-259.

The invention claimed is:

1. A cyclopropanation method, comprising:
reacting an alcohol, an ester, or an aldehyde with a phenyl sulfone in an organic solvent containing a base providing a counter cation to form a cyclopropane; and,
isolating the cyclopropane;
wherein,
the aldehyde is paraformaldehyde or $R^3CHO$, in which $R^3$ is hydrogen, alkyl, or cycloalkyl, and the alkyl is optionally intervened by oxygen, sulfur, or nitrogen;
$R^3$ is saturated or unsaturated, provided that a double bond does not exist between a β carbon and a γ carbon of the aldehyde;
$R^3$ is unsubstituted or substituted with at least one substituent selected from the group consisting of alkyl, cycloalkyl, heterocycloalkyl, aryl, and heteroaryl, provided that the α carbon of the alcohol is unsubstituted;
the substituent is further substituted or unsubstituted when the aldehyde is reacted; and,
the organic solvent further contains a catalyst having an alcohol dehydrogenation activity when the alcohol or the ester is reacted.

2. The cyclopropanation method according to claim 1;
wherein, the alcohol is reacted;
the alcohol is $R^1CH_2OH$, in which $R^1$ is hydrogen, alkyl, or cycloalkyl, and the alkyl is optionally intervened by oxygen, sulfur, or nitrogen;
$R^1$ is saturated or unsaturated, provided that a double bond does not exist between a β carbon and a γ carbon of the alcohol;
$R^1$ is unsubstituted or substituted with at least one substituent selected from the group consisting of alkyl, cycloalkyl, heterocycloalkyl, aryl, and heteroaryl, provided that the β carbon of the alcohol is unsubstituted; and,
the substituent is further substituted or unsubstituted.

3. The cyclopropanation method according to claim 2, wherein the alcohol is selected from the group consisting of:

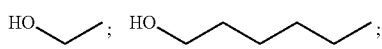

-continued

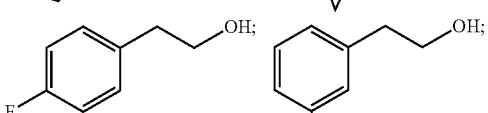

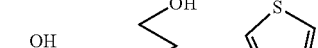

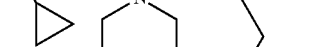

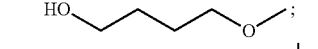

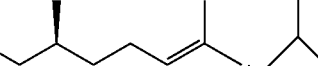

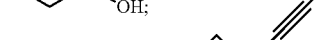

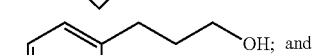

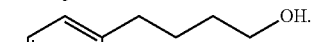

4. The cyclopropanation method according to claim 1, wherein, the ester is reacted;
the ester is formed from $R^1CH_2OH$ and $R^2COOH$;
$R^1$ is hydrogen, alkyl, or cycloalkyl, and the alkyl is optionally intervened by oxygen, sulfur, or nitrogen;
$R^1$ is saturated or unsaturated, provided that a double bond does not exist between a β carbon and a γ carbon of the alcohol;
$R^1$ is unsubstituted or substituted with at least one substituent selected from the group consisting of alkyl, cycloalkyl, heterocycloalkyl, aryl, and heteroaryl, provided that the β carbon of the alcohol is unsubstituted;
the substituent is further substituted or unsubstituted; and,
$R^2$ is saturated or unsaturated alkyl, saturated or unsaturated cycloalkyl, saturated or unsaturated heterocycloalkyl, aryl, or heteroaryl, and $R^2$ is unsubstituted or substituted.

5. The cyclopropanation method according to claim 4, wherein the ester is selected from the group consisting of

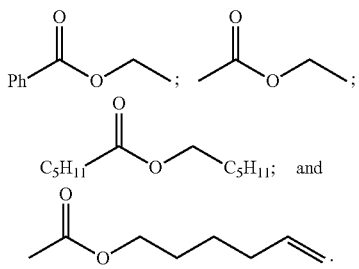

6. The cyclopropanation method according to claim 1, wherein the aldehyde is selected from the group consisting of:

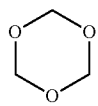

and $C_5H_{11}CHO$.

7. The cyclopropanation method according to claim 1, wherein the sulfone is represented by $R^4CH_2SO_2R^5$;
$R^4$ is hydrogen, alkyl, alkylthio, cycloalkyl, heterocloalkyl, aryl, or hetroraryl; and,
$R^5$ is unsubstituted or substituted phenyl.

8. The cyclopropanation method according to claim 1, wherein the phenyl sulfone is selected from the group consisting of:

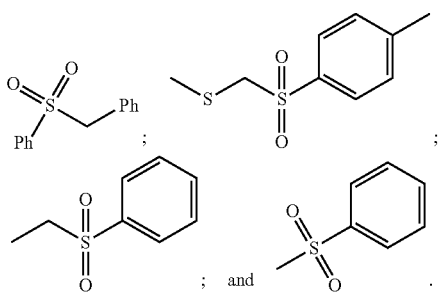

9. The cyclopropanation method according to claim 1, wherein the base provides a potassium cation or a cesium cation.

10. The cyclopropanation method according to claim 1, wherein the base is at least one selected from the group consisting of potassium hydroxide, potassium methoxide, potassium ethoxide, potassium propoxide, potassium butoxide, potassium tert-butoxide, potassium bis(trimethylsilyl)amide, and potassium hydride.

11. The cyclopropanation method according to claim 1, wherein the catalyst contains Pt, Cu, Fe, Co, Pd, Ru, V, Ni, or Os.

12. The cyclopropanation method according to claim 1, wherein the catalyst is a Ru catalyst, an Os catalyst, or a Ni catalyst.

13. The cyclopropanation method according to claim 1, wherein the catalyst is selected from the group consisting of:

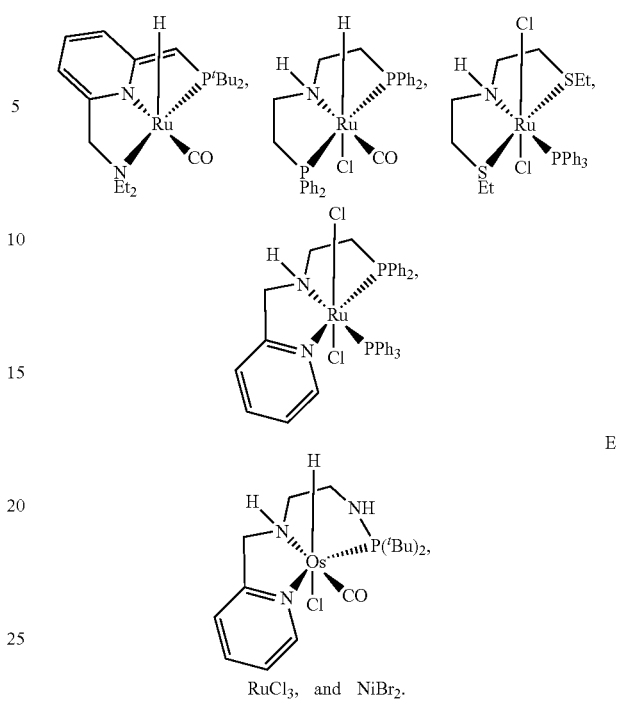

$RuCl_3$, and $NiBr_2$.

14. The cyclopropanation method according to claim 1, wherein the organic solvent is selected from ether based solvents and aromatic hydrocarbons.

15. The cyclopropanation method according to claim 1, wherein the organic solvent is selected from the group consisting of tetrahydrofuran, dioxane, 1,2-dimethoxyethane, benzene, and toluene.

16. The cyclopropanation method according to claim 1, wherein an amount of the catalyst is 0.2 to 1.0 mol % with respect to an amount of the alcohol or the ester.

17. The cyclopropanation method according to claim 1, wherein an amount of the base is 50 to 300 mol % with respect to an amount of the alcohol or the ester.

18. The cyclopropanation method according to claim 1, wherein the solvent is anhydrous.

19. The cyclopropanation method according to claim 1, wherein the molar ratio of sulfones:the alcohol, the ester, or the aldehyde is approximately 2:1.

20. The cyclopropanation method according to claim 1, wherein a cyano compound is also reacted in the reacting step.

21. The cyclopropanation method according to claim 1, wherein a yield of the cyclopropane is 70% or more.

22. The cyclopropanation method according to claim 1, wherein the isolating is carried out by a chiral chromatography.

23. The cyclopropanation method according to claim 1, wherein the reacting is carried out in a closed system.

24. The cyclopropanation method according to claim 1, wherein the reacting is carried out at above room temperature.

25. The cyclopropanation method according to claim 1, wherein the reacting is carried out at 80° C. or more.

26. The cyclopropanation method according to claim 1, wherein the reacting is carried out for 16 to 72 hours.

* * * * *